United States Patent
Soergel et al.

(10) Patent No.: US 9,474,277 B2
(45) Date of Patent: Oct. 25, 2016

(54) PYRAZOLE COMPOUND AND PESTICIDAL MIXTURES COMPRISING A PYRAZOLE COMPOUND

(71) Applicant: BASF SE, Ludwigshafen (DE)

(72) Inventors: Sebastian Soergel, Ludwigshafen (DE); Daniel Saelinger, Ludwigshafen (DE); Christian Defieber, Mannheim (DE); Juergen Langewald, Mannheim (DE); Birgit Gockel, Ludwigshafen (DE); Egon Haden, Speyer (DE); Deborah L. Culberston, Fuquay Varina, NC (US); Koshi Gunjima, Toyohashi (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/408,174

(22) PCT Filed: Jun. 12, 2013

(86) PCT No.: PCT/EP2013/062123
§ 371 (c)(1),
(2) Date: Dec. 15, 2014

(87) PCT Pub. No.: WO2013/189801
PCT Pub. Date: Dec. 27, 2013

(65) Prior Publication Data
US 2015/0150257 A1 Jun. 4, 2015

Related U.S. Application Data

(60) Provisional application No. 61/661,817, filed on Jun. 20, 2012, provisional application No. 61/717,117, filed on Oct. 23, 2012.

(51) Int. Cl.
*A01N 43/58* (2006.01)
*C07D 403/12* (2006.01)

(52) U.S. Cl.
CPC .............. *A01N 43/58* (2013.01); *C07D 403/12* (2013.01)

(58) Field of Classification Search
CPC .................................................. C07D 403/12
See application file for complete search history.

(56) References Cited

U.S. PATENT DOCUMENTS

2010/0305124 A1  12/2010  Fusslein et al.

FOREIGN PATENT DOCUMENTS

| WO | WO 2009/027393 | 3/2009 |
|---|---|---|
| WO | WO 2010/034737 | 4/2010 |
| WO | WO 2010/034738 | 4/2010 |
| WO | WO 2010/112177 | 10/2010 |
| WO | WO 2012/084670 | 6/2012 |
| WO | WO 2012/143317 | 10/2012 |

OTHER PUBLICATIONS

International Preliminary Report on Patentability dated Jul. 15, 2013, prepared in International Application No. PCT/EP2013/062123.
International Search Report dated Apr. 22, 2014, prepared in International Application No. PCT/EP2013/062123.

*Primary Examiner* — Brian McDowell
(74) *Attorney, Agent, or Firm* — Brinks Gilson & Lione

(57) ABSTRACT

The present invention relates to pesticidal mixtures comprising as active compounds 1) at least one pyrazole compound A selected from the compounds of formula I:

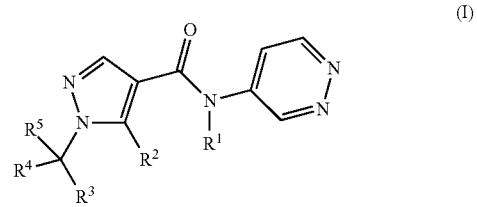

wherein the variables have the meaning as defined in the description, and 2) at least one further compound B selected from the compounds of the following groups A.1, A.2, A.3, A.4, A.5, A.6, A.7, A.8, A.9, A.10, A.11, A.12, A.13, A.14, A.15, A.16, A.17, F.1, F.2, F.3, F.4, F.5, F.6, F.7, F.8, F.9, F.10 and F.11 as defined in the specification.

The present invention also relates to novel pyrazole compounds of the formula I. The present invention also relates to methods and use of these mixtures and novel compounds for combating invertebrate pests such as insects, arachnids or nematodes in and on plants, and for protecting such plants being infested with pests, especially also for protecting plant propagation material as like seeds.

21 Claims, No Drawings

PYRAZOLE COMPOUND AND PESTICIDAL MIXTURES COMPRISING A PYRAZOLE COMPOUND

This application is a National Stage application of International Application No. PCT/EP2013/062123, filed Jun. 12, 2013, which claims the benefit of U.S. Provisional Application No. 61/661,817, filed Jun. 20, 2012 and U.S. Provisional Application No. 61/717,117, filed Oct. 23, 2012, the entire contents of which are hereby incorporated herein by reference.

The present invention relates to a pesticidal mixture comprising as active compounds at least one pyrazole compound and at least one further pesticide and to novel pyrazole compounds. Furthermore, the invention relates to methods of applying said mixture or said pyrazole compound.

The present invention thus relates to pesticidal mixtures comprising as active compounds
1) at least one pyrazole compounds of formula:

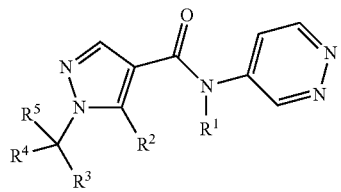

(I)

wherein
$R^1$ is H, $C_1$-$C_2$-alkyl, or $C_1$-$C_2$-alkoxy-$C_1$-$C_2$-alkyl;
$R^2$ is $CH_3$, $CH_2F$, $CHF_2$, or $CF_3$;
$R^3$ is $C_2$-$C_6$-alkyl, a radical $R^{3a}$ or a radical $R^{3b}$;
$R^4$ is $C_1$-$C_4$-alkyl, or a group mentioned for $R^{3a}$;
$R^5$ is H, halogen, or a group mentioned for $R^4$;
$R^3$ and $R^4$ together with the carbon atom, to which they are attached, may form a monocyclic three- to six-membered carbo- or heterocycle, which may contain 1 or 2 heteroatom moieties selected from N—$R^c$, O, and $S(O)_k$, with k being 0, 1 or 2, which monocyclic three- to six-membered carbo- or heterocycle is unsubstituted or may be substituted by 1, 2, 3 or 4 radicals $R^{a3}$;
$R^3$ and $R^4$ together with the carbon atom, to which they are attached, may also form a monospiro or dispiro 5- to 10-membered carbo- or heterocycle, which may contain 1 or 2 heteroatom moieties selected from N—$R^c$, O, and $S(O)_k$, with k being 0, 1 or 2, which monospiro or dispiro 5- to 10-membered carbo- or heterocycle is unsubstituted or may be substituted by 1, 2, 3 or 4 radicals $R^{a3}$;
$R^{3a}$ is selected from the group consisting of CN, $NO_2$, $S(O)_nR^b$, $C_1$-$C_4$-haloalkyl, $C_1$-$C_4$-alkyl which is partially or fully substituted by $R^{a1}$, $C_2$-$C_6$-alkenyl, $C_2$-$C_6$-alkynyl, $C_1$-$C_6$-alkoxy, wherein the C-atoms in the last 3 mentioned radicals may be unsubstituted, or partially or fully substituted by $R^{a2}$, $C_3$-$C_6$-cycloalkyl and $C_5$-$C_6$-cycloalkenyl wherein the C-atoms in the last 2 mentioned radicals may be unsubstituted, or partially or fully substituted by $R^{a3}$,
$R^{3b}$ is a monospiro or dispiro 5- to 10-membered carbo- or heterocycle, which may contain 1 or 2 heteroatom moieties selected from N—$R^c$, O, and $S(O)_k$, with k being 0 1 or 2, which monospiro or dispiro 5 to 10-membered carbo- or heterocycle is unsubstituted or may be substituted by 1, 2, 3 or 4 radicals $R^{a3}$;

$R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_nR^b$;
$R^{a2}$ is halogen, or a group mentioned for $R^{a1}$;
$R^{a3}$ is halogen, $C_1$-$C_2$-alkyl, $C_1$-$C_2$-haloalkyl, $C_1$-$C_2$-alkoxy-$C_1$-$C_2$-alkyl, $C_1$-$C_2$-alkyliden, =O, =S, =$NR^b$, =$NOR^b$, =$NSR^b$, or a group mentioned for $R^{a1}$, in particular halogen, $C_1$-$C_2$-alkyl, $C_1$-$C_2$-alkoxy-$C_1$-$C_2$-alkyl, $C_1$-$C_2$-alkyliden, or a group mentioned for $R^{a1}$; n is 0, 1, or 2;
$R^b$ is hydrogen, $C_1$-$C_2$-alkyl, $C_1$-$C_2$-haloalkyl, $C_3$-$C_6$-cycloalkyl, or $C_1$-$C_4$-alkoxy;
$R^c$ is hydrogen, $C_1$-$C_2$-alkyl, $C_1$-$C_2$-haloalkyl, $C_1$-$C_2$-alkylcarbonyl, or $C_1$-$C_2$-alkoxycarbonyl;
the stereoisomers, salts, tautomers and N-oxides thereof; and
2) at least one further compound B selected from the compounds of the following groups A.1, A.2, A.3, A.4, A.5, A.6, A.7, A.8, A.9, A.10, A.11, A.12, A.13, A.14, A.15, A.16, A.17, F.1, F.2, F.3, F.4, F.5, F.6, F.7, F.8, F.9, F.10 and F.11:

A.1 Carbamate compounds, selected from the group consisting of methiocarb and thiodicarb;

A.2 Pyrethroid compounds, selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethytfluthrin, tetramethrin, tralomethrin and transfluthrin;

A.3 Nicotinic receptor agonists/antagonists compounds, selected from the group consisting of acetamiprid, bensultap, cartap hydrochloride, clothianidin, dinotefuran, imidacloprid, thiamethoxam, nitenpyram, spinosad (allosteric agonist), spinetoram (allosteric agonist), thiacloprid, thiocydam and thiosultap-sodium A.4 GABA gated chloride channel antagonist compounds, selected from the group consisting of acetoprole, ethiprole and fipronil;

A.5 Chloride channel activators, selected from the group consisting of abamectin, emamectin benzoate, milbemectin and lepimectin;

A.6 Uncouplers of oxidative phosphorylation, namely chlorfenapyr;

A.7 Synergists, namely piperonyl butoxide;

A.8 Selective feeding blockers, selected from the group consisting of pymetrozine and flonicamid;

A.9 Chitin synthesis inhibitors, selected from the group consisting of teflubenzuron and no-valuron;

A.10 Lipid biosynthesis inhibitors, selected from the group consisting of spirodiclofen, spiromesifen and spirotetramat;

A.11 Diamide-type Ryanodine receptor modulators—Phthalamides, selected from the group consisting of flubendiamide and (R)-, (S)-3-chloro-N1-{2-methyl-4-[1,2,2,2-tetrafluoro-1-(trifluoromethyl)ethyl]phenyl}-N2-(1-methyl-2-methylsulfonylethyl)phthalamide (A11.1);

A.12 Isoxazoline compounds, selected from the group consisting of 4-[5-(3,5-dichlorophenyl)-5-trifluoromethyl-4,5-dihydro-isoxazol-3-yl]-2-methy-N-pyridin-2-ylmethyl-benzamide (A12.1), 4-[5-(3,5-dichloro-phenyl)-5- trifluoromethyl-4,5-dihydro-isoxazol-3-yl]-2-methy-N-(2,2,2-trifluoroethyl)-benzamide (A12.2), 4-[5-(3,5-dichloro-phenyl)-5-trifluoromethyl-4,5-dihydroisoxazol-3-yl]-2-methyl-N-[(2,2,2-trifluoro-ethylcarbamoyl)-methyl]-benzamide (A12.3), 4-[5-(3,5-dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (A12.4), 4-[5-(3-chloro-trifluoromethyl-phenyl)-5-trifluoromethyl-4,5-dihydro-isoxazol-3-yl]-2-methy-N-[(2,2,2-trifluoro-ethylcarbamoyl)-methyl]-benzamide (A12.5), 4-[5-(3-chloro-5-trifluoromethylphenyl)-5-trifluoromethyl-4,5-dihydro-isoxazol-3-yl]-naphthalene-1-carboxylic acid [(2,2,2-trifluoroethylcarbamoyl)-methyl]-amide (A12.6), 5-[5-(3,5-dichloro-4-fluorophenyl)-5-trifluoromethyl-4,5-dihydro-isoxazol-3-yl]-2-[1,2,4]triazol-1-yl-benzonitrile (A12.7) and 5-[5-(3,5-dichloro-phenyl)-5-trifluoromethyl-4,5-dihydro-isoxazol-3-yl]-2-[1,2,4]triazol-1-yl-benzonitrile (A12.8);

A.13 Diamide-type Ryanodine receptor modulators—Anthranilamide compounds, selected from the group consisting of chloranthraniliprole (rynaxypyr), cyantraniliprole, 5-bromo-2-(3-chloro-pyridin-2-yl)-2H-pyrazole-3-carboxylic acid [4-cyano-2-(1-cyclopropyl-ethylcarbamoyl)-6-methyl-phenyl]-amide (A13.1), 5-bromo-2-(3-chloro-pyridin-2-yl)-2H-pyrazole-3-carboxylic acid [2-chloro-4-cyano-6-(1-cyclopropyl-ethylcarbamoyl)-phenyl]-amide (A13.2), 5-bromo-2-(3-chloropyridin-2-yl)-2H-pyrazole-3-carboxylic acid [2-bromo-4-cyano-6-(1-cyclopropyl-ethylcarbamoyl)-phenyl]-amide(A13.3), 5-bromo-2-(3-chloro-pyridin-2-yl)-2H-pyrazole-3-carboxylic acid [2-bromo-4-chloro-6-(1-cyclopropyl-ethylcarbamoyl)-phenyl]-amide (A13.4), 5-bromo-2-(3-chloro-pyridin-2-yl)-2H-pyrazole-3-carboxylic acid [2,4-dichloro-6-(1-cyclopropyl-ethylcarbamoyl)-phenyl]-amide (A13.5), 5-bromo-2-(3-chloro-pyridin-2-yl)-2H-pyrazole-3-carboxylic acid [4-chloro-2-(1-cyclopropyl-ethylcarbamoyl)-6-methyl-phenyl]-amide (A13.6), N'-(2-{[5-bromo-2-(3-chloro-pyridin-2-yl)-2H-pyrazole-carbonyl]-amino}-5-chloro-3-methyl-benzoyl)-hydrazinecarboxylic acid methyl ester (A13.7), N'-(2-([5-bromo-2-(3-chloro-pyridin-2-yl)-2H-pyrazole-3-carbonyl]-amino)-5-chloro-3-methyl-benzoyl)-N'-methyl-hydrazinecarboxylic acid methyl ester (A13.8), N'-(2-{[5-bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (A13.9), N'-(3,5-dibromo-2-{[5-bromo-2-(3-chloro-pyridin-2-yl)-2H-pyrazole-3-carbonyl]-amino}-benzoyl)-hydrazinecarboxylic acid methyl ester (A13.10), N'-(3,5-dibromo-2-{[5-bromo-2-(3-chloro-pyridin-2-yl)-2H-pyrazole-3-carbonyl]-amino}-benzoyl)-N'-methy-hydrazine carboxylic acid methyl ester (A13.11) and N'-(3,5-dibromo-2-{[5-bromo-2-(3-chloropyridin-2-yl)-2H-pyrazole-3-carbonyl]-amino}-benzoyl)-N,N'-dimethyl-hydrazinecarboxylic acid methyl ester (A13.12);

A.14 Malononitrile compounds, selected from the group consisting of 2-(2,2,3,3,4,4,5,5-octafluoropentyl)-2-(3,3,3-trifluoropropyl) malononitrile ($CF_2H-CF_2-CF_2-CF_2-CH_2-C(CN)-CH_2-CH_2-CF_3$) (A14.1) and 2-(2,2,3,3,4,4,5,5-octafluoropentyl)-2-(3,3,4,4,4-pentafluorobutyl)malonodinitrile ($CF_2HCF_2-CF_2-CF_2-CH-C(CN)_2-CH_2-CH_2-CF_2-CF_3$) (A14.2);

A.15 Microbial disruptors, selected from the group consisting of *Bacillus thuringiensis* subsp. *Israelensi, Bacillus sphaericus, Bacillus thuringiensis* subsp. *Aizawai, Bacillus thuringiensis* subsp. *Kurstaki* and *Bacillus thuringiensis* subsp. *Tenebrionis;*

A.16 Aminofuranone compounds, selected from the group consisting of 4-{[(2-chloro-1,3-thiazolo-5-yl)methyl](2-fluoroethyl)amino}furan-2(5H)-on (A16.1), 4-{[(6-chloropyrid-3-yl)methyl](2-fluoroethyl)amino}furan-2(5H)-on (A16.2), 4-{[(6-chloropyrid-3-yl)methyl](2,2-difluoroethyl)amino}furan-2(5H)-on (A16.3), 4-{[(6-chloro-5-fluoropyrid-3-yl)methyl](methyl)amino}furan-2(5H)-on (A16.4), 4-{[(6-chloro-5-fluoropyrid-3-yl)methyl](cyclopropyl)amino}furan-2(5H)-on (A16.5), 4-{[(6-chloropyrid-3-yl)methyl](cycopropyl)amino}furan-2(5H)-on (A16.6) and 4-{[(6-chloropyrid-3-yl)methyl](methyl)amino}furan-2(5H)-on (A16.7);

A.17 Various compounds, selected from the group consisting of aluminium phosphide, amidoflumet, benclothiaz, benzoximate, bifenazate, borax, bromopropylate, cryolite, cyanide, cyenopyrafen, cyflumetofen, chinomethionate, dicofol, fluensulfone, fluoroacetate, phosphine, pyridalyl, pyrifluquinazon, sulfur, organic sulfur compounds, tartar emetic, sulfoxaflor, afidopyropen (cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester), 4-but-2-ynyloxy-6-(3,5-dimethyl-piperidin-1-yl)-2-fluoro-pyrimidine (A17.1), and 8-(2-cyclopropylmethoxy-4-trifluoromethyl-phenoxy)-3-(6-trifluoromethyl-pyridazin-3-yl)-3-aza-bicyclo[3.2.1]octane (A17.2).

F.1 Respiration inhibitors selected from the following groups a), b), c) and d):

a) Inhibitors of complex III at $Q_o$ site (e.g. strobilurins), selected from the group consisting of azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methylallylideneaminooxymethyl)-phenyl)-2-methoxyimino-N-methyl-acetamide, pyribencarb, triclopyricarb/chlorodincarb, famoxadone and fenamidone;

b) inhibitors of complex III at $Q_i$ site, selected from the group consisting of cyazofamid and amisulbrom;

c) inhibitors of complex II (e.g. carboxamides), selected from the group consisting of benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide;

d) other respiration inhibitors (e.g. complex I, uncouplers), selected from the group consisting of diflumetorim; the nitrophenyl derivatives: binapacryl, dinobuton, dinocap and fluazinam; ferimzone; fentin salts, such as fentin-acetate, fentin chloride or fentin hydroxide; ametoctradin; and silthiofam;

F.2 Sterol biosynthesis inhibitors (SBI fungicides) selected from the following groups a), b) and c):

a) C14 demethylase inhibitors (DMI fungicides), selected from the group consisting of the following triazoles:

azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myciobutanil, oxpoconazole, paciobutrazole, penconazole, propiconazole, prothioconazole, simeconazole, tebuconazole, tetraconazole, triadimefon, triadimenol, triticonazole and uniconazole; the following imidazoles: imazalil, pefurazoate, prochloraz and triflumizol; and the following pyrimidines, pyridines and piperazines: fenarimol, nuarimol, pyrifenox and triforine;
- b) Delta14-reductase inhibitors, selected from the group consisting of aldimorph, dodemorph, dodemorph-acetate, fenpropimorph, tridemorph, fenpropidin, piperalin and spiroxamine;
- c) Inhibitors of 3-keto reductase: fenhexamid;

F.3 Nucleic acid synthesis inhibitors selected from the following groups a) and b):
- a) phenylamides or acyl amino acid fungicides, selected from the group consisting of benalaxyl, benalaxyl-M, kiralaxyl, metalaxyl, metalaxyl-M (mefenoxam), ofurace and oxadixyl;
- b) other nucleic acid synthesis inhibitors, selected from the group consisting of hymexazole, octhilinone, oxolinic acid and bupirimate;

F.4 Inhibitors of cell division and cytoskeleton selected from the following groups a) and b):
- a) tubulin inhibitors, selected from the group consisting of benzimidazoles or thiophanates such as benomyl, carbendazim, fuberidazole, thiabendazole or thiophanatemethyl; and triazolopyrimidines such as 5-chloro-7-(4-methylpiperidin-1-yl)-6-(2,4,6-trifluorophenyl)-[1,2,4]triazolo[1,5-a]pyrimidine;
- b) other cell division inhibitors, selected from the group consisting of diethofencarb, ethaboxam, pencycuron, fluopicolide, zoxamide, metrafenone and pyriofenone;

F.5 Inhibitors of amino acid and protein synthesis selected from the following groups a) and b):
- a) methionine synthesis inhibitors (anilino-pyrimidines), selected from the group consisting of cyprodinil, mepanipyrim and pyrimethanil;
- b) protein synthesis inhibitors, selected from the group consisting of blasticidin-S, kasugamycin, kasugamycin hydrochloride-hydrate, mildiomycin, streptomycin, oxytetracyclin, polyoxine and validamycin A;

F.6 Signal transduction inhibitors selected from the following groups a) and b):
- a) MAP/histidine kinase inhibitors, selected from the group consisting of fluoroimid, iprodione, procymidone, vinclozolin, fenpicionil and fludioxonil;
- b) G protein inhibitors which is quinoxyfen;

F.7 Lipid and membrane synthesis inhibitors selected from the following groups a), b), c) and d):
- a) Phospholipid biosynthesis inhibitors, selected from the group consisting of edifenphos, iprobenfos, pyrazophos and isoprothiolane;
- b) compounds affecting lipid peroxidation, selected from the group consisting of dicloran, quintozene, tecnazene, tolclofos-methyl, biphenyl, chloroneb and etridiazole;
- c) compounds affecting phospholipid biosynthesis and cell wall deposition, selected from the group consisting of dimethomorph, flumorph, mandipropamid, pyrimorph, benthiavalicarb, iprovalicarb, valifenalate and N-(1-(1-(4-cyanophenyl)ethanesulfonyl)-but-2-yl) carbamic acid-(4-fluorophenyl) ester;
- d) compounds affecting cell membrane permeability and fatty acids selected from the group consisting of propamocarb and propamocarb-hydrochlorid;

F.8 Inhibitors with multi site action selected from the following groups a), b), c) and d):
- a) inorganic active substances selected from the group consisting of Bordeaux mixture, copper acetate, copper hydroxide, copper oxychloride, basic copper sulfate and sulfur;
- b) thio- and dithiocarbamates selected from the group consisting of ferbam, mancozeb, maneb, metam, metiram, propineb, thiram, zineb and ziram;
- c) organochlorine compounds (e.g. phthalimides, sulfamides, chloronitriles) selected from the group consisting of anilazine, chlorothalonil, captafol, captan, folpet, dichlofluanid, dichlorophen, flusulfamide, hexachlorobenzene, pentachlorphenole and its salts, phthalide, tolylfluanid and N-(4-chloro-2-nitro-phenyl)-N-ethyl-4-methylbenzenesulfonamide;
- d) guanidines and others selected from the group consisting of guanidine, dodine, dodine free base, guazatine, guazatine-acetate, iminoctadine, iminoctadinetriacetate, iminoctadine-tris(albesilate) and dithianon;

F.9 Cell wall synthesis inhibitors selected from the following groups a) and b):
- a) inhibitors of glucan synthesis selected from the group consisting of validamycin and polyoxin B;
- b) melanin synthesis inhibitors selected from the group consisting of pyroquilon, tricyclazole, carpropamid, dicyclometa and fenoxanil;

F.10 Plant defence inducers selected from the following groups a) and b):
- a) the group of acibenzolar-S-methyl, probenazole, isotianil, tiadinil and prohexadione-calcium;
- b) phosphonates selected from the group consisting of fosetyl, fosetyl-aluminum, phosphorous acid and its salts;

F.11 Fungicides having an unknown mode of action selected from the group consisting of bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-Nethyl-N-methyl formamidine, N'-(4-(4-fluoro-3-trifluoromethyl-phenoxy)-2,5-dimethylphenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanylpropoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydronaphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethylquinolin-4-yl ester, N-Methyl-2-({1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methyl-phenyl)-2,3-dimethyl-isoxazolidin-3-yl]-pyridine, 3-[5-(4-chloro-phenyl)-2,3-dimethylisoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1Hbenzoimidazole, 2-(4-chloro-phenyl)-N-[4-(3,4-dimethoxy-phenyl)-isoxazol-5-yl]-2-prop-2-ynyloxy-acetamide;

except for pesticidal mixtures comprising a pyrazole compound of formula I, wherein
$R^1$ is H, $CH_3$, $C_2H_5$, or $CH_2OCH_3$;
$R^2$ is $CH_3$, $CHF_2$, or $CF_3$;
$R^3$ is $CF_3$, or $c$-$C_3H_5$;
$R^4$ is $CH_3$; and
$R^5$ is H.

One typical problem arising in the field of pest control lies in the need to reduce the dosage rates of the active ingredient in order to reduce or avoid unfavorable environmental or toxicological effects whilst still allowing effective pest control. Another problem encountered concerns the need to have available pest control agents which are effective against a broad spectrum of pests.

Another problem underlying the present invention is the desire for compositions that improve plants, a process which is commonly and hereinafter referred to as "plant health". For example, advantageous properties that may be mentioned are improved crop characteristics including: emergence, crop yields, protein content, more developed root system, tillering increase, increase in plant height, bigger leaf blade, less dead basal leaves, stronger tillers, greener leaf color, pigment content, photosynthetic activity, less fertilizers needed, less seeds needed, more productive tillers, earlier flowering, early grain maturity, less plant verse (lodging), increased shoot growth, enhanced plant vigor, increased plant stand and early germination; or any other advantages familiar to a person skilled in the art. Methods for improving the health of plants by applying active compounds to the plants or the locus are a general need.

The combating of harmful phytopathogenic fungi is in many regions not the only problem the farmer has to face. Invertebrate pests and in particular arthropods and nematodes destroy growing and harvested crops and attack wooden dwelling and commercial structures, thereby causing large economic loss to the food supply and to property. There is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control pests, such as insects.

An efficient combination of fungicidal and insecticidal activity is also desirable. Thus, it is a further object of the present invention to provide a mixture which, on the one hand, has good fungicidal activity, and, on the other hand, good insecticidal activity, resulting in a broader pesticidal spectrum of action.

Another difficulty in relation to the use of pesticides is that the repeated and exclusive application of an individual pesticidal compound leads in many cases to a rapid selection of pests which have developed natural or adapted resistance against the active compound in question. Therefore there is a need for pest control agents that help prevent or overcome resistance.

WO 2009/027393, WO 2010/034737, WO 2010/034738, and WO 2010/112177 describe derivatives of N-(het)aryl-amides, derived from pyrazole carboxylic acids. These compounds are mentioned to be useful for combating invertebrate pests.

PCT/EP2012/056875 describes N-pyridazinyl carboxamide compounds derived from pyrazole carboxylic acids. These compounds are mentioned to be useful for combating invertebrate pests. However, this document does not describe compounds having the characteristic substituents as claimed in the present invention.

PCT/EP2011/072854 relates to pesticidal mixtures comprising N-pyridazinyl carboxamide compounds derived from pyrazole carboxylic acids. These compounds are mentioned to be useful for combating invertebrate pests and/or for controlling phytopathogenic harmful fungi. However, this document does not describe N-pyridazinyl carboxamide compounds having the characteristic substituents as claimed in the present invention.

It is therefore an object of the present invention to provide pesticidal mixtures and/or compounds which solves at least one of the discussed problems as reducing the dosage rate, enhancing the spectrum of activity or combining knock-down activity with prolonged control or as to resistance management.

It as been found that at least one of these objectives is achieved by the combination of active compounds defined in the outset or by the pyrazole compounds defined below.

Moreover, it has also been found that simultaneous, that is joint or separate, application of one or more active compounds A and one or more active compounds B or successive application of one or more active compounds A and one or more active compounds B allows enhanced control of pests compared to the control rates that are possible with the individual compounds.

The present invention also relates to novel pyrazole compounds of the formula I (hereinafter compounds I-S): wherein
$R^1$ is H, $C_1$-$C_2$-alkyl, or $C_1$-$C_2$-alkoxy-$C_1$-$C_2$-alkyl;
$R^2$ is $CH_3$, $CH_2F$, $CHF_2$, or $CF_3$;
$R^3$ is a radical $R^{3b}$,
$R^4$ is $C_1$-$C_4$-alkyl, or a radical $R^{3a}$;
  $R^{3a}$ is selected from the group consisting of CN, $NO_2$, $S(O)_nR^b$, $C_1$-$C_4$-haloalkyl, $C_1$-$C_4$-alkyl which is partially or fully substituted by $R^{a1}$, $C_2$-$C_6$-alkenyl, $C_2$-$C_6$-alkynyl, $C_1$-$C_6$-alkoxy, wherein the C-atoms in the last 3 mentioned radicals may be unsubstituted, or partially or fully substituted by $R^{a2}$, $C_3$-$C_6$-cycloalkyl and $C_5$-$C_6$-cycloalkenyl wherein the C-atoms in the last 2 mentioned radicals may be unsubstituted, or partially or fully substituted by $R^{a3}$,
  $R^{3b}$ is a monospiro or dispiro 5- to 10-membered carbo- or heterocycle, which may contain 1 or 2 heteroatom moieties selected from N—$R^c$, O, and $S(O)_k$, with k being 0 1 or 2, which monospiro or dispiro 5- to 10-membered carbo- or heterocycle is unsubstituted or may be substituted by 1, 2, 3 or 4 radicals $R^{a3}$;
    $R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_nR^b$;
    $R^{a2}$ is halogen, or a group mentioned for $R^{a1}$;
    $R^{a3}$ is halogen, $C_1$-$C_2$-alkyl, $C_1$-$C_2$-haloalkyl, $C_1$-$C_2$-alkoxy-$C_1$-$C_2$-alkyl, $C_1$-$C_2$-alkyliden, =O, =S, =$NR^b$, =$NOR^b$, =$NSR^b$, or a group mentioned for $R^{a1}$; in particular halogen, $C_1$-$C_2$-alkyl, $C_1$-$C_2$-alkoxy-$C_1$-$C_2$-alkyl, $C_1$-$C_2$-alkyliden, or a group mentioned for $R^{a1}$;
  n is 0, 1, or 2;
    $R^b$ is H, $C_1$-$C_2$-alkyl, $C_1$-$C_2$-haloalkyl, $C_3$-$C_6$-cycloalkyl, or $C_1$-$C_4$-alkoxy,
    $R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;

$R^5$ is H, halogen, or a group mentioned for $R^4$;
the stereoisomers, salts, tautomers and N-oxides thereof.

The present invention also relates to novel pyrazole compounds of the formula I (hereinafter compounds I-S'), wherein
$R^1$ is H, $C_1$-$C_2$-alkyl, or $C_1$-$C_2$-alkoxy-$C_1$-$C_2$-alkyl;
$R^2$ is $CH_3$, $CH_2F$, $CHF_2$ or $CF_3$;
$R^3$ and $R^4$ together with the carbon atom, to which they are attached, form a monospiro or dispiro 5 to 10-membered carbo- or heterocycle, which may contain 1 or 2 heteroatom moieties selected from N—$R^c$, O, and $S(O)_k$, with k being 0 1 or 2, which monospiro or dispiro 5 to 10-membered carbo- or heterocycle is unsubstituted or may be substituted by 1, 2, 3 or 4 radicals $R^{a3}$;
 $R^{3a}$ is selected from the group consisting of CN, $NO_2$, $S(O)_nR^b$, $C_1$-$C_4$-haloalkyl, $C_1$-$C_4$-alkyl which is partially or fully substituted by $R^{a1}$, $C_2$-$C_6$-alkenyl, $C_2$-$C_6$-alkynyl, $C_1$-$C_6$-alkoxy, wherein the C-atoms in the last 3 mentioned radicals may be unsubstituted, or partially or fully substituted by $R^{a2}$, $C_3$-$C_6$-cycloalkyl and $C_5$-$C_6$-cycloalkenyl wherein the C-atoms in the last 2 mentioned radicals may be unsubstituted, or partially or fully substituted by $R^{a3}$,
 $R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_nR^b$;
 $R^{a2}$ is halogen, or a group mentioned for $R^{a1}$;
 $R^{a3}$ is halogen, $C_1$-$C_2$-alkyl, $C_1$-$C_2$-haloalkyl, $C_1$-$C_2$-alkoxy-$C_1$-$C_2$-alkyl, $C_1$-$C_2$-alkyliden, =O, =S, =$NR^b$, =$NOR^b$, =$NSR^b$, or a group mentioned for $R^{a1}$; in particular halogen, $C_1$-$C_2$-alkyl, $C_1$-$C_2$-alkoxy-$C_1$-$C_2$-alkyl, $C_1$-$C_2$-alkyliden, or a group mentioned for $R^{a1}$;
 n is 0, 1, or 2;
 $R^b$ is H, $C_1$-$C_2$-alkyl, $C_1$-$C_2$-haloalkyl, $C_3$-$C_6$-cycloalkyl, or $C_1$-$C_4$-alkoxy,
 $R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;
$R^5$ is H, halogen, $C_1$-$C_4$-alkyl, or a group mentioned for $R^{3a}$;
the stereoisomers, salts, tautomers and N-oxides thereof.

The present invention also relates to novel pyrazole compounds of the formula I (hereinafter compounds I-O), wherein
$R^1$ is H, $C_1$-$C_2$-alkyl, or $C_1$-$C_2$-alkoxy-$C_1$-$C_2$-alkyl;
$R^2$ is $CH_3$, $CH_2F$, $CHF_2$, or $CF_3$;
$R^3$ and $R^4$ together with the carbon atom, to which they are attached, may form a monocyclic three- to six-membered carbo- or heterocycle, which may contain 1 or 2 heteroatom moieties selected from N—$R^c$, O, and $S(O)_k$, with k being 0, 1 or 2, which carbo- or heterocycle is substituted by 1, 2, or 3 groups =O, =S, =$NR^b$, =$NOR^b$, =$NSR^b$, and may be substituted by 1, 2, 3 or 4 radicals $R^{a3}$;
$R^3$ and $R^4$ together with the carbon atom, to which they are attached, may also form a monospiro or dispiro 5- to 10-membered carbo- or heterocycle, which may contain 1 or 2 heteroatom moieties selected from N—$R^c$, O, and $S(O)_k$, with k being 0, 1 or 2, which monospiro or dispiro 5- to 10-membered carbo- or heterocycle is unsubstituted or may be substituted by 1, 2, 3 or 4 radicals $R^{a3}$;
 $R^{3a}$ is selected from the group consisting of CN, $NO_2$, $S(O)_nR^b$, $C_1$-$C_4$-haloalkyl, $C_1$-$C_4$-alkyl which is partially or fully substituted by $R^{a1}$, $C_2$-$C_6$-alkenyl, $C_2$-$C_6$-alkynyl, $C_1$-$C_6$-alkoxy, wherein the C-atoms in the last 3 mentioned radicals may be unsubstituted, or partially or fully substituted by $R^{a2}$, $C_3$-$C_6$-cycloalkyl and $C_5$-$C_6$-cycloalkenyl wherein the C-atoms in the last 2 mentioned radicals may be unsubstituted, or partially or fully substituted by $R^{a3}$,
 $R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_nR^b$;
 n is 0, 1, or 2;
 $R^{a2}$ is halogen, or a group mentioned for $R^{a1}$;
 $R^{a33}$ is halogen, $C_1$-$C_2$-alkyl, $C_1$-$C_2$-haloalkyl, $C_1$-$C_2$-alkoxy-$C_1$-$C_2$-alkyl, $C_1$-$C_2$-alkyliden, or a group mentioned for $R^{a1}$;
 $R^b$ is H, $C_1$-$C_2$-alkyl, $C_1$-$C_2$-haloalkyl, $C_3$-$C_6$-cycloalkyl, or $C_1$-$C_4$-alkoxy;
 $R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;
$R^5$ is H, $C_1$-$C_4$-alkyl, halogen, or a group mentioned for $R^{3a}$;
the stereoisomers, salts, tautomers and N-oxides thereof.

The present invention also relates to novel pyrazole compounds of the formula I which are selected from the compounds of the following groups I-a, I-b, I-c, and I-d:

Compounds of group I-a: Compounds of the formula I, wherein:
$R^1$ is H, $C_1$-$C_2$-alkyl, or $C_1$-$C_2$-alkoxy-$C_1$-$C_2$-alkyl, in particular $CH_3$, or $C_2H_5$;
$R^2$ is $CH_3$, $CH_2F$, $CHF_2$ or $CF_3$;
$R^3$ is CN, $CH(CH_3)_2$, $CHF_2$, $CH_2OCH_3$, c-$C_3H_5$, 1-F-c-$C_3H_4$, or 1-CN-c-$C_3H_4$;
$R^4$ is $CHF_2$;
$R^5$ is H, or $CH_3$;
the stereoisomers, salts, tautomers and N-oxides thereof;
except for the following pyrazole compounds of the group I-a, where in formula I
$R^1$ is $CH_3$, or $C_2H_5$; $R^2$ is $CH_3$, $CHF_2$ or $CF_3$; $R^3$ is CN; $R^4$ is $CHF_2$; and $R^5$ is $CH_3$.

Compounds of group I-b: Compounds of the formula I, wherein:
$R^1$ is H, $C_1$-$C_2$-alkyl, or $C_1$-$C_2$-alkoxy-$C_1$-$C_2$-alkyl, in particular $CH_3$ or $C_2H_5$;
$R^2$ is $CH_3$, $CH_2F$, $CHF_2$ or $CF_3$;
$R^3$ is selected from the group consisting of
 1-$CH_3$-c-$C_3H_4$, 1-$OCH_3$-c-$C_3H_4$, 1-$CF_3$-c-$C_3H_4$, 1-$OCF_3$-c-$C_3H_4$, 1-$SCH_3$-c-$C_3H_4$, 1-$SCF_3$-c-$C_3H_4$, $C(CH_3)_3$, 1-F-1-methylethyl, 1-CN-1-methylethyl, 1-methoxy-1-methylethyl, 1-(trifluoromethoxy)-1-methylethyl, 1-(methylsulfanyl)-1-methylethyl, 1-(trifluoromethylsulfanyl)-1-methylethyl, 2,2,2-trifluoro-1,1-dimethylethyl, $CHFCH_3$, $CH(CN)CH_3$, $CF_2CH_3$, 1,1-dimethoxyethyl, 1-methoxyethyl, 1-(trifluoromethoxy)-ethyl, 1-(methylsulfanyl)ethyl, 1-(trifluoromethylsulfanyl)ethyl, 2,2,2-trifluoro-1-methylethyl, $CH_2SCH_3$, $CH_2SCF_3$, $CH_2OCF_3$, $CH_2F$, $CH_2CF_3$ and $CH_2CN$,
$R^4$ is $CH_3$, $C_2H_5$, $CHF_2$, or $CF_3$;
$R^5$ is H, or $CH_3$;
the stereoisomers, salts, tautomers and N-oxides thereof;
except for the following pyrazole compounds of the group I-b, where in formula I
$R^1$ is $CH_3$; $R^2$ is $CF_3$; $R^3$ is $C(CH_3)_3$; $R^4$ is $CH_3$; and $R^5$ is H;
and also except for the following pyrazole compounds of the group I-b where in formula I the variable $R^1$ is $CH_3$ or $C_2H_5$; $R^2$ is $CH_3$; $R^3$ is $C(CH_3)_3$, $CH_2CN$, $CH_2F$, $CHFCH_3$, 1-$CH_3$-c-$C_3H_4$, 1-CN-1-methylethyl, 1-$SCH_3$-c-$C_3H_4$, or 1-($CF_3$)cyclopropyl; $R^4$ is $CH_3$; and $R^5$ is H;
and also except for the following pyrazole compounds of the group I-b where in formula I $R^1$ is H, $CH_3$, $CH_2CH_3$, or $CH_2O\ CH_3$; $R^2$ is $CH_3$ or $CF_3$; $R^3$ is $C(CH_3)_3$, $CH_2CN$, $CH_2F$, $CHFCH_3$, $1-CH_3-cC_3H_4$. $C(CH_3)_2CN$, $CH_2CF_3$, $1-(SCH_3)-cC_3H_4$, or $1-CF_3-cC_3H_4$; $R^4$ is $CH_3$ or $CF_3$; and $R^5$ is H;

and exceptionally except within the last mentioned group the following pyrazole compounds of the group I-b where in formula I $R^1$, $R^2$, $R^3$, $R^4$ and $R^5$ have the meaning as listed in the following table:

| $R^1$ | $R^2$ | $R^3$ | $R^4$ | $R^5$ |
|---|---|---|---|---|
| H | $CH_3$ | $C(CH_3)_3$ | $CH_3$ | H |
| $CH_2OCH_3$ | $CH_3$ | $C(CH_3)_3$ | $CH_3$ | H |
| H | $CF_3$ | $C(CH_3)_3$ | $CH_3$ | H |
| $CH_2OCH_3$ | $CF_3$ | $C(CH_3)_3$ | $CH_3$ | H |
| H | $CH_3$ | $CH_2CN$ | $CH_3$ | H |
| $CH_2OCH_3$ | $CH_3$ | $CH_2CN$ | $CH_3$ | H |
| H | $CH_3$ | $CH_2F$ | $CH_3$ | H |
| H | $CH_3$ | $CHFCH_3$ | $CH_3$ | H |
| H | $CH_3$ | $1-CH_3-cC_3H_4$ | $CH_3$ | H |
| H | $CH_3$ | $C(CH_3)_2CN$ | $CH_3$ | H |
| $CH_2CH_3$ | $CH_3$ | $CH_2CF_3$ | $CH_3$ | H |
| H | $CH_3$ | $CH_2CF_3$ | $CH_3$ | H |
| H | $CH_3$ | $1-(SCH_3)-cC_3H_4$ | $CH_3$ | H |
| $CH_2CH_3$ | $CH_3$ | $C(CH_3)_3$ | $CF_3$ | H |
| $CH_3$ | $CH_3$ | $C(CH_3)_3$ | $CF_3$ | H |
| H | $CH_3$ | $C(CH_3)_3$ | $CF_3$ | H |
| H | $CH_3$ | $1-CH_3-cC_3H_4$ | $CH_3$ | H |
| H | $CH_3$ | $1-CF_3-cC_3H_4$ | $CH_3$ | H |

Compounds of group I-c: Compounds of the formula I, wherein:

$R^1$ is H, $C_1$-$C_2$-alkyl, or $C_1$-$C_2$-alkoxy-$C_1$-$C_2$-alkyl, in particular $CH_3$ or $C_2H_5$;
$R^2$ is $CH_3$, $CH_2F$, $CHF_2$, or $CF_3$;
$R^3$ together with $R^4$ forms a bivalent moiety $(CH_2)_p$ with p being 2, 4, or 5;
$R^5$ is $CH_3$, F, $OCH_3$, $SCH_3$, $OCF_3$, or $SCF_3$;
the stereoisomers, salts, tautomers and N-oxides thereof.

Compounds of group I-d: Compounds of the formula I, wherein:

$R^1$ is H, $C_1$-$C_2$-alkyl, or $C_1$-$C_2$-alkoxy-$C_1$-$C_2$-alkyl, in particular $CH_3$, or $C_2H_5$;
$R^2$ is $CH_3$, $CH_2F$, $CHF_2$ or $CF_3$;
$R^3$ together with $R^4$ forms a bivalent moiety $CH_2OCH_2OCH_2$ or $CH_2OC(CH_3)_2OCH_2$;
$R^5$ is H, $CH_3$, CN, F, $OCH_3$, $SCH_3$, $CF_3$, $OCF_3$, or $SCF_3$;
the stereoisomers, salts, tautomers and N-oxides thereof.

Moreover, the present invention relates to
- a composition comprising the pesticidal mixture as defined herein or one novel compound of the formula I as defined herein and at least one inert liquid and/or solid acceptable carrier,
- an agricultural composition comprising the pesticidal mixture as defined herein or a novel compound of the formula I as defined herein and at least one inert liquid and/or solid acceptable carrier;
- a method for controlling or combating invertebrate pests, comprising contacting said pest or its food supply, habitat, breeding grounds with a pesticidally effective amount of the pesticidal mixture as defined herein or with the novel compound of the formula I as defined herein;
- a method of protecting plants from attack or infestation by invertebrate pests, contacting a plant, a plant propagation material or soil or water in which the plant is growing, with a pesticidally effective amount of the pesticidal mixture as defined herein or with the novel pyrazole compound of the formula I as defined herein;
- a plant propagation material comprising the pesticidal mixture as defined herein or the novel pyrazole compound of the formula I as defined herein in an amount of from 0.1 g to 10 kg per 100 kg of seed;
- a method for protection of plant propagation material comprising contacting the plant propagation material with the pesticidal mixture as defined herein or with a novel pyrazole compound of the formula I as defined herein in an amount of from 0.1 g to 10 kg per 100 kg of plant propagation material;
- the use of the pesticidal mixture as defined herein or of the novel pyrazole compound of the formula I as defined herein for protecting growing plants or plant propagation material from attack or infestation by invertebrate pests;
- a method for controlling phytopathogenic harmful fungi, wherein the fungi, their habitat or the plants to be protected against fungal attack, the soil or seed are treated with an effective amount of the pesticidal mixture comprising at least one pyrazole compound A as defined herein and at least one specific compound B as defined herein;
- a method for protecting plants from phytopathogenic harmful fungi, wherein the fungi, their habitat or the plants to be protected against fungal attack, the soil or seed are treated with an effective amount of the pesticidal mixture comprising at least one pyrazole compound A as defined herein and at least one specific compound B as defined herein;
- a method for protecting animals against infestation or infection by parasites which comprises administering to the animals a parasitically effective amount of the pesticidal mixture as defined herein or of the novel pyrazole compound of the formula I as defined herein;
- a method for treating animals infested or infected by parasites which comprises administering to the animals a parasitically effective amount of the pesticidal mixture as defined herein or of the novel pyrazole compound of the formula I as defined herein to the animal in need thereof; and
- the use of the pesticidal mixture as defined herein or of the novel pyrazole compound of the formula I as defined herein for combating parasites in and on animals.

The composition according to the invention or to be used according to the invention may be a physical mixture of the at least one compound A and the at least one compound B. Accordingly, the invention also provides a mixture comprising at least one compound A and at least one compound B. However, the composition may also be any combination of at least one compound A with at least one compound B, it not being required for compounds A and B to be present together in the same formulation.

An example of a composition according to the invention or to be used according to the invention in which the at least one compound A and the at least one compound B are not present together in the same formulation is a combipack. In a combipack, two or more components of a combipack are packaged separately, i.e., not jointly pre-formulated. As such, combipacks include one or more separate containers such as vials, cans, bottles, pouches, bags or canisters, each container containing a separate component for an agrochemical composition. One example is a two-component combipack. Accordingly the present invention also relates to a two-component combipack, comprising a first component which in turn comprises at least one compound A, a liquid or solid carrier and, if appropriate, at least one surfactant and/or at least one customary auxiliary, and a second component which in turn comprises at least one compound B, a liquid or solid carrier and, if appropriate, at least one surfactant and/or at least one customary auxiliary. More details, e.g. as to suitable liquid and solid carriers, surfactants and customary auxiliaries are described below.

The "combined" use of at least one pyrazole compound A with and at least one compound B or the treatment according to the invention with the at least one pyrazole compound I "in combination with" at least one compound B on the one hand can be understood as using a physical mixture of at least one pyrazole compound A and at least one compound B. On the other hand, the combined use may also consist in using the at least one pyrazole compound A and the at least one compound B separately, but within a sufficiently short time of one another so that the desired effect can take place. More detailed illustrations of the combined use can be found in the specifications below.

The term "invertebrate pest" (also referred to as animal pests) as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "compound(s) according to the invention", or "compound(s) of formula I" or "pyrazole compound(s) A" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of formula I may have one or more centers of chirality, in which case they are present as mixtures of enantiomers or diastereomers. One center of chirality is the carbon atom carrying radicals $R^3$, $R^4$ and $R^5$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term "N-oxide" relates to a form of compounds I in which at least one nitrogen atom is present in oxidized form (as NO).

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkylthio (also referred to as alkylsulfanyl), alkylsulfinyl, and alkylsulfonyl denotes in each case a straight-chain or branched alkyl group having usually from 1 to 6 carbon atoms, preferably 1 to 4 carbon atoms and in particular from 1 to 3 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "alkenyl" as used herein denotes in each case a singly unsaturated hydrocarbon radical having usually 2 to 6, preferably 2 to 4 carbon atoms, e.g. vinyl, allyl(2-propen-1-yl), 1-propen-1-yl, 2-propen-2-yl, methallyl(2-methyl-prop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkyl" as used herein and in the haloalkyl moieties of haloalkoxy, haloalkylthio, haloalkylsulfonyl and haloalkylsulfinyl, denotes in each case a straight-chain or branched alkyl group having usually from 1 to 6 carbon atoms, frequently from 1 to 4 carbon atoms, wherein the hydrogen atoms of this group are partially or totally replaced with halogen atoms. Preferred haloalkyl moieties are selected from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 2 carbon atoms, wherein 1 carbon atom carries an alkoxy radical usually comprising 1 or 2 carbon atoms as defined above. Examples are $CH_2OCH_3$, $CH_2$—$OC_2H_5$, 2-(methoxy)ethyl, and 2-(ethoxy)ethyl.

The term "alkylcarbonyl" is a $C_1$-$C_2$-alkyl ("$C_1$-$C_2$-alkoxycarbonyl") group, as defined above, attached via a carbonyl [C(=O)] group. Examples are methylcarbonyl and ethylcarbonyl.

The term "alkoxycarbonyl" is a $C_1$-$C_2$-alkoxy ("$C_1$-$C_2$-alkoxycarbonyl") group, as defined above, attached via a carbonyl [C(=O)] group. Examples are methoxycarbonyl and ethoxycarbonyl.

The term "alkylidene" as used herein refers to a divalent group derived from an alkane usually comprising 1 to 2 carbon atoms, wherein two hydrogen atoms are removed from the same carbon atom, the free valencies being part of a double bond. Examples are methylidene (=$CH_2$) and ethylidene (=$CH(CH_3)$).

The term "cycloalkyl" as used herein and in the cycloalkyl moieties of cycloalkoxy and cycloalkylmethyl denotes in each case a monocyclic cycloaliphatic radical having usually from 3 to 6 carbon atom. Examples are cyclopropyl (c-$C_3H_5$), cyclobutyl (o-$C_4H_7$), cyclopentyl (c-$C_5H_9$), and cyclohexyl (c-$C_6H_{11}$).

The term "cycloalkenyl" as used herein denotes in each case a monocyclic monounsaturated hydrocarbon groups having 5 or 6 carbon ring members. Examples are cyclopenten-1-yl, cyclopenten-3-yl, cyclohexen-1-yl, cyclohexen-3-yl and cyclohexen-4-yl.

The term "heterocyclyl" includes in general 3- to 6-membered, in particular 5- or 6-membered monocyclic heterocyclic non-aromatic radicals. The heterocyclic non-aromatic radicals usually comprise 1 or 2 heteroatoms selected from N, O and S as ring members, where S-atoms as ring members may be present as S, SO or $SO_2$.

Examples of 5-, or 6-membered heterocyclic radicals comprise saturated or unsaturated, nonaromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S. oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like.

The term "monospiro 5- to 10-membered carbocycle" refers to a bicyclic ring system of 5-, 6-, 7-, 8-, 9- or 10 carbon atoms having one atom in common (spiroatom). Examples are spiro[2.2]pentyl, spiro[2.3]hexyl, spiro[2.4] heptyl, spiro[3.4]octyl, spiro[3.5]nonyl, spiro[3.6]deyl, spiro[4.4]nonyl and spiro[4.5]decyl.

The term "dispiro 5- to 10-membered carbocycle" refers to a tricyclic ring system of 5-, 6-, 7-, 8-, 9- or 10 carbon atoms having 2 spiroatoms. Examples are dispiro[2.0.2.1] heptyl, dispiro[2.0.3.1]octyl, dispiro[3.0.3.1]nonyl, dispiro [2.0.4.1]nonyl, dispiro[2.1.2.1]octyl, dispiro[2.1.3.1]nonyl and dispiro[3.1.3.1]decyl.

The term "monospiro or dispiro 5- to 10-membered heterocycle" refers to a bicyclic or tricyclic ring system of 5-, 6-, 7-, 8-, 9- or 10 ring atoms which has one or two spiroatoms. The heterocyclic ring system usually comprise 1 or 2 heteroatoms selected from N, O and S as ring members, where S-atoms as ring members may be present as S, SO or $SO_2$. Examples are:

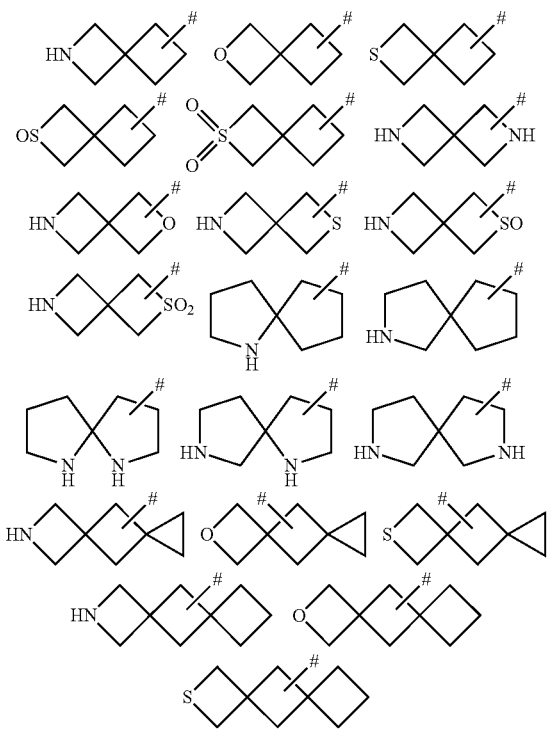

In the above structures # denotes the attachment point to the remainder of the molecule. The attachment point is not restricted to the ring on which is shown, but can be on either of the spiro rings, and may be on a carbon or on a nitrogen ring atom. If the rings carry one or more substituents, these may be bound to carbon and/or to nitrogen ring atoms.

The commercially available further compound B may be found in The Pesticide Manual, 13th Edition, British Crop Protection Council (2003) among other publications.

The phthalamide A11.1 is known from WO 2007/101540. The isoxazoline compounds A12.1 to A12.8 have been described in e.g. WO2005/085216, WO 2007/079162, WO 2007/026965, WO 2009/126668 and WO2009/051956. The anthranilamides A13.1 to A13.6 have been described in WO 2008/72743 and WO 200872783, those A13.7 to A13.12 in WO 2007/043677. Malononitrile compounds as those (A14.1) and (A14.2) have been described in WO 02/089579, WO 02/090320, WO 02/090321, WO 04/006677, WO 05/068423, WO 05/068432 and WO 05/063694. The aminofuranone compounds A16.1 to A16.7 have been described eg. in WO 2007/115644. The alkynylether compound A17.1 is described e.g. in JP 2006131529. Organic sulfur compounds have been described in WO 2007060839. The pyripyropene derivative afidopyropen has been described in WO 2008/66153 and WO 2008/108491. The pyridazin compound A17.2 has been described in JP 2008/115155.

The active compounds B mentioned above of groups F.1 to F.11, their preparation and their action against harmful fungi are generally known (cf., for example, http://www.h-clrss.demon.co.uk/index.html); they are commercially available.

Benalaxyl, methyl N-(phenylacetyl)-N-(2,6-xylyl)-DL-alaninate (DE 29 03 612); metalaxyl, methyl N-(methoxyacetyl)-N-(2,6-xylyl)-DL-alaninate (GB 15 00 581); ofurace, (RS)-α-(2-chloro-N-2,6-xylylacetamido)-γ-butyrolactone [CAS RN 58810-48-3]; oxadixyl; N-(2,6-dimethylphenyl)-2-methoxy-N-(2-oxo-3-oxazolidinyl)acetamide (GB 20 58 059); aldimorph, "4-alkyl-2,5(or 2,6) dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0]; dodine, 1-dodecylguanidinium acetate (Plant Dis. Rep., Vol. 41, p. 1029 (1957)); dodemorph, 4-cyclododecyl-2,6-dimethylmorpholine (DE-A 11 98 125); fenpropimorph, (RS)-cis-4-[3-(4-tert-butylphenyl)-2-methylpropy]-2,6-dimethylmorpholine (DE-A 27 52 096); fenpropidin, (RS)-1-[3-(4-tert-butylphenyl)-2-methylpropyl]piperidine (DE-A 27 52 096); guazatine, mixture of the reaction products from the amidation of technical grade iminodi(octamethylene)diamine, comprising various guanidines and polyamines [CAS RN 108173-90-6]; iminoctadine, 1,1'-iminodi(octamethylene)diguanidine (Congr. Plant Pathol., 1., p. 27 (1968); spiroxamine, (8-tert-butyl-1,4-dioxaspiro[4.5]dec-2-yl)diethylamine (EP-A 281 842); tridemorph, 2,6-dimethyl-4-tridecylmorpholine (DE-A 11 64 152); pyrimethanil, 4,6-dimethylpyrimidin-2-ylphenylamine (DD-A 151 404); mepanipyrim, (4-methyl-6-prop-1-ynylpyrimidin-2-yl)phenylamine (EP-A 224 339); cyprodinil, (4-cyclopropyl-6-methylpyrimidin-2-yl)phenylamine (EP-A 310 550); cycloheximide, 4-{(2R)-2-[(1S,3S,5S)-3,5-dimethyl-2-oxocyclohexyl]-2-hydroxyethyl}piperidine-2,6-dione [CAS RN 66-81-9]; griseofulvin, 7-chloro-2',4,6-trimethoxy-6'-methylspiro[benzofuran-2(3H), 1'-cyclohex-2'-ene]-3,4'-dione [CAS RN 126-07-8]; kasugamycin, 3-O-[2-amino-4-[(carboxyiminomethyl)amino]-2,3,4,6-tetradeoxy-α-D-arabino-hexopyranosyl]-D-chiro-inositol [CAS RN 6980-18-3]; natamycin, (8E,14E16E,18E,20E)-(1R,3S,5R,7R,12R,22R,24S,25R,26S)-22-(3-amino-3,6-dideoxy-β-D-mannopyranosyloxy)-1,3,26-trihydroxy-12-methyl-10-oxo-6,11,28-trioxatricyclo[22.3.1.0$^{5,7}$]octacosa-8,14,16,18,20-pentaene-25-carboxylic acid [CAS RN 7681-93-8]; polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid [CAS RN 22976-86-9]; streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. Vol. 69, p. 1234 (1947)); bitertanol, β-([1,1'-biphenyl]-4-yloxy)-α-(1,1-dimethylethyl)-1H-1,2,4-triazole-1-ethanol (DE-A 23 24 020); bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459); cyproconazole, 2-(4-chlorophenyl)-3-cyclopropyl-1-[1,2,4]triazol-1-ylbutan-2-ol (U.S. Pat. No. 4,664,696); difenoconazole, 1-{2-[2-chloro-4-(4-chlorophenoxyl)phenyl]-4-methyl-[1,3]dioxolan-2-ylmethyl}-1H-[1,2,4]triazole (GBA 2 098 607); diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575); enilconazole (imazalil), 1-[2-(2,4-dichlorophenyl)-2-(2-propenyloxyl)ethyl]-1H-imidazole (Fruits, 1973, Vol. 28, p. 545); epoxiconazole, (2RS,3SR)-1-[3-(2-chlorophenyl)-2,3-epoxy-2-(4-fluorophenyl)propyl]-1H-1,2,4-triazole (EP-A 196 038); fenbuconazole, α-[2-(4-chlorophenyl)ethyl]-α-phenyl-1H-1,2,4-triazole-1-propanenitrile (Proc. 1988 Br. Crop Prot. Conf.—Pests Dis., Vol. 1, p. 33); fluquinconazole, 3-(2,4-dichlorophenyl)-6-fluoro-2-[1,2,4]-triazol-1-yl-3H-quinazolin-4-one (Proc. Br. Crop Prot. Conf.-Pests Dis., 5-3, 411 (1992)); flusilazole, 1-{[bis(4-fluorophenyl)methylsilanyl]methyl}-1H-[1,2,4]triazole (Proc. Br. Crop Prot. Conf.-Pests Dis., Vol. 1, p. 413 (1984)); flutriafol, α-(2-fluorophenyl)-α-(4-fluorophenyl)-1H-1,2,4-triazole-1-ethanol (EP-A 15 756); hexaconazole, 2-(2,4-dichlorophenyl)-1-[1,2,4]triazol-1-ylhexan-2-ol (CAS RN 79983-71-4); ipconazole, 2-[(4-chlorophenyl)methyl]-5-(1-methylethyl)-1-(1H-1,2,4-triazol-1-ylmethyl)cyclopentanol (EP-A 267 778); metconazole, 5-(4-chlorobenzyl)-2,2-dimethyl-1-[1,2,4]triazol-1-ylmethylcyclopentanol (GB 857 383); myclobutanil, 2-(4-chlorophenyl)-2-[1,2,4]triazol-1-ylmethylpentanenitrile (CAS RN 88671-89-0); penconazole, 1-[2-(2,4-dichlorophenyl)pentyl]-1H-[1,2,4]triazole (Pesticide Manual, 12th Ed. 2000, p. 712); propiconazole, 1-[[2-(2,4-dichlorophenyl)-4-propyl-1,3-dioxolan-2-yl]methyl]-1H-1,2,4-triazole (BE 835 579); prochloraz, N-(propyl-[2-(2,4,6-trichlorophenoxyl)ethyl])imidazole-1-carboxamide (U.S. Pat. No. 3,991,071); prothioconazole, 2-[2-(1-chlorocyclopropyl)-3-(2-chlorophenyl)-2-hydroxypropyl]-2,4-dihydro[1,2,4]triazole-3-thione (WO 96/16048); simeconazole, α-(4-fluorophenyl)-α-[(trimethylsilyl)methyl]-1H-1,2,4-triazole-1-ethanol [CAS RN 149508-90-7], tebuconazole, 1-(4-chlorophenyl)-4,4-dimethyl-3-[1,2,4]triazol-1-ylmethylpentan-3-ol (EP-A 40 345); tetraconazole, 1-[2-(2,4-dichlorophenyl)-3-(1,1,2,2-tetrafluoroethoxyl)propyl]-1H-1,2,4-triazole (EP-A 234 242); triadimefon, 1-(4-chlorophenoxy)-3,3-dimethyl-1-(1H-1,2,4-triazol-1-yl)-2-butanone (BE 793 867); triadimenol, β-(4-chlorophenoxy)-α-(1,1-dimethylethyl)-1H-1,2,4-triazole-1-ethanol (DE-A 3 24 010); triflumizol, (4-chloro-2-trifluoromethylphenyl)-(2-propoxy-1-[1,2,4]triazol-1-ylethylidene)-amine (JP-A 79/119 462); triticonazole, (5E)-5-[(4-chlorophenyl)methylene]-2,2-dimethyl-1-(1H-1,2,4-triazol-1-ylmethyl)cyclopentanol (FR 26 41 277); iprodione, N-isopropyl-3-(3,5-dichlorophenyl)-2,4-dioxoimidazolidine-1-carboxamide (GB 13 12 536); myciozolin, (RS)-3-(3,5-dichlorophenyl)-5-methoxymethyl-5-methyl-1,3-oxazolidine-2,4-dione [CAS RN 54864-61-8]; procymidone, N-(3,5-dichlorophenyl)-1,2-dimethylcyclopropane-1,2-dicarboximide (U.S. Pat. No. 3,903,090); vinclozolin, 3-(3,5-dichlorophenyl)-5-methyl-5-vinyloxazolidine-2,4-dione (DE-A 22 07 576); ferbam, iron(3+) dimethyldithiocarbamate (U.S. Pat. No. 1,972,961); nabam, disodium ethylenebis(dithiocarbamate) (U.S. Pat. No. 2,317,765); maneb, manganese ethylenebis(dithiocarbamate) (U.S. Pat. No. 2,504,404); mancozeb, manganese ethylenebis(dithiocarbamate) polymer complex zinc salt (GB 996 264); metam, methyldithiocarbaminic acid (U.S. Pat. No. 2,791,605); metiram, zinc ammoniate ethylenebis(dithiocarbamate) (U.S. Pat. No. 3,248,400); propineb, zinc propylenebis(dithiocarbamate) polymer (BE 611 960); polycarbamate, bis(dimethylcarbamodithioato-κS,κS)[μ-[[1,2-ethanediylbis[carbamodithioato-κS,κS]] (2-)]]di[zinc][CAS RN 64440-88-6]; thiram, bis(dimethylthiocarbamoyl)disulfide (DE-A 642 532); ziram, dimethyldithiocarbamate [CAS RN 137-30-4]; zineb, zinc ethylenebis(dithiocarbamate) (U.S. Pat. No. 2,457,674); anilazine, 4,6-dichloro-N-(2-chlorophenyl)-1,3,5-triazine-2-amine (U.S. Pat. No. 2,720,480); benomyl, N-butyl-2-acetylaminobenzimidazole-1-carboxamide (U.S. Pat. No. 3,631,176); boscalid, 2-chloro-N-(4'-chlorobiphenyl-2-yl)nicotinamide (EP-A 545 099); carbendazim, methyl(1H-benzimidazol-2-yl)carbamate (U.S. Pat. No. 3,657,443); carboxin, 5,6-dihydro-2-methyl-N-phenyl-1,4-oxathiine-3-carboxamide (U.S. Pat. No. 3,249,499); oxycarboxin, 5,6-dihydro-2-methyl-1,4-oxathiine-3-carboxanilide 4,4-dioxide (U.S. Pat. No. 3,399,214); cyazofamid, 4-chloro-2-cyano-N,N-dimethyl-5-(4-methylphenyl)-1H-imidazole-1-sulfonamide (CAS RN 120116-88-3]; dazomet, 3,5-dimethyl-1,3,5-thiadiazinane-2-thione (Bull. Soc. Chim. Fr. Vol. 15, p. 891 (1897)); diflufenzopyr, 2-{1-[4-(3,5-difluorophenyl)semicarbazono]ethyl}nicotinic acid [CAS RN 109293-97-2]; dithianon, 5,10-dioxo-5,10-dihydronaphtho[2,3-b][1,4]dithiin-2,3-dicarbonitrile (GB 857 383); famoxadone, (RS)-3-anilino-5-methyl-5-(4-phenoxyphenyl)-1,3-oxazolidine-2,4-dione [CAS RN 131807-57-3]; fenamidone, (S)-1-anilino-4-methyl-2-methylthio-4-phenylimidazolin-5-one [CAS RN 161326-34-7]; fenarimol, α-(2-chlorophenyl)-α-(4-chlorophenyl)-5-pyrimidinemethanol (GB 12 18 623); fuberidazole, 2-(2-furanyl)-1H-benzimidazole (DE-A 12 09 799); flutolanil, α,α,α-trifluoro-3'-isopropoxy-o-toluanilide (JP 1104514); furametpyr, 5-chloro-N-(1,3-dihydro-1,1,3-trimethyl-4-isobenzofuranyl)-1,3-dimethyl-1H-pyrazole-4-carboxamide [CAS RN 123572-88-3]; isoprothiolane, diisopropyl 1,3-dithiolan-2-ylidenemalonate (Proc. Insectic. Fungic. Conf. 8. Vol. 2, p. 715 (1975)); mepronil, 3'-isopropoxy-o-toluanilide (U.S. Pat. No. 3,937,840); nuarimol, α-(2-chlorophenyl)-α-(4-fluorophenyl)-5-pyrimidinemethanol (GB 12 18 623); fluopicolide (picobenzamid), 2,6-dichloro-N-(3-chloro-5-trifluoromethylpyridin-2-ylmethyl)benzamide (WO 99/42447); probenazole, 3-allyloxy-1,2-benzothiazole 1,1-dioxide (Agric. Biol. Chem. Vol. 37, p. 737 (1973)); proquinazid, 6-iodo-2-propoxy-3-propylquinazolin-4(3H)-one (WO 97/48684); pyrifenox, 2',4'-dichloro-2-(3-pyridyl)acetophenone (EZ)—O-methyloxime (EP 49 854); pyroquilon, 1,2,5,6-tetrahydropyrrolo[3,2,1-ij] quinolin-4-one (GB 139 43 373); quinoxyfen, 5,7-dichloro-4-(4-fluorophenoxy)quinoline (U.S. Pat. No. 5,240,940); silthiofam, N-allyl-4,5-dimethyl-2-(trimethylsilyl)thiophene-3-carboxamide [CAS RN 175217-20-6]; thiabendazole, 2-(1,3-thiazol-4-yl)benzimidazole (U.S. Pat. No. 3,017,415); thifluzamide, 2',6'-dibromo-2-methyl-4'-trifluoromethoxy-4-trifluoromethyl-1,3-thiazole-5-carboxanilide [CAS RN 130000-40-7]; thiophanate-methyl, 1,2-phenylenebis(iminocarbonothioyl)bis(dimethylcarbamate) (DE-A 19 30 540); tiadinil, 3'-chloro-4,4'-dimethyl-1,2,3-thiadiazole-5-carboxanilide [CAS RN 223580-51-6]; tricyclazole, 5-methyl-1,2,4-triazolo[3,4-b][1,3]benzothiazole [CAS RN 41814-78-2]; triforine, N,N-{piperazine-1,4-diylbis[(trichloromethyl)methylene]}diformamide (DE-A 19 01 421); 5-chloro-7-(4-methylpiperidin-1-yl)-6-(2,4,6-trifluorophenyl)-[1,2,4]triazolo[1,5-a]pyrimidine (WO 98/46607) and other triazolo pyrimidine (EP-A 71 792; EP-A 141 317; WO 03/009687; WO 05/087771; WO 05/087772; WO 05/087773; WO 2006/087325; WO 2006/092428); Bordeaux mixture, mixture of $CuSO_4 \times 3Cu(OH)_2 \times 3CaSO_4$ [CAS RN 8011-63-0]; copper acetate, $Cu(OCOCH_3)_2$ [CAS RN 8011-63-0]; copper oxychloride, $Cu_2Cl(OH)_3$ [CAS RN 1332-40-7]; basic copper sulfate, $CuSO_4$ [CAS RN 1344-73-6]; binapacryl, (RS)-2-seo-butyl-4,6-dinitrophenyl 3-methylcrotonate [CAS RN 485-31-4]; dinocap, mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660); dinobuton, (RS)-2-seo-butyl-4,6-dinitrophenyl isopropyl carbonate [CAS RN 973-21-7]; nitrothal-isopropyl, diisopropyl 5-nitroisophthalate (Proc. Br. Insectic. Fungic. Conf. 7., Vol. 2, p. 673 (1973)); fenpicionil, 4-(2,3-dichlorophenyl)-1H-pyrrole-3-carbonitrile (Proc. 1988 Br. Crop Prot. Conf.—Pests Dis., Vol. 1, p. 65); fludioxonil, 4-(2,2-difluorobenzo[1,3]dioxol-4-yl)-1H-pyrrole-3-carbonitrile (The Pesticide Manual, publ. The British Crop Protection Council, 10th ed. 1995, p. 482); acibenzolar-S-methyl, methyl 1,2,3-benzothiadiazole-7-carbothioate [CAS RN 135158-54-2]; flubenthiavalicarb (benthiavalicarb), isopropyl{(S)-1-[(1R)-1-(6-fluorobenzothiazol-2-yl)-ethylcarbamoyl]-2-methylpropyl}carbamate (JP-A 09/323 984); carpropamid, 2,2-dichloro-N-[1-(4-chlorophenyl)ethyl]-1-ethyl-3-methylcyclopropanecarboxamide [CAS RN 104030-54-8]; chlorothalonil, 2,4,5,6-tetrachloroisophthalonitrile (U.S. Pat. No. 3,290,353); cyflufenamid, (2)-N-[α-(cyclopropylmethoxyimino)-2,3-difluoro-6-(trifluoromethyl)benzyl]-2-phenylacetamide (WO 96/19442); cymoxanil, 1-(2-cyano-2-methoxyiminoacetyl)-3-ethylurea (U.S. Pat. No. 3,957,847); diciomezine, 6-(3,5-dichlorophenyl-p-tolyl)pyridazin-3(2H)-one (U.S. Pat. No. 4,052,395;) diclocymet, (RS)-2-cyano-N—[(R)-1-(2,4-dichlorophenyl) ethyl]-3,3-dimethylbutyramide [CAS RN 139920-32-4]; diethofencarb, isopropyl 3,4-diethoxycarbanilate (EP-A 78 663); edifenphos, O-ethyl S,S-diphenyl phosphorodithioate (DE-A 14 93 736); ethaboxam, N-(cyano-2-thienylmethyl)-4-ethyl-2-(ethylamino)-5-thiazolecarboxamide (EP-A 639 574); fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327); fentin-acetate, triphenyltin (U.S. Pat. No. 3,499,086); fenoxanil, N-(1-cyano-1,2-dimethylpropyl)-2-(2,4-dichlorophenoxy)propanamide (EP-A 262 393); ferimzone, (2)-2'-methylacetophenone-4,6-dimethylpyrimidin-2-ylhydrazone [CAS RN 89269-64-7]; fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474); fosetyl, fosetyl-aluminum, ethylphosphonate (FR 22 54 276); iprovalicarb, isopropyl [(1S)-2-methyl-1-(1-p-tolylethylcarbamoyl)propyl]carbamate (EP-A 472 996); hexachlorobenzene (C. R. Seances Acad. Agric. Fr., Vol. 31, p. 24 (1945)); mandipropamid, (RS)-2-(4-chlorophenyl)-N-[3-methoxy-4-(prop-2-ynyloxy)phenethyl]-2-(prop-2-ynyloxy)acetamide (WO 03/042166); metrafenone, 3'-bromo-2,3,4,6'-tetramethoxy-2',6-dimethylbenzophenone (U.S. Pat. No. 5,945,567); pencycuron, 1-(4-chlorobenzyl)-1-cyclopentyl-3-phenylurea (DE-A 27 32 257); penthiopyrad, (RS)—N-[2-(1,3-dimethylbutyl)-3-thienyl]-1-methyl-3-(trifluoromethyl)-1H-pyrazole-4-carboxamide (JP 10/130268); propamocarb, isopropyl 3-(dimethylamino)propylcarbamate (DE-A 15 67 169); phthalide (DE-A 16 43 347); toloclofos-methyl, O-2,6-dichloro-p-tolyl O,O-dimethyl phosphorothioate (GB 14 67 561); quintozene, pentachloronitrobenzene (DE-A 682 048); zoxamide, (RS)-3,5-dichloro-N-(3-chloro-1-ethyl-1-methyl-2-oxopropyl)-p-toluamide [CAS RN 156052-68-5]; captafol, N-(1,1,2,2-tetrachloroethyithio)cyclohex-4-ene-1,2-dicarboximide (Phytopathology, Vol. 52, p. 754 (1962)); captan, N-(trichloromethylthio)cyclohex-4-ene-1,2-dicarboximide (U.S. Pat. No. 2,553,770); dichlofluanid, N-dichlorofluoromethylthio-N,N-dimethyl-N-phenylsulfamide (DE-A 11 93 498); folpet, N-(trichloromethylthio)phthalimide (U.S. Pat. No. 2,553,770); tolylfluanid, N-dichlorofluoromethylthio-N,N-dimethyl-N-p-tolylsulfamide (DE-A 11 93 498); dimethomorph, 3-(4-chloro-phenyl)-3-(3,4-dimethoxyphenyl)-1-morpholin-4-yl-propenone (EP-A 120 321); flumetover, 2-(3,4-dimethoxyphenyl)-N-ethyl-α,α,α-trifluoro-N-methyl-p-toluamide [AGROW no. 243, 22 (1995)]; flumorph, 3-(4-fluorophenyl)-3-(3,4-dimethoxyphenyl)-1-morpholin-4-ylpropenone (EP-A 860 438); N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide (WO 03/66610); N-(3',4'-dichloro-4-fluorobiphenyl-2-yl)-3-difluoromethyl-1-methylpyrazole-4-carboxamide and N-(3',4'-dichloro-5-fluorobiphenyl-2-yl)-3-difluoromethyl-1-methylpyrazole-4-carboxamide (WO 03/70705); N-(2-cyanophenyl)-3,4-dichloroisothiazole-5-carboxamide (WO 99/24413); N-(2-(4-[3-(4-chlorophenyl)prop-2-ynykoxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide (WO 04/49804); N-(2-bicycloprop-2-ylphenyl)-3-difluoromethyl-1-methyl-1H-pyrazole-4-carboxamide is a mixture of the diastereomers N-(trans-2-bicycloprop-2-ylphenyl)-3-difluoromethyl-1-methyl-1H-pyrazole-4-carboxamide and N-(cis-2-bicycloprop-2-ylphenyl)-3-difluoromethyl-1-methyl-1H-pyrazole-4-carboxamide (WO 03/074491 and WO 06/015866); 3-[5-(4-chlorophenyl)-2,3-dimethylisoxazolidin-3-yl]pyridine (EP-A 10 35 122); 2-butoxy-6-iodo-3-propylchromen-4-one (WO 03/14103); N,N-dimethyl-3-(3-bromo-6-fluoro-2-methylindole-1-sulfonyl)-[1,2,4]triazole-1-sulfonamide (EP-A 10 31 571); methyl(2-chloro-5-[1-(3-methylbenzyloxyimino)ethyl]benzyl)carbamate, methyl(2-chloro-5-[1-(6-methylpyridin-2-ylmethoxyimino)ethyl]benzyl)carbamate (EP-A 12 01 648); methyl 3-(4-chloro-phenyl)-3-(2-isopropoxycarbonylamino-3-methylbutyrylamino)propionate (EP-A 10 28 125); azoxystrobin, methyl 2-{2-[6-(2-cyano-1-vinylpenta-1,3-dienyloxy)pyrimidin-4-yloxy]phenyl}-3-methoxyacrylate (EP-A 382 375), dimoxystrobin, (E)-2-(methoxyimino)-N-methyl-2-[α-(2,5-xylyloxy)-o-tolyl]acetamide (EP-A 477 631); fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189); kresoxim-methyl, methyl (E)-methoxyimino[α-(o-tolyloxy)-o-tolyl]acetate (EP-A 253 213); metominostrobin, (E)-2-(methoxyimino)-N-methyl-2-(2-phenoxyphenyl)acetamide (EP-A 398 692); orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552); picoxystrobin, methyl 3-methoxy-2-[2-(6-trifluoromethylpyridin-2-yloxymethyl)phenyl]acrylate (EP-A 278 595); pyraclostrobin, methyl N-{2-[1-(4-chlorophenyl)-1H-pyrazol-3-yloxymethyl]phenyl}(N-methoxy)carbamate (WO 96/01256); trifloxystrobin, methyl(E)methoxyimino-{(E)-α-[1-(α,α,α-trifluoro-m-tolyl)ethylideneaminooxy]-o-tolyl}acetate (EP-A 460 575); methyl 2-[ortho-(2,5-dimethylphenyloxymethylene)phenyl]-3-methoxyacrylate (EP-A 226 917); 5-chloro-7-(4-methylpiperidin-1-yl)-6-(2,4,6-trifluorophenyl)-[1,2,4]triazolo[1,5-a]pyrimidine (WO 98/46608); 3,4-dichloro-N-(2-cyanophenyl)isothiazole-5-carboxamide (WO 99/24413), compounds of the formula III (WO 04/049804); N-(2-(4-[3-(4-chlorophenyl)prop-2-ynyloxy]-3-methoxyphenyl)ethyl)-2-methanesulfonylamino-3-methylbutyramide and N-(2-(4-[3-(4-chlorophenyl)prop-2-ynyloxy]-3-methoxyphenyl)ethyl)-2-ethanesulfonylamino-3-methylbutyramide (WO 03/66609); 2-butoxy-6-iodo-3-propylchromen-4-one (WO 03/14103); N,N-dimethyl-3-(3-bromo-6-fluoro-2-methylindole-1-sulfonyl)-[1,2,4]triazole-1-sulfonamide (WO 03/053145); methyl 3-(4-chlorophenyl)-3-(2-isopropoxycarbonylamino-3-methylbutyrylamino)propanoate (EP-A 1028125).

We have accordingly found that several objects can be achieved by the mixtures, defined at the outset, of the active compounds of formula I and compound B. Moreover, we have found that simultaneous, that is joint or separate, application of at least one compound I and at least one of the active compounds B or successive application of at least one of the compound(s) of formula I and at least one of the active compounds B allows better control of animal pests and/or harmful fungi than is possible with the individual compounds alone (synergistic mixtures).

The compounds of formula I can be used as synergists for a large number of different fungicidal active compounds. By simultaneous, that is joint or separate, application of compound(s) of formula I with at least one active compound B, the fungicidal and/or insecticidal activity, resp., is increased in a superadditive manner.

The compounds of the formula I can be present in different crystal modifications, which may differ in biological activity.

The remarks made below as to preferred embodiments of the variables (substituents) of the compounds of formula I are valid on their own as well as preferably in combination with each other, as well as in combination with the stereoisomers, salts, tautomers or N-oxides thereof.

The remarks made below concerning preferred embodiments of the variables further are valid on their own as well as preferably in combination with each other concerning the compounds of formula I, where applicable, as well as concerning the uses and methods according to the invention and the mixtures according to the invention.

In one embodiment of the invention the compounds of formula I have the following meanings:
$R^1$ is H, $C_1$-$C_2$-alkyl, or $C_1$-$C_2$-alkoxy-$C_1$-$C_2$-alkyl;
$R^2$ is $CH_3$, $CH_2F$, $CHF_2$, or $CF_3$;
$R^3$ is $C_2$-$C_6$-alkyl, a radical $R^{3a}$, or a radical $R^{3b}$;
$R^4$ is $C_1$-$C_4$-alkyl, or a group mentioned for $R^{3a}$;
$R^5$ is H, halogen, or a group mentioned for $R^4$;
$R^3$ and $R^4$ together with the carbon atom, to which they are attached, may form a monocyclic three- to six-membered carbo- or heterocycle, which may contain 1 or 2 heteroatom moieties selected from N—$R^c$, O, and $S(O)_k$, with k being 0, 1 or 2, which carbo- or heterocycle is unsubstituted or may be substituted by 1, 2, 3 or 4 radicals $R^{a3}$;

$R^3$ and $R^4$ together with the carbon atom, to which they are attached, may also form a monospiro or dispiro 5- to 10-membered carbo- or heterocycle, which may contain 1 or 2 heteroatom moieties selected from N—$R^c$, O, and $S(O)_k$, with k being 0, 1 or 2, which carbo- or heterocycle is unsubstituted or may be substituted by 1, 2, 3 or 4 radicals $R^{a3}$;

$R^{3a}$ is selected from the group consisting of CN, $NO_2$, $S(O)_nR^b$, $C_1$-$C_4$-haloalkyl, $C_1$-$C_4$-alkyl which is partially or fully substituted by $R^{a1}$, $C_2$-$C_6$-alkenyl, $C_2$-$C_6$-alkynyl, $C_1$-$C_6$-alkoxy, wherein the C-atoms in the last 3 mentioned radicals may be unsubstituted, or partially or fully substituted by $R^{a2}$, $C_3$-$C_6$-cycloalkyl and $C_5$-$C_6$-cycloalkenyl wherein the C-atoms in the last 2 mentioned radicals may be unsubstituted, or partially or fully substituted by $R^{a3}$, $R^{3b}$ is a monospiro or dispiro 5- to 10-membered carbo- or heterocycle, which may contain 1 or 2 heteroatom moieties selected from N—$R^c$, O, and $S(O)_k$, with k being 0 1 or 2, which monospiro or dispiro 5 to 10-membered carbo- or heterocycle is unsubstituted, or may be substituted by 1, 2, 3 or 4 radicals $R^{a3}$;

$R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_nR^b$;

$R^{a2}$ is halogen, or a group mentioned for $R^{a1}$;

$R^{a3}$ is halogen, $C_1$-$C_2$-alkyl, $C_1$-$C_2$-alkoxy-$C_1$-$C_2$-alkyl, $C_1$-$C_2$-alkyliden, or a group mentioned for $R^{a1}$;

n is 0, 1, or 2;

$R^b$ is selected from the group consisting of H, $C_1$-$C_2$-alkyl, $C_1$-$C_2$-haloalkyl, $C_3$-$C_6$-cycloalkyl, and $C_1$-$C_4$-alkoxy, $R^c$ is H, $C_1$-$C_2$-alkyl, $C_1$-$C_2$-haloalkyl, $C_1$-$C_2$-alkylcarbonyl, and $C_1$-$C_2$-alkoxycarbonyl;

the stereoisomers, salts, tautomers, and N-oxides thereof.

Particularly suitable for the mixtures according to the invention are compounds of the formula I in which $R^1$ is H, $C_1$-$C_2$-alkyl, or $C_1$-$C_2$-alkoxymethyl. More preferably, $R^1$ is $CH_3$, or $C_2H_5$.

Particularly suitable for the mixtures according to the invention are compounds of the formula I in which $R^2$ is $CH_3$, $CHF_2$, or $CF_3$, especially $CH_3$.

Particularly suitable for the mixtures according to the invention are compounds of the formula I in which $R^3$ is a radical $R^{3b}$. In this context, $R^{3b}$ is preferably a 5-, 6-, 7-, 8-, 9-, or 10-membered monospiro- or dispirocarbocycle which is unsubstituted or substituted by 1 or 2 radicals $R^{a3}$. $R^{a3}$, if present, is preferably selected from CN, $C_1$-$C_2$-haloalkyl, $C_1$-$C_2$-alkylidene, and $C_1$-$C_2$-alkoxy-$C_1$-$C_2$-alkyl. In another embodiment $R^{a3}$ is haloalkyl, preferably $CHF_2$, or $CF_3$, preferred $CF_3$. Substituents $R^{a3}$ are preferably in 1- or 4-position, if the carbocycle is monosubstituted and in 4,4-position, if the carbocycle is disubstituted. More preferably, $R^3$ is spiro[2.2]pentyl, which is unsubstituted or carries one or two radicals $R^{a3}$ or 7-dispiro[2.0.1.2]-heptyl which is unsubstituted or carries a radical R. $R^3$ is even more preferably selected from the group consisting of spiro[2.2]pentyl, 2-methylene-spiro[2.2]pentyl, 1-CN-spiro[2.2]pentyl, 1-$CF_3$-spiro[2.2]pentyl, 4-$CH_3$-spiro[2.2]pentyl, 4,4-$(CH_3)_2$-spiro[2.2]pentyl, 4-$(CH_2OCH_3)$-spiro[2.2]pentyl, 4-$CF_3$-spiro[2.2]pentyl and 7-dispiro[2.0.2.1]-heptyl.

Particularly suitable for the mixtures according to the invention are compounds of the formula I in which $R^3$ is selected from the group consisting of CN, $C_2$-$C_6$-alkyl, $C_1$-$C_4$-haloalkyl, $C_1$-$C_4$-alkyl which is substituted by one or two radicals $R^{a1}$, or $C_3$-$C_6$-cycloalkyl, wherein the C-atoms of $C_3$-$C_6$-cycloalkyl are unsubstituted or substituted by 1 or 2 radicals $R^3$. In this context, $R^{a1}$ is preferably selected from CN, $C_1$-$C_2$-alkoxy, $C_1$-$C_2$-alkylsulfanyl, $C_1$-$C_2$-haloalkoxy, and $C_1$-$C_2$-haloalkylsulfanyl. $R^{a3}$ is preferably selected from CN, $C_1$-$C_2$-alkoxy, $C_1$-$C_2$-alkylsulfanyl, $C_1$-$C_2$-haloalkoxy, and $C_1$-$C_2$-haloalkylsulfanyl. One substituent $R^{a3}$ is preferably in 1-position. More preferably, $R^3$ is selected from CN, $C_2$-$C_4$-alkyl, $C_1$-$C_4$-fluoroalkyl, $C_1$-$C_4$-alkyl which is substituted by one or two radicals $R^{a1}$, and $C_3$-$C_6$-cycloalkyl which is unsubstituted or carries one radical $R^3$. More preferably, $R^{a1}$ is selected from CN, $C_1$-$C_2$-alkoxy, $C_1$-$C_2$-alkylsulfanyl, $C_1$-$C_2$-fluoroalkoxy, and $C_1$-$C_2$-fluoroalkoxysulfanyl. $R^{a3}$ is preferably selected from CN, $C_1$-$C_2$-alkoxy, $C_1$-$C_2$-alkylsulfanyl, $C_1$-$C_2$-fluoroalkoxy, and $C_1$-$C_2$-fluoroalkylsulfanyl. Even more preferably, $R^3$ is selected from CN, $C_2$-$C_4$-alkyl, $C_1$-$C_4$-haloalkyl, especially $C_1$-$C_4$-fluoroalkyl, $C_1$-$C_2$-alkoxy-$C_1$-$C_4$-alkyl, $C_1$-$C_2$-haloalkoxy-$C_1$-$C_4$-alkyl, especially $C_1$-$C_2$-fluoroalkoxy-$C_1$-$C_4$-alkyl, cyano-$C_1$-$C_4$-alkyl, $C_1$-$C_2$-alkylsulfanyl-$C_1$-$C_4$-alkyl, $C_1$-$C_2$-haloalkylsulfanyl-$C_1$-$C_4$-alkyl, especially $C_1$-$C_2$-fluoroalkylsulfanyl-$C_1$-$C_4$-alkyl, $C_3$-$C_6$-cycloalkyl, $C_3$-$C_6$-cycloalkyl which carries one radical $R^{a3}$ selected from halogen, especially F, CN, $C_1$-$C_2$-alkyl, $C_1$-$C_4$-alkoxy, $C_1$-$C_2$-haloalkoxy, especially $C_1$-$C_2$-fluoroalkoxy, $C_1$-$C_2$-alkylsulfanyl and $C_1$-$C_2$-haloalkylsulfanyl, especially $C_1$-$C_2$-fluoroalkoxysulfanyl.

According to this embodiment, preferred examples for $R^3$ are CN, $C_2H_5$, $CH(CH_3)_2$, $CHF_2$, $CH_2F$, $CF_3$, $CH_2OCH_3$, c-$C_3H_5$, 1-F-c-$C_3H_4$, 1-CN-c-$C_3H_4$, 1-$CH_3$-c-$C_3H_4$, 1-$OCH_3$-c-$C_3H_4$, 1-$CF_3$-c-$C_3H_4$, 1-$OCF_3$—C—$C_3H_4$, 1-$SCH_3$-c-$C_3H_4$, 1-$SCF_3$-c-$C_3H_4$, $C(CH_3)_3$, 1-F-1-methylethyl, 1-CN-1-methylethyl, 1-methoxy-1-methylethyl, 1-(trifluoromethoxy)-1-methylethyl, 1-(methylsulfanyl)-1-methylethyl, 1-(trifluoromethylsulfanyl)-1-methylethyl, 2,2,2-trifluoro-1,1I-dimethylethyl, $CHFCH_3$, $CH(CN)CH_3$, $CF_2CH_3$, 1,1-dimethoxyethyl, 1-methoxyethyl, 1-(trifluoromethoxy)-ethyl, 1-(methylsulfanyl)ethyl, 1-(trifluoromethylsulfanyl)ethyl, 2,2,2-trifluoro-1-methylethyl, methylsulfanylmethyl, trifluoromethylsulfanylmethyl, trifluoromethoxymethyl, $CH_2CN$, and $CH_2CF_3$.

Preferred meanings of the variable $R^3$ are selected from the radicals R3.1, R3.2, R3.3, R3.4, R3.5, R3.6, R3.7, R3.8, R3.9, R3.10, R3.11, R3.12, R3.13, R3.14, R3.15, R3.16, R3.17, R3.18, R3.19, R3.20, R3.21, R3.22, R3.23, R3.24, R3.25, R3.26, R3.27, R3.28, R3.29, R3.30, R3.31, R3.32, R3.33, R3.34, R3.35, R3.36, R3.37, R3.38, R3.39, R3.40, R3.41, R3.42, R3.43, R3.44, R3.45, R3.46, R3.47 and R3.48 shown below:

R3.1

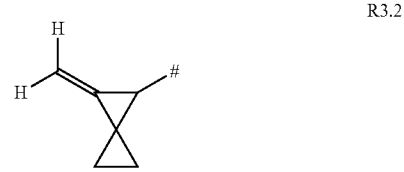

R3.2

R3.3

-continued
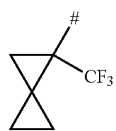 R3.4
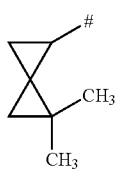 R3.5
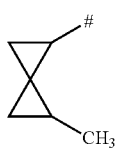 R3.6
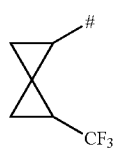 R3.7
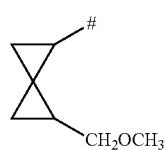 R3.8
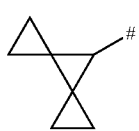 R3.9
—CN  R3.10
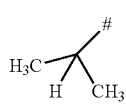 R3.11
 R3.12
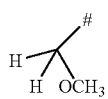 R3.13
 R3.14
 R3.15
 R3.16
-continued
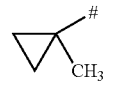 R3.17
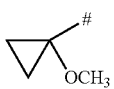 R3.18
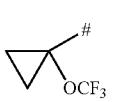 R3.19
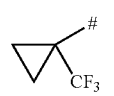 R3.20
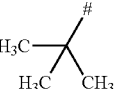 R3.21
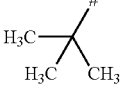 R3.22
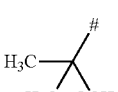 R3.23
 R3.24
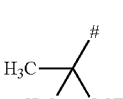 R3.25
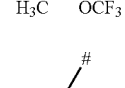 R3.26
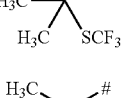 R3.27
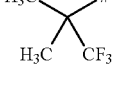 R3.28
R3.29
R3.30
R3.31

-continued

R3.32 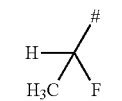

R3.33 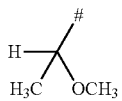

R3.34 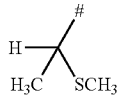

R3.35 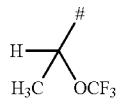

R3.36 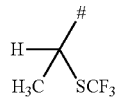

R3.37 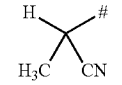

R3.38 

R3.39 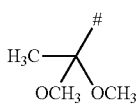

R3.40 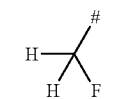

R3.41 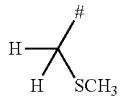

R3.42 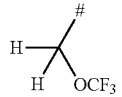

R3.43 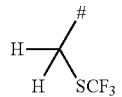

R3.44 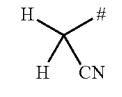

R3.45 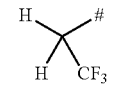

-continued

R3.46 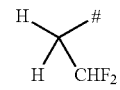

R3.47 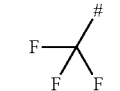

R3.48 

\# denotes the point of attachment to the remainder of the molecule.

Particularly suitable for the mixtures according to the invention are compounds of the formula I in which $R^4$ is $C_1$-$C_4$-alkyl or $C_1$-$C_4$-haloalkyl, in particular $C_1$-$C_4$-fluoroalkyl. More preferably, $R^4$ is $CH_3$, $C_2H_5$, $CHF_2$ or $CF_3$, especially $CH_3$.

Particularly suitable for the mixtures according to the invention are compounds of the formula I in which the variables $R^3$ and $R^4$ together with the carbon atom, to which they are attached, form a monocyclic three-, four-, five- or six-membered carbo- or heterocycle, which may contain 1 or 2 heteroatom moieties selected from N—$R^c$, O, and $S(O)_k$, with k being 0, 1 or 2, which monocyclic three- to six-membered carbo- or heterocycle is unsubstituted or may be substituted by 1, 2, 3 or 4 radicals $R^{a3}$. $R^c$ preferably denotes $C_1$-$C_2$-alkyl, particularly $CH_3$, or $C_1$-$C_2$-alkylcarbonyl, particularly acetyl. $R^8$ is preferably selected from $C_1$-$C_2$-alkyl and halogen, even more preferably $C_1$-$C_2$-alkyl and fluorine.

If $R^3$ and $R^4$ together with the carbon atom, to which they are attached, form a monocyclic three-, four-, five- or six-membered heterocycle, the heterocycle preferably comprises 1 or 2 heteroatom moieties selected from O and $NR^c$. $R^c$ has one of the meanings given above. More preferably, $R^3$ and $R^4$ together with the carbon atom, to which they are attached, form $C_3$-$C_6$-cycloalkyl such as cyclopropyl, cyclopentyl or cyclohexyl, 2,2-difluorocyclopropyl, 2,2-dichlorocyclopropyl, oxan-4-yl, 1,3-dioxan-5-yl or 2,2-dimethyl-1,3-dioxan-5-yl.

Preferred meanings of the variable $R^3$ and $R^4$ taken together are selected from the groups R3.49, R3.50, R3.51, R3.52 and R3.53 shown below: $(CH_2)_2$ (R3.49), $(CH_2)_4$ (R3.50), $(CH_2)_5$ (R3.51), —$CH_2OCH_2OCH_2$— (R3.52), and —$CH_2OC(CH_3)_2OCH_2$— (R3.53).

Particularly suitable for the mixtures according to the invention are compounds of the formula I in which the variables $R^3$ and $R^4$ together with the carbon atom, to which they are attached, form a monospiro or dispiro 5-, 6-, 7-, 8-, 9- or 10-membered carbo- or heterocycle, which may contain 1 or 2 heteroatom moieties selected from N—$R^c$, O, and $S(O)_k$, with k being 0, 1 or 2, which monospiro or dispiro 5- to 10-membered carbo- or heterocycle is unsubstituted or may be substituted by 1, 2, 3 or 4 radicals $R^{a3}$. $R^{a3}$, if present, is preferably selected from CN, $C_1$-$C_2$-haloalkyl, $C_1$-$C_2$-alkylidene and $C_1$-$C_2$-alkoxy-$C_1$-$C_2$-alkyl. In another embodiment $R^{a3}$ is haloalkyl, preferably $CHF_2$, or $CF_3$, preferred $CF_3$. Substituents $R^8$ are preferably in 1- or 4-position, if the carbocycle is monosubstituted and in 4,4-position, if the carbocycle is disubstituted. More preferably, $R^3$ and $R^4$ together with the carbon atom, to which they are attached, form a monospiro or dispiro 5-, 6-, 7-, 8-, 9- or 10-membered carbocycle which is unsubstituted or substituted by 1 or 2 radicals $R^{a3}$. Even more preferably, $R^3$ and $R^4$ together with the carbon atom, to which they are attached, form spiro[2.2]pentyl, which is unsubstituted or carries 1 or 2 radicals $R^3$ or 7-dispiro[2.0.1.2]-heptyl which is unsubstituted or carries a radical $R^{a3}$. Specially, $R^3$ and $R^4$ together with the carbon atom, to which they are attached, form a radical selected from spiro[2.2]pentyl, 2-methylene-spiro[2.2]pentyl, 1-CN-spiro[2.2]pentyl, 1-$CF_3$-spiro[2.2]pentyl, 4-$CH_3$-spiro[2.2]pentyl, 4,4-$(CH_3)_2$-spiro[2.2]pentyl, 4-$(CH_2OCH_3)$-spiro[2.2]pentyl, 4-$(CF_3)$-spiro[2.2]pentyl and 7-dispiro[2.0.1.2]-heptyl.

Preferred meanings of the variable $R^3$ and $R^4$ together with the carbon atom, to which they are attached, form a monospiro or dispiro carbocycle, which is unsubstituted or substituted are selected from the radicals R3.54, R3.55, R3.56, R3.57, R3.58, R3.59, R3.60, R3.61 and R3.62 shown below:

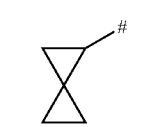
R3.54

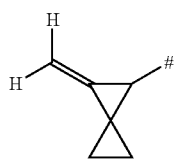
R3.55

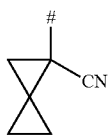
R3.56

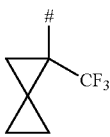
R3.57

R3.58

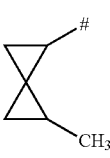
R3.59

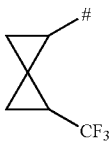
R3.60

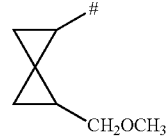
R3.61

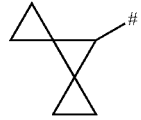
R3.62 where # denotes the point of attachment to the remainder of the molecule.

Particularly suitable for the mixtures according to the invention are compounds of the formula I in which the variable $R^5$ is H, CN, $C_1$-$C_2$-alkyl, $C_1$-$C_2$-alkoxy, $C_1$-$C_2$-alkylsulfanyl, $C_1$-$C_2$-haloalkyl, especially $C_1$-$C_2$-fluoroalkyl or $C_1$-$C_2$-haloalkylsulfanyl, especially $C_1$-$C_2$-fluoroalkyl. More preferably, $R^5$ is H, $CH_3$, CN, F, $OCH_3$, $SCH_3$, $CF_3$, $OCF_3$, or $SCF_3$. Most preferably $R^5$ is H, or CN, especially H.

Examples of preferred compounds are compounds of the formula I, where the variables have one of the general or preferred meanings given above. Especially preferred with a view to their use are the compounds I compiled in the tables I, II, III, and IV below. Moreover, the meanings mentioned below for the individual variables in the tables are per se, independently of the combination in which they are mentioned, a particularly preferred embodiment of the substituents in question.

TABLE I

| No. | $R^1$ | $R^2$ | $R^3$ | $R^4$ | $R^5$ |
|---|---|---|---|---|---|
| I-1 | $CH_3$ | $CH_3$ | R3.1 | $CH_3$ | H |
| I-2 | $C_2H_5$ | $CH_3$ | R3.1 | $CH_3$ | H |
| I-3 | $CH_3$ | $CH_2F$ | R3.1 | $CH_3$ | H |
| I-4 | $C_2H_5$ | $CH_2F$ | R3.1 | $CH_3$ | H |
| I-5 | $CH_3$ | $CF_3$ | R3.1 | $CH_3$ | H |
| I-6 | $C_2H_5$ | $CF_3$ | R3.1 | $CH_3$ | H |
| I-7 | $CH_3$ | $CH_3$ | R3.2 | $CH_3$ | H |
| I-8 | $C_2H_5$ | $CH_3$ | R3.2 | $CH_3$ | H |
| I-9 | $CH_3$ | $CH_2F$ | R3.2 | $CH_3$ | H |
| I-10 | $C_2H_5$ | $CH_2F$ | R3.2 | $CH_3$ | H |
| I-11 | $CH_3$ | $CF_3$ | R3.2 | $CH_3$ | H |
| I-12 | $C_2H_5$ | $CF_3$ | R3.2 | $CH_3$ | H |
| I-13 | $CH_3$ | $CH_3$ | R3.3 | $CH_3$ | H |
| I-14 | $C_2H_5$ | $CH_3$ | R3.3 | $CH_3$ | H |
| I-15 | $CH_3$ | $CH_2F$ | R3.3 | $CH_3$ | H |
| I-16 | $C_2H_5$ | $CH_2F$ | R3.3 | $CH_3$ | H |
| I-17 | $CH_3$ | $CF_3$ | R3.3 | $CH_3$ | H |
| I-18 | $C_2H_5$ | $CF_3$ | R3.3 | $CH_3$ | H |
| I-19 | $CH_3$ | $CH_3$ | R3.4 | $CH_3$ | H |
| I-20 | $C_2H_5$ | $CH_3$ | R3.4 | $CH_3$ | H |
| I-21 | $CH_3$ | $CH_2F$ | R3.4 | $CH_3$ | H |
| I-22 | $C_2H_5$ | $CH_2F$ | R3.4 | $CH_3$ | H |
| I-23 | $CH_3$ | $CF_3$ | R3.4 | $CH_3$ | H |
| I-24 | $C_2H_5$ | $CF_3$ | R3.4 | $CH_3$ | H |
| I-25 | $CH_3$ | $CH_3$ | R3.5 | $CH_3$ | H |
| I-26 | $C_2H_5$ | $CH_3$ | R3.5 | $CH_3$ | H |
| I-27 | $CH_3$ | $CH_2F$ | R3.5 | $CH_3$ | H |
| I-28 | $C_2H_5$ | $CH_2F$ | R3.5 | $CH_3$ | H |
| I-29 | $CH_3$ | $CF_3$ | R3.5 | $CH_3$ | H |
| I-30 | $C_2H_5$ | $CF_3$ | R3.5 | $CH_3$ | H |
| I-31 | $CH_3$ | $CH_3$ | R3.6 | $CH_3$ | H |
| I-32 | $C_2H_5$ | $CH_3$ | R3.6 | $CH_3$ | H |
| I-33 | $CH_3$ | $CH_2F$ | R3.6 | $CH_3$ | H |
| I-34 | $C_2H_5$ | $CH_2F$ | R3.6 | $CH_3$ | H |
| I-35 | $CH_3$ | $CF_3$ | R3.6 | $CH_3$ | H |

TABLE I-continued

| No. | R¹ | R² | R³ | R⁴ | R⁵ |
|---|---|---|---|---|---|
| I-36 | C₂H₅ | CF₃ | R3.6 | CH₃ | H |
| I-37 | CH₃ | CH₃ | R3.7 | CH₃ | H |
| I-38 | C₂H₅ | CH₃ | R3.7 | CH₃ | H |
| I-39 | CH₃ | CH₂F | R3.7 | CH₃ | H |
| I-40 | C₂H₅ | CH₂F | R3.7 | CH₃ | H |
| I-41 | CH₃ | CF₃ | R3.7 | CH₃ | H |
| I-42 | C₂H₅ | CF₃ | R3.7 | CH₃ | H |
| I-43 | CH₃ | CH₃ | R3.8 | CH₃ | H |
| I-44 | C₂H₅ | CH₃ | R3.8 | CH₃ | H |
| I-45 | CH₃ | CH₂F | R3.8 | CH₃ | H |
| I-46 | C₂H₅ | CH₂F | R3.8 | CH₃ | H |
| I-47 | CH₃ | CF₃ | R3.8 | CH₃ | H |
| I-48 | C₂H₅ | CF₃ | R3.8 | CH₃ | H |
| I-49 | CH₃ | CH₃ | R3.9 | CH₃ | H |
| I-50 | C₂H₅ | CH₃ | R3.9 | CH₃ | H |
| I-51 | CH₃ | CH₂F | R3.9 | CH₃ | H |
| I-52 | C₂H₅ | CH₂F | R3.9 | CH₃ | H |
| I-53 | CH₃ | CF₃ | R3.9 | CH₃ | H |
| I-54 | C₂H₅ | CF₃ | R3.9 | CH₃ | H |
| I-55 | CH₃ | CH₃ | R3.1 | C₂H₅ | H |
| I-56 | C₂H₅ | CH₃ | R3.1 | C₂H₅ | H |
| I-57 | CH₃ | CH₂F | R3.1 | C₂H₅ | H |
| I-58 | C₂H₅ | CH₂F | R3.1 | C₂H₅ | H |
| I-59 | CH₃ | CF₃ | R3.1 | C₂H₅ | H |
| I-60 | C₂H₅ | CF₃ | R3.1 | C₂H₅ | H |
| I-61 | CH₃ | CH₃ | R3.2 | C₂H₅ | H |
| I-62 | C₂H₅ | CH₃ | R3.2 | C₂H₅ | H |
| I-63 | CH₃ | CH₂F | R3.2 | C₂H₅ | H |
| I-64 | C₂H₅ | CH₂F | R3.2 | C₂H₅ | H |
| I-65 | CH₃ | CF₃ | R3.2 | C₂H₅ | H |
| I-66 | C₂H₅ | CF₃ | R3.2 | C₂H₅ | H |
| I-67 | CH₃ | CH₃ | R3.3 | C₂H₅ | H |
| I-68 | C₂H₅ | CH₃ | R3.3 | C₂H₅ | H |
| I-69 | CH₃ | CH₂F | R3.3 | C₂H₅ | H |
| I-70 | C₂H₅ | CH₂F | R3.3 | C₂H₅ | H |
| I-71 | CH₃ | CF₃ | R3.3 | C₂H₅ | H |
| I-72 | C₂H₅ | CF₃ | R3.3 | C₂H₅ | H |
| I-73 | CH₃ | CH₃ | R3.4 | C₂H₅ | H |
| I-74 | C₂H₅ | CH₃ | R3.4 | C₂H₅ | H |
| I-75 | CH₃ | CH₂F | R3.4 | C₂H₅ | H |
| I-76 | C₂H₅ | CH₂F | R3.4 | C₂H₅ | H |
| I-77 | CH₃ | CF₃ | R3.4 | C₂H₅ | H |
| I-78 | C₂H₅ | CF₃ | R3.4 | C₂H₅ | H |
| I-79 | CH₃ | CH₃ | R3.5 | C₂H₅ | H |
| I-80 | C₂H₅ | CH₃ | R3.5 | C₂H₅ | H |
| I-81 | CH₃ | CH₂F | R3.5 | C₂H₅ | H |
| I-82 | C₂H₅ | CH₂F | R3.5 | C₂H₅ | H |
| I-83 | CH₃ | CF₃ | R3.5 | C₂H₅ | H |
| I-84 | C₂H₅ | CF₃ | R3.5 | C₂H₅ | H |
| I-85 | CH₃ | CH₃ | R3.6 | C₂H₅ | H |
| I-86 | C₂H₅ | CH₃ | R3.6 | C₂H₅ | H |
| I-87 | CH₃ | CH₂F | R3.6 | C₂H₅ | H |
| I-88 | C₂H₅ | CH₂F | R3.6 | C₂H₅ | H |
| I-89 | CH₃ | CF₃ | R3.6 | C₂H₅ | H |
| I-90 | C₂H₅ | CF₃ | R3.6 | C₂H₅ | H |
| I-91 | CH₃ | CH₃ | R3.7 | C₂H₅ | H |
| I-92 | C₂H₅ | CH₃ | R3.7 | C₂H₅ | H |
| I-93 | CH₃ | CH₂F | R3.7 | C₂H₅ | H |
| I-94 | C₂H₅ | CH₂F | R3.7 | C₂H₅ | H |
| I-95 | CH₃ | CF₃ | R3.7 | C₂H₅ | H |
| I-96 | C₂H₅ | CF₃ | R3.7 | C₂H₅ | H |
| I-97 | CH₃ | CH₃ | R3.8 | C₂H₅ | H |
| I-98 | C₂H₅ | CH₃ | R3.8 | C₂H₅ | H |
| I-99 | CH₃ | CH₂F | R3.8 | C₂H₅ | H |
| I-100 | C₂H₅ | CH₂F | R3.8 | C₂H₅ | H |
| I-101 | CH₃ | CF₃ | R3.8 | C₂H₅ | H |
| I-102 | C₂H₅ | CF₃ | R3.8 | C₂H₅ | H |
| I-103 | CH₃ | CH₃ | R3.9 | C₂H₅ | H |
| I-104 | C₂H₅ | CH₃ | R3.9 | C₂H₅ | H |
| I-105 | CH₃ | CH₂F | R3.9 | C₂H₅ | H |
| I-106 | C₂H₅ | CH₂F | R3.9 | C₂H₅ | H |
| I-107 | CH₃ | CF₃ | R3.9 | C₂H₅ | H |
| I-108 | C₂H₅ | CF₃ | R3.9 | C₂H₅ | H |
| I-109 | CH₃ | CH₃ | R3.1 | CF₃ | H |
| I-110 | C₂H₅ | CH₃ | R3.1 | CF₃ | H |
| I-111 | CH₃ | CH₂F | R3.1 | CF₃ | H |
| I-112 | C₂H₅ | CH₂F | R3.1 | CF₃ | H |
| I-113 | CH₃ | CF₃ | R3.1 | CF₃ | H |
| I-114 | C₂H₅ | CF₃ | R3.1 | CF₃ | H |
| I-115 | CH₃ | CH₃ | R3.2 | CF₃ | H |
| I-116 | C₂H₅ | CH₃ | R3.2 | CF₃ | H |
| I-117 | CH₃ | CH₂F | R3.2 | CF₃ | H |
| I-118 | C₂H₅ | CH₂F | R3.2 | CF₃ | H |
| I-119 | CH₃ | CF₃ | R3.2 | CF₃ | H |
| I-120 | C₂H₅ | CF₃ | R3.2 | CF₃ | H |
| I-121 | CH₃ | CH₃ | R3.3 | CF₃ | H |
| I-122 | C₂H₅ | CH₃ | R3.3 | CF₃ | H |
| I-123 | CH₃ | CH₂F | R3.3 | CF₃ | H |
| I-124 | C₂H₅ | CH₂F | R3.3 | CF₃ | H |
| I-125 | CH₃ | CF₃ | R3.3 | CF₃ | H |
| I-126 | C₂H₅ | CF₃ | R3.3 | CF₃ | H |
| I-127 | CH₃ | CH₃ | R3.4 | CF₃ | H |
| I-128 | C₂H₅ | CH₃ | R3.4 | CF₃ | H |
| I-129 | CH₃ | CH₂F | R3.4 | CF₃ | H |
| I-130 | C₂H₅ | CH₂F | R3.4 | CF₃ | H |
| I-131 | CH₃ | CF₃ | R3.4 | CF₃ | H |
| I-132 | C₂H₅ | CF₃ | R3.4 | CF₃ | H |
| I-133 | CH₃ | CH₃ | R3.5 | CF₃ | H |
| I-134 | C₂H₅ | CH₃ | R3.5 | CF₃ | H |
| I-135 | CH₃ | CH₂F | R3.5 | CF₃ | H |
| I-136 | C₂H₅ | CH₂F | R3.5 | CF₃ | H |
| I-137 | CH₃ | CF₃ | R3.5 | CF₃ | H |
| I-138 | C₂H₅ | CF₃ | R3.5 | CF₃ | H |
| I-139 | CH₃ | CH₃ | R3.6 | CF₃ | H |
| I-140 | C₂H₅ | CH₃ | R3.6 | CF₃ | H |
| I-141 | CH₃ | CH₂F | R3.6 | CF₃ | H |
| I-142 | C₂H₅ | CH₂F | R3.6 | CF₃ | H |
| I-143 | CH₃ | CF₃ | R3.6 | CF₃ | H |
| I-144 | C₂H₅ | CF₃ | R3.6 | CF₃ | H |
| I-145 | CH₃ | CH₃ | R3.7 | CF₃ | H |
| I-146 | C₂H₅ | CH₃ | R3.7 | CF₃ | H |
| I-147 | CH₃ | CH₂F | R3.7 | CF₃ | H |
| I-148 | C₂H₅ | CH₂F | R3.7 | CF₃ | H |
| I-149 | CH₃ | CF₃ | R3.7 | CF₃ | H |
| I-150 | C₂H₅ | CF₃ | R3.7 | CF₃ | H |
| I-151 | CH₃ | CH₃ | R3.8 | CF₃ | H |
| I-152 | C₂H₅ | CH₃ | R3.8 | CF₃ | H |
| I-153 | CH₃ | CH₂F | R3.8 | CF₃ | H |
| I-154 | C₂H₅ | CH₂F | R3.8 | CF₃ | H |
| I-155 | CH₃ | CF₃ | R3.8 | CF₃ | H |
| I-156 | C₂H₅ | CF₃ | R3.8 | CF₃ | H |
| I-157 | CH₃ | CH₃ | R3.9 | CF₃ | H |
| I-158 | C₂H₅ | CH₃ | R3.9 | CF₃ | H |
| I-159 | CH₃ | CH₂F | R3.9 | CF₃ | H |
| I-160 | C₂H₅ | CH₂F | R3.9 | CF₃ | H |
| I-161 | CH₃ | CF₃ | R3.9 | CF₃ | H |
| I-162 | C₂H₅ | CF₃ | R3.9 | CF₃ | H |
| I-163 | CH₃ | CH₃ | R3.1 | CHF₂ | H |
| I-164 | C₂H₅ | CH₃ | R3.1 | CHF₂ | H |
| I-165 | CH₃ | CH₂F | R3.1 | CHF₂ | H |
| I-166 | C₂H₅ | CH₂F | R3.1 | CHF₂ | H |
| I-167 | CH₃ | CF₃ | R3.1 | CHF₂ | H |
| I-168 | C₂H₅ | CF₃ | R3.1 | CHF₂ | H |
| I-169 | CH₃ | CH₃ | R3.2 | CHF₂ | H |
| I-170 | C₂H₅ | CH₃ | R3.2 | CHF₂ | H |
| I-171 | CH₃ | CH₂F | R3.2 | CHF₂ | H |
| I-172 | C₂H₅ | CH₂F | R3.2 | CHF₂ | H |
| I-173 | CH₃ | CF₃ | R3.2 | CHF₂ | H |
| I-174 | C₂H₅ | CF₃ | R3.2 | CHF₂ | H |
| I-175 | CH₃ | CH₃ | R3.3 | CHF₂ | H |
| I-176 | C₂H₅ | CH₃ | R3.3 | CHF₂ | H |
| I-177 | CH₃ | CH₂F | R3.3 | CHF₂ | H |
| I-178 | C₂H₅ | CH₂F | R3.3 | CHF₂ | H |
| I-179 | CH₃ | CF₃ | R3.3 | CHF₂ | H |
| I-180 | C₂H₅ | CF₃ | R3.3 | CHF₂ | H |
| I-181 | CH₃ | CH₃ | R3.4 | CHF₂ | H |
| I-182 | C₂H₅ | CH₃ | R3.4 | CHF₂ | H |
| I-183 | CH₃ | CH₂F | R3.4 | CHF₂ | H |
| I-184 | C₂H₅ | CH₂F | R3.4 | CHF₂ | H |
| I-185 | CH₃ | CF₃ | R3.4 | CHF₂ | H |
| I-186 | C₂H₅ | CF₃ | R3.4 | CHF₂ | H |
| I-187 | CH₃ | CH₃ | R3.5 | CHF₂ | H |
| I-188 | C₂H₅ | CH₃ | R3.5 | CHF₂ | H |
| I-189 | CH₃ | CH₂F | R3.5 | CHF₂ | H |
| I-190 | C₂H₅ | CH₂F | R3.5 | CHF₂ | H |
| I-191 | CH₃ | CF₃ | R3.5 | CHF₂ | H |

TABLE I-continued

| No. | R¹ | R² | R³ | R⁴ | R⁵ |
|---|---|---|---|---|---|
| I-192 | $C_2H_5$ | $CF_3$ | R3.5 | $CHF_2$ | H |
| I-193 | $CH_3$ | $CH_3$ | R3.6 | $CHF_2$ | H |
| I-194 | $C_2H_5$ | $CH_3$ | R3.6 | $CHF_2$ | H |
| I-195 | $CH_3$ | $CH_2F$ | R3.6 | $CHF_2$ | H |
| I-196 | $C_2H_5$ | $CH_2F$ | R3.6 | $CHF_2$ | H |
| I-197 | $CH_3$ | $CF_3$ | R3.6 | $CHF_2$ | H |
| I-198 | $C_2H_5$ | $CF_3$ | R3.6 | $CHF_2$ | H |
| I-199 | $CH_3$ | $CH_3$ | R3.7 | $CHF_2$ | H |
| I-200 | $C_2H_5$ | $CH_3$ | R3.7 | $CHF_2$ | H |
| I-201 | $CH_3$ | $CH_2F$ | R3.7 | $CHF_2$ | H |
| I-202 | $C_2H_5$ | $CH_2F$ | R3.7 | $CHF_2$ | H |
| I-203 | $CH_3$ | $CF_3$ | R3.7 | $CHF_2$ | H |
| I-204 | $C_2H_5$ | $CF_3$ | R3.7 | $CHF_2$ | H |
| I-205 | $CH_3$ | $CH_3$ | R3.8 | $CHF_2$ | H |
| I-206 | $C_2H_5$ | $CH_3$ | R3.8 | $CHF_2$ | H |
| I-207 | $CH_3$ | $CH_2F$ | R3.8 | $CHF_2$ | H |
| I-208 | $C_2H_5$ | $CH_2F$ | R3.8 | $CHF_2$ | H |
| I-209 | $CH_3$ | $CF_3$ | R3.8 | $CHF_2$ | H |
| I-210 | $C_2H_5$ | $CF_3$ | R3.8 | $CHF_2$ | H |
| I-211 | $CH_3$ | $CH_3$ | R3.9 | $CHF_2$ | H |
| I-212 | $C_2H_5$ | $CH_3$ | R3.9 | $CHF_2$ | H |
| I-213 | $CH_3$ | $CH_2F$ | R3.9 | $CHF_2$ | H |
| I-214 | $C_2H_5$ | $CH_2F$ | R3.9 | $CHF_2$ | H |
| I-215 | $CH_3$ | $CF_3$ | R3.9 | $CHF_2$ | H |
| I-216 | $C_2H_5$ | $CF_3$ | R3.9 | $CHF_2$ | H |
| I-217 | $CH_3$ | $CH_3$ | R3.1 | $CH_3$ | $CH_3$ |
| I-218 | $C_2H_5$ | $CH_3$ | R3.1 | $CH_3$ | $CH_3$ |
| I-219 | $CH_3$ | $CH_2F$ | R3.1 | $CH_3$ | $CH_3$ |
| I-220 | $C_2H_5$ | $CH_2F$ | R3.1 | $CH_3$ | $CH_3$ |
| I-221 | $CH_3$ | $CF_3$ | R3.1 | $CH_3$ | $CH_3$ |
| I-222 | $C_2H_5$ | $CF_3$ | R3.1 | $CH_3$ | $CH_3$ |
| I-223 | $CH_3$ | $CH_3$ | R3.2 | $CH_3$ | $CH_3$ |
| I-224 | $C_2H_5$ | $CH_3$ | R3.2 | $CH_3$ | $CH_3$ |
| I-225 | $CH_3$ | $CH_2F$ | R3.2 | $CH_3$ | $CH_3$ |
| I-226 | $C_2H_5$ | $CH_2F$ | R3.2 | $CH_3$ | $CH_3$ |
| I-227 | $CH_3$ | $CF_3$ | R3.2 | $CH_3$ | $CH_3$ |
| I-228 | $C_2H_5$ | $CF_3$ | R3.2 | $CH_3$ | $CH_3$ |
| I-229 | $CH_3$ | $CH_3$ | R3.3 | $CH_3$ | $CH_3$ |
| I-230 | $C_2H_5$ | $CH_3$ | R3.3 | $CH_3$ | $CH_3$ |
| I-231 | $CH_3$ | $CH_2F$ | R3.3 | $CH_3$ | $CH_3$ |
| I-232 | $C_2H_5$ | $CH_2F$ | R3.3 | $CH_3$ | $CH_3$ |
| I-233 | $CH_3$ | $CF_3$ | R3.3 | $CH_3$ | $CH_3$ |
| I-234 | $C_2H_5$ | $CF_3$ | R3.3 | $CH_3$ | $CH_3$ |
| I-235 | $CH_3$ | $CH_3$ | R3.4 | $CH_3$ | $CH_3$ |
| I-236 | $C_2H_5$ | $CH_3$ | R3.4 | $CH_3$ | $CH_3$ |
| I-237 | $CH_3$ | $CH_2F$ | R3.4 | $CH_3$ | $CH_3$ |
| I-238 | $C_2H_5$ | $CH_2F$ | R3.4 | $CH_3$ | $CH_3$ |
| I-239 | $CH_3$ | $CF_3$ | R3.4 | $CH_3$ | $CH_3$ |
| I-240 | $C_2H_5$ | $CF_3$ | R3.4 | $CH_3$ | $CH_3$ |
| I-241 | $CH_3$ | $CH_3$ | R3.5 | $CH_3$ | $CH_3$ |
| I-242 | $C_2H_5$ | $CH_3$ | R3.5 | $CH_3$ | $CH_3$ |
| I-243 | $CH_3$ | $CH_2F$ | R3.5 | $CH_3$ | $CH_3$ |
| I-244 | $C_2H_5$ | $CH_2F$ | R3.5 | $CH_3$ | $CH_3$ |
| I-245 | $CH_3$ | $CF_3$ | R3.5 | $CH_3$ | $CH_3$ |
| I-246 | $C_2H_5$ | $CF_3$ | R3.5 | $CH_3$ | $CH_3$ |
| I-247 | $CH_3$ | $CH_3$ | R3.6 | $CH_3$ | $CH_3$ |
| I-248 | $C_2H_5$ | $CH_3$ | R3.6 | $CH_3$ | $CH_3$ |
| I-249 | $CH_3$ | $CH_2F$ | R3.6 | $CH_3$ | $CH_3$ |
| I-250 | $C_2H_5$ | $CH_2F$ | R3.6 | $CH_3$ | $CH_3$ |
| I-251 | $CH_3$ | $CF_3$ | R3.6 | $CH_3$ | $CH_3$ |
| I-252 | $C_2H_5$ | $CF_3$ | R3.6 | $CH_3$ | $CH_3$ |
| I-253 | $CH_3$ | $CH_3$ | R3.7 | $CH_3$ | $CH_3$ |
| I-254 | $C_2H_5$ | $CH_3$ | R3.7 | $CH_3$ | $CH_3$ |
| I-255 | $CH_3$ | $CH_2F$ | R3.7 | $CH_3$ | $CH_3$ |
| I-256 | $C_2H_5$ | $CH_2F$ | R3.7 | $CH_3$ | $CH_3$ |
| I-257 | $CH_3$ | $CF_3$ | R3.7 | $CH_3$ | $CH_3$ |
| I-258 | $C_2H_5$ | $CF_3$ | R3.7 | $CH_3$ | $CH_3$ |
| I-259 | $CH_3$ | $CH_3$ | R3.8 | $CH_3$ | $CH_3$ |
| I-260 | $C_2H_5$ | $CH_3$ | R3.8 | $CH_3$ | $CH_3$ |
| I-261 | $CH_3$ | $CH_2F$ | R3.8 | $CH_3$ | $CH_3$ |
| I-262 | $C_2H_5$ | $CH_2F$ | R3.8 | $CH_3$ | $CH_3$ |
| I-263 | $CH_3$ | $CF_3$ | R3.8 | $CH_3$ | $CH_3$ |
| I-264 | $C_2H_5$ | $CF_3$ | R3.8 | $CH_3$ | $CH_3$ |
| I-265 | $CH_3$ | $CH_3$ | R3.9 | $CH_3$ | $CH_3$ |
| I-266 | $C_2H_5$ | $CH_3$ | R3.9 | $CH_3$ | $CH_3$ |
| I-267 | $CH_3$ | $CH_2F$ | R3.9 | $CH_3$ | $CH_3$ |
| I-268 | $C_2H_5$ | $CH_2F$ | R3.9 | $CH_3$ | $CH_3$ |
| I-269 | $CH_3$ | $CF_3$ | R3.9 | $CH_3$ | $CH_3$ |
| I-270 | $C_2H_5$ | $CF_3$ | R3.9 | $CH_3$ | $CH_3$ |
| I-271 | $CH_3$ | $CH_3$ | R3.1 | $C_2H_5$ | $CH_3$ |
| I-272 | $C_2H_5$ | $CH_3$ | R3.1 | $C_2H_5$ | $CH_3$ |
| I-273 | $CH_3$ | $CH_2F$ | R3.1 | $C_2H_5$ | $CH_3$ |
| I-274 | $C_2H_5$ | $CH_2F$ | R3.1 | $C_2H_5$ | $CH_3$ |
| I-275 | $CH_3$ | $CF_3$ | R3.1 | $C_2H_5$ | $CH_3$ |
| I-276 | $C_2H_5$ | $CF_3$ | R3.1 | $C_2H_5$ | $CH_3$ |
| I-277 | $CH_3$ | $CH_3$ | R3.2 | $C_2H_5$ | $CH_3$ |
| I-278 | $C_2H_5$ | $CH_3$ | R3.2 | $C_2H_5$ | $CH_3$ |
| I-279 | $CH_3$ | $CH_2F$ | R3.2 | $C_2H_5$ | $CH_3$ |
| I-280 | $C_2H_5$ | $CH_2F$ | R3.2 | $C_2H_5$ | $CH_3$ |
| I-281 | $CH_3$ | $CF_3$ | R3.2 | $C_2H_5$ | $CH_3$ |
| I-282 | $C_2H_5$ | $CF_3$ | R3.2 | $C_2H_5$ | $CH_3$ |
| I-283 | $CH_3$ | $CH_3$ | R3.3 | $C_2H_5$ | $CH_3$ |
| I-284 | $C_2H_5$ | $CH_3$ | R3.3 | $C_2H_5$ | $CH_3$ |
| I-285 | $CH_3$ | $CH_2F$ | R3.3 | $C_2H_5$ | $CH_3$ |
| I-286 | $C_2H_5$ | $CH_2F$ | R3.3 | $C_2H_5$ | $CH_3$ |
| I-287 | $CH_3$ | $CF_3$ | R3.3 | $C_2H_5$ | $CH_3$ |
| I-288 | $C_2H_5$ | $CF_3$ | R3.3 | $C_2H_5$ | $CH_3$ |
| I-289 | $CH_3$ | $CH_3$ | R3.4 | $C_2H_5$ | $CH_3$ |
| I-290 | $C_2H_5$ | $CH_3$ | R3.4 | $C_2H_5$ | $CH_3$ |
| I-291 | $CH_3$ | $CH_2F$ | R3.4 | $C_2H_5$ | $CH_3$ |
| I-292 | $C_2H_5$ | $CH_2F$ | R3.4 | $C_2H_5$ | $CH_3$ |
| I-293 | $CH_3$ | $CF_3$ | R3.4 | $C_2H_5$ | $CH_3$ |
| I-294 | $C_2H_5$ | $CF_3$ | R3.4 | $C_2H_5$ | $CH_3$ |
| I-295 | $CH_3$ | $CH_3$ | R3.5 | $C_2H_5$ | $CH_3$ |
| I-296 | $C_2H_5$ | $CH_3$ | R3.5 | $C_2H_5$ | $CH_3$ |
| I-297 | $CH_3$ | $CH_2F$ | R3.5 | $C_2H_5$ | $CH_3$ |
| I-298 | $C_2H_5$ | $CH_2F$ | R3.5 | $C_2H_5$ | $CH_3$ |
| I-299 | $CH_3$ | $CF_3$ | R3.5 | $C_2H_5$ | $CH_3$ |
| I-300 | $C_2H_5$ | $CF_3$ | R3.5 | $C_2H_5$ | $CH_3$ |
| I-301 | $CH_3$ | $CH_3$ | R3.6 | $C_2H_5$ | $CH_3$ |
| I-302 | $C_2H_5$ | $CH_3$ | R3.6 | $C_2H_5$ | $CH_3$ |
| I-303 | $CH_3$ | $CH_2F$ | R3.6 | $C_2H_5$ | $CH_3$ |
| I-304 | $C_2H_5$ | $CH_2F$ | R3.6 | $C_2H_5$ | $CH_3$ |
| I-305 | $CH_3$ | $CF_3$ | R3.6 | $C_2H_5$ | $CH_3$ |
| I-306 | $C_2H_5$ | $CF_3$ | R3.6 | $C_2H_5$ | $CH_3$ |
| I-307 | $CH_3$ | $CH_3$ | R3.7 | $C_2H_5$ | $CH_3$ |
| I-308 | $C_2H_5$ | $CH_3$ | R3.7 | $C_2H_5$ | $CH_3$ |
| I-309 | $CH_3$ | $CH_2F$ | R3.7 | $C_2H_5$ | $CH_3$ |
| I-310 | $C_2H_5$ | $CH_2F$ | R3.7 | $C_2H_5$ | $CH_3$ |
| I-311 | $CH_3$ | $CF_3$ | R3.7 | $C_2H_5$ | $CH_3$ |
| I-312 | $C_2H_5$ | $CF_3$ | R3.7 | $C_2H_5$ | $CH_3$ |
| I-313 | $CH_3$ | $CH_3$ | R3.8 | $C_2H_5$ | $CH_3$ |
| I-314 | $C_2H_5$ | $CH_3$ | R3.8 | $C_2H_5$ | $CH_3$ |
| I-315 | $CH_3$ | $CH_2F$ | R3.8 | $C_2H_5$ | $CH_3$ |
| I-316 | $C_2H_5$ | $CH_2F$ | R3.8 | $C_2H_5$ | $CH_3$ |
| I-317 | $CH_3$ | $CF_3$ | R3.8 | $C_2H_5$ | $CH_3$ |
| I-318 | $C_2H_5$ | $CF_3$ | R3.8 | $C_2H_5$ | $CH_3$ |
| I-319 | $CH_3$ | $CH_3$ | R3.9 | $C_2H_5$ | $CH_3$ |
| I-320 | $C_2H_5$ | $CH_3$ | R3.9 | $C_2H_5$ | $CH_3$ |
| I-321 | $CH_3$ | $CH_2F$ | R3.9 | $C_2H_5$ | $CH_3$ |
| I-322 | $C_2H_5$ | $CH_2F$ | R3.9 | $C_2H_5$ | $CH_3$ |
| I-323 | $CH_3$ | $CF_3$ | R3.9 | $C_2H_5$ | $CH_3$ |
| I-324 | $C_2H_5$ | $CF_3$ | R3.9 | $C_2H_5$ | $CH_3$ |
| I-325 | $CH_3$ | $CH_3$ | R3.1 | $CF_3$ | $CH_3$ |
| I-326 | $C_2H_5$ | $CH_3$ | R3.1 | $CF_3$ | $CH_3$ |
| I-327 | $CH_3$ | $CH_2F$ | R3.1 | $CF_3$ | $CH_3$ |
| I-328 | $C_2H_5$ | $CH_2F$ | R3.1 | $CF_3$ | $CH_3$ |
| I-329 | $CH_3$ | $CF_3$ | R3.1 | $CF_3$ | $CH_3$ |
| I-330 | $C_2H_5$ | $CF_3$ | R3.1 | $CF_3$ | $CH_3$ |
| I-331 | $CH_3$ | $CH_3$ | R3.2 | $CF_3$ | $CH_3$ |
| I-332 | $C_2H_5$ | $CH_3$ | R3.2 | $CF_3$ | $CH_3$ |
| I-333 | $CH_3$ | $CH_2F$ | R3.2 | $CF_3$ | $CH_3$ |
| I-334 | $C_2H_5$ | $CH_2F$ | R3.2 | $CF_3$ | $CH_3$ |
| I-335 | $CH_3$ | $CF_3$ | R3.2 | $CF_3$ | $CH_3$ |
| I-336 | $C_2H_5$ | $CF_3$ | R3.2 | $CF_3$ | $CH_3$ |
| I-337 | $CH_3$ | $CH_3$ | R3.3 | $CF_3$ | $CH_3$ |
| I-338 | $C_2H_5$ | $CH_3$ | R3.3 | $CF_3$ | $CH_3$ |
| I-339 | $CH_3$ | $CH_2F$ | R3.3 | $CF_3$ | $CH_3$ |
| I-340 | $C_2H_5$ | $CH_2F$ | R3.3 | $CF_3$ | $CH_3$ |
| I-341 | $CH_3$ | $CF_3$ | R3.3 | $CF_3$ | $CH_3$ |
| I-342 | $C_2H_5$ | $CF_3$ | R3.3 | $CF_3$ | $CH_3$ |
| I-343 | $CH_3$ | $CH_3$ | R3.4 | $CF_3$ | $CH_3$ |
| I-344 | $C_2H_5$ | $CH_3$ | R3.4 | $CF_3$ | $CH_3$ |
| I-345 | $CH_3$ | $CH_2F$ | R3.4 | $CF_3$ | $CH_3$ |
| I-346 | $C_2H_5$ | $CH_2F$ | R3.4 | $CF_3$ | $CH_3$ |
| I-347 | $CH_3$ | $CF_3$ | R3.4 | $CF_3$ | $CH_3$ |

TABLE I-continued

| No. | R¹ | R² | R³ | R⁴ | R⁵ |
|---|---|---|---|---|---|
| I-348 | $C_2H_5$ | $CF_3$ | R3.4 | $CF_3$ | $CH_3$ |
| I-349 | $CH_3$ | $CH_3$ | R3.5 | $CF_3$ | $CH_3$ |
| I-350 | $C_2H_5$ | $CH_3$ | R3.5 | $CF_3$ | $CH_3$ |
| I-351 | $CH_3$ | $CH_2F$ | R3.5 | $CF_3$ | $CH_3$ |
| I-352 | $C_2H_5$ | $CH_2F$ | R3.5 | $CF_3$ | $CH_3$ |
| I-353 | $CH_3$ | $CF_3$ | R3.5 | $CF_3$ | $CH_3$ |
| I-354 | $C_2H_5$ | $CF_3$ | R3.5 | $CF_3$ | $CH_3$ |
| I-355 | $CH_3$ | $CH_3$ | R3.6 | $CF_3$ | $CH_3$ |
| I-356 | $C_2H_5$ | $CH_3$ | R3.6 | $CF_3$ | $CH_3$ |
| I-357 | $CH_3$ | $CH_2F$ | R3.6 | $CF_3$ | $CH_3$ |
| I-358 | $C_2H_5$ | $CH_2F$ | R3.6 | $CF_3$ | $CH_3$ |
| I-359 | $CH_3$ | $CF_3$ | R3.6 | $CF_3$ | $CH_3$ |
| I-360 | $C_2H_5$ | $CF_3$ | R3.6 | $CF_3$ | $CH_3$ |
| I-361 | $CH_3$ | $CH_3$ | R3.7 | $CF_3$ | $CH_3$ |
| I-362 | $C_2H_5$ | $CH_3$ | R3.7 | $CF_3$ | $CH_3$ |
| I-363 | $CH_3$ | $CH_2F$ | R3.7 | $CF_3$ | $CH_3$ |
| I-364 | $C_2H_5$ | $CH_2F$ | R3.7 | $CF_3$ | $CH_3$ |
| I-365 | $CH_3$ | $CF_3$ | R3.7 | $CF_3$ | $CH_3$ |
| I-366 | $C_2H_5$ | $CF_3$ | R3.7 | $CF_3$ | $CH_3$ |
| I-367 | $CH_3$ | $CH_3$ | R3.8 | $CF_3$ | $CH_3$ |
| I-368 | $C_2H_5$ | $CH_3$ | R3.8 | $CF_3$ | $CH_3$ |
| I-369 | $CH_3$ | $CH_2F$ | R3.8 | $CF_3$ | $CH_3$ |
| I-370 | $C_2H_5$ | $CH_2F$ | R3.8 | $CF_3$ | $CH_3$ |
| I-371 | $CH_3$ | $CF_3$ | R3.8 | $CF_3$ | $CH_3$ |
| I-372 | $C_2H_5$ | $CF_3$ | R3.8 | $CF_3$ | $CH_3$ |
| I-373 | $CH_3$ | $CH_3$ | R3.9 | $CF_3$ | $CH_3$ |
| I-374 | $C_2H_5$ | $CH_3$ | R3.9 | $CF_3$ | $CH_3$ |
| I-375 | $CH_3$ | $CH_2F$ | R3.9 | $CF_3$ | $CH_3$ |
| I-376 | $C_2H_5$ | $CH_2F$ | R3.9 | $CF_3$ | $CH_3$ |
| I-377 | $CH_3$ | $CF_3$ | R3.9 | $CF_3$ | $CH_3$ |
| I-378 | $C_2H_5$ | $CF_3$ | R3.9 | $CF_3$ | $CH_3$ |
| I-379 | $CH_3$ | $CH_3$ | R3.1 | $CHF_2$ | $CH_3$ |
| I-380 | $C_2H_5$ | $CH_3$ | R3.1 | $CHF_2$ | $CH_3$ |
| I-381 | $CH_3$ | $CH_2F$ | R3.1 | $CHF_2$ | $CH_3$ |
| I-382 | $C_2H_5$ | $CH_2F$ | R3.1 | $CHF_2$ | $CH_3$ |
| I-383 | $CH_3$ | $CF_3$ | R3.1 | $CHF_2$ | $CH_3$ |
| I-384 | $C_2H_5$ | $CF_3$ | R3.1 | $CHF_2$ | $CH_3$ |
| I-385 | $CH_3$ | $CH_3$ | R3.2 | $CHF_2$ | $CH_3$ |
| I-386 | $C_2H_5$ | $CH_3$ | R3.2 | $CHF_2$ | $CH_3$ |
| I-387 | $CH_3$ | $CH_2F$ | R3.2 | $CHF_2$ | $CH_3$ |
| I-388 | $C_2H_5$ | $CH_2F$ | R3.2 | $CHF_2$ | $CH_3$ |
| I-389 | $CH_3$ | $CF_3$ | R3.2 | $CHF_2$ | $CH_3$ |
| I-390 | $C_2H_5$ | $CF_3$ | R3.2 | $CHF_2$ | $CH_3$ |
| I-391 | $CH_3$ | $CH_3$ | R3.3 | $CHF_2$ | $CH_3$ |
| I-392 | $C_2H_5$ | $CH_3$ | R3.3 | $CHF_2$ | $CH_3$ |
| I-393 | $CH_3$ | $CH_2F$ | R3.3 | $CHF_2$ | $CH_3$ |
| I-394 | $C_2H_5$ | $CH_2F$ | R3.3 | $CHF_2$ | $CH_3$ |
| I-395 | $CH_3$ | $CF_3$ | R3.3 | $CHF_2$ | $CH_3$ |
| I-396 | $C_2H_5$ | $CF_3$ | R3.3 | $CHF_2$ | $CH_3$ |
| I-397 | $CH_3$ | $CH_3$ | R3.4 | $CHF_2$ | $CH_3$ |
| I-398 | $C_2H_5$ | $CH_3$ | R3.4 | $CHF_2$ | $CH_3$ |
| I-399 | $CH_3$ | $CH_2F$ | R3.4 | $CHF_2$ | $CH_3$ |
| I-400 | $C_2H_5$ | $CH_2F$ | R3.4 | $CHF_2$ | $CH_3$ |
| I-401 | $CH_3$ | $CF_3$ | R3.4 | $CHF_2$ | $CH_3$ |
| I-402 | $C_2H_5$ | $CF_3$ | R3.4 | $CHF_2$ | $CH_3$ |
| I-403 | $CH_3$ | $CH_3$ | R3.5 | $CHF_2$ | $CH_3$ |
| I-404 | $C_2H_5$ | $CH_3$ | R3.5 | $CHF_2$ | $CH_3$ |
| I-405 | $CH_3$ | $CH_2F$ | R3.5 | $CHF_2$ | $CH_3$ |
| I-406 | $C_2H_5$ | $CH_2F$ | R3.5 | $CHF_2$ | $CH_3$ |
| I-407 | $CH_3$ | $CF_3$ | R3.5 | $CHF_2$ | $CH_3$ |
| I-408 | $C_2H_5$ | $CF_3$ | R3.5 | $CHF_2$ | $CH_3$ |
| I-409 | $CH_3$ | $CH_3$ | R3.6 | $CHF_2$ | $CH_3$ |
| I-410 | $C_2H_5$ | $CH_3$ | R3.6 | $CHF_2$ | $CH_3$ |
| I-411 | $CH_3$ | $CH_2F$ | R3.6 | $CHF_2$ | $CH_3$ |
| I-412 | $C_2H_5$ | $CH_2F$ | R3.6 | $CHF_2$ | $CH_3$ |
| I-413 | $CH_3$ | $CF_3$ | R3.6 | $CHF_2$ | $CH_3$ |
| I-414 | $C_2H_5$ | $CF_3$ | R3.6 | $CHF_2$ | $CH_3$ |
| I-415 | $CH_3$ | $CH_3$ | R3.7 | $CHF_2$ | $CH_3$ |
| I-416 | $C_2H_5$ | $CH_3$ | R3.7 | $CHF_2$ | $CH_3$ |
| I-417 | $CH_3$ | $CH_2F$ | R3.7 | $CHF_2$ | $CH_3$ |
| I-418 | $C_2H_5$ | $CH_2F$ | R3.7 | $CHF_2$ | $CH_3$ |
| I-419 | $CH_3$ | $CF_3$ | R3.7 | $CHF_2$ | $CH_3$ |
| I-420 | $C_2H_5$ | $CF_3$ | R3.7 | $CHF_2$ | $CH_3$ |
| I-421 | $CH_3$ | $CH_3$ | R3.8 | $CHF_2$ | $CH_3$ |
| I-422 | $C_2H_5$ | $CH_3$ | R3.8 | $CHF_2$ | $CH_3$ |
| I-423 | $CH_3$ | $CH_2F$ | R3.8 | $CHF_2$ | $CH_3$ |
| I-424 | $C_2H_5$ | $CH_2F$ | R3.8 | $CHF_2$ | $CH_3$ |
| I-425 | $CH_3$ | $CF_3$ | R3.8 | $CHF_2$ | $CH_3$ |
| I-426 | $C_2H_5$ | $CF_3$ | R3.8 | $CHF_2$ | $CH_3$ |
| I-427 | $CH_3$ | $CH_3$ | R3.9 | $CHF_2$ | $CH_3$ |
| I-428 | $C_2H_5$ | $CH_3$ | R3.9 | $CHF_2$ | $CH_3$ |
| I-429 | $CH_3$ | $CH_2F$ | R3.9 | $CHF_2$ | $CH_3$ |
| I-430 | $C_2H_5$ | $CH_2F$ | R3.9 | $CHF_2$ | $CH_3$ |
| I-431 | $CH_3$ | $CF_3$ | R3.9 | $CHF_2$ | $CH_3$ |
| I-432 | $C_2H_5$ | $CF_3$ | R3.9 | $CHF_2$ | $CH_3$ |

TABLE II

| No. | R¹ | R² | R³ | R⁴ | R⁵ |
|---|---|---|---|---|---|
| I-433 | $CH_3$ | $CH_3$ | R3.10 | $CHF_2$ | H |
| I-434 | $C_2H_5$ | $CH_3$ | R3.10 | $CHF_2$ | H |
| I-435 | $CH_3$ | $CHF_2$ | R3.10 | $CHF_2$ | H |
| I-436 | $C_2H_5$ | $CHF_2$ | R3.10 | $CHF_2$ | H |
| I-437 | $CH_3$ | $CF_3$ | R3.10 | $CHF_2$ | H |
| I-438 | $C_2H_5$ | $CF_3$ | R3.10 | $CHF_2$ | H |
| I-439 | $CH_3$ | $CH_3$ | R3.11 | $CHF_2$ | H |
| I-440 | $C_2H_5$ | $CH_3$ | R3.11 | $CHF_2$ | H |
| I-441 | $CH_3$ | $CHF_2$ | R3.11 | $CHF_2$ | H |
| I-442 | $C_2H_5$ | $CHF_2$ | R3.11 | $CHF_2$ | H |
| I-443 | $CH_3$ | $CF_3$ | R3.11 | $CHF_2$ | H |
| I-444 | $C_2H_5$ | $CF_3$ | R3.11 | $CHF_2$ | H |
| I-445 | $CH_3$ | $CH_3$ | R3.12 | $CHF_2$ | H |
| I-446 | $C_2H_5$ | $CH_3$ | R3.12 | $CHF_2$ | H |
| I-447 | $CH_3$ | $CHF_2$ | R3.12 | $CHF_2$ | H |
| I-448 | $C_2H_5$ | $CHF_2$ | R3.12 | $CHF_2$ | H |
| I-449 | $CH_3$ | $CF_3$ | R3.12 | $CHF_2$ | H |
| I-450 | $C_2H_5$ | $CF_3$ | R3.12 | $CHF_2$ | H |
| I-451 | $CH_3$ | $CH_3$ | R3.13 | $CHF_2$ | H |
| I-452 | $C_2H_5$ | $CH_3$ | R3.13 | $CHF_2$ | H |
| I-453 | $CH_3$ | $CHF_2$ | R3.13 | $CHF_2$ | H |
| I-454 | $C_2H_5$ | $CHF_2$ | R3.13 | $CHF_2$ | H |
| I-455 | $CH_3$ | $CF_3$ | R3.13 | $CHF_2$ | H |
| I-456 | $C_2H_5$ | $CF_3$ | R3.13 | $CHF_2$ | H |
| I-457 | $CH_3$ | $CH_3$ | R3.14 | $CHF_2$ | H |
| I-458 | $C_2H_5$ | $CH_3$ | R3.14 | $CHF_2$ | H |
| I-459 | $CH_3$ | $CHF_2$ | R3.14 | $CHF_2$ | H |
| I-460 | $C_2H_5$ | $CHF_2$ | R3.14 | $CHF_2$ | H |
| I-461 | $CH_3$ | $CF_3$ | R3.14 | $CHF_2$ | H |
| I-462 | $C_2H_5$ | $CF_3$ | R3.14 | $CHF_2$ | H |
| I-463 | $CH_3$ | $CH_3$ | R3.15 | $CHF_2$ | H |
| I-464 | $C_2H_5$ | $CH_3$ | R3.15 | $CHF_2$ | H |
| I-465 | $CH_3$ | $CHF_2$ | R3.15 | $CHF_2$ | H |
| I-466 | $C_2H_5$ | $CHF_2$ | R3.15 | $CHF_2$ | H |
| I-467 | $CH_3$ | $CF_3$ | R3.15 | $CHF_2$ | H |
| I-468 | $C_2H_5$ | $CF_3$ | R3.15 | $CHF_2$ | H |
| I-469 | $CH_3$ | $CH_3$ | R3.16 | $CHF_2$ | H |
| I-470 | $C_2H_5$ | $CH_3$ | R3.16 | $CHF_2$ | H |
| I-471 | $CH_3$ | $CHF_2$ | R3.16 | $CHF_2$ | H |
| I-472 | $C_2H_5$ | $CHF_2$ | R3.16 | $CHF_2$ | H |
| I-473 | $CH_3$ | $CF_3$ | R3.16 | $CHF_2$ | H |
| I-474 | $C_2H_5$ | $CF_3$ | R3.16 | $CHF_2$ | H |
| I-475 | $CH_3$ | $CH_3$ | R3.17 | $CHF_2$ | H |
| I-476 | $C_2H_5$ | $CH_3$ | R3.17 | $CHF_2$ | H |
| I-477 | $CH_3$ | $CHF_2$ | R3.17 | $CHF_2$ | H |
| I-478 | $C_2H_5$ | $CHF_2$ | R3.17 | $CHF_2$ | H |
| I-479 | $CH_3$ | $CF_3$ | R3.17 | $CHF_2$ | H |
| I-480 | $C_2H_5$ | $CF_3$ | R3.17 | $CHF_2$ | H |
| I-481 | $CH_3$ | $CH_3$ | R3.18 | $CHF_2$ | H |
| I-482 | $C_2H_5$ | $CH_3$ | R3.18 | $CHF_2$ | H |
| I-483 | $CH_3$ | $CHF_2$ | R3.18 | $CHF_2$ | H |
| I-484 | $C_2H_5$ | $CHF_2$ | R3.18 | $CHF_2$ | H |
| I-485 | $CH_3$ | $CF_3$ | R3.18 | $CHF_2$ | H |
| I-486 | $C_2H_5$ | $CF_3$ | R3.18 | $CHF_2$ | H |
| I-487 | $CH_3$ | $CH_3$ | R3.19 | $CHF_2$ | H |
| I-488 | $C_2H_5$ | $CH_3$ | R3.19 | $CHF_2$ | H |
| I-489 | $CH_3$ | $CHF_2$ | R3.19 | $CHF_2$ | H |
| I-490 | $C_2H_5$ | $CHF_2$ | R3.19 | $CHF_2$ | H |
| I-491 | $CH_3$ | $CF_3$ | R3.19 | $CHF_2$ | H |
| I-492 | $C_2H_5$ | $CF_3$ | R3.19 | $CHF_2$ | H |
| I-493 | $CH_3$ | $CH_3$ | R3.20 | $CHF_2$ | H |
| I-494 | $C_2H_5$ | $CH_3$ | R3.20 | $CHF_2$ | H |
| I-495 | $CH_3$ | $CHF_2$ | R3.20 | $CHF_2$ | H |

TABLE II-continued

| No. | R¹ | R² | R³ | R⁴ | R⁵ |
|---|---|---|---|---|---|
| I-496 | $C_2H_5$ | $CHF_2$ | R3.20 | $CHF_2$ | H |
| I-497 | $CH_3$ | $CF_3$ | R3.20 | $CHF_2$ | H |
| I-498 | $C_2H_5$ | $CF_3$ | R3.20 | $CHF_2$ | H |
| I-499 | $CH_3$ | $CH_3$ | R3.21 | $CHF_2$ | H |
| I-500 | $C_2H_5$ | $CH_3$ | R3.21 | $CHF_2$ | H |
| I-501 | $CH_3$ | $CHF_2$ | R3.21 | $CHF_2$ | H |
| I-502 | $C_2H_5$ | $CHF_2$ | R3.21 | $CHF_2$ | H |
| I-503 | $CH_3$ | $CF_3$ | R3.21 | $CHF_2$ | H |
| I-504 | $C_2H_5$ | $CF_3$ | R3.21 | $CHF_2$ | H |
| I-505 | $CH_3$ | $CH_3$ | R3.22 | $CHF_2$ | H |
| I-506 | $C_2H_5$ | $CH_3$ | R3.22 | $CHF_2$ | H |
| I-507 | $CH_3$ | $CHF_2$ | R3.22 | $CHF_2$ | H |
| I-508 | $C_2H_5$ | $CHF_2$ | R3.22 | $CHF_2$ | H |
| I-509 | $CH_3$ | $CF_3$ | R3.22 | $CHF_2$ | H |
| I-510 | $C_2H_5$ | $CF_3$ | R3.22 | $CHF_2$ | H |
| I-511 | $CH_3$ | $CH_3$ | R3.23 | $CHF_2$ | H |
| I-512 | $C_2H_5$ | $CH_3$ | R3.23 | $CHF_2$ | H |
| I-513 | $CH_3$ | $CHF_2$ | R3.23 | $CHF_2$ | H |
| I-514 | $C_2H_5$ | $CHF_2$ | R3.23 | $CHF_2$ | H |
| I-515 | $CH_3$ | $CF_3$ | R3.23 | $CHF_2$ | H |
| I-516 | $C_2H_5$ | $CF_3$ | R3.23 | $CHF_2$ | H |
| I-517 | $CH_3$ | $CH_3$ | R3.24 | $CHF_2$ | H |
| I-518 | $C_2H_5$ | $CH_3$ | R3.24 | $CHF_2$ | H |
| I-519 | $CH_3$ | $CHF_2$ | R3.24 | $CHF_2$ | H |
| I-520 | $C_2H_5$ | $CHF_2$ | R3.24 | $CHF_2$ | H |
| I-521 | $CH_3$ | $CF_3$ | R3.24 | $CHF_2$ | H |
| I-522 | $C_2H_5$ | $CF_3$ | R3.24 | $CHF_2$ | H |
| I-523 | $CH_3$ | $CH_3$ | R3.25 | $CHF_2$ | H |
| I-524 | $C_2H_5$ | $CH_3$ | R3.25 | $CHF_2$ | H |
| I-525 | $CH_3$ | $CHF_2$ | R3.25 | $CHF_2$ | H |
| I-526 | $C_2H_5$ | $CHF_2$ | R3.25 | $CHF_2$ | H |
| I-527 | $CH_3$ | $CF_3$ | R3.25 | $CHF_2$ | H |
| I-528 | $C_2H_5$ | $CF_3$ | R3.25 | $CHF_2$ | H |
| I-529 | $CH_3$ | $CH_3$ | R3.26 | $CHF_2$ | H |
| I-530 | $C_2H_5$ | $CH_3$ | R3.26 | $CHF_2$ | H |
| I-531 | $CH_3$ | $CHF_2$ | R3.26 | $CHF_2$ | H |
| I-532 | $C_2H_5$ | $CHF_2$ | R3.26 | $CHF_2$ | H |
| I-533 | $CH_3$ | $CF_3$ | R3.26 | $CHF_2$ | H |
| I-534 | $C_2H_5$ | $CF_3$ | R3.26 | $CHF_2$ | H |
| I-535 | $CH_3$ | $CH_3$ | R3.27 | $CHF_2$ | H |
| I-536 | $C_2H_5$ | $CH_3$ | R3.27 | $CHF_2$ | H |
| I-537 | $CH_3$ | $CHF_2$ | R3.27 | $CHF_2$ | H |
| I-538 | $C_2H_5$ | $CHF_2$ | R3.27 | $CHF_2$ | H |
| I-539 | $CH_3$ | $CF_3$ | R3.27 | $CHF_2$ | H |
| I-540 | $C_2H_5$ | $CF_3$ | R3.27 | $CHF_2$ | H |
| I-541 | $CH_3$ | $CH_3$ | R3.28 | $CHF_2$ | H |
| I-542 | $C_2H_5$ | $CH_3$ | R3.28 | $CHF_2$ | H |
| I-543 | $CH_3$ | $CHF_2$ | R3.28 | $CHF_2$ | H |
| I-544 | $C_2H_5$ | $CHF_2$ | R3.28 | $CHF_2$ | H |
| I-545 | $CH_3$ | $CF_3$ | R3.28 | $CHF_2$ | H |
| I-546 | $C_2H_5$ | $CF_3$ | R3.28 | $CHF_2$ | H |
| I-547 | $CH_3$ | $CH_3$ | R3.29 | $CHF_2$ | H |
| I-548 | $C_2H_5$ | $CH_3$ | R3.29 | $CHF_2$ | H |
| I-549 | $CH_3$ | $CHF_2$ | R3.29 | $CHF_2$ | H |
| I-550 | $C_2H_5$ | $CHF_2$ | R3.29 | $CHF_2$ | H |
| I-551 | $CH_3$ | $CF_3$ | R3.29 | $CHF_2$ | H |
| I-552 | $C_2H_5$ | $CF_3$ | R3.29 | $CHF_2$ | H |
| I-553 | $CH_3$ | $CH_3$ | R3.30 | $CHF_2$ | H |
| I-554 | $C_2H_5$ | $CH_3$ | R3.30 | $CHF_2$ | H |
| I-555 | $CH_3$ | $CHF_2$ | R3.30 | $CHF_2$ | H |
| I-556 | $C_2H_5$ | $CHF_2$ | R3.30 | $CHF_2$ | H |
| I-557 | $CH_3$ | $CF_3$ | R3.30 | $CHF_2$ | H |
| I-558 | $C_2H_5$ | $CF_3$ | R3.30 | $CHF_2$ | H |
| I-559 | $CH_3$ | $CH_3$ | R3.31 | $CHF_2$ | H |
| I-560 | $C_2H_5$ | $CH_3$ | R3.31 | $CHF_2$ | H |
| I-561 | $CH_3$ | $CHF_2$ | R3.31 | $CHF_2$ | H |
| I-562 | $C_2H_5$ | $CHF_2$ | R3.31 | $CHF_2$ | H |
| I-563 | $CH_3$ | $CF_3$ | R3.31 | $CHF_2$ | H |
| I-564 | $C_2H_5$ | $CF_3$ | R3.31 | $CHF_2$ | H |
| I-565 | $CH_3$ | $CH_3$ | R3.32 | $CHF_2$ | H |
| I-566 | $C_2H_5$ | $CH_3$ | R3.32 | $CHF_2$ | H |
| I-567 | $CH_3$ | $CHF_2$ | R3.32 | $CHF_2$ | H |
| I-568 | $C_2H_5$ | $CHF_2$ | R3.32 | $CHF_2$ | H |
| I-569 | $CH_3$ | $CF_3$ | R3.32 | $CHF_2$ | H |
| I-570 | $C_2H_5$ | $CF_3$ | R3.32 | $CHF_2$ | H |
| I-571 | $CH_3$ | $CH_3$ | R3.33 | $CHF_2$ | H |
| I-572 | $C_2H_5$ | $CH_3$ | R3.33 | $CHF_2$ | H |
| I-573 | $CH_3$ | $CHF_2$ | R3.33 | $CHF_2$ | H |
| I-574 | $C_2H_5$ | $CHF_2$ | R3.33 | $CHF_2$ | H |
| I-575 | $CH_3$ | $CF_3$ | R3.33 | $CHF_2$ | H |
| I-576 | $C_2H_5$ | $CF_3$ | R3.33 | $CHF_2$ | H |
| I-577 | $CH_3$ | $CH_3$ | R3.34 | $CHF_2$ | H |
| I-578 | $C_2H_5$ | $CH_3$ | R3.34 | $CHF_2$ | H |
| I-579 | $CH_3$ | $CHF_2$ | R3.34 | $CHF_2$ | H |
| I-580 | $C_2H_5$ | $CHF_2$ | R3.34 | $CHF_2$ | H |
| I-581 | $CH_3$ | $CF_3$ | R3.34 | $CHF_2$ | H |
| I-582 | $C_2H_5$ | $CF_3$ | R3.34 | $CHF_2$ | H |
| I-583 | $CH_3$ | $CH_3$ | R3.35 | $CHF_2$ | H |
| I-584 | $C_2H_5$ | $CH_3$ | R3.35 | $CHF_2$ | H |
| I-585 | $CH_3$ | $CHF_2$ | R3.35 | $CHF_2$ | H |
| I-586 | $C_2H_5$ | $CHF_2$ | R3.35 | $CHF_2$ | H |
| I-587 | $CH_3$ | $CF_3$ | R3.35 | $CHF_2$ | H |
| I-588 | $C_2H_5$ | $CF_3$ | R3.35 | $CHF_2$ | H |
| I-589 | $CH_3$ | $CH_3$ | R3.36 | $CHF_2$ | H |
| I-590 | $C_2H_5$ | $CH_3$ | R3.36 | $CHF_2$ | H |
| I-591 | $CH_3$ | $CHF_2$ | R3.36 | $CHF_2$ | H |
| I-592 | $C_2H_5$ | $CHF_2$ | R3.36 | $CHF_2$ | H |
| I-593 | $CH_3$ | $CF_3$ | R3.36 | $CHF_2$ | H |
| I-594 | $C_2H_5$ | $CF_3$ | R3.36 | $CHF_2$ | H |
| I-595 | $CH_3$ | $CH_3$ | R3.37 | $CHF_2$ | H |
| I-596 | $C_2H_5$ | $CH_3$ | R3.37 | $CHF_2$ | H |
| I-597 | $CH_3$ | $CHF_2$ | R3.37 | $CHF_2$ | H |
| I-598 | $C_2H_5$ | $CHF_2$ | R3.37 | $CHF_2$ | H |
| I-599 | $CH_3$ | $CF_3$ | R3.37 | $CHF_2$ | H |
| I-600 | $C_2H_5$ | $CF_3$ | R3.37 | $CHF_2$ | H |
| I-601 | $CH_3$ | $CH_3$ | R3.38 | $CHF_2$ | H |
| I-602 | $C_2H_5$ | $CH_3$ | R3.38 | $CHF_2$ | H |
| I-603 | $CH_3$ | $CHF_2$ | R3.38 | $CHF_2$ | H |
| I-604 | $C_2H_5$ | $CHF_2$ | R3.38 | $CHF_2$ | H |
| I-605 | $CH_3$ | $CF_3$ | R3.38 | $CHF_2$ | H |
| I-606 | $C_2H_5$ | $CF_3$ | R3.38 | $CHF_2$ | H |
| I-607 | $CH_3$ | $CH_3$ | R3.39 | $CHF_2$ | H |
| I-608 | $C_2H_5$ | $CH_3$ | R3.39 | $CHF_2$ | H |
| I-609 | $CH_3$ | $CHF_2$ | R3.39 | $CHF_2$ | H |
| I-610 | $C_2H_5$ | $CHF_2$ | R3.39 | $CHF_2$ | H |
| I-611 | $CH_3$ | $CF_3$ | R3.39 | $CHF_2$ | H |
| I-612 | $C_2H_5$ | $CF_3$ | R3.39 | $CHF_2$ | H |
| I-613 | $CH_3$ | $CH_3$ | R3.40 | $CHF_2$ | H |
| I-614 | $C_2H_5$ | $CH_3$ | R3.40 | $CHF_2$ | H |
| I-615 | $CH_3$ | $CHF_2$ | R3.40 | $CHF_2$ | H |
| I-616 | $C_2H_5$ | $CHF_2$ | R3.40 | $CHF_2$ | H |
| I-617 | $CH_3$ | $CF_3$ | R3.40 | $CHF_2$ | H |
| I-618 | $C_2H_5$ | $CF_3$ | R3.40 | $CHF_2$ | H |
| I-619 | $CH_3$ | $CH_3$ | R3.41 | $CHF_2$ | H |
| I-620 | $C_2H_5$ | $CH_3$ | R3.41 | $CHF_2$ | H |
| I-621 | $CH_3$ | $CHF_2$ | R3.41 | $CHF_2$ | H |
| I-622 | $C_2H_5$ | $CHF_2$ | R3.41 | $CHF_2$ | H |
| I-623 | $CH_3$ | $CF_3$ | R3.41 | $CHF_2$ | H |
| I-624 | $C_2H_5$ | $CF_3$ | R3.41 | $CHF_2$ | H |
| I-625 | $CH_3$ | $CH_3$ | R3.42 | $CHF_2$ | H |
| I-626 | $C_2H_5$ | $CH_3$ | R3.42 | $CHF_2$ | H |
| I-627 | $CH_3$ | $CHF_2$ | R3.42 | $CHF_2$ | H |
| I-628 | $C_2H_5$ | $CHF_2$ | R3.42 | $CHF_2$ | H |
| I-629 | $CH_3$ | $CF_3$ | R3.42 | $CHF_2$ | H |
| I-630 | $C_2H_5$ | $CF_3$ | R3.42 | $CHF_2$ | H |
| I-631 | $CH_3$ | $CH_3$ | R3.43 | $CHF_2$ | H |
| I-632 | $C_2H_5$ | $CH_3$ | R3.43 | $CHF_2$ | H |
| I-633 | $CH_3$ | $CHF_2$ | R3.43 | $CHF_2$ | H |
| I-634 | $C_2H_5$ | $CHF_2$ | R3.43 | $CHF_2$ | H |
| I-635 | $CH_3$ | $CF_3$ | R3.43 | $CHF_2$ | H |
| I-636 | $C_2H_5$ | $CF_3$ | R3.43 | $CHF_2$ | H |
| I-637 | $CH_3$ | $CH_3$ | R3.44 | $CHF_2$ | H |
| I-638 | $C_2H_5$ | $CH_3$ | R3.44 | $CHF_2$ | H |
| I-639 | $CH_3$ | $CHF_2$ | R3.44 | $CHF_2$ | H |
| I-640 | $C_2H_5$ | $CHF_2$ | R3.44 | $CHF_2$ | H |
| I-641 | $CH_3$ | $CF_3$ | R3.44 | $CHF_2$ | H |
| I-642 | $C_2H_5$ | $CF_3$ | R3.44 | $CHF_2$ | H |
| I-643 | $CH_3$ | $CH_3$ | R3.45 | $CHF_2$ | H |
| I-644 | $C_2H_5$ | $CH_3$ | R3.45 | $CHF_2$ | H |
| I-645 | $CH_3$ | $CHF_2$ | R3.45 | $CHF_2$ | H |
| I-646 | $C_2H_5$ | $CHF_2$ | R3.45 | $CHF_2$ | H |
| I-647 | $CH_3$ | $CF_3$ | R3.45 | $CHF_2$ | H |
| I-648 | $C_2H_5$ | $CF_3$ | R3.45 | $CHF_2$ | H |
| I-649 | $CH_3$ | $CH_3$ | R3.46 | $CHF_2$ | H |
| I-650 | $C_2H_5$ | $CH_3$ | R3.46 | $CHF_2$ | H |
| I-651 | $CH_3$ | $CHF_2$ | R3.46 | $CHF_2$ | H |

TABLE II-continued

| No. | R¹ | R² | R³ | R⁴ | R⁵ |
|---|---|---|---|---|---|
| I-652 | C₂H₅ | CHF₂ | R3.46 | CHF₂ | H |
| I-653 | CH₃ | CF₃ | R3.46 | CHF₂ | H |
| I-654 | C₂H₅ | CF₃ | R3.46 | CHF₂ | H |
| I-655 | CH₃ | CH₃ | R3.47 | CHF₂ | H |
| I-656 | C₂H₅ | CH₃ | R3.47 | CHF₂ | H |
| I-657 | CH₃ | CHF₂ | R3.47 | CHF₂ | H |
| I-658 | C₂H₅ | CHF₂ | R3.47 | CHF₂ | H |
| I-659 | CH₃ | CF₃ | R3.47 | CHF₂ | H |
| I-660 | C₂H₅ | CF₃ | R3.47 | CHF₂ | H |
| I-661 | CH₃ | CH₃ | R3.48 | CHF₂ | H |
| I-662 | C₂H₅ | CH₃ | R3.48 | CHF₂ | H |
| I-663 | CH₃ | CHF₂ | R3.48 | CHF₂ | H |
| I-664 | C₂H₅ | CHF₂ | R3.48 | CHF₂ | H |
| I-665 | CH₃ | CF₃ | R3.48 | CHF₂ | H |
| I-666 | C₂H₅ | CF₃ | R3.48 | CHF₂ | H |
| I-667 | CH₃ | CH₃ | R3.10 | CH₃ | H |
| I-668 | C₂H₅ | CH₃ | R3.10 | CH₃ | H |
| I-669 | CH₃ | CHF₂ | R3.10 | CH₃ | H |
| I-670 | C₂H₅ | CHF₂ | R3.10 | CH₃ | H |
| I-671 | CH₃ | CF₃ | R3.10 | CH₃ | H |
| I-672 | C₂H₅ | CF₃ | R3.10 | CH₃ | H |
| I-673 | CH₃ | CH₃ | R3.11 | CH₃ | H |
| I-674 | C₂H₅ | CH₃ | R3.11 | CH₃ | H |
| I-675 | CH₃ | CHF₂ | R3.11 | CH₃ | H |
| I-676 | C₂H₅ | CHF₂ | R3.11 | CH₃ | H |
| I-677 | CH₃ | CF₃ | R3.11 | CH₃ | H |
| I-678 | C₂H₅ | CF₃ | R3.11 | CH₃ | H |
| I-679 | CH₃ | CH₃ | R3.12 | CH₃ | H |
| I-680 | C₂H₅ | CH₃ | R3.12 | CH₃ | H |
| I-681 | CH₃ | CHF₂ | R3.12 | CH₃ | H |
| I-682 | C₂H₅ | CHF₂ | R3.12 | CH₃ | H |
| I-683 | CH₃ | CF₃ | R3.12 | CH₃ | H |
| I-684 | C₂H₅ | CF₃ | R3.12 | CH₃ | H |
| I-685 | CH₃ | CH₃ | R3.13 | CH₃ | H |
| I-686 | C₂H₅ | CH₃ | R3.13 | CH₃ | H |
| I-687 | CH₃ | CHF₂ | R3.13 | CH₃ | H |
| I-688 | C₂H₅ | CHF₂ | R3.13 | CH₃ | H |
| I-689 | CH₃ | CF₃ | R3.13 | CH₃ | H |
| I-690 | C₂H₅ | CF₃ | R3.13 | CH₃ | H |
| I-691 | CH₃ | CH₃ | R3.15 | CH₃ | H |
| I-692 | C₂H₅ | CH₃ | R3.15 | CH₃ | H |
| I-693 | CH₃ | CHF₂ | R3.15 | CH₃ | H |
| I-694 | C₂H₅ | CHF₂ | R3.15 | CH₃ | H |
| I-695 | CH₃ | CF₃ | R3.15 | CH₃ | H |
| I-696 | C₂H₅ | CF₃ | R3.15 | CH₃ | H |
| I-697 | CH₃ | CH₃ | R3.16 | CH₃ | H |
| I-698 | C₂H₅ | CH₃ | R3.16 | CH₃ | H |
| I-699 | CH₃ | CHF₂ | R3.16 | CH₃ | H |
| I-700 | C₂H₅ | CHF₂ | R3.16 | CH₃ | H |
| I-701 | CH₃ | CF₃ | R3.16 | CH₃ | H |
| I-702 | C₂H₅ | CF₃ | R3.16 | CH₃ | H |
| I-703 | CH₃ | CH₃ | R3.17 | CH₃ | H |
| I-704 | C₂H₅ | CH₃ | R3.17 | CH₃ | H |
| I-705 | CH₃ | CHF₂ | R3.17 | CH₃ | H |
| I-706 | C₂H₅ | CHF₂ | R3.17 | CH₃ | H |
| I-707 | CH₃ | CF₃ | R3.17 | CH₃ | H |
| I-708 | C₂H₅ | CF₃ | R3.17 | CH₃ | H |
| I-709 | CH₃ | CH₃ | R3.18 | CH₃ | H |
| I-710 | C₂H₅ | CH₃ | R3.18 | CH₃ | H |
| I-711 | CH₃ | CHF₂ | R3.18 | CH₃ | H |
| I-712 | C₂H₅ | CHF₂ | R3.18 | CH₃ | H |
| I-713 | CH₃ | CF₃ | R3.18 | CH₃ | H |
| I-714 | C₂H₅ | CF₃ | R3.18 | CH₃ | H |
| I-715 | CH₃ | CH₃ | R3.19 | CH₃ | H |
| I-716 | C₂H₅ | CH₃ | R3.19 | CH₃ | H |
| I-717 | CH₃ | CHF₂ | R3.19 | CH₃ | H |
| I-718 | C₂H₅ | CHF₂ | R3.19 | CH₃ | H |
| I-719 | CH₃ | CF₃ | R3.19 | CH₃ | H |
| I-720 | C₂H₅ | CF₃ | R3.19 | CH₃ | H |
| I-721 | CH₃ | CH₃ | R3.20 | CH₃ | H |
| I-722 | C₂H₅ | CH₃ | R3.20 | CH₃ | H |
| I-723 | CH₃ | CHF₂ | R3.20 | CH₃ | H |
| I-724 | C₂H₅ | CHF₂ | R3.20 | CH₃ | H |
| I-725 | CH₃ | CF₃ | R3.20 | CH₃ | H |
| I-726 | C₂H₅ | CF₃ | R3.20 | CH₃ | H |
| I-727 | CH₃ | CH₃ | R3.21 | CH₃ | H |
| I-728 | C₂H₅ | CH₃ | R3.21 | CH₃ | H |
| I-729 | CH₃ | CHF₂ | R3.21 | CH₃ | H |
| I-730 | C₂H₅ | CHF₂ | R3.21 | CH₃ | H |
| I-731 | CH₃ | CF₃ | R3.21 | CH₃ | H |
| I-732 | C₂H₅ | CF₃ | R3.21 | CH₃ | H |
| I-733 | CH₃ | CH₃ | R3.22 | CH₃ | H |
| I-734 | C₂H₅ | CH₃ | R3.22 | CH₃ | H |
| I-735 | CH₃ | CHF₂ | R3.22 | CH₃ | H |
| I-736 | C₂H₅ | CHF₂ | R3.22 | CH₃ | H |
| I-737 | CH₃ | CF₃ | R3.22 | CH₃ | H |
| I-738 | C₂H₅ | CF₃ | R3.22 | CH₃ | H |
| I-739 | CH₃ | CH₃ | R3.23 | CH₃ | H |
| I-740 | C₂H₅ | CH₃ | R3.23 | CH₃ | H |
| I-741 | CH₃ | CHF₂ | R3.23 | CH₃ | H |
| I-742 | C₂H₅ | CHF₂ | R3.23 | CH₃ | H |
| I-743 | CH₃ | CF₃ | R3.23 | CH₃ | H |
| I-744 | C₂H₅ | CF₃ | R3.23 | CH₃ | H |
| I-745 | CH₃ | CH₃ | R3.24 | CH₃ | H |
| I-746 | C₂H₅ | CH₃ | R3.24 | CH₃ | H |
| I-747 | CH₃ | CHF₂ | R3.24 | CH₃ | H |
| I-748 | C₂H₅ | CHF₂ | R3.24 | CH₃ | H |
| I-749 | CH₃ | CF₃ | R3.24 | CH₃ | H |
| I-750 | C₂H₅ | CF₃ | R3.24 | CH₃ | H |
| I-751 | CH₃ | CH₃ | R3.25 | CH₃ | H |
| I-752 | C₂H₅ | CH₃ | R3.25 | CH₃ | H |
| I-753 | CH₃ | CHF₂ | R3.25 | CH₃ | H |
| I-754 | C₂H₅ | CHF₂ | R3.25 | CH₃ | H |
| I-755 | CH₃ | CF₃ | R3.25 | CH₃ | H |
| I-756 | C₂H₅ | CF₃ | R3.25 | CH₃ | H |
| I-757 | CH₃ | CH₃ | R3.26 | CH₃ | H |
| I-758 | C₂H₅ | CH₃ | R3.26 | CH₃ | H |
| I-759 | CH₃ | CHF₂ | R3.26 | CH₃ | H |
| I-760 | C₂H₅ | CHF₂ | R3.26 | CH₃ | H |
| I-761 | CH₃ | CF₃ | R3.26 | CH₃ | H |
| I-762 | C₂H₅ | CF₃ | R3.26 | CH₃ | H |
| I-763 | CH₃ | CH₃ | R3.27 | CH₃ | H |
| I-764 | C₂H₅ | CH₃ | R3.27 | CH₃ | H |
| I-765 | CH₃ | CHF₂ | R3.27 | CH₃ | H |
| I-766 | C₂H₅ | CHF₂ | R3.27 | CH₃ | H |
| I-767 | CH₃ | CF₃ | R3.27 | CH₃ | H |
| I-768 | C₂H₅ | CF₃ | R3.27 | CH₃ | H |
| I-769 | CH₃ | CH₃ | R3.28 | CH₃ | H |
| I-770 | C₂H₅ | CH₃ | R3.28 | CH₃ | H |
| I-771 | CH₃ | CHF₂ | R3.28 | CH₃ | H |
| I-772 | C₂H₅ | CHF₂ | R3.28 | CH₃ | H |
| I-773 | CH₃ | CF₃ | R3.28 | CH₃ | H |
| I-774 | C₂H₅ | CF₃ | R3.28 | CH₃ | H |
| I-775 | CH₃ | CH₃ | R3.29 | CH₃ | H |
| I-776 | C₂H₅ | CH₃ | R3.29 | CH₃ | H |
| I-777 | CH₃ | CHF₂ | R3.29 | CH₃ | H |
| I-778 | C₂H₅ | CHF₂ | R3.29 | CH₃ | H |
| I-779 | CH₃ | CF₃ | R3.29 | CH₃ | H |
| I-780 | C₂H₅ | CF₃ | R3.29 | CH₃ | H |
| I-781 | CH₃ | CH₃ | R3.30 | CH₃ | H |
| I-782 | C₂H₅ | CH₃ | R3.30 | CH₃ | H |
| I-783 | CH₃ | CHF₂ | R3.30 | CH₃ | H |
| I-784 | C₂H₅ | CHF₂ | R3.30 | CH₃ | H |
| I-785 | CH₃ | CF₃ | R3.30 | CH₃ | H |
| I-786 | C₂H₅ | CF₃ | R3.30 | CH₃ | H |
| I-787 | CH₃ | CH₃ | R3.31 | CH₃ | H |
| I-788 | C₂H₅ | CH₃ | R3.31 | CH₃ | H |
| I-789 | CH₃ | CHF₂ | R3.31 | CH₃ | H |
| I-790 | C₂H₅ | CHF₂ | R3.31 | CH₃ | H |
| I-791 | CH₃ | CF₃ | R3.31 | CH₃ | H |
| I-792 | C₂H₅ | CF₃ | R3.31 | CH₃ | H |
| I-793 | CH₃ | CH₃ | R3.32 | CH₃ | H |
| I-794 | C₂H₅ | CH₃ | R3.32 | CH₃ | H |
| I-795 | CH₃ | CHF₂ | R3.32 | CH₃ | H |
| I-796 | C₂H₅ | CHF₂ | R3.32 | CH₃ | H |
| I-797 | CH₃ | CF₃ | R3.32 | CH₃ | H |
| I-798 | C₂H₅ | CF₃ | R3.32 | CH₃ | H |
| I-799 | CH₃ | CH₃ | R3.33 | CH₃ | H |
| I-800 | C₂H₅ | CH₃ | R3.33 | CH₃ | H |
| I-801 | CH₃ | CHF₂ | R3.33 | CH₃ | H |
| I-802 | C₂H₅ | CHF₂ | R3.33 | CH₃ | H |
| I-803 | CH₃ | CF₃ | R3.33 | CH₃ | H |
| I-804 | C₂H₅ | CF₃ | R3.33 | CH₃ | H |
| I-805 | CH₃ | CH₃ | R3.34 | CH₃ | H |
| I-806 | C₂H₅ | CH₃ | R3.34 | CH₃ | H |
| I-807 | CH₃ | CHF₂ | R3.34 | CH₃ | H |

TABLE II-continued

| No. | R¹ | R² | R³ | R⁴ | R⁵ |
|---|---|---|---|---|---|
| I-808 | C₂H₅ | CHF₂ | R3.34 | CH₃ | H |
| I-809 | CH₃ | CF₃ | R3.34 | CH₃ | H |
| I-810 | C₂H₅ | CF₃ | R3.34 | CH₃ | H |
| I-811 | CH₃ | CH₃ | R3.35 | CH₃ | H |
| I-812 | C₂H₅ | CH₃ | R3.35 | CH₃ | H |
| I-813 | CH₃ | CHF₂ | R3.35 | CH₃ | H |
| I-814 | C₂H₅ | CHF₂ | R3.35 | CH₃ | H |
| I-815 | CH₃ | CF₃ | R3.35 | CH₃ | H |
| I-816 | C₂H₅ | CF₃ | R3.35 | CH₃ | H |
| I-817 | CH₃ | CH₃ | R3.36 | CH₃ | H |
| I-818 | C₂H₅ | CH₃ | R3.36 | CH₃ | H |
| I-819 | CH₃ | CHF₂ | R3.36 | CH₃ | H |
| I-820 | C₂H₅ | CHF₂ | R3.36 | CH₃ | H |
| I-821 | CH₃ | CF₃ | R3.36 | CH₃ | H |
| I-822 | C₂H₅ | CF₃ | R3.36 | CH₃ | H |
| I-823 | CH₃ | CH₃ | R3.37 | CH₃ | H |
| I-824 | C₂H₅ | CH₃ | R3.37 | CH₃ | H |
| I-825 | CH₃ | CHF₂ | R3.37 | CH₃ | H |
| I-826 | C₂H₅ | CHF₂ | R3.37 | CH₃ | H |
| I-827 | CH₃ | CF₃ | R3.37 | CH₃ | H |
| I-828 | C₂H₅ | CF₃ | R3.37 | CH₃ | H |
| I-829 | CH₃ | CH₃ | R3.38 | CH₃ | H |
| I-830 | C₂H₅ | CH₃ | R3.38 | CH₃ | H |
| I-831 | CH₃ | CHF₂ | R3.38 | CH₃ | H |
| I-832 | C₂H₅ | CHF₂ | R3.38 | CH₃ | H |
| I-833 | CH₃ | CF₃ | R3.38 | CH₃ | H |
| I-834 | C₂H₅ | CF₃ | R3.38 | CH₃ | H |
| I-835 | CH₃ | CH₃ | R3.39 | CH₃ | H |
| I-836 | C₂H₅ | CH₃ | R3.39 | CH₃ | H |
| I-837 | CH₃ | CHF₂ | R3.39 | CH₃ | H |
| I-838 | C₂H₅ | CHF₂ | R3.39 | CH₃ | H |
| I-839 | CH₃ | CF₃ | R3.39 | CH₃ | H |
| I-840 | C₂H₅ | CF₃ | R3.39 | CH₃ | H |
| I-841 | CH₃ | CH₃ | R3.40 | CH₃ | H |
| I-842 | C₂H₅ | CH₃ | R3.40 | CH₃ | H |
| I-843 | CH₃ | CHF₂ | R3.40 | CH₃ | H |
| I-844 | C₂H₅ | CHF₂ | R3.40 | CH₃ | H |
| I-845 | CH₃ | CF₃ | R3.40 | CH₃ | H |
| I-846 | C₂H₅ | CF₃ | R3.40 | CH₃ | H |
| I-847 | CH₃ | CH₃ | R3.41 | CH₃ | H |
| I-848 | C₂H₅ | CH₃ | R3.41 | CH₃ | H |
| I-849 | CH₃ | CHF₂ | R3.41 | CH₃ | H |
| I-850 | C₂H₅ | CHF₂ | R3.41 | CH₃ | H |
| I-851 | CH₃ | CF₃ | R3.41 | CH₃ | H |
| I-852 | C₂H₅ | CF₃ | R3.41 | CH₃ | H |
| I-853 | CH₃ | CH₃ | R3.42 | CH₃ | H |
| I-854 | C₂H₅ | CH₃ | R3.42 | CH₃ | H |
| I-855 | CH₃ | CHF₂ | R3.42 | CH₃ | H |
| I-856 | C₂H₅ | CHF₂ | R3.42 | CH₃ | H |
| I-857 | CH₃ | CF₃ | R3.42 | CH₃ | H |
| I-858 | C₂H₅ | CF₃ | R3.42 | CH₃ | H |
| I-859 | CH₃ | CH₃ | R3.43 | CH₃ | H |
| I-860 | C₂H₅ | CH₃ | R3.43 | CH₃ | H |
| I-861 | CH₃ | CHF₂ | R3.43 | CH₃ | H |
| I-862 | C₂H₅ | CHF₂ | R3.43 | CH₃ | H |
| I-863 | CH₃ | CF₃ | R3.43 | CH₃ | H |
| I-864 | C₂H₅ | CF₃ | R3.43 | CH₃ | H |
| I-865 | CH₃ | CH₃ | R3.44 | CH₃ | H |
| I-866 | C₂H₅ | CH₃ | R3.44 | CH₃ | H |
| I-867 | CH₃ | CHF₂ | R3.44 | CH₃ | H |
| I-868 | C₂H₅ | CHF₂ | R3.44 | CH₃ | H |
| I-869 | CH₃ | CF₃ | R3.44 | CH₃ | H |
| I-870 | C₂H₅ | CF₃ | R3.44 | CH₃ | H |
| I-871 | CH₃ | CH₃ | R3.45 | CH₃ | H |
| I-872 | C₂H₅ | CH₃ | R3.45 | CH₃ | H |
| I-873 | CH₃ | CHF₂ | R3.45 | CH₃ | H |
| I-874 | C₂H₅ | CHF₂ | R3.45 | CH₃ | H |
| I-875 | CH₃ | CF₃ | R3.45 | CH₃ | H |
| I-876 | C₂H₅ | CF₃ | R3.45 | CH₃ | H |
| I-877 | CH₃ | CH₃ | R3.46 | CH₃ | H |
| I-878 | C₂H₅ | CH₃ | R3.46 | CH₃ | H |
| I-879 | CH₃ | CHF₂ | R3.46 | CH₃ | H |
| I-880 | C₂H₅ | CHF₂ | R3.46 | CH₃ | H |
| I-881 | CH₃ | CF₃ | R3.46 | CH₃ | H |
| I-882 | C₂H₅ | CF₃ | R3.46 | CH₃ | H |
| I-883 | CH₃ | CH₃ | R3.48 | CH₃ | H |
| I-884 | C₂H₅ | CH₃ | R3.48 | CH₃ | H |
| I-885 | CH₃ | CHF₂ | R3.48 | CH₃ | H |
| I-886 | C₂H₅ | CHF₂ | R3.48 | CH₃ | H |
| I-887 | CH₃ | CF₃ | R3.48 | CH₃ | H |
| I-888 | C₂H₅ | CF₃ | R3.48 | CH₃ | H |
| I-889 | CH₃ | CH₃ | R3.10 | C₂H₅ | H |
| I-890 | C₂H₅ | CH₃ | R3.10 | C₂H₅ | H |
| I-891 | CH₃ | CHF₂ | R3.10 | C₂H₅ | H |
| I-892 | C₂H₅ | CHF₂ | R3.10 | C₂H₅ | H |
| I-893 | CH₃ | CF₃ | R3.10 | C₂H₅ | H |
| I-894 | C₂H₅ | CF₃ | R3.10 | C₂H₅ | H |
| I-895 | CH₃ | CH₃ | R3.11 | C₂H₅ | H |
| I-896 | C₂H₅ | CH₃ | R3.11 | C₂H₅ | H |
| I-897 | CH₃ | CHF₂ | R3.11 | C₂H₅ | H |
| I-898 | C₂H₅ | CHF₂ | R3.11 | C₂H₅ | H |
| I-899 | CH₃ | CF₃ | R3.11 | C₂H₅ | H |
| I-900 | C₂H₅ | CF₃ | R3.11 | C₂H₅ | H |
| I-901 | CH₃ | CH₃ | R3.12 | C₂H₅ | H |
| I-902 | C₂H₅ | CH₃ | R3.12 | C₂H₅ | H |
| I-903 | CH₃ | CHF₂ | R3.12 | C₂H₅ | H |
| I-904 | C₂H₅ | CHF₂ | R3.12 | C₂H₅ | H |
| I-905 | CH₃ | CF₃ | R3.12 | C₂H₅ | H |
| I-906 | C₂H₅ | CF₃ | R3.12 | C₂H₅ | H |
| I-907 | CH₃ | CH₃ | R3.13 | C₂H₅ | H |
| I-908 | C₂H₅ | CH₃ | R3.13 | C₂H₅ | H |
| I-909 | CH₃ | CHF₂ | R3.13 | C₂H₅ | H |
| I-910 | C₂H₅ | CHF₂ | R3.13 | C₂H₅ | H |
| I-911 | CH₃ | CF₃ | R3.13 | C₂H₅ | H |
| I-912 | C₂H₅ | CF₃ | R3.13 | C₂H₅ | H |
| I-913 | CH₃ | CH₃ | R3.14 | C₂H₅ | H |
| I-914 | C₂H₅ | CH₃ | R3.14 | C₂H₅ | H |
| I-915 | CH₃ | CHF₂ | R3.14 | C₂H₅ | H |
| I-916 | C₂H₅ | CHF₂ | R3.14 | C₂H₅ | H |
| I-917 | CH₃ | CF₃ | R3.14 | C₂H₅ | H |
| I-918 | C₂H₅ | CF₃ | R3.14 | C₂H₅ | H |
| I-919 | CH₃ | CH₃ | R3.15 | C₂H₅ | H |
| I-920 | C₂H₅ | CH₃ | R3.15 | C₂H₅ | H |
| I-921 | CH₃ | CHF₂ | R3.15 | C₂H₅ | H |
| I-922 | C₂H₅ | CHF₂ | R3.15 | C₂H₅ | H |
| I-923 | CH₃ | CF₃ | R3.15 | C₂H₅ | H |
| I-924 | C₂H₅ | CF₃ | R3.15 | C₂H₅ | H |
| I-925 | CH₃ | CH₃ | R3.16 | C₂H₅ | H |
| I-926 | C₂H₅ | CH₃ | R3.16 | C₂H₅ | H |
| I-927 | CH₃ | CHF₂ | R3.16 | C₂H₅ | H |
| I-928 | C₂H₅ | CHF₂ | R3.16 | C₂H₅ | H |
| I-929 | CH₃ | CF₃ | R3.16 | C₂H₅ | H |
| I-930 | C₂H₅ | CF₃ | R3.16 | C₂H₅ | H |
| I-931 | CH₃ | CH₃ | R3.17 | C₂H₅ | H |
| I-932 | C₂H₅ | CH₃ | R3.17 | C₂H₅ | H |
| I-933 | CH₃ | CHF₂ | R3.17 | C₂H₅ | H |
| I-934 | C₂H₅ | CHF₂ | R3.17 | C₂H₅ | H |
| I-935 | CH₃ | CF₃ | R3.17 | C₂H₅ | H |
| I-936 | C₂H₅ | CF₃ | R3.17 | C₂H₅ | H |
| I-937 | CH₃ | CH₃ | R3.18 | C₂H₅ | H |
| I-938 | C₂H₅ | CH₃ | R3.18 | C₂H₅ | H |
| I-939 | CH₃ | CHF₂ | R3.18 | C₂H₅ | H |
| I-940 | C₂H₅ | CHF₂ | R3.18 | C₂H₅ | H |
| I-941 | CH₃ | CF₃ | R3.18 | C₂H₅ | H |
| I-942 | C₂H₅ | CF₃ | R3.18 | C₂H₅ | H |
| I-943 | CH₃ | CH₃ | R3.19 | C₂H₅ | H |
| I-944 | C₂H₅ | CH₃ | R3.19 | C₂H₅ | H |
| I-945 | CH₃ | CHF₂ | R3.19 | C₂H₅ | H |
| I-946 | C₂H₅ | CHF₂ | R3.19 | C₂H₅ | H |
| I-947 | CH₃ | CF₃ | R3.19 | C₂H₅ | H |
| I-948 | C₂H₅ | CF₃ | R3.19 | C₂H₅ | H |
| I-949 | CH₃ | CH₃ | R3.20 | C₂H₅ | H |
| I-950 | C₂H₅ | CH₃ | R3.20 | C₂H₅ | H |
| I-951 | CH₃ | CHF₂ | R3.20 | C₂H₅ | H |
| I-952 | C₂H₅ | CHF₂ | R3.20 | C₂H₅ | H |
| I-953 | CH₃ | CF₃ | R3.20 | C₂H₅ | H |
| I-954 | C₂H₅ | CF₃ | R3.20 | C₂H₅ | H |
| I-955 | CH₃ | CH₃ | R3.21 | C₂H₅ | H |
| I-956 | C₂H₅ | CH₃ | R3.21 | C₂H₅ | H |
| I-957 | CH₃ | CHF₂ | R3.21 | C₂H₅ | H |
| I-958 | C₂H₅ | CHF₂ | R3.21 | C₂H₅ | H |
| I-959 | CH₃ | CF₃ | R3.21 | C₂H₅ | H |
| I-960 | C₂H₅ | CF₃ | R3.21 | C₂H₅ | H |
| I-961 | CH₃ | CH₃ | R3.22 | C₂H₅ | H |
| I-962 | C₂H₅ | CH₃ | R3.22 | C₂H₅ | H |
| I-963 | CH₃ | CHF₂ | R3.22 | C₂H₅ | H |

TABLE II-continued

| No. | R¹ | R² | R³ | R⁴ | R⁵ |
|---|---|---|---|---|---|
| I-964 | C₂H₅ | CHF₂ | R3.22 | C₂H₅ | H |
| I-965 | CH₃ | CF₃ | R3.22 | C₂H₅ | H |
| I-966 | C₂H₅ | CF₃ | R3.22 | C₂H₅ | H |
| I-967 | CH₃ | CH₃ | R3.23 | C₂H₅ | H |
| I-968 | C₂H₅ | CH₃ | R3.23 | C₂H₅ | H |
| I-969 | CH₃ | CHF₂ | R3.23 | C₂H₅ | H |
| I-970 | C₂H₅ | CHF₂ | R3.23 | C₂H₅ | H |
| I-971 | CH₃ | CF₃ | R3.23 | C₂H₅ | H |
| I-972 | C₂H₅ | CF₃ | R3.23 | C₂H₅ | H |
| I-973 | CH₃ | CH₃ | R3.24 | C₂H₅ | H |
| I-974 | C₂H₅ | CH₃ | R3.24 | C₂H₅ | H |
| I-975 | CH₃ | CHF₂ | R3.24 | C₂H₅ | H |
| I-976 | C₂H₅ | CHF₂ | R3.24 | C₂H₅ | H |
| I-977 | CH₃ | CF₃ | R3.24 | C₂H₅ | H |
| I-978 | C₂H₅ | CF₃ | R3.24 | C₂H₅ | H |
| I-979 | CH₃ | CH₃ | R3.25 | C₂H₅ | H |
| I-980 | C₂H₅ | CH₃ | R3.25 | C₂H₅ | H |
| I-981 | CH₃ | CHF₂ | R3.25 | C₂H₅ | H |
| I-982 | C₂H₅ | CHF₂ | R3.25 | C₂H₅ | H |
| I-983 | CH₃ | CF₃ | R3.25 | C₂H₅ | H |
| I-984 | C₂H₅ | CF₃ | R3.25 | C₂H₅ | H |
| I-985 | CH₃ | CH₃ | R3.26 | C₂H₅ | H |
| I-986 | C₂H₅ | CH₃ | R3.26 | C₂H₅ | H |
| I-987 | CH₃ | CHF₂ | R3.26 | C₂H₅ | H |
| I-988 | C₂H₅ | CHF₂ | R3.26 | C₂H₅ | H |
| I-989 | CH₃ | CF₃ | R3.26 | C₂H₅ | H |
| I-990 | C₂H₅ | CF₃ | R3.26 | C₂H₅ | H |
| I-991 | CH₃ | CH₃ | R3.27 | C₂H₅ | H |
| I-992 | C₂H₅ | CH₃ | R3.27 | C₂H₅ | H |
| I-993 | CH₃ | CHF₂ | R3.27 | C₂H₅ | H |
| I-994 | C₂H₅ | CHF₂ | R3.27 | C₂H₅ | H |
| I-995 | CH₃ | CF₃ | R3.27 | C₂H₅ | H |
| I-996 | C₂H₅ | CF₃ | R3.27 | C₂H₅ | H |
| I-997 | CH₃ | CH₃ | R3.28 | C₂H₅ | H |
| I-998 | C₂H₅ | CH₃ | R3.28 | C₂H₅ | H |
| I-999 | CH₃ | CHF₂ | R3.28 | C₂H₅ | H |
| I-1000 | C₂H₅ | CHF₂ | R3.28 | C₂H₅ | H |
| I-1001 | CH₃ | CF₃ | R3.28 | C₂H₅ | H |
| I-1002 | C₂H₅ | CF₃ | R3.28 | C₂H₅ | H |
| I-1003 | CH₃ | CH₃ | R3.29 | C₂H₅ | H |
| I-1004 | C₂H₅ | CH₃ | R3.29 | C₂H₅ | H |
| I-1005 | CH₃ | CHF₂ | R3.29 | C₂H₅ | H |
| I-1006 | C₂H₅ | CHF₂ | R3.29 | C₂H₅ | H |
| I-1007 | CH₃ | CF₃ | R3.29 | C₂H₅ | H |
| I-1008 | C₂H₅ | CF₃ | R3.29 | C₂H₅ | H |
| I-1009 | CH₃ | CH₃ | R3.30 | C₂H₅ | H |
| I-1010 | C₂H₅ | CH₃ | R3.30 | C₂H₅ | H |
| I-1011 | CH₃ | CHF₂ | R3.30 | C₂H₅ | H |
| I-1012 | C₂H₅ | CHF₂ | R3.30 | C₂H₅ | H |
| I-1013 | CH₃ | CF₃ | R3.30 | C₂H₅ | H |
| I-1014 | C₂H₅ | CF₃ | R3.30 | C₂H₅ | H |
| I-1015 | CH₃ | CH₃ | R3.31 | C₂H₅ | H |
| I-1016 | C₂H₅ | CH₃ | R3.31 | C₂H₅ | H |
| I-1017 | CH₃ | CHF₂ | R3.31 | C₂H₅ | H |
| I-1018 | C₂H₅ | CHF₂ | R3.31 | C₂H₅ | H |
| I-1019 | CH₃ | CF₃ | R3.31 | C₂H₅ | H |
| I-1020 | C₂H₅ | CF₃ | R3.31 | C₂H₅ | H |
| I-1021 | CH₃ | CH₃ | R3.32 | C₂H₅ | H |
| I-1022 | C₂H₅ | CH₃ | R3.32 | C₂H₅ | H |
| I-1023 | CH₃ | CHF₂ | R3.32 | C₂H₅ | H |
| I-1024 | C₂H₅ | CHF₂ | R3.32 | C₂H₅ | H |
| I-1025 | CH₃ | CF₃ | R3.32 | C₂H₅ | H |
| I-1026 | C₂H₅ | CF₃ | R3.32 | C₂H₅ | H |
| I-1027 | CH₃ | CH₃ | R3.33 | C₂H₅ | H |
| I-1028 | C₂H₅ | CH₃ | R3.33 | C₂H₅ | H |
| I-1029 | CH₃ | CHF₂ | R3.33 | C₂H₅ | H |
| I-1030 | C₂H₅ | CHF₂ | R3.33 | C₂H₅ | H |
| I-1031 | CH₃ | CF₃ | R3.33 | C₂H₅ | H |
| I-1032 | C₂H₅ | CF₃ | R3.33 | C₂H₅ | H |
| I-1033 | CH₃ | CH₃ | R3.34 | C₂H₅ | H |
| I-1034 | C₂H₅ | CH₃ | R3.34 | C₂H₅ | H |
| I-1035 | CH₃ | CHF₂ | R3.34 | C₂H₅ | H |
| I-1036 | C₂H₅ | CHF₂ | R3.34 | C₂H₅ | H |
| I-1037 | CH₃ | CF₃ | R3.34 | C₂H₅ | H |
| I-1038 | C₂H₅ | CF₃ | R3.34 | C₂H₅ | H |
| I-1039 | CH₃ | CH₃ | R3.35 | C₂H₅ | H |
| I-1040 | C₂H₅ | CH₃ | R3.35 | C₂H₅ | H |
| I-1041 | CH₃ | CHF₂ | R3.35 | C₂H₅ | H |
| I-1042 | C₂H₅ | CHF₂ | R3.35 | C₂H₅ | H |
| I-1043 | CH₃ | CF₃ | R3.35 | C₂H₅ | H |
| I-1044 | C₂H₅ | CF₃ | R3.35 | C₂H₅ | H |
| I-1045 | CH₃ | CH₃ | R3.36 | C₂H₅ | H |
| I-1046 | C₂H₅ | CH₃ | R3.36 | C₂H₅ | H |
| I-1047 | CH₃ | CHF₂ | R3.36 | C₂H₅ | H |
| I-1048 | C₂H₅ | CHF₂ | R3.36 | C₂H₅ | H |
| I-1049 | CH₃ | CF₃ | R3.36 | C₂H₅ | H |
| I-1050 | C₂H₅ | CF₃ | R3.36 | C₂H₅ | H |
| I-1051 | CH₃ | CH₃ | R3.37 | C₂H₅ | H |
| I-1052 | C₂H₅ | CH₃ | R3.37 | C₂H₅ | H |
| I-1053 | CH₃ | CHF₂ | R3.37 | C₂H₅ | H |
| I-1054 | C₂H₅ | CHF₂ | R3.37 | C₂H₅ | H |
| I-1055 | CH₃ | CF₃ | R3.37 | C₂H₅ | H |
| I-1056 | C₂H₅ | CF₃ | R3.37 | C₂H₅ | H |
| I-1057 | CH₃ | CH₃ | R3.38 | C₂H₅ | H |
| I-1058 | C₂H₅ | CH₃ | R3.38 | C₂H₅ | H |
| I-1059 | CH₃ | CHF₂ | R3.38 | C₂H₅ | H |
| I-1060 | C₂H₅ | CHF₂ | R3.38 | C₂H₅ | H |
| I-1061 | CH₃ | CF₃ | R3.38 | C₂H₅ | H |
| I-1062 | C₂H₅ | CF₃ | R3.38 | C₂H₅ | H |
| I-1063 | CH₃ | CH₃ | R3.39 | C₂H₅ | H |
| I-1064 | C₂H₅ | CH₃ | R3.39 | C₂H₅ | H |
| I-1065 | CH₃ | CHF₂ | R3.39 | C₂H₅ | H |
| I-1066 | C₂H₅ | CHF₂ | R3.39 | C₂H₅ | H |
| I-1067 | CH₃ | CF₃ | R3.39 | C₂H₅ | H |
| I-1068 | C₂H₅ | CF₃ | R3.39 | C₂H₅ | H |
| I-1069 | CH₃ | CH₃ | R3.40 | C₂H₅ | H |
| I-1070 | C₂H₅ | CH₃ | R3.40 | C₂H₅ | H |
| I-1071 | CH₃ | CHF₂ | R3.40 | C₂H₅ | H |
| I-1072 | C₂H₅ | CHF₂ | R3.40 | C₂H₅ | H |
| I-1073 | CH₃ | CF₃ | R3.40 | C₂H₅ | H |
| I-1074 | C₂H₅ | CF₃ | R3.40 | C₂H₅ | H |
| I-1075 | CH₃ | CH₃ | R3.41 | C₂H₅ | H |
| I-1076 | C₂H₅ | CH₃ | R3.41 | C₂H₅ | H |
| I-1077 | CH₃ | CHF₂ | R3.41 | C₂H₅ | H |
| I-1078 | C₂H₅ | CHF₂ | R3.41 | C₂H₅ | H |
| I-1079 | CH₃ | CF₃ | R3.41 | C₂H₅ | H |
| I-1080 | C₂H₅ | CF₃ | R3.41 | C₂H₅ | H |
| I-1081 | CH₃ | CH₃ | R3.42 | C₂H₅ | H |
| I-1082 | C₂H₅ | CH₃ | R3.42 | C₂H₅ | H |
| I-1083 | CH₃ | CHF₂ | R3.42 | C₂H₅ | H |
| I-1084 | C₂H₅ | CHF₂ | R3.42 | C₂H₅ | H |
| I-1085 | CH₃ | CF₃ | R3.42 | C₂H₅ | H |
| I-1086 | C₂H₅ | CF₃ | R3.42 | C₂H₅ | H |
| I-1087 | CH₃ | CH₃ | R3.43 | C₂H₅ | H |
| I-1088 | C₂H₅ | CH₃ | R3.43 | C₂H₅ | H |
| I-1089 | CH₃ | CHF₂ | R3.43 | C₂H₅ | H |
| I-1090 | C₂H₅ | CHF₂ | R3.43 | C₂H₅ | H |
| I-1091 | CH₃ | CF₃ | R3.43 | C₂H₅ | H |
| I-1092 | C₂H₅ | CF₃ | R3.43 | C₂H₅ | H |
| I-1093 | CH₃ | CH₃ | R3.44 | C₂H₅ | H |
| I-1094 | C₂H₅ | CH₃ | R3.44 | C₂H₅ | H |
| I-1095 | CH₃ | CHF₂ | R3.44 | C₂H₅ | H |
| I-1096 | C₂H₅ | CHF₂ | R3.44 | C₂H₅ | H |
| I-1097 | CH₃ | CF₃ | R3.44 | C₂H₅ | H |
| I-1098 | C₂H₅ | CF₃ | R3.44 | C₂H₅ | H |
| I-1099 | CH₃ | CH₃ | R3.45 | C₂H₅ | H |
| I-1100 | C₂H₅ | CH₃ | R3.45 | C₂H₅ | H |
| I-1101 | CH₃ | CHF₂ | R3.45 | C₂H₅ | H |
| I-1102 | C₂H₅ | CHF₂ | R3.45 | C₂H₅ | H |
| I-1103 | CH₃ | CF₃ | R3.45 | C₂H₅ | H |
| I-1104 | C₂H₅ | CF₃ | R3.45 | C₂H₅ | H |
| I-1105 | CH₃ | CH₃ | R3.46 | C₂H₅ | H |
| I-1106 | C₂H₅ | CH₃ | R3.46 | C₂H₅ | H |
| I-1107 | CH₃ | CHF₂ | R3.46 | C₂H₅ | H |
| I-1108 | C₂H₅ | CHF₂ | R3.46 | C₂H₅ | H |
| I-1109 | CH₃ | CF₃ | R3.46 | C₂H₅ | H |
| I-1110 | C₂H₅ | CF₃ | R3.46 | C₂H₅ | H |
| I-1111 | CH₃ | CH₃ | R3.47 | C₂H₅ | H |
| I-1112 | C₂H₅ | CH₃ | R3.47 | C₂H₅ | H |
| I-1113 | CH₃ | CHF₂ | R3.47 | C₂H₅ | H |
| I-1114 | C₂H₅ | CHF₂ | R3.47 | C₂H₅ | H |
| I-1115 | CH₃ | CF₃ | R3.47 | C₂H₅ | H |
| I-1116 | C₂H₅ | CF₃ | R3.47 | C₂H₅ | H |
| I-1117 | CH₃ | CH₃ | R3.48 | C₂H₅ | H |
| I-1118 | C₂H₅ | CH₃ | R3.48 | C₂H₅ | H |
| I-1119 | CH₃ | CHF₂ | R3.48 | C₂H₅ | H |

TABLE II-continued

| No. | R¹ | R² | R³ | R⁴ | R⁵ |
|---|---|---|---|---|---|
| I-1120 | C₂H₅ | CHF₂ | R3.48 | C₂H₅ | H |
| I-1121 | CH₃ | CF₃ | R3.48 | C₂H₅ | H |
| I-1122 | C₂H₅ | CF₃ | R3.48 | C₂H₅ | H |
| I-1123 | CH₃ | CH₃ | R3.10 | CF₃ | H |
| I-1124 | C₂H₅ | CH₃ | R3.10 | CF₃ | H |
| I-1125 | CH₃ | CHF₂ | R3.10 | CF₃ | H |
| I-1126 | C₂H₅ | CHF₂ | R3.10 | CF₃ | H |
| I-1127 | CH₃ | CF₃ | R3.10 | CF₃ | H |
| I-1128 | C₂H₅ | CF₃ | R3.10 | CF₃ | H |
| I-1129 | CH₃ | CH₃ | R3.11 | CF₃ | H |
| I-1130 | C₂H₅ | CH₃ | R3.11 | CF₃ | H |
| I-1131 | CH₃ | CHF₂ | R3.11 | CF₃ | H |
| I-1132 | C₂H₅ | CHF₂ | R3.11 | CF₃ | H |
| I-1133 | CH₃ | CF₃ | R3.11 | CF₃ | H |
| I-1134 | C₂H₅ | CF₃ | R3.11 | CF₃ | H |
| I-1135 | CH₃ | CH₃ | R3.12 | CF₃ | H |
| I-1136 | C₂H₅ | CH₃ | R3.12 | CF₃ | H |
| I-1137 | CH₃ | CHF₂ | R3.12 | CF₃ | H |
| I-1138 | C₂H₅ | CHF₂ | R3.12 | CF₃ | H |
| I-1139 | CH₃ | CF₃ | R3.12 | CF₃ | H |
| I-1140 | C₂H₅ | CF₃ | R3.12 | CF₃ | H |
| I-1141 | CH₃ | CH₃ | R3.13 | CF₃ | H |
| I-1142 | C₂H₅ | CH₃ | R3.13 | CF₃ | H |
| I-1143 | CH₃ | CHF₂ | R3.13 | CF₃ | H |
| I-1144 | C₂H₅ | CHF₂ | R3.13 | CF₃ | H |
| I-1145 | CH₃ | CF₃ | R3.13 | CF₃ | H |
| I-1146 | C₂H₅ | CF₃ | R3.13 | CF₃ | H |
| I-1147 | CH₃ | CH₃ | R3.14 | CF₃ | H |
| I-1148 | C₂H₅ | CH₃ | R3.14 | CF₃ | H |
| I-1149 | CH₃ | CHF₂ | R3.14 | CF₃ | H |
| I-1150 | C₂H₅ | CHF₂ | R3.14 | CF₃ | H |
| I-1151 | CH₃ | CF₃ | R3.14 | CF₃ | H |
| I-1152 | C₂H₅ | CF₃ | R3.14 | CF₃ | H |
| I-1153 | CH₃ | CH₃ | R3.15 | CF₃ | H |
| I-1154 | C₂H₅ | CH₃ | R3.15 | CF₃ | H |
| I-1155 | CH₃ | CHF₂ | R3.15 | CF₃ | H |
| I-1156 | C₂H₅ | CHF₂ | R3.15 | CF₃ | H |
| I-1157 | CH₃ | CF₃ | R3.15 | CF₃ | H |
| I-1158 | C₂H₅ | CF₃ | R3.15 | CF₃ | H |
| I-1159 | CH₃ | CH₃ | R3.16 | CF₃ | H |
| I-1160 | C₂H₅ | CH₃ | R3.16 | CF₃ | H |
| I-1161 | CH₃ | CHF₂ | R3.16 | CF₃ | H |
| I-1162 | C₂H₅ | CHF₂ | R3.16 | CF₃ | H |
| I-1163 | CH₃ | CF₃ | R3.16 | CF₃ | H |
| I-1164 | C₂H₅ | CF₃ | R3.16 | CF₃ | H |
| I-1165 | CH₃ | CH₃ | R3.17 | CF₃ | H |
| I-1166 | C₂H₅ | CH₃ | R3.17 | CF₃ | H |
| I-1167 | CH₃ | CHF₂ | R3.17 | CF₃ | H |
| I-1168 | C₂H₅ | CHF₂ | R3.17 | CF₃ | H |
| I-1169 | CH₃ | CF₃ | R3.17 | CF₃ | H |
| I-1170 | C₂H₅ | CF₃ | R3.17 | CF₃ | H |
| I-1171 | CH₃ | CH₃ | R3.18 | CF₃ | H |
| I-1172 | C₂H₅ | CH₃ | R3.18 | CF₃ | H |
| I-1173 | CH₃ | CHF₂ | R3.18 | CF₃ | H |
| I-1174 | C₂H₅ | CHF₂ | R3.18 | CF₃ | H |
| I-1175 | CH₃ | CF₃ | R3.18 | CF₃ | H |
| I-1176 | C₂H₅ | CF₃ | R3.18 | CF₃ | H |
| I-1177 | CH₃ | CH₃ | R3.19 | CF₃ | H |
| I-1178 | C₂H₅ | CH₃ | R3.19 | CF₃ | H |
| I-1179 | CH₃ | CHF₂ | R3.19 | CF₃ | H |
| I-1180 | C₂H₅ | CHF₂ | R3.19 | CF₃ | H |
| I-1181 | CH₃ | CF₃ | R3.19 | CF₃ | H |
| I-1182 | C₂H₅ | CF₃ | R3.19 | CF₃ | H |
| I-1183 | CH₃ | CH₃ | R3.20 | CF₃ | H |
| I-1184 | C₂H₅ | CH₃ | R3.20 | CF₃ | H |
| I-1185 | CH₃ | CHF₂ | R3.20 | CF₃ | H |
| I-1186 | C₂H₅ | CHF₂ | R3.20 | CF₃ | H |
| I-1187 | CH₃ | CF₃ | R3.20 | CF₃ | H |
| I-1188 | C₂H₅ | CF₃ | R3.20 | CF₃ | H |
| I-1189 | CH₃ | CH₃ | R3.21 | CF₃ | H |
| I-1190 | C₂H₅ | CH₃ | R3.21 | CF₃ | H |
| I-1191 | CH₃ | CHF₂ | R3.21 | CF₃ | H |
| I-1192 | C₂H₅ | CHF₂ | R3.21 | CF₃ | H |
| I-1193 | CH₃ | CF₃ | R3.21 | CF₃ | H |
| I-1194 | C₂H₅ | CF₃ | R3.21 | CF₃ | H |
| I-1195 | CH₃ | CH₃ | R3.22 | CF₃ | H |
| I-1196 | C₂H₅ | CH₃ | R3.22 | CF₃ | H |
| I-1197 | CH₃ | CHF₂ | R3.22 | CF₃ | H |
| I-1198 | C₂H₅ | CHF₂ | R3.22 | CF₃ | H |
| I-1199 | CH₃ | CF₃ | R3.22 | CF₃ | H |
| I-1200 | C₂H₅ | CF₃ | R3.22 | CF₃ | H |
| I-1201 | CH₃ | CH₃ | R3.23 | CF₃ | H |
| I-1202 | C₂H₅ | CH₃ | R3.23 | CF₃ | H |
| I-1203 | CH₃ | CHF₂ | R3.23 | CF₃ | H |
| I-1204 | C₂H₅ | CHF₂ | R3.23 | CF₃ | H |
| I-1205 | CH₃ | CF₃ | R3.23 | CF₃ | H |
| I-1206 | C₂H₅ | CF₃ | R3.23 | CF₃ | H |
| I-1207 | CH₃ | CH₃ | R3.24 | CF₃ | H |
| I-1208 | C₂H₅ | CH₃ | R3.24 | CF₃ | H |
| I-1209 | CH₃ | CHF₂ | R3.24 | CF₃ | H |
| I-1210 | C₂H₅ | CHF₂ | R3.24 | CF₃ | H |
| I-1211 | CH₃ | CF₃ | R3.24 | CF₃ | H |
| I-1212 | C₂H₅ | CF₃ | R3.24 | CF₃ | H |
| I-1213 | CH₃ | CH₃ | R3.25 | CF₃ | H |
| I-1214 | C₂H₅ | CH₃ | R3.25 | CF₃ | H |
| I-1215 | CH₃ | CHF₂ | R3.25 | CF₃ | H |
| I-1216 | C₂H₅ | CHF₂ | R3.25 | CF₃ | H |
| I-1217 | CH₃ | CF₃ | R3.25 | CF₃ | H |
| I-1218 | C₂H₅ | CF₃ | R3.25 | CF₃ | H |
| I-1219 | CH₃ | CH₃ | R3.26 | CF₃ | H |
| I-1220 | C₂H₅ | CH₃ | R3.26 | CF₃ | H |
| I-1221 | CH₃ | CHF₂ | R3.26 | CF₃ | H |
| I-1222 | C₂H₅ | CHF₂ | R3.26 | CF₃ | H |
| I-1223 | CH₃ | CF₃ | R3.26 | CF₃ | H |
| I-1224 | C₂H₅ | CF₃ | R3.26 | CF₃ | H |
| I-1225 | CH₃ | CH₃ | R3.27 | CF₃ | H |
| I-1226 | C₂H₅ | CH₃ | R3.27 | CF₃ | H |
| I-1227 | CH₃ | CHF₂ | R3.27 | CF₃ | H |
| I-1228 | C₂H₅ | CHF₂ | R3.27 | CF₃ | H |
| I-1229 | CH₃ | CF₃ | R3.27 | CF₃ | H |
| I-1230 | C₂H₅ | CF₃ | R3.27 | CF₃ | H |
| I-1231 | CH₃ | CH₃ | R3.28 | CF₃ | H |
| I-1232 | C₂H₅ | CH₃ | R3.28 | CF₃ | H |
| I-1233 | CH₃ | CHF₂ | R3.28 | CF₃ | H |
| I-1234 | C₂H₅ | CHF₂ | R3.28 | CF₃ | H |
| I-1235 | CH₃ | CF₃ | R3.28 | CF₃ | H |
| I-1236 | C₂H₅ | CF₃ | R3.28 | CF₃ | H |
| I-1237 | CH₃ | CH₃ | R3.29 | CF₃ | H |
| I-1238 | C₂H₅ | CH₃ | R3.29 | CF₃ | H |
| I-1239 | CH₃ | CHF₂ | R3.29 | CF₃ | H |
| I-1240 | C₂H₅ | CHF₂ | R3.29 | CF₃ | H |
| I-1241 | CH₃ | CF₃ | R3.29 | CF₃ | H |
| I-1242 | C₂H₅ | CF₃ | R3.29 | CF₃ | H |
| I-1243 | CH₃ | CH₃ | R3.30 | CF₃ | H |
| I-1244 | C₂H₅ | CH₃ | R3.30 | CF₃ | H |
| I-1245 | CH₃ | CHF₂ | R3.30 | CF₃ | H |
| I-1246 | C₂H₅ | CHF₂ | R3.30 | CF₃ | H |
| I-1247 | CH₃ | CF₃ | R3.30 | CF₃ | H |
| I-1248 | C₂H₅ | CF₃ | R3.30 | CF₃ | H |
| I-1249 | CH₃ | CH₃ | R3.31 | CF₃ | H |
| I-1250 | C₂H₅ | CH₃ | R3.31 | CF₃ | H |
| I-1251 | CH₃ | CHF₂ | R3.31 | CF₃ | H |
| I-1252 | C₂H₅ | CHF₂ | R3.31 | CF₃ | H |
| I-1253 | CH₃ | CF₃ | R3.31 | CF₃ | H |
| I-1254 | C₂H₅ | CF₃ | R3.31 | CF₃ | H |
| I-1255 | CH₃ | CH₃ | R3.32 | CF₃ | H |
| I-1256 | C₂H₅ | CH₃ | R3.32 | CF₃ | H |
| I-1257 | CH₃ | CHF₂ | R3.32 | CF₃ | H |
| I-1258 | C₂H₅ | CHF₂ | R3.32 | CF₃ | H |
| I-1259 | CH₃ | CF₃ | R3.32 | CF₃ | H |
| I-1260 | C₂H₅ | CF₃ | R3.32 | CF₃ | H |
| I-1261 | CH₃ | CH₃ | R3.33 | CF₃ | H |
| I-1262 | C₂H₅ | CH₃ | R3.33 | CF₃ | H |
| I-1263 | CH₃ | CHF₂ | R3.33 | CF₃ | H |
| I-1264 | C₂H₅ | CHF₂ | R3.33 | CF₃ | H |
| I-1265 | CH₃ | CF₃ | R3.33 | CF₃ | H |
| I-1266 | C₂H₅ | CF₃ | R3.33 | CF₃ | H |
| I-1267 | CH₃ | CH₃ | R3.34 | CF₃ | H |
| I-1268 | C₂H₅ | CH₃ | R3.34 | CF₃ | H |
| I-1269 | CH₃ | CHF₂ | R3.34 | CF₃ | H |
| I-1270 | C₂H₅ | CHF₂ | R3.34 | CF₃ | H |
| I-1271 | CH₃ | CF₃ | R3.34 | CF₃ | H |
| I-1272 | C₂H₅ | CF₃ | R3.34 | CF₃ | H |
| I-1273 | CH₃ | CH₃ | R3.35 | CF₃ | H |
| I-1274 | C₂H₅ | CH₃ | R3.35 | CF₃ | H |
| I-1275 | CH₃ | CHF₂ | R3.35 | CF₃ | H |

TABLE II-continued

| No. | R¹ | R² | R³ | R⁴ | R⁵ |
|---|---|---|---|---|---|
| I-1276 | $C_2H_5$ | $CHF_2$ | R3.35 | $CF_3$ | H |
| I-1277 | $CH_3$ | $CF_3$ | R3.35 | $CF_3$ | H |
| I-1278 | $C_2H_5$ | $CF_3$ | R3.35 | $CF_3$ | H |
| I-1279 | $CH_3$ | $CH_3$ | R3.36 | $CF_3$ | H |
| I-1280 | $C_2H_5$ | $CH_3$ | R3.36 | $CF_3$ | H |
| I-1281 | $CH_3$ | $CHF_2$ | R3.36 | $CF_3$ | H |
| I-1282 | $C_2H_5$ | $CHF_2$ | R3.36 | $CF_3$ | H |
| I-1283 | $CH_3$ | $CF_3$ | R3.36 | $CF_3$ | H |
| I-1284 | $C_2H_5$ | $CF_3$ | R3.36 | $CF_3$ | H |
| I-1285 | $CH_3$ | $CH_3$ | R3.37 | $CF_3$ | H |
| I-1286 | $C_2H_5$ | $CH_3$ | R3.37 | $CF_3$ | H |
| I-1287 | $CH_3$ | $CHF_2$ | R3.37 | $CF_3$ | H |
| I-1288 | $C_2H_5$ | $CHF_2$ | R3.37 | $CF_3$ | H |
| I-1289 | $CH_3$ | $CF_3$ | R3.37 | $CF_3$ | H |
| I-1290 | $C_2H_5$ | $CF_3$ | R3.37 | $CF_3$ | H |
| I-1291 | $CH_3$ | $CH_3$ | R3.38 | $CF_3$ | H |
| I-1292 | $C_2H_5$ | $CH_3$ | R3.38 | $CF_3$ | H |
| I-1293 | $CH_3$ | $CHF_2$ | R3.38 | $CF_3$ | H |
| I-1294 | $C_2H_5$ | $CHF_2$ | R3.38 | $CF_3$ | H |
| I-1295 | $CH_3$ | $CF_3$ | R3.38 | $CF_3$ | H |
| I-1296 | $C_2H_5$ | $CF_3$ | R3.38 | $CF_3$ | H |
| I-1297 | $CH_3$ | $CH_3$ | R3.39 | $CF_3$ | H |
| I-1298 | $C_2H_5$ | $CH_3$ | R3.39 | $CF_3$ | H |
| I-1299 | $CH_3$ | $CHF_2$ | R3.39 | $CF_3$ | H |
| I-1300 | $C_2H_5$ | $CHF_2$ | R3.39 | $CF_3$ | H |
| I-1301 | $CH_3$ | $CF_3$ | R3.39 | $CF_3$ | H |
| I-1302 | $C_2H_5$ | $CF_3$ | R3.39 | $CF_3$ | H |
| I-1303 | $CH_3$ | $CH_3$ | R3.40 | $CF_3$ | H |
| I-1304 | $C_2H_5$ | $CH_3$ | R3.40 | $CF_3$ | H |
| I-1305 | $CH_3$ | $CHF_2$ | R3.40 | $CF_3$ | H |
| I-1306 | $C_2H_5$ | $CHF_2$ | R3.40 | $CF_3$ | H |
| I-1307 | $CH_3$ | $CF_3$ | R3.40 | $CF_3$ | H |
| I-1308 | $C_2H_5$ | $CF_3$ | R3.40 | $CF_3$ | H |
| I-1309 | $CH_3$ | $CH_3$ | R3.41 | $CF_3$ | H |
| I-1310 | $C_2H_5$ | $CH_3$ | R3.41 | $CF_3$ | H |
| I-1311 | $CH_3$ | $CHF_2$ | R3.41 | $CF_3$ | H |
| I-1312 | $C_2H_5$ | $CHF_2$ | R3.41 | $CF_3$ | H |
| I-1313 | $CH_3$ | $CF_3$ | R3.41 | $CF_3$ | H |
| I-1314 | $C_2H_5$ | $CF_3$ | R3.41 | $CF_3$ | H |
| I-1315 | $CH_3$ | $CH_3$ | R3.42 | $CF_3$ | H |
| I-1316 | $C_2H_5$ | $CH_3$ | R3.42 | $CF_3$ | H |
| I-1317 | $CH_3$ | $CHF_2$ | R3.42 | $CF_3$ | H |
| I-1318 | $C_2H_5$ | $CHF_2$ | R3.42 | $CF_3$ | H |
| I-1319 | $CH_3$ | $CF_3$ | R3.42 | $CF_3$ | H |
| I-1320 | $C_2H_5$ | $CF_3$ | R3.42 | $CF_3$ | H |
| I-1321 | $CH_3$ | $CH_3$ | R3.43 | $CF_3$ | H |
| I-1322 | $C_2H_5$ | $CH_3$ | R3.43 | $CF_3$ | H |
| I-1323 | $CH_3$ | $CHF_2$ | R3.43 | $CF_3$ | H |
| I-1324 | $C_2H_5$ | $CHF_2$ | R3.43 | $CF_3$ | H |
| I-1325 | $CH_3$ | $CF_3$ | R3.43 | $CF_3$ | H |
| I-1326 | $C_2H_5$ | $CF_3$ | R3.43 | $CF_3$ | H |
| I-1327 | $CH_3$ | $CH_3$ | R3.44 | $CF_3$ | H |
| I-1328 | $C_2H_5$ | $CH_3$ | R3.44 | $CF_3$ | H |
| I-1329 | $CH_3$ | $CHF_2$ | R3.44 | $CF_3$ | H |
| I-1330 | $C_2H_5$ | $CHF_2$ | R3.44 | $CF_3$ | H |
| I-1331 | $CH_3$ | $CF_3$ | R3.44 | $CF_3$ | H |
| I-1332 | $C_2H_5$ | $CF_3$ | R3.44 | $CF_3$ | H |
| I-1333 | $CH_3$ | $CH_3$ | R3.45 | $CF_3$ | H |
| I-1334 | $C_2H_5$ | $CH_3$ | R3.45 | $CF_3$ | H |
| I-1335 | $CH_3$ | $CHF_2$ | R3.45 | $CF_3$ | H |
| I-1336 | $C_2H_5$ | $CHF_2$ | R3.45 | $CF_3$ | H |
| I-1337 | $CH_3$ | $CF_3$ | R3.45 | $CF_3$ | H |
| I-1338 | $C_2H_5$ | $CF_3$ | R3.45 | $CF_3$ | H |
| I-1339 | $CH_3$ | $CH_3$ | R3.46 | $CF_3$ | H |
| I-1340 | $C_2H_5$ | $CH_3$ | R3.46 | $CF_3$ | H |
| I-1341 | $CH_3$ | $CHF_2$ | R3.46 | $CF_3$ | H |
| I-1342 | $C_2H_5$ | $CHF_2$ | R3.46 | $CF_3$ | H |
| I-1343 | $CH_3$ | $CF_3$ | R3.46 | $CF_3$ | H |
| I-1344 | $C_2H_5$ | $CF_3$ | R3.46 | $CF_3$ | H |
| I-1345 | $CH_3$ | $CH_3$ | R3.47 | $CF_3$ | H |
| I-1346 | $C_2H_5$ | $CH_3$ | R3.47 | $CF_3$ | H |
| I-1347 | $CH_3$ | $CHF_2$ | R3.47 | $CF_3$ | H |
| I-1348 | $C_2H_5$ | $CHF_2$ | R3.47 | $CF_3$ | H |
| I-1349 | $CH_3$ | $CF_3$ | R3.47 | $CF_3$ | H |
| I-1350 | $C_2H_5$ | $CF_3$ | R3.47 | $CF_3$ | H |
| I-1351 | $CH_3$ | $CH_3$ | R3.48 | $CF_3$ | H |
| I-1352 | $C_2H_5$ | $CH_3$ | R3.48 | $CF_3$ | H |
| I-1353 | $CH_3$ | $CHF_2$ | R3.48 | $CF_3$ | H |
| I-1354 | $C_2H_5$ | $CHF_2$ | R3.48 | $CF_3$ | H |
| I-1355 | $CH_3$ | $CF_3$ | R3.48 | $CF_3$ | H |
| I-1356 | $C_2H_5$ | $CF_3$ | R3.48 | $CF_3$ | H |
| I-1357 | $CH_3$ | $CH_3$ | R3.10 | $CHF_2$ | $CH_3$ |
| I-1358 | $C_2H_5$ | $CH_3$ | R3.10 | $CHF_2$ | $CH_3$ |
| I-1359 | $CH_3$ | $CHF_2$ | R3.10 | $CHF_2$ | $CH_3$ |
| I-1360 | $C_2H_5$ | $CHF_2$ | R3.10 | $CHF_2$ | $CH_3$ |
| I-1361 | $CH_3$ | $CF_3$ | R3.10 | $CHF_2$ | $CH_3$ |
| I-1362 | $C_2H_5$ | $CF_3$ | R3.10 | $CHF_2$ | $CH_3$ |
| I-1363 | $CH_3$ | $CH_3$ | R3.11 | $CHF_2$ | $CH_3$ |
| I-1364 | $C_2H_5$ | $CH_3$ | R3.11 | $CHF_2$ | $CH_3$ |
| I-1365 | $CH_3$ | $CHF_2$ | R3.11 | $CHF_2$ | $CH_3$ |
| I-1366 | $C_2H_5$ | $CHF_2$ | R3.11 | $CHF_2$ | $CH_3$ |
| I-1367 | $CH_3$ | $CF_3$ | R3.11 | $CHF_2$ | $CH_3$ |
| I-1368 | $C_2H_5$ | $CF_3$ | R3.11 | $CHF_2$ | $CH_3$ |
| I-1369 | $CH_3$ | $CH_3$ | R3.12 | $CHF_2$ | $CH_3$ |
| I-1370 | $C_2H_5$ | $CH_3$ | R3.12 | $CHF_2$ | $CH_3$ |
| I-1371 | $CH_3$ | $CHF_2$ | R3.12 | $CHF_2$ | $CH_3$ |
| I-1372 | $C_2H_5$ | $CHF_2$ | R3.12 | $CHF_2$ | $CH_3$ |
| I-1373 | $CH_3$ | $CF_3$ | R3.12 | $CHF_2$ | $CH_3$ |
| I-1374 | $C_2H_5$ | $CF_3$ | R3.12 | $CHF_2$ | $CH_3$ |
| I-1375 | $CH_3$ | $CH_3$ | R3.13 | $CHF_2$ | $CH_3$ |
| I-1376 | $C_2H_5$ | $CH_3$ | R3.13 | $CHF_2$ | $CH_3$ |
| I-1377 | $CH_3$ | $CHF_2$ | R3.13 | $CHF_2$ | $CH_3$ |
| I-1378 | $C_2H_5$ | $CHF_2$ | R3.13 | $CHF_2$ | $CH_3$ |
| I-1379 | $CH_3$ | $CF_3$ | R3.13 | $CHF_2$ | $CH_3$ |
| I-1380 | $C_2H_5$ | $CF_3$ | R3.13 | $CHF_2$ | $CH_3$ |
| I-1381 | $CH_3$ | $CH_3$ | R3.14 | $CHF_2$ | $CH_3$ |
| I-1382 | $C_2H_5$ | $CH_3$ | R3.14 | $CHF_2$ | $CH_3$ |
| I-1383 | $CH_3$ | $CHF_2$ | R3.14 | $CHF_2$ | $CH_3$ |
| I-1384 | $C_2H_5$ | $CHF_2$ | R3.14 | $CHF_2$ | $CH_3$ |
| I-1385 | $CH_3$ | $CF_3$ | R3.14 | $CHF_2$ | $CH_3$ |
| I-1386 | $C_2H_5$ | $CF_3$ | R3.14 | $CHF_2$ | $CH_3$ |
| I-1387 | $CH_3$ | $CH_3$ | R3.15 | $CHF_2$ | $CH_3$ |
| I-1388 | $C_2H_5$ | $CH_3$ | R3.15 | $CHF_2$ | $CH_3$ |
| I-1389 | $CH_3$ | $CHF_2$ | R3.15 | $CHF_2$ | $CH_3$ |
| I-1390 | $C_2H_5$ | $CHF_2$ | R3.15 | $CHF_2$ | $CH_3$ |
| I-1391 | $CH_3$ | $CF_3$ | R3.15 | $CHF_2$ | $CH_3$ |
| I-1392 | $C_2H_5$ | $CF_3$ | R3.15 | $CHF_2$ | $CH_3$ |
| I-1393 | $CH_3$ | $CH_3$ | R3.16 | $CHF_2$ | $CH_3$ |
| I-1394 | $C_2H_5$ | $CH_3$ | R3.16 | $CHF_2$ | $CH_3$ |
| I-1395 | $CH_3$ | $CHF_2$ | R3.16 | $CHF_2$ | $CH_3$ |
| I-1396 | $C_2H_5$ | $CHF_2$ | R3.16 | $CHF_2$ | $CH_3$ |
| I-1397 | $CH_3$ | $CF_3$ | R3.16 | $CHF_2$ | $CH_3$ |
| I-1398 | $C_2H_5$ | $CF_3$ | R3.16 | $CHF_2$ | $CH_3$ |
| I-1399 | $CH_3$ | $CH_3$ | R3.17 | $CHF_2$ | $CH_3$ |
| I-1400 | $C_2H_5$ | $CH_3$ | R3.17 | $CHF_2$ | $CH_3$ |
| I-1401 | $CH_3$ | $CHF_2$ | R3.17 | $CHF_2$ | $CH_3$ |
| I-1402 | $C_2H_5$ | $CHF_2$ | R3.17 | $CHF_2$ | $CH_3$ |
| I-1403 | $CH_3$ | $CF_3$ | R3.17 | $CHF_2$ | $CH_3$ |
| I-1404 | $C_2H_5$ | $CF_3$ | R3.17 | $CHF_2$ | $CH_3$ |
| I-1405 | $CH_3$ | $CH_3$ | R3.18 | $CHF_2$ | $CH_3$ |
| I-1406 | $C_2H_5$ | $CH_3$ | R3.18 | $CHF_2$ | $CH_3$ |
| I-1407 | $CH_3$ | $CHF_2$ | R3.18 | $CHF_2$ | $CH_3$ |
| I-1408 | $C_2H_5$ | $CHF_2$ | R3.18 | $CHF_2$ | $CH_3$ |
| I-1409 | $CH_3$ | $CF_3$ | R3.18 | $CHF_2$ | $CH_3$ |
| I-1410 | $C_2H_5$ | $CF_3$ | R3.18 | $CHF_2$ | $CH_3$ |
| I-1411 | $CH_3$ | $CH_3$ | R3.19 | $CHF_2$ | $CH_3$ |
| I-1412 | $C_2H_5$ | $CH_3$ | R3.19 | $CHF_2$ | $CH_3$ |
| I-1413 | $CH_3$ | $CHF_2$ | R3.19 | $CHF_2$ | $CH_3$ |
| I-1414 | $C_2H_5$ | $CHF_2$ | R3.19 | $CHF_2$ | $CH_3$ |
| I-1415 | $CH_3$ | $CF_3$ | R3.19 | $CHF_2$ | $CH_3$ |
| I-1416 | $C_2H_5$ | $CF_3$ | R3.19 | $CHF_2$ | $CH_3$ |
| I-1417 | $CH_3$ | $CH_3$ | R3.20 | $CHF_2$ | $CH_3$ |
| I-1418 | $C_2H_5$ | $CH_3$ | R3.20 | $CHF_2$ | $CH_3$ |
| I-1419 | $CH_3$ | $CHF_2$ | R3.20 | $CHF_2$ | $CH_3$ |
| I-1420 | $C_2H_5$ | $CHF_2$ | R3.20 | $CHF_2$ | $CH_3$ |
| I-1421 | $CH_3$ | $CF_3$ | R3.20 | $CHF_2$ | $CH_3$ |
| I-1422 | $C_2H_5$ | $CF_3$ | R3.20 | $CHF_2$ | $CH_3$ |
| I-1423 | $CH_3$ | $CH_3$ | R3.21 | $CHF_2$ | $CH_3$ |
| I-1424 | $C_2H_5$ | $CH_3$ | R3.21 | $CHF_2$ | $CH_3$ |
| I-1425 | $CH_3$ | $CHF_2$ | R3.21 | $CHF_2$ | $CH_3$ |
| I-1426 | $C_2H_5$ | $CHF_2$ | R3.21 | $CHF_2$ | $CH_3$ |
| I-1427 | $CH_3$ | $CF_3$ | R3.21 | $CHF_2$ | $CH_3$ |
| I-1428 | $C_2H_5$ | $CF_3$ | R3.21 | $CHF_2$ | $CH_3$ |
| I-1429 | $CH_3$ | $CH_3$ | R3.22 | $CHF_2$ | $CH_3$ |
| I-1430 | $C_2H_5$ | $CH_3$ | R3.22 | $CHF_2$ | $CH_3$ |
| I-1431 | $CH_3$ | $CHF_2$ | R3.22 | $CHF_2$ | $CH_3$ |

TABLE II-continued

| No. | R¹ | R² | R³ | R⁴ | R⁵ |
|---|---|---|---|---|---|
| I-1432 | C₂H₅ | CHF₂ | R3.22 | CHF₂ | CH₃ |
| I-1433 | CH₃ | CF₃ | R3.22 | CHF₂ | CH₃ |
| I-1434 | C₂H₅ | CF₃ | R3.22 | CHF₂ | CH₃ |
| I-1435 | CH₃ | CH₃ | R3.23 | CHF₂ | CH₃ |
| I-1436 | C₂H₅ | CH₃ | R3.23 | CHF₂ | CH₃ |
| I-1437 | CH₃ | CHF₂ | R3.23 | CHF₂ | CH₃ |
| I-1438 | C₂H₅ | CHF₂ | R3.23 | CHF₂ | CH₃ |
| I-1439 | CH₃ | CF₃ | R3.23 | CHF₂ | CH₃ |
| I-1440 | C₂H₅ | CF₃ | R3.23 | CHF₂ | CH₃ |
| I-1441 | CH₃ | CH₃ | R3.24 | CHF₂ | CH₃ |
| I-1442 | C₂H₅ | CH₃ | R3.24 | CHF₂ | CH₃ |
| I-1443 | CH₃ | CHF₂ | R3.24 | CHF₂ | CH₃ |
| I-1444 | C₂H₅ | CHF₂ | R3.24 | CHF₂ | CH₃ |
| I-1445 | CH₃ | CF₃ | R3.24 | CHF₂ | CH₃ |
| I-1446 | C₂H₅ | CF₃ | R3.24 | CHF₂ | CH₃ |
| I-1447 | CH₃ | CH₃ | R3.25 | CHF₂ | CH₃ |
| I-1448 | C₂H₅ | CH₃ | R3.25 | CHF₂ | CH₃ |
| I-1449 | CH₃ | CHF₂ | R3.25 | CHF₂ | CH₃ |
| I-1450 | C₂H₅ | CHF₂ | R3.25 | CHF₂ | CH₃ |
| I-1451 | CH₃ | CF₃ | R3.25 | CHF₂ | CH₃ |
| I-1452 | C₂H₅ | CF₃ | R3.25 | CHF₂ | CH₃ |
| I-1453 | CH₃ | CH₃ | R3.26 | CHF₂ | CH₃ |
| I-1454 | C₂H₅ | CH₃ | R3.26 | CHF₂ | CH₃ |
| I-1455 | CH₃ | CHF₂ | R3.26 | CHF₂ | CH₃ |
| I-1456 | C₂H₅ | CHF₂ | R3.26 | CHF₂ | CH₃ |
| I-1457 | CH₃ | CF₃ | R3.26 | CHF₂ | CH₃ |
| I-1458 | C₂H₅ | CF₃ | R3.26 | CHF₂ | CH₃ |
| I-1459 | CH₃ | CH₃ | R3.27 | CHF₂ | CH₃ |
| I-1460 | C₂H₅ | CH₃ | R3.27 | CHF₂ | CH₃ |
| I-1461 | CH₃ | CHF₂ | R3.27 | CHF₂ | CH₃ |
| I-1462 | C₂H₅ | CHF₂ | R3.27 | CHF₂ | CH₃ |
| I-1463 | CH₃ | CF₃ | R3.27 | CHF₂ | CH₃ |
| I-1464 | C₂H₅ | CF₃ | R3.27 | CHF₂ | CH₃ |
| I-1465 | CH₃ | CH₃ | R3.28 | CHF₂ | CH₃ |
| I-1466 | C₂H₅ | CH₃ | R3.28 | CHF₂ | CH₃ |
| I-1467 | CH₃ | CHF₂ | R3.28 | CHF₂ | CH₃ |
| I-1468 | C₂H₅ | CHF₂ | R3.28 | CHF₂ | CH₃ |
| I-1469 | CH₃ | CF₃ | R3.28 | CHF₂ | CH₃ |
| I-1470 | C₂H₅ | CF₃ | R3.28 | CHF₂ | CH₃ |
| I-1471 | CH₃ | CH₃ | R3.29 | CHF₂ | CH₃ |
| I-1472 | C₂H₅ | CH₃ | R3.29 | CHF₂ | CH₃ |
| I-1473 | CH₃ | CHF₂ | R3.29 | CHF₂ | CH₃ |
| I-1474 | C₂H₅ | CHF₂ | R3.29 | CHF₂ | CH₃ |
| I-1475 | CH₃ | CF₃ | R3.29 | CHF₂ | CH₃ |
| I-1476 | C₂H₅ | CF₃ | R3.29 | CHF₂ | CH₃ |
| I-1477 | CH₃ | CH₃ | R3.30 | CHF₂ | CH₃ |
| I-1478 | C₂H₅ | CH₃ | R3.30 | CHF₂ | CH₃ |
| I-1479 | CH₃ | CHF₂ | R3.30 | CHF₂ | CH₃ |
| I-1480 | C₂H₅ | CHF₂ | R3.30 | CHF₂ | CH₃ |
| I-1481 | CH₃ | CF₃ | R3.30 | CHF₂ | CH₃ |
| I-1482 | C₂H₅ | CF₃ | R3.30 | CHF₂ | CH₃ |
| I-1483 | CH₃ | CH₃ | R3.31 | CHF₂ | CH₃ |
| I-1484 | C₂H₅ | CH₃ | R3.31 | CHF₂ | CH₃ |
| I-1485 | CH₃ | CHF₂ | R3.31 | CHF₂ | CH₃ |
| I-1486 | C₂H₅ | CHF₂ | R3.31 | CHF₂ | CH₃ |
| I-1487 | CH₃ | CF₃ | R3.31 | CHF₂ | CH₃ |
| I-1488 | C₂H₅ | CF₃ | R3.31 | CHF₂ | CH₃ |
| I-1489 | CH₃ | CH₃ | R3.32 | CHF₂ | CH₃ |
| I-1490 | C₂H₅ | CH₃ | R3.32 | CHF₂ | CH₃ |
| I-1491 | CH₃ | CHF₂ | R3.32 | CHF₂ | CH₃ |
| I-1492 | C₂H₅ | CHF₂ | R3.32 | CHF₂ | CH₃ |
| I-1493 | CH₃ | CF₃ | R3.32 | CHF₂ | CH₃ |
| I-1494 | C₂H₅ | CF₃ | R3.32 | CHF₂ | CH₃ |
| I-1495 | CH₃ | CH₃ | R3.33 | CHF₂ | CH₃ |
| I-1496 | C₂H₅ | CH₃ | R3.33 | CHF₂ | CH₃ |
| I-1497 | CH₃ | CHF₂ | R3.33 | CHF₂ | CH₃ |
| I-1498 | C₂H₅ | CHF₂ | R3.33 | CHF₂ | CH₃ |
| I-1499 | CH₃ | CF₃ | R3.33 | CHF₂ | CH₃ |
| I-1500 | C₂H₅ | CF₃ | R3.33 | CHF₂ | CH₃ |
| I-1501 | CH₃ | CH₃ | R3.34 | CHF₂ | CH₃ |
| I-1502 | C₂H₅ | CH₃ | R3.34 | CHF₂ | CH₃ |
| I-1503 | CH₃ | CHF₂ | R3.34 | CHF₂ | CH₃ |
| I-1504 | C₂H₅ | CHF₂ | R3.34 | CHF₂ | CH₃ |
| I-1505 | CH₃ | CF₃ | R3.34 | CHF₂ | CH₃ |
| I-1506 | C₂H₅ | CF₃ | R3.34 | CHF₂ | CH₃ |
| I-1507 | CH₃ | CH₃ | R3.35 | CHF₂ | CH₃ |
| I-1508 | C₂H₅ | CH₃ | R3.35 | CHF₂ | CH₃ |
| I-1509 | CH₃ | CHF₂ | R3.35 | CHF₂ | CH₃ |
| I-1510 | C₂H₅ | CHF₂ | R3.35 | CHF₂ | CH₃ |
| I-1511 | CH₃ | CF₃ | R3.35 | CHF₂ | CH₃ |
| I-1512 | C₂H₅ | CF₃ | R3.35 | CHF₂ | CH₃ |
| I-1513 | CH₃ | CH₃ | R3.36 | CHF₂ | CH₃ |
| I-1514 | C₂H₅ | CH₃ | R3.36 | CHF₂ | CH₃ |
| I-1515 | CH₃ | CHF₂ | R3.36 | CHF₂ | CH₃ |
| I-1516 | C₂H₅ | CHF₂ | R3.36 | CHF₂ | CH₃ |
| I-1517 | CH₃ | CF₃ | R3.36 | CHF₂ | CH₃ |
| I-1518 | C₂H₅ | CF₃ | R3.36 | CHF₂ | CH₃ |
| I-1519 | CH₃ | CH₃ | R3.37 | CHF₂ | CH₃ |
| I-1520 | C₂H₅ | CH₃ | R3.37 | CHF₂ | CH₃ |
| I-1521 | CH₃ | CHF₂ | R3.37 | CHF₂ | CH₃ |
| I-1522 | C₂H₅ | CHF₂ | R3.37 | CHF₂ | CH₃ |
| I-1523 | CH₃ | CF₃ | R3.37 | CHF₂ | CH₃ |
| I-1524 | C₂H₅ | CF₃ | R3.37 | CHF₂ | CH₃ |
| I-1525 | CH₃ | CH₃ | R3.38 | CHF₂ | CH₃ |
| I-1526 | C₂H₅ | CH₃ | R3.38 | CHF₂ | CH₃ |
| I-1527 | CH₃ | CHF₂ | R3.38 | CHF₂ | CH₃ |
| I-1528 | C₂H₅ | CHF₂ | R3.38 | CHF₂ | CH₃ |
| I-1529 | CH₃ | CF₃ | R3.38 | CHF₂ | CH₃ |
| I-1530 | C₂H₅ | CF₃ | R3.38 | CHF₂ | CH₃ |
| I-1531 | CH₃ | CH₃ | R3.39 | CHF₂ | CH₃ |
| I-1532 | C₂H₅ | CH₃ | R3.39 | CHF₂ | CH₃ |
| I-1533 | CH₃ | CHF₂ | R3.39 | CHF₂ | CH₃ |
| I-1534 | C₂H₅ | CHF₂ | R3.39 | CHF₂ | CH₃ |
| I-1535 | CH₃ | CF₃ | R3.39 | CHF₂ | CH₃ |
| I-1536 | C₂H₅ | CF₃ | R3.39 | CHF₂ | CH₃ |
| I-1537 | CH₃ | CH₃ | R3.40 | CHF₂ | CH₃ |
| I-1538 | C₂H₅ | CH₃ | R3.40 | CHF₂ | CH₃ |
| I-1539 | CH₃ | CHF₂ | R3.40 | CHF₂ | CH₃ |
| I-1540 | C₂H₅ | CHF₂ | R3.40 | CHF₂ | CH₃ |
| I-1541 | CH₃ | CF₃ | R3.40 | CHF₂ | CH₃ |
| I-1542 | C₂H₅ | CF₃ | R3.40 | CHF₂ | CH₃ |
| I-1543 | CH₃ | CH₃ | R3.41 | CHF₂ | CH₃ |
| I-1544 | C₂H₅ | CH₃ | R3.41 | CHF₂ | CH₃ |
| I-1545 | CH₃ | CHF₂ | R3.41 | CHF₂ | CH₃ |
| I-1546 | C₂H₅ | CHF₂ | R3.41 | CHF₂ | CH₃ |
| I-1547 | CH₃ | CF₃ | R3.41 | CHF₂ | CH₃ |
| I-1548 | C₂H₅ | CF₃ | R3.41 | CHF₂ | CH₃ |
| I-1549 | CH₃ | CH₃ | R3.42 | CHF₂ | CH₃ |
| I-1550 | C₂H₅ | CH₃ | R3.42 | CHF₂ | CH₃ |
| I-1551 | CH₃ | CHF₂ | R3.42 | CHF₂ | CH₃ |
| I-1552 | C₂H₅ | CHF₂ | R3.42 | CHF₂ | CH₃ |
| I-1553 | CH₃ | CF₃ | R3.42 | CHF₂ | CH₃ |
| I-1554 | C₂H₅ | CF₃ | R3.42 | CHF₂ | CH₃ |
| I-1555 | CH₃ | CH₃ | R3.43 | CHF₂ | CH₃ |
| I-1556 | C₂H₅ | CH₃ | R3.43 | CHF₂ | CH₃ |
| I-1557 | CH₃ | CHF₂ | R3.43 | CHF₂ | CH₃ |
| I-1558 | C₂H₅ | CHF₂ | R3.43 | CHF₂ | CH₃ |
| I-1559 | CH₃ | CF₃ | R3.43 | CHF₂ | CH₃ |
| I-1560 | C₂H₅ | CF₃ | R3.43 | CHF₂ | CH₃ |
| I-1561 | CH₃ | CH₃ | R3.44 | CHF₂ | CH₃ |
| I-1562 | C₂H₅ | CH₃ | R3.44 | CHF₂ | CH₃ |
| I-1563 | CH₃ | CHF₂ | R3.44 | CHF₂ | CH₃ |
| I-1564 | C₂H₅ | CHF₂ | R3.44 | CHF₂ | CH₃ |
| I-1565 | CH₃ | CF₃ | R3.44 | CHF₂ | CH₃ |
| I-1566 | C₂H₅ | CF₃ | R3.44 | CHF₂ | CH₃ |
| I-1567 | CH₃ | CH₃ | R3.45 | CHF₂ | CH₃ |
| I-1568 | C₂H₅ | CH₃ | R3.45 | CHF₂ | CH₃ |
| I-1569 | CH₃ | CHF₂ | R3.45 | CHF₂ | CH₃ |
| I-1570 | C₂H₅ | CHF₂ | R3.45 | CHF₂ | CH₃ |
| I-1571 | CH₃ | CF₃ | R3.45 | CHF₂ | CH₃ |
| I-1572 | C₂H₅ | CF₃ | R3.45 | CHF₂ | CH₃ |
| I-1573 | CH₃ | CH₃ | R3.46 | CHF₂ | CH₃ |
| I-1574 | C₂H₅ | CH₃ | R3.46 | CHF₂ | CH₃ |
| I-1575 | CH₃ | CHF₂ | R3.46 | CHF₂ | CH₃ |
| I-1576 | C₂H₅ | CHF₂ | R3.46 | CHF₂ | CH₃ |
| I-1577 | CH₃ | CF₃ | R3.46 | CHF₂ | CH₃ |
| I-1578 | C₂H₅ | CF₃ | R3.46 | CHF₂ | CH₃ |
| I-1579 | CH₃ | CH₃ | R3.47 | CHF₂ | CH₃ |
| I-1580 | C₂H₅ | CH₃ | R3.47 | CHF₂ | CH₃ |
| I-1581 | CH₃ | CHF₂ | R3.47 | CHF₂ | CH₃ |
| I-1582 | C₂H₅ | CHF₂ | R3.47 | CHF₂ | CH₃ |
| I-1583 | CH₃ | CF₃ | R3.47 | CHF₂ | CH₃ |
| I-1584 | C₂H₅ | CF₃ | R3.47 | CHF₂ | CH₃ |
| I-1585 | CH₃ | CH₃ | R3.48 | CHF₂ | CH₃ |
| I-1586 | C₂H₅ | CH₃ | R3.48 | CHF₂ | CH₃ |
| I-1587 | CH₃ | CHF₂ | R3.48 | CHF₂ | CH₃ |

TABLE II-continued

| No. | R¹ | R² | R³ | R⁴ | R⁵ |
|---|---|---|---|---|---|
| I-1588 | C₂H₅ | CHF₂ | R3.48 | CHF₂ | CH₃ |
| I-1589 | CH₃ | CF₃ | R3.48 | CHF₂ | CH₃ |
| I-1590 | C₂H₅ | CF₃ | R3.48 | CHF₂ | CH₃ |
| I-1591 | CH₃ | CH₃ | R3.10 | CH₃ | CH₃ |
| I-1592 | C₂H₅ | CH₃ | R3.10 | CH₃ | CH₃ |
| I-1593 | CH₃ | CHF₂ | R3.10 | CH₃ | CH₃ |
| I-1594 | C₂H₅ | CHF₂ | R3.10 | CH₃ | CH₃ |
| I-1595 | CH₃ | CF₃ | R3.10 | CH₃ | CH₃ |
| I-1596 | C₂H₅ | CF₃ | R3.10 | CH₃ | CH₃ |
| I-1597 | CH₃ | CH₃ | R3.11 | CH₃ | CH₃ |
| I-1598 | C₂H₅ | CH₃ | R3.11 | CH₃ | CH₃ |
| I-1599 | CH₃ | CHF₂ | R3.11 | CH₃ | CH₃ |
| I-1600 | C₂H₅ | CHF₂ | R3.11 | CH₃ | CH₃ |
| I-1601 | CH₃ | CF₃ | R3.11 | CH₃ | CH₃ |
| I-1602 | C₂H₅ | CF₃ | R3.11 | CH₃ | CH₃ |
| I-1603 | CH₃ | CH₃ | R3.12 | CH₃ | CH₃ |
| I-1604 | C₂H₅ | CH₃ | R3.12 | CH₃ | CH₃ |
| I-1605 | CH₃ | CHF₂ | R3.12 | CH₃ | CH₃ |
| I-1606 | C₂H₅ | CHF₂ | R3.12 | CH₃ | CH₃ |
| I-1607 | CH₃ | CF₃ | R3.12 | CH₃ | CH₃ |
| I-1608 | C₂H₅ | CF₃ | R3.12 | CH₃ | CH₃ |
| I-1609 | CH₃ | CH₃ | R3.13 | CH₃ | CH₃ |
| I-1610 | C₂H₅ | CH₃ | R3.13 | CH₃ | CH₃ |
| I-1611 | CH₃ | CHF₂ | R3.13 | CH₃ | CH₃ |
| I-1612 | C₂H₅ | CHF₂ | R3.13 | CH₃ | CH₃ |
| I-1613 | CH₃ | CF₃ | R3.13 | CH₃ | CH₃ |
| I-1614 | C₂H₅ | CF₃ | R3.13 | CH₃ | CH₃ |
| I-1615 | CH₃ | CH₃ | R3.14 | CH₃ | CH₃ |
| I-1616 | C₂H₅ | CH₃ | R3.14 | CH₃ | CH₃ |
| I-1617 | CH₃ | CHF₂ | R3.14 | CH₃ | CH₃ |
| I-1618 | C₂H₅ | CHF₂ | R3.14 | CH₃ | CH₃ |
| I-1619 | CH₃ | CF₃ | R3.14 | CH₃ | CH₃ |
| I-1620 | C₂H₅ | CF₃ | R3.14 | CH₃ | CH₃ |
| I-1621 | CH₃ | CH₃ | R3.15 | CH₃ | CH₃ |
| I-1622 | C₂H₅ | CH₃ | R3.15 | CH₃ | CH₃ |
| I-1623 | CH₃ | CHF₂ | R3.15 | CH₃ | CH₃ |
| I-1624 | C₂H₅ | CHF₂ | R3.15 | CH₃ | CH₃ |
| I-1625 | CH₃ | CF₃ | R3.15 | CH₃ | CH₃ |
| I-1626 | C₂H₅ | CF₃ | R3.15 | CH₃ | CH₃ |
| I-1627 | CH₃ | CH₃ | R3.16 | CH₃ | CH₃ |
| I-1628 | C₂H₅ | CH₃ | R3.16 | CH₃ | CH₃ |
| I-1629 | CH₃ | CHF₂ | R3.16 | CH₃ | CH₃ |
| I-1630 | C₂H₅ | CHF₂ | R3.16 | CH₃ | CH₃ |
| I-1631 | CH₃ | CF₃ | R3.16 | CH₃ | CH₃ |
| I-1632 | C₂H₅ | CF₃ | R3.16 | CH₃ | CH₃ |
| I-1633 | CH₃ | CH₃ | R3.17 | CH₃ | CH₃ |
| I-1634 | C₂H₅ | CH₃ | R3.17 | CH₃ | CH₃ |
| I-1635 | CH₃ | CHF₂ | R3.17 | CH₃ | CH₃ |
| I-1636 | C₂H₅ | CHF₂ | R3.17 | CH₃ | CH₃ |
| I-1637 | CH₃ | CF₃ | R3.17 | CH₃ | CH₃ |
| I-1638 | C₂H₅ | CF₃ | R3.17 | CH₃ | CH₃ |
| I-1639 | CH₃ | CH₃ | R3.18 | CH₃ | CH₃ |
| I-1640 | C₂H₅ | CH₃ | R3.18 | CH₃ | CH₃ |
| I-1641 | CH₃ | CHF₂ | R3.18 | CH₃ | CH₃ |
| I-1642 | C₂H₅ | CHF₂ | R3.18 | CH₃ | CH₃ |
| I-1643 | CH₃ | CF₃ | R3.18 | CH₃ | CH₃ |
| I-1644 | C₂H₅ | CF₃ | R3.18 | CH₃ | CH₃ |
| I-1645 | CH₃ | CH₃ | R3.19 | CH₃ | CH₃ |
| I-1646 | C₂H₅ | CH₃ | R3.19 | CH₃ | CH₃ |
| I-1647 | CH₃ | CHF₂ | R3.19 | CH₃ | CH₃ |
| I-1648 | C₂H₅ | CHF₂ | R3.19 | CH₃ | CH₃ |
| I-1649 | CH₃ | CF₃ | R3.19 | CH₃ | CH₃ |
| I-1650 | C₂H₅ | CF₃ | R3.19 | CH₃ | CH₃ |
| I-1651 | CH₃ | CH₃ | R3.20 | CH₃ | CH₃ |
| I-1652 | C₂H₅ | CH₃ | R3.20 | CH₃ | CH₃ |
| I-1653 | CH₃ | CHF₂ | R3.20 | CH₃ | CH₃ |
| I-1654 | C₂H₅ | CHF₂ | R3.20 | CH₃ | CH₃ |
| I-1655 | CH₃ | CF₃ | R3.20 | CH₃ | CH₃ |
| I-1656 | C₂H₅ | CF₃ | R3.20 | CH₃ | CH₃ |
| I-1657 | CH₃ | CH₃ | R3.21 | CH₃ | CH₃ |
| I-1658 | C₂H₅ | CH₃ | R3.21 | CH₃ | CH₃ |
| I-1659 | CH₃ | CHF₂ | R3.21 | CH₃ | CH₃ |
| I-1660 | C₂H₅ | CHF₂ | R3.21 | CH₃ | CH₃ |
| I-1661 | CH₃ | CF₃ | R3.21 | CH₃ | CH₃ |
| I-1662 | C₂H₅ | CF₃ | R3.21 | CH₃ | CH₃ |
| I-1663 | CH₃ | CH₃ | R3.22 | CH₃ | CH₃ |
| I-1664 | C₂H₅ | CH₃ | R3.22 | CH₃ | CH₃ |
| I-1665 | CH₃ | CHF₂ | R3.22 | CH₃ | CH₃ |
| I-1666 | C₂H₅ | CHF₂ | R3.22 | CH₃ | CH₃ |
| I-1667 | CH₃ | CF₃ | R3.22 | CH₃ | CH₃ |
| I-1668 | C₂H₅ | CF₃ | R3.22 | CH₃ | CH₃ |
| I-1669 | CH₃ | CH₃ | R3.23 | CH₃ | CH₃ |
| I-1670 | C₂H₅ | CH₃ | R3.23 | CH₃ | CH₃ |
| I-1671 | CH₃ | CHF₂ | R3.23 | CH₃ | CH₃ |
| I-1672 | C₂H₅ | CHF₂ | R3.23 | CH₃ | CH₃ |
| I-1673 | CH₃ | CF₃ | R3.23 | CH₃ | CH₃ |
| I-1674 | C₂H₅ | CF₃ | R3.23 | CH₃ | CH₃ |
| I-1675 | CH₃ | CH₃ | R3.24 | CH₃ | CH₃ |
| I-1676 | C₂H₅ | CH₃ | R3.24 | CH₃ | CH₃ |
| I-1677 | CH₃ | CHF₂ | R3.24 | CH₃ | CH₃ |
| I-1678 | C₂H₅ | CHF₂ | R3.24 | CH₃ | CH₃ |
| I-1679 | CH₃ | CF₃ | R3.24 | CH₃ | CH₃ |
| I-1680 | C₂H₅ | CF₃ | R3.24 | CH₃ | CH₃ |
| I-1681 | CH₃ | CH₃ | R3.25 | CH₃ | CH₃ |
| I-1682 | C₂H₅ | CH₃ | R3.25 | CH₃ | CH₃ |
| I-1683 | CH₃ | CHF₂ | R3.25 | CH₃ | CH₃ |
| I-1684 | C₂H₅ | CHF₂ | R3.25 | CH₃ | CH₃ |
| I-1685 | CH₃ | CF₃ | R3.25 | CH₃ | CH₃ |
| I-1686 | C₂H₅ | CF₃ | R3.25 | CH₃ | CH₃ |
| I-1687 | CH₃ | CH₃ | R3.26 | CH₃ | CH₃ |
| I-1688 | C₂H₅ | CH₃ | R3.26 | CH₃ | CH₃ |
| I-1689 | CH₃ | CHF₂ | R3.26 | CH₃ | CH₃ |
| I-1690 | C₂H₅ | CHF₂ | R3.26 | CH₃ | CH₃ |
| I-1691 | CH₃ | CF₃ | R3.26 | CH₃ | CH₃ |
| I-1692 | C₂H₅ | CF₃ | R3.26 | CH₃ | CH₃ |
| I-1693 | CH₃ | CH₃ | R3.27 | CH₃ | CH₃ |
| I-1694 | C₂H₅ | CH₃ | R3.27 | CH₃ | CH₃ |
| I-1695 | CH₃ | CHF₂ | R3.27 | CH₃ | CH₃ |
| I-1696 | C₂H₅ | CHF₂ | R3.27 | CH₃ | CH₃ |
| I-1697 | CH₃ | CF₃ | R3.27 | CH₃ | CH₃ |
| I-1698 | C₂H₅ | CF₃ | R3.27 | CH₃ | CH₃ |
| I-1699 | CH₃ | CH₃ | R3.28 | CH₃ | CH₃ |
| I-1700 | C₂H₅ | CH₃ | R3.28 | CH₃ | CH₃ |
| I-1701 | CH₃ | CHF₂ | R3.28 | CH₃ | CH₃ |
| I-1702 | C₂H₅ | CHF₂ | R3.28 | CH₃ | CH₃ |
| I-1703 | CH₃ | CF₃ | R3.28 | CH₃ | CH₃ |
| I-1704 | C₂H₅ | CF₃ | R3.28 | CH₃ | CH₃ |
| I-1705 | CH₃ | CH₃ | R3.29 | CH₃ | CH₃ |
| I-1706 | C₂H₅ | CH₃ | R3.29 | CH₃ | CH₃ |
| I-1707 | CH₃ | CHF₂ | R3.29 | CH₃ | CH₃ |
| I-1708 | C₂H₅ | CHF₂ | R3.29 | CH₃ | CH₃ |
| I-1709 | CH₃ | CF₃ | R3.29 | CH₃ | CH₃ |
| I-1710 | C₂H₅ | CF₃ | R3.29 | CH₃ | CH₃ |
| I-1711 | CH₃ | CH₃ | R3.30 | CH₃ | CH₃ |
| I-1712 | C₂H₅ | CH₃ | R3.30 | CH₃ | CH₃ |
| I-1713 | CH₃ | CHF₂ | R3.30 | CH₃ | CH₃ |
| I-1714 | C₂H₅ | CHF₂ | R3.30 | CH₃ | CH₃ |
| I-1715 | CH₃ | CF₃ | R3.30 | CH₃ | CH₃ |
| I-1716 | C₂H₅ | CF₃ | R3.30 | CH₃ | CH₃ |
| I-1717 | CH₃ | CH₃ | R3.31 | CH₃ | CH₃ |
| I-1718 | C₂H₅ | CH₃ | R3.31 | CH₃ | CH₃ |
| I-1719 | CH₃ | CHF₂ | R3.31 | CH₃ | CH₃ |
| I-1720 | C₂H₅ | CHF₂ | R3.31 | CH₃ | CH₃ |
| I-1721 | CH₃ | CF₃ | R3.31 | CH₃ | CH₃ |
| I-1722 | C₂H₅ | CF₃ | R3.31 | CH₃ | CH₃ |
| I-1723 | CH₃ | CH₃ | R3.32 | CH₃ | CH₃ |
| I-1724 | C₂H₅ | CH₃ | R3.32 | CH₃ | CH₃ |
| I-1725 | CH₃ | CHF₂ | R3.32 | CH₃ | CH₃ |
| I-1726 | C₂H₅ | CHF₂ | R3.32 | CH₃ | CH₃ |
| I-1727 | CH₃ | CF₃ | R3.32 | CH₃ | CH₃ |
| I-1728 | C₂H₅ | CF₃ | R3.32 | CH₃ | CH₃ |
| I-1729 | CH₃ | CH₃ | R3.33 | CH₃ | CH₃ |
| I-1730 | C₂H₅ | CH₃ | R3.33 | CH₃ | CH₃ |
| I-1731 | CH₃ | CHF₂ | R3.33 | CH₃ | CH₃ |
| I-1732 | C₂H₅ | CHF₂ | R3.33 | CH₃ | CH₃ |
| I-1733 | CH₃ | CF₃ | R3.33 | CH₃ | CH₃ |
| I-1734 | C₂H₅ | CF₃ | R3.33 | CH₃ | CH₃ |
| I-1735 | CH₃ | CH₃ | R3.34 | CH₃ | CH₃ |
| I-1736 | C₂H₅ | CH₃ | R3.34 | CH₃ | CH₃ |
| I-1737 | CH₃ | CHF₂ | R3.34 | CH₃ | CH₃ |
| I-1738 | C₂H₅ | CHF₂ | R3.34 | CH₃ | CH₃ |
| I-1739 | CH₃ | CF₃ | R3.34 | CH₃ | CH₃ |
| I-1740 | C₂H₅ | CF₃ | R3.34 | CH₃ | CH₃ |
| I-1741 | CH₃ | CH₃ | R3.35 | CH₃ | CH₃ |
| I-1742 | C₂H₅ | CH₃ | R3.35 | CH₃ | CH₃ |
| I-1743 | CH₃ | CHF₂ | R3.35 | CH₃ | CH₃ |

TABLE II-continued

| No. | R¹ | R² | R³ | R⁴ | R⁵ |
|---|---|---|---|---|---|
| I-1744 | $C_2H_5$ | $CHF_2$ | R3.35 | $CH_3$ | $CH_3$ |
| I-1745 | $CH_3$ | $CF_3$ | R3.35 | $CH_3$ | $CH_3$ |
| I-1746 | $C_2H_5$ | $CF_3$ | R3.35 | $CH_3$ | $CH_3$ |
| I-1747 | $CH_3$ | $CH_3$ | R3.36 | $CH_3$ | $CH_3$ |
| I-1748 | $C_2H_5$ | $CH_3$ | R3.36 | $CH_3$ | $CH_3$ |
| I-1749 | $CH_3$ | $CHF_2$ | R3.36 | $CH_3$ | $CH_3$ |
| I-1750 | $C_2H_5$ | $CHF_2$ | R3.36 | $CH_3$ | $CH_3$ |
| I-1751 | $CH_3$ | $CF_3$ | R3.36 | $CH_3$ | $CH_3$ |
| I-1752 | $C_2H_5$ | $CF_3$ | R3.36 | $CH_3$ | $CH_3$ |
| I-1753 | $CH_3$ | $CH_3$ | R3.37 | $CH_3$ | $CH_3$ |
| I-1754 | $C_2H_5$ | $CH_3$ | R3.37 | $CH_3$ | $CH_3$ |
| I-1755 | $CH_3$ | $CHF_2$ | R3.37 | $CH_3$ | $CH_3$ |
| I-1756 | $C_2H_5$ | $CHF_2$ | R3.37 | $CH_3$ | $CH_3$ |
| I-1757 | $CH_3$ | $CF_3$ | R3.37 | $CH_3$ | $CH_3$ |
| I-1758 | $C_2H_5$ | $CF_3$ | R3.37 | $CH_3$ | $CH_3$ |
| I-1759 | $CH_3$ | $CH_3$ | R3.38 | $CH_3$ | $CH_3$ |
| I-1760 | $C_2H_5$ | $CH_3$ | R3.38 | $CH_3$ | $CH_3$ |
| I-1761 | $CH_3$ | $CHF_2$ | R3.38 | $CH_3$ | $CH_3$ |
| I-1762 | $C_2H_5$ | $CHF_2$ | R3.38 | $CH_3$ | $CH_3$ |
| I-1763 | $CH_3$ | $CF_3$ | R3.38 | $CH_3$ | $CH_3$ |
| I-1764 | $C_2H_5$ | $CF_3$ | R3.38 | $CH_3$ | $CH_3$ |
| I-1765 | $CH_3$ | $CH_3$ | R3.39 | $CH_3$ | $CH_3$ |
| I-1766 | $C_2H_5$ | $CH_3$ | R3.39 | $CH_3$ | $CH_3$ |
| I-1767 | $CH_3$ | $CHF_2$ | R3.39 | $CH_3$ | $CH_3$ |
| I-1768 | $C_2H_5$ | $CHF_2$ | R3.39 | $CH_3$ | $CH_3$ |
| I-1769 | $CH_3$ | $CF_3$ | R3.39 | $CH_3$ | $CH_3$ |
| I-1770 | $C_2H_5$ | $CF_3$ | R3.39 | $CH_3$ | $CH_3$ |
| I-1771 | $CH_3$ | $CH_3$ | R3.40 | $CH_3$ | $CH_3$ |
| I-1772 | $C_2H_5$ | $CH_3$ | R3.40 | $CH_3$ | $CH_3$ |
| I-1773 | $CH_3$ | $CHF_2$ | R3.40 | $CH_3$ | $CH_3$ |
| I-1774 | $C_2H_5$ | $CHF_2$ | R3.40 | $CH_3$ | $CH_3$ |
| I-1775 | $CH_3$ | $CF_3$ | R3.40 | $CH_3$ | $CH_3$ |
| I-1776 | $C_2H_5$ | $CF_3$ | R3.40 | $CH_3$ | $CH_3$ |
| I-1777 | $CH_3$ | $CH_3$ | R3.41 | $CH_3$ | $CH_3$ |
| I-1778 | $C_2H_5$ | $CH_3$ | R3.41 | $CH_3$ | $CH_3$ |
| I-1779 | $CH_3$ | $CHF_2$ | R3.41 | $CH_3$ | $CH_3$ |
| I-1780 | $C_2H_5$ | $CHF_2$ | R3.41 | $CH_3$ | $CH_3$ |
| I-1781 | $CH_3$ | $CF_3$ | R3.41 | $CH_3$ | $CH_3$ |
| I-1782 | $C_2H_5$ | $CF_3$ | R3.41 | $CH_3$ | $CH_3$ |
| I-1783 | $CH_3$ | $CH_3$ | R3.42 | $CH_3$ | $CH_3$ |
| I-1784 | $C_2H_5$ | $CH_3$ | R3.42 | $CH_3$ | $CH_3$ |
| I-1785 | $CH_3$ | $CHF_2$ | R3.42 | $CH_3$ | $CH_3$ |
| I-1786 | $C_2H_5$ | $CHF_2$ | R3.42 | $CH_3$ | $CH_3$ |
| I-1787 | $CH_3$ | $CF_3$ | R3.42 | $CH_3$ | $CH_3$ |
| I-1788 | $C_2H_5$ | $CF_3$ | R3.42 | $CH_3$ | $CH_3$ |
| I-1789 | $CH_3$ | $CH_3$ | R3.43 | $CH_3$ | $CH_3$ |
| I-1790 | $C_2H_5$ | $CH_3$ | R3.43 | $CH_3$ | $CH_3$ |
| I-1791 | $CH_3$ | $CHF_2$ | R3.43 | $CH_3$ | $CH_3$ |
| I-1792 | $C_2H_5$ | $CHF_2$ | R3.43 | $CH_3$ | $CH_3$ |
| I-1793 | $CH_3$ | $CF_3$ | R3.43 | $CH_3$ | $CH_3$ |
| I-1794 | $C_2H_5$ | $CF_3$ | R3.43 | $CH_3$ | $CH_3$ |
| I-1795 | $CH_3$ | $CH_3$ | R3.44 | $CH_3$ | $CH_3$ |
| I-1796 | $C_2H_5$ | $CH_3$ | R3.44 | $CH_3$ | $CH_3$ |
| I-1797 | $CH_3$ | $CHF_2$ | R3.44 | $CH_3$ | $CH_3$ |
| I-1798 | $C_2H_5$ | $CHF_2$ | R3.44 | $CH_3$ | $CH_3$ |
| I-1799 | $CH_3$ | $CF_3$ | R3.44 | $CH_3$ | $CH_3$ |
| I-1800 | $C_2H_5$ | $CF_3$ | R3.44 | $CH_3$ | $CH_3$ |
| I-1801 | $CH_3$ | $CH_3$ | R3.45 | $CH_3$ | $CH_3$ |
| I-1802 | $C_2H_5$ | $CH_3$ | R3.45 | $CH_3$ | $CH_3$ |
| I-1803 | $CH_3$ | $CHF_2$ | R3.45 | $CH_3$ | $CH_3$ |
| I-1804 | $C_2H_5$ | $CHF_2$ | R3.45 | $CH_3$ | $CH_3$ |
| I-1805 | $CH_3$ | $CF_3$ | R3.45 | $CH_3$ | $CH_3$ |
| I-1806 | $C_2H_5$ | $CF_3$ | R3.45 | $CH_3$ | $CH_3$ |
| I-1807 | $CH_3$ | $CH_3$ | R3.46 | $CH_3$ | $CH_3$ |
| I-1808 | $C_2H_5$ | $CH_3$ | R3.46 | $CH_3$ | $CH_3$ |
| I-1809 | $CH_3$ | $CHF_2$ | R3.46 | $CH_3$ | $CH_3$ |
| I-1810 | $C_2H_5$ | $CHF_2$ | R3.46 | $CH_3$ | $CH_3$ |
| I-1811 | $CH_3$ | $CF_3$ | R3.46 | $CH_3$ | $CH_3$ |
| I-1812 | $C_2H_5$ | $CF_3$ | R3.46 | $CH_3$ | $CH_3$ |
| I-1813 | $CH_3$ | $CH_3$ | R3.47 | $CH_3$ | $CH_3$ |
| I-1814 | $C_2H_5$ | $CH_3$ | R3.47 | $CH_3$ | $CH_3$ |
| I-1815 | $CH_3$ | $CHF_2$ | R3.47 | $CH_3$ | $CH_3$ |
| I-1816 | $C_2H_5$ | $CHF_2$ | R3.47 | $CH_3$ | $CH_3$ |
| I-1817 | $CH_3$ | $CF_3$ | R3.47 | $CH_3$ | $CH_3$ |
| I-1818 | $C_2H_5$ | $CF_3$ | R3.47 | $CH_3$ | $CH_3$ |
| I-1819 | $CH_3$ | $CH_3$ | R3.48 | $CH_3$ | $CH_3$ |
| I-1820 | $C_2H_5$ | $CH_3$ | R3.48 | $CH_3$ | $CH_3$ |
| I-1821 | $CH_3$ | $CHF_2$ | R3.48 | $CH_3$ | $CH_3$ |
| I-1822 | $C_2H_5$ | $CHF_2$ | R3.48 | $CH_3$ | $CH_3$ |
| I-1823 | $CH_3$ | $CF_3$ | R3.48 | $CH_3$ | $CH_3$ |
| I-1824 | $C_2H_5$ | $CF_3$ | R3.48 | $CH_3$ | $CH_3$ |
| I-1825 | $CH_3$ | $CH_3$ | R3.10 | $C_2H_5$ | $CH_3$ |
| I-1826 | $C_2H_5$ | $CH_3$ | R3.10 | $C_2H_5$ | $CH_3$ |
| I-1827 | $CH_3$ | $CHF_2$ | R3.10 | $C_2H_5$ | $CH_3$ |
| I-1828 | $C_2H_5$ | $CHF_2$ | R3.10 | $C_2H_5$ | $CH_3$ |
| I-1829 | $CH_3$ | $CF_3$ | R3.10 | $C_2H_5$ | $CH_3$ |
| I-1830 | $C_2H_5$ | $CF_3$ | R3.10 | $C_2H_5$ | $CH_3$ |
| I-1831 | $CH_3$ | $CH_3$ | R3.11 | $C_2H_5$ | $CH_3$ |
| I-1832 | $C_2H_5$ | $CH_3$ | R3.11 | $C_2H_5$ | $CH_3$ |
| I-1833 | $CH_3$ | $CHF_2$ | R3.11 | $C_2H_5$ | $CH_3$ |
| I-1834 | $C_2H_5$ | $CHF_2$ | R3.11 | $C_2H_5$ | $CH_3$ |
| I-1835 | $CH_3$ | $CF_3$ | R3.11 | $C_2H_5$ | $CH_3$ |
| I-1836 | $C_2H_5$ | $CF_3$ | R3.11 | $C_2H_5$ | $CH_3$ |
| I-1837 | $CH_3$ | $CH_3$ | R3.12 | $C_2H_5$ | $CH_3$ |
| I-1838 | $C_2H_5$ | $CH_3$ | R3.12 | $C_2H_5$ | $CH_3$ |
| I-1839 | $CH_3$ | $CHF_2$ | R3.12 | $C_2H_5$ | $CH_3$ |
| I-1840 | $C_2H_5$ | $CHF_2$ | R3.12 | $C_2H_5$ | $CH_3$ |
| I-1841 | $CH_3$ | $CF_3$ | R3.12 | $C_2H_5$ | $CH_3$ |
| I-1842 | $C_2H_5$ | $CF_3$ | R3.12 | $C_2H_5$ | $CH_3$ |
| I-1843 | $CH_3$ | $CH_3$ | R3.13 | $C_2H_5$ | $CH_3$ |
| I-1844 | $C_2H_5$ | $CH_3$ | R3.13 | $C_2H_5$ | $CH_3$ |
| I-1845 | $CH_3$ | $CHF_2$ | R3.13 | $C_2H_5$ | $CH_3$ |
| I-1846 | $C_2H_5$ | $CHF_2$ | R3.13 | $C_2H_5$ | $CH_3$ |
| I-1847 | $CH_3$ | $CF_3$ | R3.13 | $C_2H_5$ | $CH_3$ |
| I-1848 | $C_2H_5$ | $CF_3$ | R3.13 | $C_2H_5$ | $CH_3$ |
| I-1849 | $CH_3$ | $CH_3$ | R3.14 | $C_2H_5$ | $CH_3$ |
| I-1850 | $C_2H_5$ | $CH_3$ | R3.14 | $C_2H_5$ | $CH_3$ |
| I-1851 | $CH_3$ | $CHF_2$ | R3.14 | $C_2H_5$ | $CH_3$ |
| I-1852 | $C_2H_5$ | $CHF_2$ | R3.14 | $C_2H_5$ | $CH_3$ |
| I-1853 | $CH_3$ | $CF_3$ | R3.14 | $C_2H_5$ | $CH_3$ |
| I-1854 | $C_2H_5$ | $CF_3$ | R3.14 | $C_2H_5$ | $CH_3$ |
| I-1855 | $CH_3$ | $CH_3$ | R3.15 | $C_2H_5$ | $CH_3$ |
| I-1856 | $C_2H_5$ | $CH_3$ | R3.15 | $C_2H_5$ | $CH_3$ |
| I-1857 | $CH_3$ | $CHF_2$ | R3.15 | $C_2H_5$ | $CH_3$ |
| I-1858 | $C_2H_5$ | $CHF_2$ | R3.15 | $C_2H_5$ | $CH_3$ |
| I-1859 | $CH_3$ | $CF_3$ | R3.15 | $C_2H_5$ | $CH_3$ |
| I-1860 | $C_2H_5$ | $CF_3$ | R3.15 | $C_2H_5$ | $CH_3$ |
| I-1861 | $CH_3$ | $CH_3$ | R3.16 | $C_2H_5$ | $CH_3$ |
| I-1862 | $C_2H_5$ | $CH_3$ | R3.16 | $C_2H_5$ | $CH_3$ |
| I-1863 | $CH_3$ | $CHF_2$ | R3.16 | $C_2H_5$ | $CH_3$ |
| I-1864 | $C_2H_5$ | $CHF_2$ | R3.16 | $C_2H_5$ | $CH_3$ |
| I-1865 | $CH_3$ | $CF_3$ | R3.16 | $C_2H_5$ | $CH_3$ |
| I-1866 | $C_2H_5$ | $CF_3$ | R3.16 | $C_2H_5$ | $CH_3$ |
| I-1867 | $CH_3$ | $CH_3$ | R3.17 | $C_2H_5$ | $CH_3$ |
| I-1868 | $C_2H_5$ | $CH_3$ | R3.17 | $C_2H_5$ | $CH_3$ |
| I-1869 | $CH_3$ | $CHF_2$ | R3.17 | $C_2H_5$ | $CH_3$ |
| I-1870 | $C_2H_5$ | $CHF_2$ | R3.17 | $C_2H_5$ | $CH_3$ |
| I-1871 | $CH_3$ | $CF_3$ | R3.17 | $C_2H_5$ | $CH_3$ |
| I-1872 | $C_2H_5$ | $CF_3$ | R3.17 | $C_2H_5$ | $CH_3$ |
| I-1873 | $CH_3$ | $CH_3$ | R3.18 | $C_2H_5$ | $CH_3$ |
| I-1874 | $C_2H_5$ | $CH_3$ | R3.18 | $C_2H_5$ | $CH_3$ |
| I-1875 | $CH_3$ | $CHF_2$ | R3.18 | $C_2H_5$ | $CH_3$ |
| I-1876 | $C_2H_5$ | $CHF_2$ | R3.18 | $C_2H_5$ | $CH_3$ |
| I-1877 | $CH_3$ | $CF_3$ | R3.18 | $C_2H_5$ | $CH_3$ |
| I-1878 | $C_2H_5$ | $CF_3$ | R3.18 | $C_2H_5$ | $CH_3$ |
| I-1879 | $CH_3$ | $CH_3$ | R3.19 | $C_2H_5$ | $CH_3$ |
| I-1880 | $C_2H_5$ | $CH_3$ | R3.19 | $C_2H_5$ | $CH_3$ |
| I-1881 | $CH_3$ | $CHF_2$ | R3.19 | $C_2H_5$ | $CH_3$ |
| I-1882 | $C_2H_5$ | $CHF_2$ | R3.19 | $C_2H_5$ | $CH_3$ |
| I-1883 | $CH_3$ | $CF_3$ | R3.19 | $C_2H_5$ | $CH_3$ |
| I-1884 | $C_2H_5$ | $CF_3$ | R3.19 | $C_2H_5$ | $CH_3$ |
| I-1885 | $CH_3$ | $CH_3$ | R3.20 | $C_2H_5$ | $CH_3$ |
| I-1886 | $C_2H_5$ | $CH_3$ | R3.20 | $C_2H_5$ | $CH_3$ |
| I-1887 | $CH_3$ | $CHF_2$ | R3.20 | $C_2H_5$ | $CH_3$ |
| I-1888 | $C_2H_5$ | $CHF_2$ | R3.20 | $C_2H_5$ | $CH_3$ |
| I-1889 | $CH_3$ | $CF_3$ | R3.20 | $C_2H_5$ | $CH_3$ |
| I-1890 | $C_2H_5$ | $CF_3$ | R3.20 | $C_2H_5$ | $CH_3$ |
| I-1891 | $CH_3$ | $CH_3$ | R3.21 | $C_2H_5$ | $CH_3$ |
| I-1892 | $C_2H_5$ | $CH_3$ | R3.21 | $C_2H_5$ | $CH_3$ |
| I-1893 | $CH_3$ | $CHF_2$ | R3.21 | $C_2H_5$ | $CH_3$ |
| I-1894 | $C_2H_5$ | $CHF_2$ | R3.21 | $C_2H_5$ | $CH_3$ |
| I-1895 | $CH_3$ | $CF_3$ | R3.21 | $C_2H_5$ | $CH_3$ |
| I-1896 | $C_2H_5$ | $CF_3$ | R3.21 | $C_2H_5$ | $CH_3$ |
| I-1897 | $CH_3$ | $CH_3$ | R3.22 | $C_2H_5$ | $CH_3$ |
| I-1898 | $C_2H_5$ | $CH_3$ | R3.22 | $C_2H_5$ | $CH_3$ |
| I-1899 | $CH_3$ | $CHF_2$ | R3.22 | $C_2H_5$ | $CH_3$ |

TABLE II-continued

| No. | R¹ | R² | R³ | R⁴ | R⁵ |
|---|---|---|---|---|---|
| I-1900 | $C_2H_5$ | $CHF_2$ | R3.22 | $C_2H_5$ | $CH_3$ |
| I-1901 | $CH_3$ | $CF_3$ | R3.22 | $C_2H_5$ | $CH_3$ |
| I-1902 | $C_2H_5$ | $CF_3$ | R3.22 | $C_2H_5$ | $CH_3$ |
| I-1903 | $CH_3$ | $CH_3$ | R3.23 | $C_2H_5$ | $CH_3$ |
| I-1904 | $C_2H_5$ | $CH_3$ | R3.23 | $C_2H_5$ | $CH_3$ |
| I-1905 | $CH_3$ | $CHF_2$ | R3.23 | $C_2H_5$ | $CH_3$ |
| I-1906 | $C_2H_5$ | $CHF_2$ | R3.23 | $C_2H_5$ | $CH_3$ |
| I-1907 | $CH_3$ | $CF_3$ | R3.23 | $C_2H_5$ | $CH_3$ |
| I-1908 | $C_2H_5$ | $CF_3$ | R3.23 | $C_2H_5$ | $CH_3$ |
| I-1909 | $CH_3$ | $CH_3$ | R3.24 | $C_2H_5$ | $CH_3$ |
| I-1910 | $C_2H_5$ | $CH_3$ | R3.24 | $C_2H_5$ | $CH_3$ |
| I-1911 | $CH_3$ | $CHF_2$ | R3.24 | $C_2H_5$ | $CH_3$ |
| I-1912 | $C_2H_5$ | $CHF_2$ | R3.24 | $C_2H_5$ | $CH_3$ |
| I-1913 | $CH_3$ | $CF_3$ | R3.24 | $C_2H_5$ | $CH_3$ |
| I-1914 | $C_2H_5$ | $CF_3$ | R3.24 | $C_2H_5$ | $CH_3$ |
| I-1915 | $CH_3$ | $CH_3$ | R3.25 | $C_2H_5$ | $CH_3$ |
| I-1916 | $C_2H_5$ | $CH_3$ | R3.25 | $C_2H_5$ | $CH_3$ |
| I-1917 | $CH_3$ | $CHF_2$ | R3.25 | $C_2H_5$ | $CH_3$ |
| I-1918 | $C_2H_5$ | $CHF_2$ | R3.25 | $C_2H_5$ | $CH_3$ |
| I-1919 | $CH_3$ | $CF_3$ | R3.25 | $C_2H_5$ | $CH_3$ |
| I-1920 | $C_2H_5$ | $CF_3$ | R3.25 | $C_2H_5$ | $CH_3$ |
| I-1921 | $CH_3$ | $CH_3$ | R3.26 | $C_2H_5$ | $CH_3$ |
| I-1922 | $C_2H_5$ | $CH_3$ | R3.26 | $C_2H_5$ | $CH_3$ |
| I-1923 | $CH_3$ | $CHF_2$ | R3.26 | $C_2H_5$ | $CH_3$ |
| I-1924 | $C_2H_5$ | $CHF_2$ | R3.26 | $C_2H_5$ | $CH_3$ |
| I-1925 | $CH_3$ | $CF_3$ | R3.26 | $C_2H_5$ | $CH_3$ |
| I-1926 | $C_2H_5$ | $CF_3$ | R3.26 | $C_2H_5$ | $CH_3$ |
| I-1927 | $CH_3$ | $CH_3$ | R3.27 | $C_2H_5$ | $CH_3$ |
| I-1928 | $C_2H_5$ | $CH_3$ | R3.27 | $C_2H_5$ | $CH_3$ |
| I-1929 | $CH_3$ | $CHF_2$ | R3.27 | $C_2H_5$ | $CH_3$ |
| I-1930 | $C_2H_5$ | $CHF_2$ | R3.27 | $C_2H_5$ | $CH_3$ |
| I-1931 | $CH_3$ | $CF_3$ | R3.27 | $C_2H_5$ | $CH_3$ |
| I-1932 | $C_2H_5$ | $CF_3$ | R3.27 | $C_2H_5$ | $CH_3$ |
| I-1933 | $CH_3$ | $CH_3$ | R3.28 | $C_2H_5$ | $CH_3$ |
| I-1934 | $C_2H_5$ | $CH_3$ | R3.28 | $C_2H_5$ | $CH_3$ |
| I-1935 | $CH_3$ | $CHF_2$ | R3.28 | $C_2H_5$ | $CH_3$ |
| I-1936 | $C_2H_5$ | $CHF_2$ | R3.28 | $C_2H_5$ | $CH_3$ |
| I-1937 | $CH_3$ | $CF_3$ | R3.28 | $C_2H_5$ | $CH_3$ |
| I-1938 | $C_2H_5$ | $CF_3$ | R3.28 | $C_2H_5$ | $CH_3$ |
| I-1939 | $CH_3$ | $CH_3$ | R3.29 | $C_2H_5$ | $CH_3$ |
| I-1940 | $C_2H_5$ | $CH_3$ | R3.29 | $C_2H_5$ | $CH_3$ |
| I-1941 | $CH_3$ | $CHF_2$ | R3.29 | $C_2H_5$ | $CH_3$ |
| I-1942 | $C_2H_5$ | $CHF_2$ | R3.29 | $C_2H_5$ | $CH_3$ |
| I-1943 | $CH_3$ | $CF_3$ | R3.29 | $C_2H_5$ | $CH_3$ |
| I-1944 | $C_2H_5$ | $CF_3$ | R3.29 | $C_2H_5$ | $CH_3$ |
| I-1945 | $CH_3$ | $CH_3$ | R3.30 | $C_2H_5$ | $CH_3$ |
| I-1946 | $C_2H_5$ | $CH_3$ | R3.30 | $C_2H_5$ | $CH_3$ |
| I-1947 | $CH_3$ | $CHF_2$ | R3.30 | $C_2H_5$ | $CH_3$ |
| I-1948 | $C_2H_5$ | $CHF_2$ | R3.30 | $C_2H_5$ | $CH_3$ |
| I-1949 | $CH_3$ | $CF_3$ | R3.30 | $C_2H_5$ | $CH_3$ |
| I-1950 | $C_2H_5$ | $CF_3$ | R3.30 | $C_2H_5$ | $CH_3$ |
| I-1951 | $CH_3$ | $CH_3$ | R3.31 | $C_2H_5$ | $CH_3$ |
| I-1952 | $C_2H_5$ | $CH_3$ | R3.31 | $C_2H_5$ | $CH_3$ |
| I-1953 | $CH_3$ | $CHF_2$ | R3.31 | $C_2H_5$ | $CH_3$ |
| I-1954 | $C_2H_5$ | $CHF_2$ | R3.31 | $C_2H_5$ | $CH_3$ |
| I-1955 | $CH_3$ | $CF_3$ | R3.31 | $C_2H_5$ | $CH_3$ |
| I-1956 | $C_2H_5$ | $CF_3$ | R3.31 | $C_2H_5$ | $CH_3$ |
| I-1957 | $CH_3$ | $CH_3$ | R3.32 | $C_2H_5$ | $CH_3$ |
| I-1958 | $C_2H_5$ | $CH_3$ | R3.32 | $C_2H_5$ | $CH_3$ |
| I-1959 | $CH_3$ | $CHF_2$ | R3.32 | $C_2H_5$ | $CH_3$ |
| I-1960 | $C_2H_5$ | $CHF_2$ | R3.32 | $C_2H_5$ | $CH_3$ |
| I-1961 | $CH_3$ | $CF_3$ | R3.32 | $C_2H_5$ | $CH_3$ |
| I-1962 | $C_2H_5$ | $CF_3$ | R3.32 | $C_2H_5$ | $CH_3$ |
| I-1963 | $CH_3$ | $CH_3$ | R3.33 | $C_2H_5$ | $CH_3$ |
| I-1964 | $C_2H_5$ | $CH_3$ | R3.33 | $C_2H_5$ | $CH_3$ |
| I-1965 | $CH_3$ | $CHF_2$ | R3.33 | $C_2H_5$ | $CH_3$ |
| I-1966 | $C_2H_5$ | $CHF_2$ | R3.33 | $C_2H_5$ | $CH_3$ |
| I-1967 | $CH_3$ | $CF_3$ | R3.33 | $C_2H_5$ | $CH_3$ |
| I-1968 | $C_2H_5$ | $CF_3$ | R3.33 | $C_2H_5$ | $CH_3$ |
| I-1969 | $CH_3$ | $CH_3$ | R3.34 | $C_2H_5$ | $CH_3$ |
| I-1970 | $C_2H_5$ | $CH_3$ | R3.34 | $C_2H_5$ | $CH_3$ |
| I-1971 | $CH_3$ | $CHF_2$ | R3.34 | $C_2H_5$ | $CH_3$ |
| I-1972 | $C_2H_5$ | $CHF_2$ | R3.34 | $C_2H_5$ | $CH_3$ |
| I-1973 | $CH_3$ | $CF_3$ | R3.34 | $C_2H_5$ | $CH_3$ |
| I-1974 | $C_2H_5$ | $CF_3$ | R3.34 | $C_2H_5$ | $CH_3$ |
| I-1975 | $CH_3$ | $CH_3$ | R3.35 | $C_2H_5$ | $CH_3$ |
| I-1976 | $C_2H_5$ | $CH_3$ | R3.35 | $C_2H_5$ | $CH_3$ |
| I-1977 | $CH_3$ | $CHF_2$ | R3.35 | $C_2H_5$ | $CH_3$ |
| I-1978 | $C_2H_5$ | $CHF_2$ | R3.35 | $C_2H_5$ | $CH_3$ |
| I-1979 | $CH_3$ | $CF_3$ | R3.35 | $C_2H_5$ | $CH_3$ |
| I-1980 | $C_2H_5$ | $CF_3$ | R3.35 | $C_2H_5$ | $CH_3$ |
| I-1981 | $CH_3$ | $CH_3$ | R3.36 | $C_2H_5$ | $CH_3$ |
| I-1982 | $C_2H_5$ | $CH_3$ | R3.36 | $C_2H_5$ | $CH_3$ |
| I-1983 | $CH_3$ | $CHF_2$ | R3.36 | $C_2H_5$ | $CH_3$ |
| I-1984 | $C_2H_5$ | $CHF_2$ | R3.36 | $C_2H_5$ | $CH_3$ |
| I-1985 | $CH_3$ | $CF_3$ | R3.36 | $C_2H_5$ | $CH_3$ |
| I-1986 | $C_2H_5$ | $CF_3$ | R3.36 | $C_2H_5$ | $CH_3$ |
| I-1987 | $CH_3$ | $CH_3$ | R3.37 | $C_2H_5$ | $CH_3$ |
| I-1988 | $C_2H_5$ | $CH_3$ | R3.37 | $C_2H_5$ | $CH_3$ |
| I-1989 | $CH_3$ | $CHF_2$ | R3.37 | $C_2H_5$ | $CH_3$ |
| I-1990 | $C_2H_5$ | $CHF_2$ | R3.37 | $C_2H_5$ | $CH_3$ |
| I-1991 | $CH_3$ | $CF_3$ | R3.37 | $C_2H_5$ | $CH_3$ |
| I-1992 | $C_2H_5$ | $CF_3$ | R3.37 | $C_2H_5$ | $CH_3$ |
| I-1993 | $CH_3$ | $CH_3$ | R3.38 | $C_2H_5$ | $CH_3$ |
| I-1994 | $C_2H_5$ | $CH_3$ | R3.38 | $C_2H_5$ | $CH_3$ |
| I-1995 | $CH_3$ | $CHF_2$ | R3.38 | $C_2H_5$ | $CH_3$ |
| I-1996 | $C_2H_5$ | $CHF_2$ | R3.38 | $C_2H_5$ | $CH_3$ |
| I-1997 | $CH_3$ | $CF_3$ | R3.38 | $C_2H_5$ | $CH_3$ |
| I-1998 | $C_2H_5$ | $CF_3$ | R3.38 | $C_2H_5$ | $CH_3$ |
| I-1999 | $CH_3$ | $CH_3$ | R3.39 | $C_2H_5$ | $CH_3$ |
| I-2000 | $C_2H_5$ | $CH_3$ | R3.39 | $C_2H_5$ | $CH_3$ |
| I-2001 | $CH_3$ | $CHF_2$ | R3.39 | $C_2H_5$ | $CH_3$ |
| I-2002 | $C_2H_5$ | $CHF_2$ | R3.39 | $C_2H_5$ | $CH_3$ |
| I-2003 | $CH_3$ | $CF_3$ | R3.39 | $C_2H_5$ | $CH_3$ |
| I-2004 | $C_2H_5$ | $CF_3$ | R3.39 | $C_2H_5$ | $CH_3$ |
| I-2005 | $CH_3$ | $CH_3$ | R3.40 | $C_2H_5$ | $CH_3$ |
| I-2006 | $C_2H_5$ | $CH_3$ | R3.40 | $C_2H_5$ | $CH_3$ |
| I-2007 | $CH_3$ | $CHF_2$ | R3.40 | $C_2H_5$ | $CH_3$ |
| I-2008 | $C_2H_5$ | $CHF_2$ | R3.40 | $C_2H_5$ | $CH_3$ |
| I-2009 | $CH_3$ | $CF_3$ | R3.40 | $C_2H_5$ | $CH_3$ |
| I-2010 | $C_2H_5$ | $CF_3$ | R3.40 | $C_2H_5$ | $CH_3$ |
| I-2011 | $CH_3$ | $CH_3$ | R3.41 | $C_2H_5$ | $CH_3$ |
| I-2012 | $C_2H_5$ | $CH_3$ | R3.41 | $C_2H_5$ | $CH_3$ |
| I-2013 | $CH_3$ | $CHF_2$ | R3.41 | $C_2H_5$ | $CH_3$ |
| I-2014 | $C_2H_5$ | $CHF_2$ | R3.41 | $C_2H_5$ | $CH_3$ |
| I-2015 | $CH_3$ | $CF_3$ | R3.41 | $C_2H_5$ | $CH_3$ |
| I-2016 | $C_2H_5$ | $CF_3$ | R3.41 | $C_2H_5$ | $CH_3$ |
| I-2017 | $CH_3$ | $CH_3$ | R3.42 | $C_2H_5$ | $CH_3$ |
| I-2018 | $C_2H_5$ | $CH_3$ | R3.42 | $C_2H_5$ | $CH_3$ |
| I-2019 | $CH_3$ | $CHF_2$ | R3.42 | $C_2H_5$ | $CH_3$ |
| I-2020 | $C_2H_5$ | $CHF_2$ | R3.42 | $C_2H_5$ | $CH_3$ |
| I-2021 | $CH_3$ | $CF_3$ | R3.42 | $C_2H_5$ | $CH_3$ |
| I-2022 | $C_2H_5$ | $CF_3$ | R3.42 | $C_2H_5$ | $CH_3$ |
| I-2023 | $CH_3$ | $CH_3$ | R3.43 | $C_2H_5$ | $CH_3$ |
| I-2024 | $C_2H_5$ | $CH_3$ | R3.43 | $C_2H_5$ | $CH_3$ |
| I-2025 | $CH_3$ | $CHF_2$ | R3.43 | $C_2H_5$ | $CH_3$ |
| I-2026 | $C_2H_5$ | $CHF_2$ | R3.43 | $C_2H_5$ | $CH_3$ |
| I-2027 | $CH_3$ | $CF_3$ | R3.43 | $C_2H_5$ | $CH_3$ |
| I-2028 | $C_2H_5$ | $CF_3$ | R3.43 | $C_2H_5$ | $CH_3$ |
| I-2029 | $CH_3$ | $CH_3$ | R3.44 | $C_2H_5$ | $CH_3$ |
| I-2030 | $C_2H_5$ | $CH_3$ | R3.44 | $C_2H_5$ | $CH_3$ |
| I-2031 | $CH_3$ | $CHF_2$ | R3.44 | $C_2H_5$ | $CH_3$ |
| I-2032 | $C_2H_5$ | $CHF_2$ | R3.44 | $C_2H_5$ | $CH_3$ |
| I-2033 | $CH_3$ | $CF_3$ | R3.44 | $C_2H_5$ | $CH_3$ |
| I-2034 | $C_2H_5$ | $CF_3$ | R3.44 | $C_2H_5$ | $CH_3$ |
| I-2035 | $CH_3$ | $CH_3$ | R3.45 | $C_2H_5$ | $CH_3$ |
| I-2036 | $C_2H_5$ | $CH_3$ | R3.45 | $C_2H_5$ | $CH_3$ |
| I-2037 | $CH_3$ | $CHF_2$ | R3.45 | $C_2H_5$ | $CH_3$ |
| I-2038 | $C_2H_5$ | $CHF_2$ | R3.45 | $C_2H_5$ | $CH_3$ |
| I-2039 | $CH_3$ | $CF_3$ | R3.45 | $C_2H_5$ | $CH_3$ |
| I-2040 | $C_2H_5$ | $CF_3$ | R3.45 | $C_2H_5$ | $CH_3$ |
| I-2041 | $CH_3$ | $CH_3$ | R3.46 | $C_2H_5$ | $CH_3$ |
| I-2042 | $C_2H_5$ | $CH_3$ | R3.46 | $C_2H_5$ | $CH_3$ |
| I-2043 | $CH_3$ | $CHF_2$ | R3.46 | $C_2H_5$ | $CH_3$ |
| I-2044 | $C_2H_5$ | $CHF_2$ | R3.46 | $C_2H_5$ | $CH_3$ |
| I-2045 | $CH_3$ | $CF_3$ | R3.46 | $C_2H_5$ | $CH_3$ |
| I-2046 | $C_2H_5$ | $CF_3$ | R3.46 | $C_2H_5$ | $CH_3$ |
| I-2047 | $CH_3$ | $CH_3$ | R3.47 | $C_2H_5$ | $CH_3$ |
| I-2048 | $C_2H_5$ | $CH_3$ | R3.47 | $C_2H_5$ | $CH_3$ |
| I-2049 | $CH_3$ | $CHF_2$ | R3.47 | $C_2H_5$ | $CH_3$ |
| I-2050 | $C_2H_5$ | $CHF_2$ | R3.47 | $C_2H_5$ | $CH_3$ |
| I-2051 | $CH_3$ | $CF_3$ | R3.47 | $C_2H_5$ | $CH_3$ |
| I-2052 | $C_2H_5$ | $CF_3$ | R3.47 | $C_2H_5$ | $CH_3$ |
| I-2053 | $CH_3$ | $CH_3$ | R3.48 | $C_2H_5$ | $CH_3$ |
| I-2054 | $C_2H_5$ | $CH_3$ | R3.48 | $C_2H_5$ | $CH_3$ |
| I-2055 | $CH_3$ | $CHF_2$ | R3.48 | $C_2H_5$ | $CH_3$ |

TABLE II-continued

| No. | R¹ | R² | R³ | R⁴ | R⁵ |
|---|---|---|---|---|---|
| I-2056 | C₂H₅ | CHF₂ | R3.48 | C₂H₅ | CH₃ |
| I-2057 | CH₃ | CF₃ | R3.48 | C₂H₅ | CH₃ |
| I-2058 | C₂H₅ | CF₃ | R3.48 | C₂H₅ | CH₃ |
| I-2059 | CH₃ | CH₃ | R3.10 | CF₃ | CH₃ |
| I-2060 | C₂H₅ | CH₃ | R3.10 | CF₃ | CH₃ |
| I-2061 | CH₃ | CHF₂ | R3.10 | CF₃ | CH₃ |
| I-2062 | C₂H₅ | CHF₂ | R3.10 | CF₃ | CH₃ |
| I-2063 | CH₃ | CF₃ | R3.10 | CF₃ | CH₃ |
| I-2064 | C₂H₅ | CF₃ | R3.10 | CF₃ | CH₃ |
| I-2065 | CH₃ | CH₃ | R3.11 | CF₃ | CH₃ |
| I-2066 | C₂H₅ | CH₃ | R3.11 | CF₃ | CH₃ |
| I-2067 | CH₃ | CHF₂ | R3.11 | CF₃ | CH₃ |
| I-2068 | C₂H₅ | CHF₂ | R3.11 | CF₃ | CH₃ |
| I-2069 | CH₃ | CF₃ | R3.11 | CF₃ | CH₃ |
| I-2070 | C₂H₅ | CF₃ | R3.11 | CF₃ | CH₃ |
| I-2071 | CH₃ | CH₃ | R3.12 | CF₃ | CH₃ |
| I-2072 | C₂H₅ | CH₃ | R3.12 | CF₃ | CH₃ |
| I-2073 | CH₃ | CHF₂ | R3.12 | CF₃ | CH₃ |
| I-2074 | C₂H₅ | CHF₂ | R3.12 | CF₃ | CH₃ |
| I-2075 | CH₃ | CF₃ | R3.12 | CF₃ | CH₃ |
| I-2076 | C₂H₅ | CF₃ | R3.12 | CF₃ | CH₃ |
| I-2077 | CH₃ | CH₃ | R3.13 | CF₃ | CH₃ |
| I-2078 | C₂H₅ | CH₃ | R3.13 | CF₃ | CH₃ |
| I-2079 | CH₃ | CHF₂ | R3.13 | CF₃ | CH₃ |
| I-2080 | C₂H₅ | CHF₂ | R3.13 | CF₃ | CH₃ |
| I-2081 | CH₃ | CF₃ | R3.13 | CF₃ | CH₃ |
| I-2082 | C₂H₅ | CF₃ | R3.13 | CF₃ | CH₃ |
| I-2083 | CH₃ | CH₃ | R3.14 | CF₃ | CH₃ |
| I-2084 | C₂H₅ | CH₃ | R3.14 | CF₃ | CH₃ |
| I-2085 | CH₃ | CHF₂ | R3.14 | CF₃ | CH₃ |
| I-2086 | C₂H₅ | CHF₂ | R3.14 | CF₃ | CH₃ |
| I-2087 | CH₃ | CF₃ | R3.14 | CF₃ | CH₃ |
| I-2088 | C₂H₅ | CF₃ | R3.14 | CF₃ | CH₃ |
| I-2089 | CH₃ | CH₃ | R3.15 | CF₃ | CH₃ |
| I-2090 | C₂H₅ | CH₃ | R3.15 | CF₃ | CH₃ |
| I-2091 | CH₃ | CHF₂ | R3.15 | CF₃ | CH₃ |
| I-2092 | C₂H₅ | CHF₂ | R3.15 | CF₃ | CH₃ |
| I-2093 | CH₃ | CF₃ | R3.15 | CF₃ | CH₃ |
| I-2094 | C₂H₅ | CF₃ | R3.15 | CF₃ | CH₃ |
| I-2095 | CH₃ | CH₃ | R3.16 | CF₃ | CH₃ |
| I-2096 | C₂H₅ | CH₃ | R3.16 | CF₃ | CH₃ |
| I-2097 | CH₃ | CHF₂ | R3.16 | CF₃ | CH₃ |
| I-2098 | C₂H₅ | CHF₂ | R3.16 | CF₃ | CH₃ |
| I-2099 | CH₃ | CF₃ | R3.16 | CF₃ | CH₃ |
| I-2100 | C₂H₅ | CF₃ | R3.16 | CF₃ | CH₃ |
| I-2101 | CH₃ | CH₃ | R3.17 | CF₃ | CH₃ |
| I-2102 | C₂H₅ | CH₃ | R3.17 | CF₃ | CH₃ |
| I-2103 | CH₃ | CHF₂ | R3.17 | CF₃ | CH₃ |
| I-2104 | C₂H₅ | CHF₂ | R3.17 | CF₃ | CH₃ |
| I-2105 | CH₃ | CF₃ | R3.17 | CF₃ | CH₃ |
| I-2106 | C₂H₅ | CF₃ | R3.17 | CF₃ | CH₃ |
| I-2107 | CH₃ | CH₃ | R3.18 | CF₃ | CH₃ |
| I-2108 | C₂H₅ | CH₃ | R3.18 | CF₃ | CH₃ |
| I-2109 | CH₃ | CHF₂ | R3.18 | CF₃ | CH₃ |
| I-2110 | C₂H₅ | CHF₂ | R3.18 | CF₃ | CH₃ |
| I-2111 | CH₃ | CF₃ | R3.18 | CF₃ | CH₃ |
| I-2112 | C₂H₅ | CF₃ | R3.18 | CF₃ | CH₃ |
| I-2113 | CH₃ | CH₃ | R3.19 | CF₃ | CH₃ |
| I-2114 | C₂H₅ | CH₃ | R3.19 | CF₃ | CH₃ |
| I-2115 | CH₃ | CHF₂ | R3.19 | CF₃ | CH₃ |
| I-2116 | C₂H₅ | CHF₂ | R3.19 | CF₃ | CH₃ |
| I-2117 | CH₃ | CF₃ | R3.19 | CF₃ | CH₃ |
| I-2118 | C₂H₅ | CF₃ | R3.19 | CF₃ | CH₃ |
| I-2119 | CH₃ | CH₃ | R3.20 | CF₃ | CH₃ |
| I-2120 | C₂H₅ | CH₃ | R3.20 | CF₃ | CH₃ |
| I-2121 | CH₃ | CHF₂ | R3.20 | CF₃ | CH₃ |
| I-2122 | C₂H₅ | CHF₂ | R3.20 | CF₃ | CH₃ |
| I-2123 | CH₃ | CF₃ | R3.20 | CF₃ | CH₃ |
| I-2124 | C₂H₅ | CF₃ | R3.20 | CF₃ | CH₃ |
| I-2125 | CH₃ | CH₃ | R3.21 | CF₃ | CH₃ |
| I-2126 | C₂H₅ | CH₃ | R3.21 | CF₃ | CH₃ |
| I-2127 | CH₃ | CHF₂ | R3.21 | CF₃ | CH₃ |
| I-2128 | C₂H₅ | CHF₂ | R3.21 | CF₃ | CH₃ |
| I-2129 | CH₃ | CF₃ | R3.21 | CF₃ | CH₃ |
| I-2130 | C₂H₅ | CF₃ | R3.21 | CF₃ | CH₃ |
| I-2131 | CH₃ | CH₃ | R3.22 | CF₃ | CH₃ |
| I-2132 | C₂H₅ | CH₃ | R3.22 | CF₃ | CH₃ |
| I-2133 | CH₃ | CHF₂ | R3.22 | CF₃ | CH₃ |
| I-2134 | C₂H₅ | CHF₂ | R3.22 | CF₃ | CH₃ |
| I-2135 | CH₃ | CF₃ | R3.22 | CF₃ | CH₃ |
| I-2136 | C₂H₅ | CF₃ | R3.22 | CF₃ | CH₃ |
| I-2137 | CH₃ | CH₃ | R3.23 | CF₃ | CH₃ |
| I-2138 | C₂H₅ | CH₃ | R3.23 | CF₃ | CH₃ |
| I-2139 | CH₃ | CHF₂ | R3.23 | CF₃ | CH₃ |
| I-2140 | C₂H₅ | CHF₂ | R3.23 | CF₃ | CH₃ |
| I-2141 | CH₃ | CF₃ | R3.23 | CF₃ | CH₃ |
| I-2142 | C₂H₅ | CF₃ | R3.23 | CF₃ | CH₃ |
| I-2143 | CH₃ | CH₃ | R3.24 | CF₃ | CH₃ |
| I-2144 | C₂H₅ | CH₃ | R3.24 | CF₃ | CH₃ |
| I-2145 | CH₃ | CHF₂ | R3.24 | CF₃ | CH₃ |
| I-2146 | C₂H₅ | CHF₂ | R3.24 | CF₃ | CH₃ |
| I-2147 | CH₃ | CF₃ | R3.24 | CF₃ | CH₃ |
| I-2148 | C₂H₅ | CF₃ | R3.24 | CF₃ | CH₃ |
| I-2149 | CH₃ | CH₃ | R3.25 | CF₃ | CH₃ |
| I-2150 | C₂H₅ | CH₃ | R3.25 | CF₃ | CH₃ |
| I-2151 | CH₃ | CHF₂ | R3.25 | CF₃ | CH₃ |
| I-2152 | C₂H₅ | CHF₂ | R3.25 | CF₃ | CH₃ |
| I-2153 | CH₃ | CF₃ | R3.25 | CF₃ | CH₃ |
| I-2154 | C₂H₅ | CF₃ | R3.25 | CF₃ | CH₃ |
| I-2155 | CH₃ | CH₃ | R3.26 | CF₃ | CH₃ |
| I-2156 | C₂H₅ | CH₃ | R3.26 | CF₃ | CH₃ |
| I-2157 | CH₃ | CHF₂ | R3.26 | CF₃ | CH₃ |
| I-2158 | C₂H₅ | CHF₂ | R3.26 | CF₃ | CH₃ |
| I-2159 | CH₃ | CF₃ | R3.26 | CF₃ | CH₃ |
| I-2160 | C₂H₅ | CF₃ | R3.26 | CF₃ | CH₃ |
| I-2161 | CH₃ | CH₃ | R3.27 | CF₃ | CH₃ |
| I-2162 | C₂H₅ | CH₃ | R3.27 | CF₃ | CH₃ |
| I-2163 | CH₃ | CHF₂ | R3.27 | CF₃ | CH₃ |
| I-2164 | C₂H₅ | CHF₂ | R3.27 | CF₃ | CH₃ |
| I-2165 | CH₃ | CF₃ | R3.27 | CF₃ | CH₃ |
| I-2166 | C₂H₅ | CF₃ | R3.27 | CF₃ | CH₃ |
| I-2167 | CH₃ | CH₃ | R3.28 | CF₃ | CH₃ |
| I-2168 | C₂H₅ | CH₃ | R3.28 | CF₃ | CH₃ |
| I-2169 | CH₃ | CHF₂ | R3.28 | CF₃ | CH₃ |
| I-2170 | C₂H₅ | CHF₂ | R3.28 | CF₃ | CH₃ |
| I-2171 | CH₃ | CF₃ | R3.28 | CF₃ | CH₃ |
| I-2172 | C₂H₅ | CF₃ | R3.28 | CF₃ | CH₃ |
| I-2173 | CH₃ | CH₃ | R3.29 | CF₃ | CH₃ |
| I-2174 | C₂H₅ | CH₃ | R3.29 | CF₃ | CH₃ |
| I-2175 | CH₃ | CHF₂ | R3.29 | CF₃ | CH₃ |
| I-2176 | C₂H₅ | CHF₂ | R3.29 | CF₃ | CH₃ |
| I-2177 | CH₃ | CF₃ | R3.29 | CF₃ | CH₃ |
| I-2178 | C₂H₅ | CF₃ | R3.29 | CF₃ | CH₃ |
| I-2179 | CH₃ | CH₃ | R3.30 | CF₃ | CH₃ |
| I-2180 | C₂H₅ | CH₃ | R3.30 | CF₃ | CH₃ |
| I-2181 | CH₃ | CHF₂ | R3.30 | CF₃ | CH₃ |
| I-2182 | C₂H₅ | CHF₂ | R3.30 | CF₃ | CH₃ |
| I-2183 | CH₃ | CF₃ | R3.30 | CF₃ | CH₃ |
| I-2184 | C₂H₅ | CF₃ | R3.30 | CF₃ | CH₃ |
| I-2185 | CH₃ | CH₃ | R3.31 | CF₃ | CH₃ |
| I-2186 | C₂H₅ | CH₃ | R3.31 | CF₃ | CH₃ |
| I-2187 | CH₃ | CHF₂ | R3.31 | CF₃ | CH₃ |
| I-2188 | C₂H₅ | CHF₂ | R3.31 | CF₃ | CH₃ |
| I-2189 | CH₃ | CF₃ | R3.31 | CF₃ | CH₃ |
| I-2190 | C₂H₅ | CF₃ | R3.31 | CF₃ | CH₃ |
| I-2191 | CH₃ | CH₃ | R3.32 | CF₃ | CH₃ |
| I-2192 | C₂H₅ | CH₃ | R3.32 | CF₃ | CH₃ |
| I-2193 | CH₃ | CHF₂ | R3.32 | CF₃ | CH₃ |
| I-2194 | C₂H₅ | CHF₂ | R3.32 | CF₃ | CH₃ |
| I-2195 | CH₃ | CF₃ | R3.32 | CF₃ | CH₃ |
| I-2196 | C₂H₅ | CF₃ | R3.32 | CF₃ | CH₃ |
| I-2197 | CH₃ | CH₃ | R3.33 | CF₃ | CH₃ |
| I-2198 | C₂H₅ | CH₃ | R3.33 | CF₃ | CH₃ |
| I-2199 | CH₃ | CHF₂ | R3.33 | CF₃ | CH₃ |
| I-2200 | C₂H₅ | CHF₂ | R3.33 | CF₃ | CH₃ |
| I-2201 | CH₃ | CF₃ | R3.33 | CF₃ | CH₃ |
| I-2202 | C₂H₅ | CF₃ | R3.33 | CF₃ | CH₃ |
| I-2203 | CH₃ | CH₃ | R3.34 | CF₃ | CH₃ |
| I-2204 | C₂H₅ | CH₃ | R3.34 | CF₃ | CH₃ |
| I-2205 | CH₃ | CHF₂ | R3.34 | CF₃ | CH₃ |
| I-2206 | C₂H₅ | CHF₂ | R3.34 | CF₃ | CH₃ |
| I-2207 | CH₃ | CF₃ | R3.34 | CF₃ | CH₃ |
| I-2208 | C₂H₅ | CF₃ | R3.34 | CF₃ | CH₃ |
| I-2209 | CH₃ | CH₃ | R3.35 | CF₃ | CH₃ |
| I-2210 | C₂H₅ | CH₃ | R3.35 | CF₃ | CH₃ |
| I-2211 | CH₃ | CHF₂ | R3.35 | CF₃ | CH₃ |

TABLE II-continued

| No. | R¹ | R² | R³ | R⁴ | R⁵ |
|---|---|---|---|---|---|
| I-2212 | $C_2H_5$ | $CHF_2$ | R3.35 | $CF_3$ | $CH_3$ |
| I-2213 | $CH_3$ | $CF_3$ | R3.35 | $CF_3$ | $CH_3$ |
| I-2214 | $C_2H_5$ | $CF_3$ | R3.35 | $CF_3$ | $CH_3$ |
| I-2215 | $CH_3$ | $CH_3$ | R3.36 | $CF_3$ | $CH_3$ |
| I-2216 | $C_2H_5$ | $CH_3$ | R3.36 | $CF_3$ | $CH_3$ |
| I-2217 | $CH_3$ | $CHF_2$ | R3.36 | $CF_3$ | $CH_3$ |
| I-2218 | $C_2H_5$ | $CHF_2$ | R3.36 | $CF_3$ | $CH_3$ |
| I-2219 | $CH_3$ | $CF_3$ | R3.36 | $CF_3$ | $CH_3$ |
| I-2220 | $C_2H_5$ | $CF_3$ | R3.36 | $CF_3$ | $CH_3$ |
| I-2221 | $CH_3$ | $CH_3$ | R3.37 | $CF_3$ | $CH_3$ |
| I-2222 | $C_2H_5$ | $CH_3$ | R3.37 | $CF_3$ | $CH_3$ |
| I-2223 | $CH_3$ | $CHF_2$ | R3.37 | $CF_3$ | $CH_3$ |
| I-2224 | $C_2H_5$ | $CHF_2$ | R3.37 | $CF_3$ | $CH_3$ |
| I-2225 | $CH_3$ | $CF_3$ | R3.37 | $CF_3$ | $CH_3$ |
| I-2226 | $C_2H_5$ | $CF_3$ | R3.37 | $CF_3$ | $CH_3$ |
| I-2227 | $CH_3$ | $CH_3$ | R3.38 | $CF_3$ | $CH_3$ |
| I-2228 | $C_2H_5$ | $CH_3$ | R3.38 | $CF_3$ | $CH_3$ |
| I-2229 | $CH_3$ | $CHF_2$ | R3.38 | $CF_3$ | $CH_3$ |
| I-2230 | $C_2H_5$ | $CHF_2$ | R3.38 | $CF_3$ | $CH_3$ |
| I-2231 | $CH_3$ | $CF_3$ | R3.38 | $CF_3$ | $CH_3$ |
| I-2232 | $C_2H_5$ | $CF_3$ | R3.38 | $CF_3$ | $CH_3$ |
| I-2233 | $CH_3$ | $CH_3$ | R3.39 | $CF_3$ | $CH_3$ |
| I-2234 | $C_2H_5$ | $CH_3$ | R3.39 | $CF_3$ | $CH_3$ |
| I-2235 | $CH_3$ | $CHF_2$ | R3.39 | $CF_3$ | $CH_3$ |
| I-2236 | $C_2H_5$ | $CHF_2$ | R3.39 | $CF_3$ | $CH_3$ |
| I-2237 | $CH_3$ | $CF_3$ | R3.39 | $CF_3$ | $CH_3$ |
| I-2238 | $C_2H_5$ | $CF_3$ | R3.39 | $CF_3$ | $CH_3$ |
| I-2239 | $CH_3$ | $CH_3$ | R3.40 | $CF_3$ | $CH_3$ |
| I-2240 | $C_2H_5$ | $CH_3$ | R3.40 | $CF_3$ | $CH_3$ |
| I-2241 | $CH_3$ | $CHF_2$ | R3.40 | $CF_3$ | $CH_3$ |
| I-2242 | $C_2H_5$ | $CHF_2$ | R3.40 | $CF_3$ | $CH_3$ |
| I-2243 | $CH_3$ | $CF_3$ | R3.40 | $CF_3$ | $CH_3$ |
| I-2244 | $C_2H_5$ | $CF_3$ | R3.40 | $CF_3$ | $CH_3$ |
| I-2245 | $CH_3$ | $CH_3$ | R3.41 | $CF_3$ | $CH_3$ |
| I-2246 | $C_2H_5$ | $CH_3$ | R3.41 | $CF_3$ | $CH_3$ |
| I-2247 | $CH_3$ | $CHF_2$ | R3.41 | $CF_3$ | $CH_3$ |
| I-2248 | $C_2H_5$ | $CHF_2$ | R3.41 | $CF_3$ | $CH_3$ |
| I-2249 | $CH_3$ | $CF_3$ | R3.41 | $CF_3$ | $CH_3$ |
| I-2250 | $C_2H_5$ | $CF_3$ | R3.41 | $CF_3$ | $CH_3$ |
| I-2251 | $CH_3$ | $CH_3$ | R3.42 | $CF_3$ | $CH_3$ |
| I-2252 | $C_2H_5$ | $CH_3$ | R3.42 | $CF_3$ | $CH_3$ |
| I-2253 | $CH_3$ | $CHF_2$ | R3.42 | $CF_3$ | $CH_3$ |
| I-2254 | $C_2H_5$ | $CHF_2$ | R3.42 | $CF_3$ | $CH_3$ |
| I-2255 | $CH_3$ | $CF_3$ | R3.42 | $CF_3$ | $CH_3$ |
| I-2256 | $C_2H_5$ | $CF_3$ | R3.42 | $CF_3$ | $CH_3$ |
| I-2257 | $CH_3$ | $CH_3$ | R3.43 | $CF_3$ | $CH_3$ |
| I-2258 | $C_2H_5$ | $CH_3$ | R3.43 | $CF_3$ | $CH_3$ |
| I-2259 | $CH_3$ | $CHF_2$ | R3.43 | $CF_3$ | $CH_3$ |
| I-2260 | $C_2H_5$ | $CHF_2$ | R3.43 | $CF_3$ | $CH_3$ |
| I-2261 | $CH_3$ | $CF_3$ | R3.43 | $CF_3$ | $CH_3$ |
| I-2262 | $C_2H_5$ | $CF_3$ | R3.43 | $CF_3$ | $CH_3$ |
| I-2263 | $CH_3$ | $CH_3$ | R3.44 | $CF_3$ | $CH_3$ |
| I-2264 | $C_2H_5$ | $CH_3$ | R3.44 | $CF_3$ | $CH_3$ |
| I-2265 | $CH_3$ | $CHF_2$ | R3.44 | $CF_3$ | $CH_3$ |
| I-2266 | $C_2H_5$ | $CHF_2$ | R3.44 | $CF_3$ | $CH_3$ |
| I-2267 | $CH_3$ | $CF_3$ | R3.44 | $CF_3$ | $CH_3$ |
| I-2268 | $C_2H_5$ | $CF_3$ | R3.44 | $CF_3$ | $CH_3$ |
| I-2269 | $CH_3$ | $CH_3$ | R3.45 | $CF_3$ | $CH_3$ |
| I-2270 | $C_2H_5$ | $CH_3$ | R3.45 | $CF_3$ | $CH_3$ |
| I-2271 | $CH_3$ | $CHF_2$ | R3.45 | $CF_3$ | $CH_3$ |
| I-2272 | $C_2H_5$ | $CHF_2$ | R3.45 | $CF_3$ | $CH_3$ |
| I-2273 | $CH_3$ | $CF_3$ | R3.45 | $CF_3$ | $CH_3$ |
| I-2274 | $C_2H_5$ | $CF_3$ | R3.45 | $CF_3$ | $CH_3$ |
| I-2275 | $CH_3$ | $CH_3$ | R3.46 | $CF_3$ | $CH_3$ |
| I-2276 | $C_2H_5$ | $CH_3$ | R3.46 | $CF_3$ | $CH_3$ |
| I-2277 | $CH_3$ | $CHF_2$ | R3.46 | $CF_3$ | $CH_3$ |
| I-2278 | $C_2H_5$ | $CHF_2$ | R3.46 | $CF_3$ | $CH_3$ |
| I-2279 | $CH_3$ | $CF_3$ | R3.46 | $CF_3$ | $CH_3$ |
| I-2280 | $C_2H_5$ | $CF_3$ | R3.46 | $CF_3$ | $CH_3$ |
| I-2281 | $CH_3$ | $CH_3$ | R3.47 | $CF_3$ | $CH_3$ |
| I-2282 | $C_2H_5$ | $CH_3$ | R3.47 | $CF_3$ | $CH_3$ |
| I-2283 | $CH_3$ | $CHF_2$ | R3.47 | $CF_3$ | $CH_3$ |
| I-2284 | $C_2H_5$ | $CHF_2$ | R3.47 | $CF_3$ | $CH_3$ |
| I-2285 | $CH_3$ | $CF_3$ | R3.47 | $CF_3$ | $CH_3$ |
| I-2286 | $C_2H_5$ | $CF_3$ | R3.47 | $CF_3$ | $CH_3$ |
| I-2287 | $CH_3$ | $CH_3$ | R3.48 | $CF_3$ | $CH_3$ |
| I-2288 | $C_2H_5$ | $CH_3$ | R3.48 | $CF_3$ | $CH_3$ |
| I-2289 | $CH_3$ | $CHF_2$ | R3.48 | $CF_3$ | $CH_3$ |
| I-2290 | $C_2H_5$ | $CHF_2$ | R3.48 | $CF_3$ | $CH_3$ |
| I-2291 | $CH_3$ | $CF_3$ | R3.48 | $CF_3$ | $CH_3$ |
| I-2292 | $C_2H_5$ | $CF_3$ | R3.48 | $CF_3$ | $CH_3$ |

TABLE III

| No. | R¹ | R² | R³ | R⁴ | R⁵ |
|---|---|---|---|---|---|
| I-2293 | $CH_3$ | $CH_3$ | R3.49 | H | |
| I-2294 | $C_2H_5$ | $CH_3$ | R3.49 | H | |
| I-2295 | $CH_3$ | $CHF_2$ | R3.49 | H | |
| I-2296 | $C_2H_5$ | $CHF_2$ | R3.49 | H | |
| I-2297 | $CH_3$ | $CF_3$ | R3.49 | H | |
| I-2298 | $C_2H_5$ | $CF_3$ | R3.49 | H | |
| I-2299 | $CH_3$ | $CH_3$ | R3.50 | H | |
| I-2300 | $C_2H_5$ | $CH_3$ | R3.50 | H | |
| I-2301 | $CH_3$ | $CHF_2$ | R3.50 | H | |
| I-2302 | $C_2H_5$ | $CHF_2$ | R3.50 | H | |
| I-2303 | $CH_3$ | $CF_3$ | R3.50 | H | |
| I-2304 | $C_2H_5$ | $CF_3$ | R3.50 | H | |
| I-2305 | $CH_3$ | $CH_3$ | R3.51 | H | |
| I-2306 | $C_2H_5$ | $CH_3$ | R3.51 | H | |
| I-2307 | $CH_3$ | $CHF_2$ | R3.51 | H | |
| I-2308 | $C_2H_5$ | $CHF_2$ | R3.51 | H | |
| I-2309 | $CH_3$ | $CF_3$ | R3.51 | H | |
| I-2310 | $C_2H_5$ | $CF_3$ | R3.51 | H | |
| I-2311 | $CH_3$ | $CH_3$ | R3.52 | H | |
| I-2312 | $C_2H_5$ | $CH_3$ | R3.52 | H | |
| I-2313 | $CH_3$ | $CHF_2$ | R3.52 | H | |
| I-2314 | $C_2H_5$ | $CHF_2$ | R3.52 | H | |
| I-2315 | $CH_3$ | $CF_3$ | R3.52 | H | |
| I-2316 | $C_2H_5$ | $CF_3$ | R3.52 | H | |
| I-2317 | $CH_3$ | $CH_3$ | R3.53 | H | |
| I-2318 | $C_2H_5$ | $CH_3$ | R3.53 | H | |
| I-2319 | $CH_3$ | $CHF_2$ | R3.53 | H | |
| I-2320 | $C_2H_5$ | $CHF_2$ | R3.53 | H | |
| I-2321 | $CH_3$ | $CF_3$ | R3.53 | H | |
| I-2322 | $C_2H_5$ | $CF_3$ | R3.53 | H | |
| I-2323 | $CH_3$ | $CH_3$ | R3.49 | $CH_3$ | |
| I-2324 | $C_2H_5$ | $CH_3$ | R3.49 | $CH_3$ | |
| I-2325 | $CH_3$ | $CHF_2$ | R3.49 | $CH_3$ | |
| I-2326 | $C_2H_5$ | $CHF_2$ | R3.49 | $CH_3$ | |
| I-2327 | $CH_3$ | $CF_3$ | R3.49 | $CH_3$ | |
| I-2328 | $C_2H_5$ | $CF_3$ | R3.49 | $CH_3$ | |
| I-2329 | $CH_3$ | $CH_3$ | R3.50 | $CH_3$ | |
| I-2330 | $C_2H_5$ | $CH_3$ | R3.50 | $CH_3$ | |
| I-2331 | $CH_3$ | $CHF_2$ | R3.50 | $CH_3$ | |
| I-2332 | $C_2H_5$ | $CHF_2$ | R3.50 | $CH_3$ | |
| I-2333 | $CH_3$ | $CF_3$ | R3.50 | $CH_3$ | |
| I-2334 | $C_2H_5$ | $CF_3$ | R3.50 | $CH_3$ | |
| I-2335 | $CH_3$ | $CH_3$ | R3.51 | $CH_3$ | |
| I-2336 | $C_2H_5$ | $CH_3$ | R3.51 | $CH_3$ | |
| I-2337 | $CH_3$ | $CHF_2$ | R3.51 | $CH_3$ | |
| I-2338 | $C_2H_5$ | $CHF_2$ | R3.51 | $CH_3$ | |
| I-2339 | $CH_3$ | $CF_3$ | R3.51 | $CH_3$ | |
| I-2340 | $C_2H_5$ | $CF_3$ | R3.51 | $CH_3$ | |
| I-2341 | $CH_3$ | $CH_3$ | R3.52 | $CH_3$ | |
| I-2342 | $C_2H_5$ | $CH_3$ | R3.52 | $CH_3$ | |
| I-2343 | $CH_3$ | $CHF_2$ | R3.52 | $CH_3$ | |
| I-2344 | $C_2H_5$ | $CHF_2$ | R3.52 | $CH_3$ | |
| I-2345 | $CH_3$ | $CF_3$ | R3.52 | $CH_3$ | |
| I-2346 | $C_2H_5$ | $CF_3$ | R3.52 | $CH_3$ | |
| I-2347 | $CH_3$ | $CH_3$ | R3.53 | $CH_3$ | |
| I-2348 | $C_2H_5$ | $CH_3$ | R3.53 | $CH_3$ | |
| I-2349 | $CH_3$ | $CHF_2$ | R3.53 | $CH_3$ | |
| I-2350 | $C_2H_5$ | $CHF_2$ | R3.53 | $CH_3$ | |
| I-2351 | $CH_3$ | $CF_3$ | R3.53 | $CH_3$ | |
| I-2352 | $C_2H_5$ | $CF_3$ | R3.53 | $CH_3$ | |
| I-2353 | $CH_3$ | $CH_3$ | R3.49 | CN | |
| I-2354 | $C_2H_5$ | $CH_3$ | R3.49 | CN | |
| I-2355 | $CH_3$ | $CHF_2$ | R3.49 | CN | |
| I-2356 | $C_2H_5$ | $CHF_2$ | R3.49 | CN | |
| I-2357 | $CH_3$ | $CF_3$ | R3.49 | CN | |
| I-2358 | $C_2H_5$ | $CF_3$ | R3.49 | CN | |
| I-2359 | $CH_3$ | $CH_3$ | R3.50 | CN | |

TABLE III-continued

| No. | R¹ | R² | R³ | R⁴ | R⁵ |
|---|---|---|---|---|---|
| I-2360 | C₂H₅ | CH₃ | | R3.50 | CN |
| I-2361 | CH₃ | CHF₂ | | R3.50 | CN |
| I-2362 | C₂H₅ | CHF₂ | | R3.50 | CN |
| I-2363 | CH₃ | CF₃ | | R3.50 | CN |
| I-2364 | C₂H₅ | CF₃ | | R3.50 | CN |
| I-2365 | CH₃ | CH₃ | | R3.51 | CN |
| I-2366 | C₂H₅ | CH₃ | | R3.51 | CN |
| I-2367 | CH₃ | CHF₂ | | R3.51 | CN |
| I-2368 | C₂H₅ | CHF₂ | | R3.51 | CN |
| I-2369 | CH₃ | CF₃ | | R3.51 | CN |
| I-2370 | C₂H₅ | CF₃ | | R3.51 | CN |
| I-2371 | CH₃ | CH₃ | | R3.52 | CN |
| I-2372 | C₂H₅ | CH₃ | | R3.52 | CN |
| I-2373 | CH₃ | CHF₂ | | R3.52 | CN |
| I-2374 | C₂H₅ | CHF₂ | | R3.52 | CN |
| I-2375 | CH₃ | CF₃ | | R3.52 | CN |
| I-2376 | C₂H₅ | CF₃ | | R3.52 | CN |
| I-2377 | CH₃ | CH₃ | | R3.53 | CN |
| I-2378 | C₂H₅ | CH₃ | | R3.53 | CN |
| I-2379 | CH₃ | CHF₂ | | R3.53 | CN |
| I-2380 | C₂H₅ | CHF₂ | | R3.53 | CN |
| I-2381 | CH₃ | CF₃ | | R3.53 | CN |
| I-2382 | C₂H₅ | CF₃ | | R3.53 | CN |
| I-2383 | CH₃ | CH₃ | | R3.49 | F |
| I-2384 | C₂H₅ | CH₃ | | R3.49 | F |
| I-2385 | CH₃ | CHF₂ | | R3.49 | F |
| I-2386 | C₂H₅ | CHF₂ | | R3.49 | F |
| I-2387 | CH₃ | CF₃ | | R3.49 | F |
| I-2388 | C₂H₅ | CF₃ | | R3.49 | F |
| I-2389 | CH₃ | CH₃ | | R3.50 | F |
| I-2390 | C₂H₅ | CH₃ | | R3.50 | F |
| I-2391 | CH₃ | CHF₂ | | R3.50 | F |
| I-2392 | C₂H₅ | CHF₂ | | R3.50 | F |
| I-2393 | CH₃ | CF₃ | | R3.50 | F |
| I-2394 | C₂H₅ | CF₃ | | R3.50 | F |
| I-2395 | CH₃ | CH₃ | | R3.51 | F |
| I-2396 | C₂H₅ | CH₃ | | R3.51 | F |
| I-2397 | CH₃ | CHF₂ | | R3.51 | F |
| I-2398 | C₂H₅ | CHF₂ | | R3.51 | F |
| I-2399 | CH₃ | CF₃ | | R3.51 | F |
| I-2400 | C₂H₅ | CF₃ | | R3.51 | F |
| I-2401 | CH₃ | CH₃ | | R3.52 | F |
| I-2402 | C₂H₅ | CH₃ | | R3.52 | F |
| I-2403 | CH₃ | CHF₂ | | R3.52 | F |
| I-2404 | C₂H₅ | CHF₂ | | R3.52 | F |
| I-2405 | CH₃ | CF₃ | | R3.52 | F |
| I-2406 | C₂H₅ | CF₃ | | R3.52 | F |
| I-2407 | CH₃ | CH₃ | | R3.53 | F |
| I-2408 | C₂H₅ | CH₃ | | R3.53 | F |
| I-2409 | CH₃ | CHF₂ | | R3.53 | F |
| I-2410 | C₂H₅ | CHF₂ | | R3.53 | F |
| I-2411 | CH₃ | CF₃ | | R3.53 | F |
| I-2412 | C₂H₅ | CF₃ | | R3.53 | F |
| I-2413 | CH₃ | CH₃ | | R3.49 | CF₃ |
| I-2414 | C₂H₅ | CH₃ | | R3.49 | CF₃ |
| I-2415 | CH₃ | CHF₂ | | R3.49 | CF₃ |
| I-2416 | C₂H₅ | CHF₂ | | R3.49 | CF₃ |
| I-2417 | CH₃ | CF₃ | | R3.49 | CF₃ |
| I-2418 | C₂H₅ | CF₃ | | R3.49 | CF₃ |
| I-2419 | CH₃ | CH₃ | | R3.50 | CF₃ |
| I-2420 | C₂H₅ | CH₃ | | R3.50 | CF₃ |
| I-2421 | CH₃ | CHF₂ | | R3.50 | CF₃ |
| I-2422 | C₂H₅ | CHF₂ | | R3.50 | CF₃ |
| I-2423 | CH₃ | CF₃ | | R3.50 | CF₃ |
| I-2424 | C₂H₅ | CF₃ | | R3.50 | CF₃ |
| I-2425 | CH₃ | CH₃ | | R3.51 | CF₃ |
| I-2426 | C₂H₅ | CH₃ | | R3.51 | CF₃ |
| I-2427 | CH₃ | CHF₂ | | R3.51 | CF₃ |
| I-2428 | C₂H₅ | CHF₂ | | R3.51 | CF₃ |
| I-2429 | CH₃ | CF₃ | | R3.51 | CF₃ |
| I-2430 | C₂H₅ | CF₃ | | R3.51 | CF₃ |
| I-2431 | CH₃ | CH₃ | | R3.52 | CF₃ |
| I-2432 | C₂H₅ | CH₃ | | R3.52 | CF₃ |
| I-2433 | CH₃ | CHF₂ | | R3.52 | CF₃ |
| I-2434 | C₂H₅ | CHF₂ | | R3.52 | CF₃ |
| I-2435 | CH₃ | CF₃ | | R3.52 | CF₃ |
| I-2436 | C₂H₅ | CF₃ | | R3.52 | CF₃ |
| I-2437 | CH₃ | CH₃ | | R3.53 | CF₃ |
| I-2438 | C₂H₅ | CH₃ | | R3.53 | CF₃ |
| I-2439 | CH₃ | CHF₂ | | R3.53 | CF₃ |
| I-2440 | C₂H₅ | CHF₂ | | R3.53 | CF₃ |
| I-2441 | CH₃ | CF₃ | | R3.53 | CF₃ |
| I-2442 | C₂H₅ | CF₃ | | R3.53 | CF₃ |
| I-2443 | CH₃ | CH₃ | | R3.49 | OCH₃ |
| I-2444 | C₂H₅ | CH₃ | | R3.49 | OCH₃ |
| I-2445 | CH₃ | CHF₂ | | R3.49 | OCH₃ |
| I-2446 | C₂H₅ | CHF₂ | | R3.49 | OCH₃ |
| I-2447 | CH₃ | CF₃ | | R3.49 | OCH₃ |
| I-2448 | C₂H₅ | CF₃ | | R3.49 | OCH₃ |
| I-2449 | CH₃ | CH₃ | | R3.50 | OCH₃ |
| I-2450 | C₂H₅ | CH₃ | | R3.50 | OCH₃ |
| I-2451 | CH₃ | CHF₂ | | R3.50 | OCH₃ |
| I-2452 | C₂H₅ | CHF₂ | | R3.50 | OCH₃ |
| I-2453 | CH₃ | CF₃ | | R3.50 | OCH₃ |
| I-2454 | C₂H₅ | CF₃ | | R3.50 | OCH₃ |
| I-2455 | CH₃ | CH₃ | | R3.51 | OCH₃ |
| I-2456 | C₂H₅ | CH₃ | | R3.51 | OCH₃ |
| I-2457 | CH₃ | CHF₂ | | R3.51 | OCH₃ |
| I-2458 | C₂H₅ | CHF₂ | | R3.51 | OCH₃ |
| I-2459 | CH₃ | CF₃ | | R3.51 | OCH₃ |
| I-2460 | C₂H₅ | CF₃ | | R3.51 | OCH₃ |
| I-2461 | CH₃ | CH₃ | | R3.52 | OCH₃ |
| I-2462 | C₂H₅ | CH₃ | | R3.52 | OCH₃ |
| I-2463 | CH₃ | CHF₂ | | R3.52 | OCH₃ |
| I-2464 | C₂H₅ | CHF₂ | | R3.52 | OCH₃ |
| I-2465 | CH₃ | CF₃ | | R3.52 | OCH₃ |
| I-2466 | C₂H₅ | CF₃ | | R3.52 | OCH₃ |
| I-2467 | CH₃ | CH₃ | | R3.53 | OCH₃ |
| I-2468 | C₂H₅ | CH₃ | | R3.53 | OCH₃ |
| I-2469 | CH₃ | CHF₂ | | R3.53 | OCH₃ |
| I-2470 | C₂H₅ | CHF₂ | | R3.53 | OCH₃ |
| I-2471 | CH₃ | CF₃ | | R3.53 | OCH₃ |
| I-2472 | C₂H₅ | CF₃ | | R3.53 | OCH₃ |
| I-2473 | CH₃ | CH₃ | | R3.49 | SCH₃ |
| I-2474 | C₂H₅ | CH₃ | | R3.49 | SCH₃ |
| I-2475 | CH₃ | CHF₂ | | R3.49 | SCH₃ |
| I-2476 | C₂H₅ | CHF₂ | | R3.49 | SCH₃ |
| I-2477 | CH₃ | CF₃ | | R3.49 | SCH₃ |
| I-2478 | C₂H₅ | CF₃ | | R3.49 | SCH₃ |
| I-2479 | CH₃ | CH₃ | | R3.50 | SCH₃ |
| I-2480 | C₂H₅ | CH₃ | | R3.50 | SCH₃ |
| I-2481 | CH₃ | CHF₂ | | R3.50 | SCH₃ |
| I-2482 | C₂H₅ | CHF₂ | | R3.50 | SCH₃ |
| I-2483 | CH₃ | CF₃ | | R3.50 | SCH₃ |
| I-2484 | C₂H₅ | CF₃ | | R3.50 | SCH₃ |
| I-2485 | CH₃ | CH₃ | | R3.51 | SCH₃ |
| I-2486 | C₂H₅ | CH₃ | | R3.51 | SCH₃ |
| I-2487 | CH₃ | CHF₂ | | R3.51 | SCH₃ |
| I-2488 | C₂H₅ | CHF₂ | | R3.51 | SCH₃ |
| I-2489 | CH₃ | CF₃ | | R3.51 | SCH₃ |
| I-2490 | C₂H₅ | CF₃ | | R3.51 | SCH₃ |
| I-2491 | CH₃ | CH₃ | | R3.52 | SCH₃ |
| I-2492 | C₂H₅ | CH₃ | | R3.52 | SCH₃ |
| I-2493 | CH₃ | CHF₂ | | R3.52 | SCH₃ |
| I-2494 | C₂H₅ | CHF₂ | | R3.52 | SCH₃ |
| I-2495 | CH₃ | CF₃ | | R3.52 | SCH₃ |
| I-2496 | C₂H₅ | CF₃ | | R3.52 | SCH₃ |
| I-2497 | CH₃ | CH₃ | | R3.53 | SCH₃ |
| I-2498 | C₂H₅ | CH₃ | | R3.53 | SCH₃ |
| I-2499 | CH₃ | CHF₂ | | R3.53 | SCH₃ |
| I-2500 | C₂H₅ | CHF₂ | | R3.53 | SCH₃ |
| I-2501 | CH₃ | CF₃ | | R3.53 | SCH₃ |
| I-2502 | C₂H₅ | CF₃ | | R3.53 | SCH₃ |
| I-2503 | CH₃ | CH₃ | | R3.49 | OCF₃ |
| I-2504 | C₂H₅ | CH₃ | | R3.49 | OCF₃ |
| I-2505 | CH₃ | CHF₂ | | R3.49 | OCF₃ |
| I-2506 | C₂H₅ | CHF₂ | | R3.49 | OCF₃ |
| I-2507 | CH₃ | CF₃ | | R3.49 | OCF₃ |
| I-2508 | C₂H₅ | CF₃ | | R3.49 | OCF₃ |
| I-2509 | CH₃ | CH₃ | | R3.50 | OCF₃ |
| I-2510 | C₂H₅ | CH₃ | | R3.50 | OCF₃ |
| I-2511 | CH₃ | CHF₂ | | R3.50 | OCF₃ |
| I-2512 | C₂H₅ | CHF₂ | | R3.50 | OCF₃ |
| I-2513 | CH₃ | CF₃ | | R3.50 | OCF₃ |
| I-2514 | C₂H₅ | CF₃ | | R3.50 | OCF₃ |
| I-2515 | CH₃ | CH₃ | | R3.51 | OCF₃ |

TABLE III-continued

| No. | R¹ | R² | R³ | R⁴ | R⁵ |
|---|---|---|---|---|---|
| I-2516 | C₂H₅ | CH₃ | | R3.51 | OCF₃ |
| I-2517 | CH₃ | CHF₂ | | R3.51 | OCF₃ |
| I-2518 | C₂H₅ | CHF₂ | | R3.51 | OCF₃ |
| I-2519 | CH₃ | CF₃ | | R3.51 | OCF₃ |
| I-2520 | C₂H₅ | CF₃ | | R3.51 | OCF₃ |
| I-2521 | CH₃ | CH₃ | | R3.52 | OCF₃ |
| I-2522 | C₂H₅ | CH₃ | | R3.52 | OCF₃ |
| I-2523 | CH₃ | CHF₂ | | R3.52 | OCF₃ |
| I-2524 | C₂H₅ | CHF₂ | | R3.52 | OCF₃ |
| I-2525 | CH₃ | CF₃ | | R3.52 | OCF₃ |
| I-2526 | C₂H₅ | CF₃ | | R3.52 | OCF₃ |
| I-2527 | CH₃ | CH₃ | | R3.53 | OCF₃ |
| I-2528 | C₂H₅ | CH₃ | | R3.53 | OCF₃ |
| I-2529 | CH₃ | CHF₂ | | R3.53 | OCF₃ |
| I-2530 | C₂H₅ | CHF₂ | | R3.53 | OCF₃ |
| I-2531 | CH₃ | CF₃ | | R3.53 | OCF₃ |
| I-2532 | C₂H₅ | CF₃ | | R3.53 | OCF₃ |
| I-2533 | CH₃ | CH₃ | | R3.49 | SCF₃ |
| I-2534 | C₂H₅ | CH₃ | | R3.49 | SCF₃ |
| I-2535 | CH₃ | CHF₂ | | R3.49 | SCF₃ |
| I-2536 | C₂H₅ | CHF₂ | | R3.49 | SCF₃ |
| I-2537 | CH₃ | CF₃ | | R3.49 | SCF₃ |
| I-2538 | C₂H₅ | CF₃ | | R3.49 | SCF₃ |
| I-2539 | CH₃ | CH₃ | | R3.50 | SCF₃ |
| I-2540 | C₂H₅ | CH₃ | | R3.50 | SCF₃ |
| I-2541 | CH₃ | CHF₂ | | R3.50 | SCF₃ |
| I-2542 | C₂H₅ | CHF₂ | | R3.50 | SCF₃ |
| I-2543 | CH₃ | CF₃ | | R3.50 | SCF₃ |
| I-2544 | C₂H₅ | CF₃ | | R3.50 | SCF₃ |
| I-2545 | CH₃ | CH₃ | | R3.51 | SCF₃ |
| I-2546 | C₂H₅ | CH₃ | | R3.51 | SCF₃ |
| I-2547 | CH₃ | CHF₂ | | R3.51 | SCF₃ |
| I-2548 | C₂H₅ | CHF₂ | | R3.51 | SCF₃ |
| I-2549 | CH₃ | CF₃ | | R3.51 | SCF₃ |
| I-2550 | C₂H₅ | CF₃ | | R3.51 | SCF₃ |
| I-2551 | CH₃ | CH₃ | | R3.52 | SCF₃ |
| I-2552 | C₂H₅ | CH₃ | | R3.52 | SCF₃ |
| I-2553 | CH₃ | CHF₂ | | R3.52 | SCF₃ |
| I-2554 | C₂H₅ | CHF₂ | | R3.52 | SCF₃ |
| I-2555 | CH₃ | CF₃ | | R3.52 | SCF₃ |
| I-2556 | C₂H₅ | CF₃ | | R3.52 | SCF₃ |
| I-2557 | CH₃ | CH₃ | | R3.53 | SCF₃ |
| I-2558 | C₂H₅ | CH₃ | | R3.53 | SCF₃ |
| I-2559 | CH₃ | CHF₂ | | R3.53 | SCF₃ |
| I-2560 | C₂H₅ | CHF₂ | | R3.53 | SCF₃ |
| I-2561 | CH₃ | CF₃ | | R3.53 | SCF₃ |
| I-2562 | C₂H₅ | CF₃ | | R3.53 | SCF₃ |

TABLE IV

| No | R¹ | R² | R³ | R⁴ | R⁵ |
|---|---|---|---|---|---|
| I-2563 | CH₃ | CH₃ | | R3.54 | H |
| I-2564 | C₂H₅ | CH₃ | | R3.54 | H |
| I-2565 | CH₃ | CH₂F | | R3.54 | H |
| I-2566 | C₂H₅ | CH₂F | | R3.54 | H |
| I-2567 | CH₃ | CF₃ | | R3.54 | H |
| I-2568 | C₂H₅ | CF₃ | | R3.54 | H |
| I-2569 | CH₃ | CH₃ | | R3.55 | H |
| I-2570 | C₂H₅ | CH₃ | | R3.55 | H |
| I-2571 | CH₃ | CH₂F | | R3.55 | H |
| I-2572 | C₂H₅ | CH₂F | | R3.55 | H |
| I-2573 | CH₃ | CF₃ | | R3.55 | H |
| I-2574 | C₂H₅ | CF₃ | | R3.55 | H |
| I-2575 | CH₃ | CH₃ | | R3.56 | H |
| I-2576 | C₂H₅ | CH₃ | | R3.56 | H |
| I-2577 | CH₃ | CH₂F | | R3.56 | H |
| I-2578 | C₂H₅ | CH₂F | | R3.56 | H |
| I-2579 | CH₃ | CF₃ | | R3.56 | H |
| I-2580 | C₂H₅ | CF₃ | | R3.56 | H |
| I-2581 | CH₃ | CH₃ | | R3.57 | H |
| I-2582 | C₂H₅ | CH₃ | | R3.57 | H |
| I-2583 | CH₃ | CH₂F | | R3.57 | H |
| I-2584 | C₂H₅ | CH₂F | | R3.57 | H |
| I-2585 | CH₃ | CF₃ | | R3.57 | H |

TABLE IV-continued

| No | R¹ | R² | R³ | R⁴ | R⁵ |
|---|---|---|---|---|---|
| I-2586 | C₂H₅ | CF₃ | | R3.57 | H |
| I-2587 | CH₃ | CH₃ | | R3.58 | H |
| I-2588 | C₂H₅ | CH₃ | | R3.58 | H |
| I-2589 | CH₃ | CH₂F | | R3.58 | H |
| I-2590 | C₂H₅ | CH₂F | | R3.58 | H |
| I-2591 | CH₃ | CF₃ | | R3.58 | H |
| I-2592 | C₂H₅ | CF₃ | | R3.58 | H |
| I-2593 | CH₃ | CH₃ | | R3.59 | H |
| I-2594 | C₂H₅ | CH₃ | | R3.59 | H |
| I-2595 | CH₃ | CH₂F | | R3.59 | H |
| I-2596 | C₂H₅ | CH₂F | | R3.59 | H |
| I-2597 | CH₃ | CF₃ | | R3.59 | H |
| I-2598 | C₂H₅ | CF₃ | | R3.59 | H |
| I-2599 | CH₃ | CH₃ | | R3.60 | H |
| I-2600 | C₂H₅ | CH₃ | | R3.60 | H |
| I-2601 | CH₃ | CH₂F | | R3.60 | H |
| I-2602 | C₂H₅ | CH₂F | | R3.60 | H |
| I-2603 | CH₃ | CF₃ | | R3.60 | H |
| I-2604 | C₂H₅ | CF₃ | | R3.60 | H |
| I-2605 | CH₃ | CH₃ | | R3.61 | H |
| I-2606 | C₂H₅ | CH₃ | | R3.61 | H |
| I-2607 | CH₃ | CH₂F | | R3.61 | H |
| I-2608 | C₂H₅ | CH₂F | | R3.61 | H |
| I-2609 | CH₃ | CF₃ | | R3.61 | H |
| I-2610 | C₂H₅ | CF₃ | | R3.61 | H |
| I-2611 | CH₃ | CH₃ | | R3.62 | H |
| I-2612 | C₂H₅ | CH₃ | | R3.62 | H |
| I-2613 | CH₃ | CH₂F | | R3.62 | H |
| I-2614 | C₂H₅ | CH₂F | | R3.62 | H |
| I-2615 | CH₃ | CF₃ | | R3.62 | H |
| I-2616 | C₂H₅ | CF₃ | | R3.62 | H |
| I-2617 | CH₃ | CH₃ | | R3.54 | CH₃ |
| I-2618 | C₂H₅ | CH₃ | | R3.54 | CH₃ |
| I-2619 | CH₃ | CH₂F | | R3.54 | CH₃ |
| I-2620 | C₂H₅ | CH₂F | | R3.54 | CH₃ |
| I-2621 | CH₃ | CF₃ | | R3.54 | CH₃ |
| I-2622 | C₂H₅ | CF₃ | | R3.54 | CH₃ |
| I-2623 | CH₃ | CH₃ | | R3.55 | CH₃ |
| I-2624 | C₂H₅ | CH₃ | | R3.55 | CH₃ |
| I-2625 | CH₃ | CH₂F | | R3.55 | CH₃ |
| I-2626 | C₂H₅ | CH₂F | | R3.55 | CH₃ |
| I-2627 | CH₃ | CF₃ | | R3.55 | CH₃ |
| I-2628 | C₂H₅ | CF₃ | | R3.55 | CH₃ |
| I-2629 | CH₃ | CH₃ | | R3.56 | CH₃ |
| I-2630 | C₂H₅ | CH₃ | | R3.56 | CH₃ |
| I-2631 | CH₃ | CH₂F | | R3.56 | CH₃ |
| I-2632 | C₂H₅ | CH₂F | | R3.56 | CH₃ |
| I-2633 | CH₃ | CF₃ | | R3.56 | CH₃ |
| I-2634 | C₂H₅ | CF₃ | | R3.56 | CH₃ |
| I-2635 | CH₃ | CH₃ | | R3.57 | CH₃ |
| I-2636 | C₂H₅ | CH₃ | | R3.57 | CH₃ |
| I-2637 | CH₃ | CH₂F | | R3.57 | CH₃ |
| I-2638 | C₂H₅ | CH₂F | | R3.57 | CH₃ |
| I-2639 | CH₃ | CF₃ | | R3.57 | CH₃ |
| I-2640 | C₂H₅ | CF₃ | | R3.57 | CH₃ |
| I-2641 | CH₃ | CH₃ | | R3.58 | CH₃ |
| I-2642 | C₂H₅ | CH₃ | | R3.58 | CH₃ |
| I-2643 | CH₃ | CH₂F | | R3.58 | CH₃ |
| I-2644 | C₂H₅ | CH₂F | | R3.58 | CH₃ |
| I-2645 | CH₃ | CF₃ | | R3.58 | CH₃ |
| I-2646 | C₂H₅ | CF₃ | | R3.58 | CH₃ |
| I-2647 | CH₃ | CH₃ | | R3.59 | CH₃ |
| I-2648 | C₂H₅ | CH₃ | | R3.59 | CH₃ |
| I-2649 | CH₃ | CH₂F | | R3.59 | CH₃ |
| I-2650 | C₂H₅ | CH₂F | | R3.59 | CH₃ |
| I-2651 | CH₃ | CF₃ | | R3.59 | CH₃ |
| I-2652 | C₂H₅ | CF₃ | | R3.59 | CH₃ |
| I-2653 | CH₃ | CH₃ | | R3.60 | CH₃ |
| I-2654 | C₂H₅ | CH₃ | | R3.60 | CH₃ |
| I-2655 | CH₃ | CH₂F | | R3.60 | CH₃ |
| I-2656 | C₂H₅ | CH2F | | R3.60 | CH₃ |
| I-2657 | CH₃ | CF₃ | | R3.60 | CH₃ |
| I-2658 | C₂H₅ | CF₃ | | R3.60 | CH₃ |
| I-2659 | CH₃ | CH₃ | | R3.61 | CH₃ |
| I-2660 | C₂H₅ | CH₃ | | R3.61 | CH₃ |
| I-2661 | CH₃ | CH₂F | | R3.61 | CH₃ |
| I-2662 | C₂H₅ | CH₂F | | R3.61 | CH₃ |
| I-2663 | CH₃ | CF₃ | | R3.61 | CH₃ |

TABLE IV-continued

| No | $R^1$ | $R^2$ | $R^3$ | $R^4$ | $R^5$ |
|---|---|---|---|---|---|
| I-2664 | $C_2H_5$ | $CF_3$ | R3.61 | | $CH_3$ |
| I-2665 | $CH_3$ | $CH_3$ | R3.62 | | $CH_3$ |
| I-2666 | $C_2H_5$ | $CH_3$ | R3.62 | | $CH_3$ |
| I-2667 | $CH_3$ | $CH_2F$ | R3.62 | | $CH_3$ |
| I-2668 | $C_2H_5$ | $CH_2F$ | R3.62 | | $CH_3$ |
| I-2669 | $CH_3$ | $CF_3$ | R3.62 | | $CH_3$ |
| I-2670 | $C_2H_5$ | $CF_3$ | R3.62 | | $CH_3$ |
| I-2671 | $CH_3$ | $CH_3$ | R3.54 | | CN |
| I-2672 | $C_2H_5$ | $CH_3$ | R3.54 | | CN |
| I-2673 | $CH_3$ | $CH_2F$ | R3.54 | | CN |
| I-2674 | $C_2H_5$ | $CH_2F$ | R3.54 | | CN |
| I-2675 | $CH_3$ | $CF_3$ | R3.54 | | CN |
| I-2676 | $C_2H_5$ | $CF_3$ | R3.54 | | CN |
| I-2677 | $CH_3$ | $CH_3$ | R3.55 | | CN |
| I-2678 | $C_2H_5$ | $CH_3$ | R3.55 | | CN |
| I-2697 | $CH_3$ | $CH_2F$ | R3.58 | | CN |
| I-2698 | $C_2H_5$ | $CH_2F$ | R3.58 | | CN |
| I-2699 | $CH_3$ | $CF_3$ | R3.58 | | CN |
| I-2700 | $C_2H_5$ | $CF_3$ | R3.58 | | CN |
| I-2701 | $CH_3$ | $CH_3$ | R3.59 | | CN |
| I-2702 | $C_2H_5$ | $CH_3$ | R3.59 | | CN |
| I-2703 | $CH_3$ | $CH_2F$ | R3.59 | | CN |
| I-2704 | $C_2H_5$ | $CH_2F$ | R3.59 | | CN |
| I-2705 | $CH_3$ | $CF_3$ | R3.59 | | CN |
| I-2706 | $C_2H_5$ | $CF_3$ | R3.59 | | CN |
| I-2707 | $CH_3$ | $CH_3$ | R3.60 | | CN |
| I-2708 | $C_2H_5$ | $CH_3$ | R3.60 | | CN |
| I-2709 | $CH_3$ | $CH_2F$ | R3.60 | | CN |
| I-2710 | $C_2H_5$ | $CH_2F$ | R3.60 | | CN |
| I-2711 | $CH_3$ | $CF_3$ | R3.60 | | CN |
| I-2712 | $C_2H_5$ | $CF_3$ | R3.60 | | CN |
| I-2713 | $CH_3$ | $CH_3$ | R3.61 | | CN |
| I-2714 | $C_2H_5$ | $CH_3$ | R3.61 | | CN |
| I-2715 | $CH_3$ | $CH_2F$ | R3.61 | | CN |
| I-2716 | $C_2H_5$ | $CH_2F$ | R3.61 | | CN |
| I-2717 | $CH_3$ | $CF_3$ | R3.61 | | CN |
| I-2718 | $C_2H_5$ | $CF_3$ | R3.61 | | CN |
| I-2719 | $CH_3$ | $CH_3$ | R3.62 | | CN |
| I-2720 | $C_2H_5$ | $CH_3$ | R3.62 | | CN |
| I-2721 | $CH_3$ | $CH_2F$ | R3.62 | | CN |
| I-2722 | $C_2H_5$ | $CH_2F$ | R3.62 | | CN |
| I-2723 | $CH_3$ | $CF_3$ | R3.62 | | CN |
| I-2724 | $C_2H_5$ | $CF_3$ | R3.62 | | CN |

The examples of compounds of formula I of table I include their tautomers, racemic mixtures, individual pure enantiomers and diasteroemers and their optically active mixtures.

Some of the compounds of the formula I are novel. Thus the present invention also relates to the novel compounds I-S as defined above.

In compounds I-S, $R^1$ is preferably H, $C_1$-$C_2$-alkyl, or $C_1$-$C_2$-alkoxymethyl, in particular $CH_3$ or $C_2H_5$. $R^2$ is preferably $CH_3$, $CHF_2$, or $CF_3$.

In compounds I-S, the variable $R^3$ is preferably a monospiro or dispiro 5-, 6-, 7-, 8-, 9- or 10-membered carbocycle which is unsubstituted or substituted by 1 or 2 radicals $R^{a3}$. $R^{a3}$, if present, is preferably selected from cyano, $C_1$-$C_2$-haloalkyl, $C_1$-$C_2$-alkylidene and $C_1$-$C_2$-alkoxy-$C_1$-$C_2$-alkyl. Substituents $R^{a3}$ are preferably in 1- or 4-position, if the carbocycle is monosubstituted and in 4,4-position, if the carbocycle is disubstituted. More preferably, $R^3$ is spiro[2.2]pentyl, which is unsubstituted or carries one or two radicals $R^{a3}$ or 7-dispiro[2.0.1.2]-heptyl which is unsubstituted or carries a radical $R^3$. $R^3$ is even more preferably selected from the group consisting of spiro[2.2]pentyl(R3.1), 2-methylene-spiro[2.2]pentyl(R3.2), 1-CN-spiro[2.2]pentyl(R3.3), 1-($CF_3$)spiro[2.2]pentyl(R3.4), 4,4-($CH_3$)$_2$-spiro[2.2]pentyl (R3.5), 4-$CH_3$-spiro[2.2]pentyl(R3.6), 4-($CF_3$)-spiro[2.2] pentyl(R3.7), 4-($CH_2OCH_3$)-spiro[2.2]pentyl(R3.8), and 7-dispiro[2.0.2.1]-heptyl(R3.9).

In compounds I-S, the variable $R^4$ is preferably $C_1$-$C_4$-alkyl or $C_1$-$C_4$-haloalkyl, in particular $CH_3$, $C_2H_5$, $CHF_2$, or $CF_3$.

In compounds I-S, the variable $R^5$ is preferably H, $CH_3$, CN, F, $OCH_3$, $SCH_3$, $CF_3$, $OCF_3$, or $SCF_3$ Examples for compounds I-S are compounds I-1 to I-432 compiled in table I above.

Specific compounds of this embodiment are compiled in table V below.

TABLE V

| No. | $R^1$ | $R^2$ | $R^3$ | R4 | $R^5$ |
|---|---|---|---|---|---|
| V-1 | H | $CH_3$ | spiro[2.2]pentyl | $CH_3$ | H |
| V-2 | $CH_3$ | $CH_3$ | spiro[2.2]pentyl | $CH_3$ | H |
| V-3 | $CH_2CH_3$ | $CH_3$ | spiro[2.2]pentyl | $CH_3$ | H |
| V-4 | H | $CH_3$ | 1-CN-spiro[2.2]pentyl | $CH_3$ | H |
| V-5 | $CH_3$ | $CH_3$ | 1-CN-spiro[2.2]pentyl | $CH_3$ | H |
| V-6 | $CH_2CH_3$ | $CH_3$ | 1-CN-spiro[2.2]pentyl | $CH_3$ | H |
| V-7 | H | $CH_3$ | 4,4-($CH_3$)$_2$-spiro[2.2]pentyl | $CH_3$ | H |
| V-8 | $CH_3$ | $CH_3$ | 4,4-($CH_3$)$_2$-spiro[2.2]pentyl | $CH_3$ | H |
| V-9 | $CH_2CH_3$ | $CH_3$ | 4,4-($CH_3$)$_2$-spiro[2.2]pentyl | $CH_3$ | H |
| V-10 | H | $CH_3$ | 4-($CH_2OCH_3$)-spiro[2.2]pentyl | $CH_3$ | H |
| V-11 | $CH_3$ | $CH_3$ | 4-($CH_2OCH_3$)-spiro[2.2]pentyl | $CH_3$ | H |
| V-12 | $CH_2CH_3$ | $CH_3$ | 4-($CH_2OCH_3$)-spiro[2.2]pentyl | $CH_3$ | H |
| V-13 | H | $CH_3$ | 1-[C(=)$NH_2$]-spiro[2.2]pentyl | $CH_3$ | H |
| V-14 | $CH_3$ | $CH_3$ | 1-[C(=)$NH_2$]-spiro[2.2]pentyl | $CH_3$ | H |
| V-15 | $CH_2CH_3$ | $CH_3$ | 1-[C(=)$NH_2$]-spiro[2.2]pentyl | $CH_3$ | H |

The present invention also relates to compounds I-S' as defined above:

In compounds I-S', the variable $R^1$ is preferably H, $C_1$-$C_2$-alkyl, or $C_1$-$C_2$-alkoxymethyl, in particular $CH_3$ or $C_2H_5$. In compounds I-S', the variable $R^2$ is preferably $CH_3$, $CHF_2$, or $CF_3$. In compounds I-S', the variable $R^5$ is preferably H, $CH_3$, CN, F, $OCH_3$, $SCH_3$, $CF_3$, $OCF_3$, or $SCF_3$.

In compounds I-S', the variables $R^3$ and $R^4$ together with the carbon atom, to which they are attached, form a monospiro or dispiro 5-, 6-, 7-, 8-, 9- or 10-membered carbour heterocycle, which may contain 1 or 2 heteroatom moieties selected from N—$R^c$, O, and S(O)$_k$ with k being 0, 1 or 2, which monospiro or dispiro 5- to 10-membered carbour heterocycle is unsubstituted or may be substituted by 1, 2, 3 or 4 radicals $R^{a3}$. $R^{a3}$, if present, is preferably selected from CN, $C_1$-$C_2$-haloalkyl, $C_1$-$C_2$-alkylidene, and $C_1$-$C_2$-alkoxy-$C_1$-$C_2$-alkyl. In another embodiment $R^{a3}$ is haloalkyl, preferably $CHF_2$, or $CF_3$, preferred $CF_3$. Substituents $R^{a3}$ are preferably in 1- or 4-position, if the carbocycle is monosubstituted and in 4,4-position, if the carbocycle is disubstituted. More preferably, $R^3$ and $R^4$ together with the carbon atom, to which they are attached, form a monospiro or dispiro 5-, 6-, 7-, 8-, 9- or 10-membered carbocycle which is unsubstituted or substituted by 1 or 2 radicals $R^{a3}$. Even more preferably, $R^3$ and $R^4$ together with the carbon atom, to which they are attached, form spiro[2.2]pentyl, which is unsubstituted or carries 1 or 2 radicals $R^{a3}$ or 7-dispiro [2.0.1.2]-heptyl which is unsubstituted or carries a radical $R^{a3}$. Specially, $R^3$ and $R^4$ together with the carbon atom, to which they are attached, form a radical selected from spiro[2.2]pentyl(R3.54), 2-methylene-spiro[2.2]pentyl (R3.55), 1-CN-spiro[2.2]pentyl(R3.56), 1-$CF_3$-spiro[2.2] pentyl(R3.57), 4,4-($CH_3$)$_2$-spiro[2.2]pentyl(R3.58), 4-$CH_3$-spiro[2.2]pentyl(R3.59), 4-($CF_3$)-spiro[2.2]pentyl(R3.60) 4-($CH_2OCH_3$)-spiro[2.2]pentyl(R3.61), and 7-dispiro [2.0.1.2]-heptyl(R3.62).

Examples of compounds I-S' are compounds I-2563 to I-2724 compiled in table IV above. Specific examples are compiled in table VI below:

| No. | R¹ | R² | R³ | R⁵ |
|---|---|---|---|---|
| VI-1 | H | CH₃ | spiro[2.2]pentyl | H |
| VI-2 | CH₃ | CH₃ | spiro[2.2]pentyl | H |
| VI-3 | CH₂CH₃ | CH₃ | spiro[2.2]pentyl | H |
| VI-4 | H | CH₃ | 7-dispiro[2.0.1.2]-heptyl | H |
| VI-5 | CH₃ | CH₃ | 7-dispiro[2.0.1.2]-heptyl | H |
| VI-6 | CH₂CH₃ | CH₃ | 7-dispiro[2.0.1.2]-heptyl | H |
| VI-7 | H | CH₃ | 4,4-(CH₃)₂-spiro[2.2]pentyl | H |
| VI-8 | CH₃ | CH₃ | 4,4-(CH₃)₂-spiro[2.2]pentyl | H |
| VI-9 | CH₂CH₃ | CH₃ | 4,4-(CH₃)₂-spiro[2.2]pentyl | H |
| VI-10 | H | CH₃ | 4-CH₃-spiro[2.2]pentyl | H |
| VI-11 | CH₃ | CH₃ | 4-CH₃-spiro[2.2]pentyl | H |
| VI-12 | CH₂CH₃ | CH₃ | 4-CH₃-spiro[2.2]pentyl | H |
| VI-13 | H | CH₃ | 4-(CF₃)-spiro[2.2]pentyl | H |
| VI-14 | CH₃ | CH₃ | 4-(CF₃)-spiro[2.2]pentyl | H |
| VI-15 | CH₂CH₃ | CH₃ | 4-(CF₃)-spiro[2.2]pentyl | H |
| VI-16 | H | CH₃ | 4-(CH₂OCH₃)-spiro[2.2]pentyl | H |
| VI-17 | CH₃ | CH₃ | 4-(CH₂OCH₃)-spiro[2.2]pentyl | H |
| VI-18 | CH₂CH₃ | CH₃ | 4-(CH₂OCH₃)-spiro[2.2]pentyl | H |
| VI-19 | H | CH₃ | 2-methylene-spiro[2.2]pentyl | H |
| VI-20 | CH₃ | CH₃ | 2-methylene-spiro[2.2]pentyl | H |
| VI-21 | CH₂CH₃ | CH₃ | 2-methylene-spiro[2.2]pentyl | H |
| VI-22 | H | CH₃ | 1,4-dioxaspiro[4.5]decan-8-yl | H |
| VI-23 | CH₃ | CH₃ | 1,4-dioxaspiro[4.5]decan-8-yl | H |
| VI-24 | CH₂CH₃ | CH₃ | 1,4-dioxaspiro[4.5]decan-8-yl | H |
| VI-25 | H | CH₃ | 5-oxaspiro[2.5]octan-8-yl | H |
| VI-26 | CH₃ | CH₃ | 5-oxaspiro[2.5]octan-8-yl | H |
| VI-27 | CH₂CH₃ | CH₃ | 5-oxaspiro[2.5]octan-8-yl | H |
| VI-28 | H | CH₃ | 5,8-dioxaspiro[3.4]octan-2-yl | H |
| VI-29 | CH₃ | CH₃ | 5,8-dioxaspiro[3.4]octan-2-yl | H |
| VI-30 | CH₂CH₃ | CH₃ | 5,8-dioxaspiro[3.4]octan-2-yl | H |

The present invention also relates to compounds of the formula I, which are selected from the compounds of the following groups I-a, I-b, I-c and I-d as defined above.

The present invention also relates to compounds of the formula I, which are selected from the compounds of the following groups I-a, I-c and I-d.

In an embodiment, the invention relates to compounds of the group I-a.

In another embodiment, the invention relates to compounds of the group I-b.

In another embodiment, the invention relates to compounds of the group I-c.

In another embodiment, the invention relates to compounds of the group I-d.

In compounds I-a, the variable $R^3$ is a variable R3.10, R3.11, R3.12, R3.13, R3.14, R3.15 or R3.16 as defined above. Examples of the compounds I-a are the compounds I-433 to I-474 and I-1363 to I-1398 compiled in table II.

In compounds I-b, the variable $R^3$ is a variable R3.17, R3.18, R3.19, R3.20, R3.21, R3.22, R3.23, R3.24, R3.25, R3.26, R3.27, R3.28, R3.29, R3.30, R3.31, R3.32, R3.33, R3.34, R3.35, R3.36, R3.37, R3.38, R3.39, R3.40, R3.41, R3.42, R3.43, R3.44, or R3.45 as defined above. In compounds I-b, the variable $R^3$ is preferably a variable R3.18, R3.20, R3.21, R3.24, R3.25, R3.26, R3.27, R3.28, R3.30, R3.31, R3.33, R3.34, R3.35, R3.36, R3.37, R3.38, R3.39, R3.41, R3.42, or R3.43 as defined above. Examples of compounds I-b are the compounds I-475 to I-648, I-705 to I-714, I-717 to I-732, I-735 to I-738, I-741 to I-742, I-744 to I-792, I-793 to I-822, I-825 to I-864, I-867 to I-876, I-931 to I-1104, I-1165 to I-1338, I-1399 to I-1572, I-1633 to I-1806, I-1867 to I-2040, and 1-2101 to I-2274 compiled in table II. A preferred group of examples of compounds I-b are the compounds I-475 to I-648, I-705, I-706, I-709 to I-714, I-717, I-718, I-721 to I-732, I-735, I-736, I-741 to I-742, I-745 to I-774, I-777, I-778, I-781 to I-792, I-795, I-796, I-799 to I-822, I-825 to I-840, I-843, I-844, I-847 to I-864, I-867, I-868, I-873, I-874, I-931 to I-1104, I-1167 to I-1168, I-1171 to I-1176, I-1179, I-1180, I-1183 to I-1194, I-1197, I-1198, I-1203, I-1204, I-1207 to I-1236, I-1239, I-1240, I-1243 to I-1254, I-1257, I-1258, I-1261 to I-1302, I-1305, I-1306, I-1309 to I-1326, I-1329, I-1330, I-1335, I-1336, I-1399 to I-1572, I-1633 to I-1806, I-1867 to I-2040, and I-2101 to I-2274 compiled in table II.

In compounds I-c, the variables $R^3$ and $R^4$ together are a variable R3.49, R3.50 or R3.51 as defined above. Examples of compounds I-c are compiled in table III as compounds I-2293 to I-2310, I-2323 to I-2340, I-2353 to I-2370, I-2383 to I-2400, I-2413 to I-2430, I-2443 to I-2460, I-2473 to I-2490, I-2503 to I-2521 and I-2534 to I-2550.

In compounds I-d, the variables $R^3$ and $R^4$ together are a variable R3.52 and R3.53 as defined above. Examples of compounds I-d are compiled in table III as compounds I-2311 to I-2322, I-2341 to I-2352, I-2371 to I-2382, I-2401 to I-2412, I-2431 to I-2442, I-2461 to I-2472, I-2491 to I-2502, I-2521 to I-2532 and I-2551 to I-2562.

The compounds according to the invention can be prepared analogously to the synthesis routes described in WO 2009/027393 and WO 2010/034737 according to standard processes of organic chemistry, for example according to the following synthesis route:

Compounds of formula I, can be prepared e.g. by reacting activated pyrazole carboxylic acid derivative II with a 3-aminopyridine, or 4-aminopyridazine of formula III (e.g. Houben-Weyl: "Methoden der organ. Chemie" [Methods of Organic Chemistry], Georg-Thieme-Verlag, Stuttgart, N.Y. 1985, Volume E5, pp. 941-1045) as outlined in scheme 1

Scheme 1:

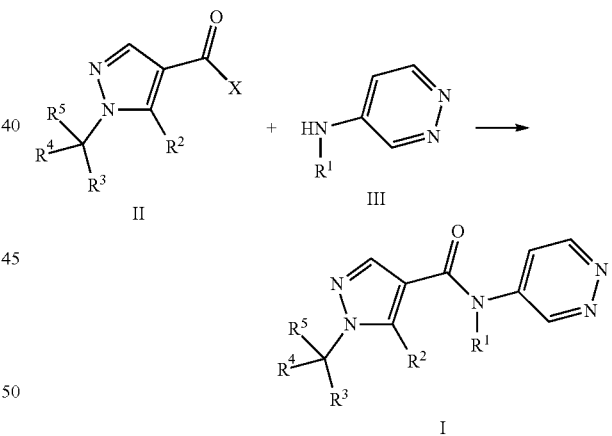

In scheme 1, $R^1$, $R^2$, $R^3$, $R^4$ and $R^5$ are as defined above. Activated pyrazole carboxylic acid derivatives II are preferably halides, activated esters, anhydrides, azides, for example chlorides, fluorides, bromides, para-nitrophenyl esters, pentafluorophenyl esters, N-hydroxysuccinimides, hydroxybenzotriazol-1-yl esters. For example, X is a suitable leaving group such as halogen, $N_3$, p-nitrophenoxy or pentafluorophenoxy and the like.

Compounds of formula I, wherein $R^1$ is different from hydrogen can also be prepared by alkylating the amides I, in which $R^1$ is hydrogen, using suitable alkylating agents in the presence of bases. The alkylation can be effected under standard conditions known from literature.

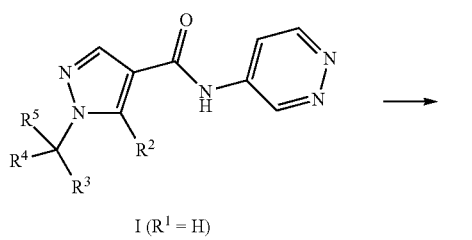

I (R¹ = H)

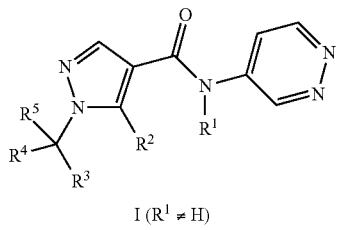

I (R¹ ≠ H)

Formula I compounds may be present in three isomeric forms:

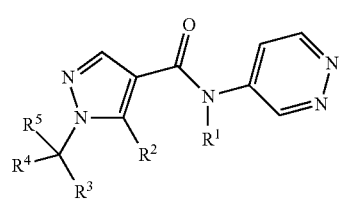

T-A

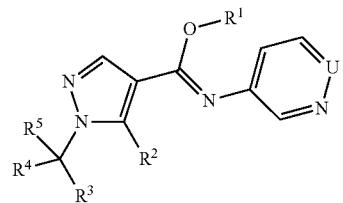

T-B

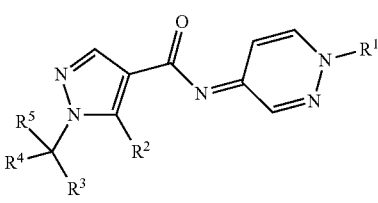

T-C

For reasons of clarity it is referred to isomer T-A only throughout the specification, but its description embraces disclosure of the other isomers as well.

Isomer T-C can be obtained by alkylation of compounds I, wherein R¹ is hydrogen. The reaction can be performed by analogy to known N-alkylation of pyridazines. N-alkylation of pyridazines is known in literature and can be found in e.g.: J. Chem. Soc., Perkin Trans. Vol. 1, p. 401 (1988), and J. Org. Chem. Vol. 46, p. 2467 (1981).

The compounds II and III are known in the art or are commercially available or can be prepared by methods known from the literature (cf. WO 05/040169; WO 08/074824; Journal of Fluorine chemistry 132(11), p. 995 (2011)).

N-oxides of the compounds of formula I, can be prepared by oxidation of compounds I according to standard methods of preparing heteroaromatic N-oxides, e.g. by the method described in Journal of Organometallic Chemistry 1989, 370, 17-31.

If individual compounds cannot be prepared via the above-described routes, they can be prepared by derivatization of other compounds I or by customary modifications of the synthesis routes described. For example, in individual cases, certain compounds I can advantageously be prepared from other compounds I by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

A particular group of preferred embodiments of the invention are pesticidal combinations, where the pyrazole compound A is a compound of formula I, a stereoisomer, salt, tautomer or N-oxides thereof, wherein the variables $R^1$, $R^2$, $R^3$, $R^4$ and $R^5$ have the following meanings: $R^1$ is $CH_3$, or $C_2H_5$; $R^2$ is $CH_3$; $R^3$ is $CH(CH_3)_2$, $CHF_2$, 1-cyanocyclopropyl, 2,2-difluoroethyl, 2,2,2-trifluoroethyl, 1-cyano-1-methylethyl, 1-fluoroethyl or spiro[2.2]pentyl, 1-cyanospiro[2.2]pentyl; $R^4$ is $CH_3$, or $R^3$ and $R^4$ together with the carbon atom, to which they are bound, form a spiro[2.2]pentyl radical; and $R^5$ is H or CN.

Especially preferred embodiments of the invention are pesticidal combinations wherein in each case the pyrazole compound A is selected from a compound of the formula I, where $R^1$ is $C_2H_5$, $R^2$ is $CH_3$, $R^3$ is $CHF_2$, $R^4$ is $CH_3$ and $R^5$ is H (compound I-680); a compound of the formula I, where $R^1$ is $C_2H_5$, $R^2$ is $CH_3$, $R^3$ is 1-CN-c-$C_3H_4$, $R^4$ is $CH_3$ and $R^5$ is H (compound I-698); a compound of the formula I, where $R^1$ is $CH_3$, $R^2$ is $CH_3$, $R^3$ is $CH(CH_3)_2$, $R^4$ is $CH_3$ and $R^5$ is H (compound I-673); and a compound of the formula I, where $R^1$ is $C_2H_5$, $R^2$ is $CH_3$, $R^3$ is $CH(CH_3)_2$, $R^4$ is $CH_3$ and $R^5$ is H (compound I-674).

Further especially preferred embodiments of the invention are pesticidal combinations wherein in each case the pyrazole compound A selected from compounds I is selected from compounds I-1, I-2, I-13, I-14, I-679, I-697, I-775, I-776, I-793, I-794, I-871, I-872, I-877, 878, I-2563, I-2564, I-2671 and I-2672.

One embodiment of the invention relates to pesticidal mixtures of at least a compound of formula I with at least one compound B from the groups A.1 to A.17.

A preferred embodiment of the invention relates to pesticidal mixtures of a compound of formula I with one compound B from the groups A.1 to A.17.

A further embodiment of relates to mixtures of a compound of the formula I with at least one active compound B selected from the group A.1.

A further embodiment of relates to mixtures of a compound of the formula I with at least one active compound B selected from the group A.2.

A further embodiment of relates to mixtures of a compound of the formula I with at least one active compound B selected from the group A.3.

A further embodiment of relates to mixtures of a compound of the formula I with at least one active compound B selected from the group A.4.

A further embodiment of relates to mixtures of a compound of the formula I with at least one active compound B selected from the group A.5.

A further embodiment of relates to mixtures of a compound of the formula I with at least one active compound B selected from the group A.6.

A further embodiment of relates to mixtures of a compound of the formula I with at least one active compound B selected from the group A.7.

A further embodiment of relates to mixtures of a compound of the formula I with at least one active compound B selected from the group A.8.

A further embodiment of relates to mixtures of a compound of the formula I with at least one active compound B selected from the group A.9.

A further embodiment of relates to mixtures of a compound of the formula I with at least one active compound B selected from the group A.10.

A further embodiment of relates to mixtures of a compound of the formula I with at least one active compound B selected from the group A.11.

A further embodiment of relates to mixtures of a compound of the formula I with at least one active compound B selected from the group A.12.

A further embodiment of relates to mixtures of a compound of the formula I with at least one active compound B selected from the group A.13.

A further embodiment of relates to mixtures of a compound of the formula I with at least one active compound B selected from the group A.14.

A further embodiment of relates to mixtures of a compound of the formula I with at least one active compound B selected from the group A.15.

A further embodiment of relates to mixtures of a compound of the formula I with at least one active compound B selected from the group A.16.

A further embodiment of relates to mixtures of a compound of the formula I with at least one active compound B selected from the group A.17.

Binary mixtures of a compound of formula I and a compound B from the groups A.1 to A.17 are one preferred embodiment of the invention.

Ternary mixtures of a compound of formula I and two compounds B from the groups A.1 to A.17 are another preferred embodiment of the invention.

With respect to their use in the pesticidal mixtures of the present invention, particular preference is given to the compounds B from the groups A.1 to A.17 as listed in the paragraphs below:

The compound B selected from group A.2 as defined above is preferably acrinathrin, bifenthrin, cyfluthrin, lambda-cyhalothrin, cypermethrin, alpha-cypermethrin, beta-cypermethrin, zeta-cypermethin, deltamethrin, esfenvalerate, etofenprox, fenpropathrin, flucythrinate, tau-fluvalinate, silafluofen or tralomethrin.

The compound B selected from group A.3 as defined above is preferably acetamiprid, clothianidin, dinotefuran, imidacloprid, thiamethoxam, nitenpyram or thiacloprid.

The compound B selected from group A.4 as defined above is preferably ethiprole or fipronil.

The compound B selected from group A.5 as defined above is preferably abamectin, emamectin benzoate or lepimectin.

The compound B selected from group A.6 as defined above is preferably chlorfenapyr.

The compound B selected from group A.8 as defined above is preferably flonicamid or pymetrozine.

The compound B selected from group A.10 as defined above is preferably spiromesifen or spirotetramat.

The compound B selected from group A.11 as defined above is preferably flubendiamide.

The compound B selected from group A.13 as defined above is preferably chloranthraniliprole (rynaxypyr) or cyantraniliprole.

The compound B selected from group A.16 as defined above is preferably 4-{[(6-chloropyrid-3-yl)methyl](2,2-difluoroethyl)amino}furan-2(5H)-on (A16.3).

The compound B selected from group A.17 is preferably pyrifluquinazon, sulfoxaflor or afidopyropen (cyclopropaneacetic acid, [(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester).

A particular group of embodiments of relates to mixtures of a compound of the formula I with at least one active compound B selected from the group consisting of fipronil, alpha-cypermethrin, thiamethoxam, abamectin, spirotetramat, imidacioprid, flonicamid, chloranthraniliprole, pymetrozine, sulfoxaflor and afidopyropen.

In another embodiment, the invention relates to mixtures of a compound of formula I with at least one active compound B selected from the group consisting of the compound A17.3, and A17.4a) to A17.4h): A17.3) 3,4-dihydro-2,4-dioxo-1-(pyrimidin-5-ylmethyl)-3-[3-(trifluoromethyl)phenyl]-2H-pyrido[1,2-a]pyrimidin-1-ium-3-ide, A17.4a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; A17.4b)-N-[4-chloro-2-[(diethyl-lambda-4-sulfanylidene)carbamoyl]-6-methy-phenyl]-2-(3-chloro-2-pyridyl)-5-(trifluoromethyl)pyrazole-3-carboxamide; A17.4c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; A17.4d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

A17.4e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; A17.4f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; A17.4g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; A17.4h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide.

Especially preferred are inventive mixtures wherein the compound B is fipronil and the compound I of formula I is a compound of Table I, Table II, Table III, or Table IV.

Especially preferred are inventive mixtures wherein the compound B is alpha-cypermethrin and the compound I of formula I is a compound of Table I, Table II, Table III, or Table IV.

Especially preferred are inventive mixtures wherein the compound B is thiamethoxam and the compound I of formula I is a compound of Table I, Table II, Table III, or Table IV.

Especially preferred are inventive mixtures wherein the compound B is abamectin and the compound I of formula I is a compound of Table I, Table II, Table III, or Table IV.

Especially preferred are inventive mixtures wherein the compound B is spirotetramat and the compound I of formula I is a compound of Table I, Table II, Table III, or Table IV.

Especially preferred are inventive mixtures wherein the compound B is imidacloprid and the compound I of formula I is a compound of Table I, Table II, Table III, or Table IV.

Especially preferred are inventive mixtures wherein the compound B is flonicamid and the compound I of formula I is a compound of Table I, Table II, Table III, or Table IV.

Especially preferred are inventive mixtures wherein the compound B is chloranthraniliprole (rynaxypyr) and the compound I of formula I is a compound of Table I, Table II, Table III, or Table IV.

Especially preferred are inventive mixtures wherein the compound B is pymetrozine and the compound I of formula I is a compound of Table I, Table II, Table III, or Table IV.

Especially preferred are inventive mixtures wherein the compound B is sulfoxaflor and the compound I of formula I is a compound of Table I, Table II, Table III, or Table IV.

Especially preferred are inventive mixtures wherein the compound B is afidopyren and the compound I of formula I is a compound of Table I, Table II, Table III, or Table IV.

The following table M-I represents preferred combinations of the active compounds I of formula I as defined in Tables I, II, III, or IV and the active compounds B in mixtures according to the invention

TABLE M-I

| No. | Comp. I | Comp. B |
|---|---|---|
| M.1 | I-1 | acrinathrin |
| M.2 | I-2 | acrinathrin |
| M.3 | I-13 | acrinathrin |
| M.4 | I-14 | acrinathrin |
| M.5 | I-673 | acrinathrin |
| M.6 | I-674 | acrinathrin |
| M.7 | I-679 | acrinathrin |
| M.8 | I-680 | acrinathrin |
| M.9 | I-697 | acrinathrin |
| M.10 | I-698 | acrinathrin |
| M.11 | I-775 | acrinathrin |
| M.12 | I-776 | acrinathrin |
| M.13 | I-793 | acrinathrin |
| M.14 | I-794 | acrinathrin |
| M.15 | I-871 | acrinathrin |
| M.16 | I-872 | acrinathrin |
| M.17 | I-877 | acrinathrin |
| M.18 | I-878 | acrinathrin |
| M.19 | I-2563 | acrinathrin |
| M.20 | I-2564 | acrinathrin |
| M.21 | I-2671 | acrinathrin |
| M.22 | I-2672 | acrinathrin |
| M.23 | I-1 | bifenthrin |
| M.24 | I-2 | bifenthrin |
| M.25 | I-13 | bifenthrin |
| M.26 | I-14 | bifenthrin |
| M.27 | I-673 | bifenthrin |
| M.28 | I-674 | bifenthrin |
| M.29 | I-679 | bifenthrin |
| M.30 | I-680 | bifenthrin |
| M.31 | I-697 | bifenthrin |
| M.32 | I-698 | bifenthrin |
| M.33 | I-775 | bifenthrin |
| M.34 | I-776 | bifenthrin |
| M.35 | I-793 | bifenthrin |
| M.36 | I-794 | bifenthrin |
| M.37 | I-871 | bifenthrin |
| M.38 | I-872 | bifenthrin |
| M.39 | I-877 | bifenthrin |
| M.40 | I-878 | bifenthrin |
| M.41 | I-2563 | bifenthrin |
| M.42 | I-2564 | bifenthrin |
| M.43 | I-2671 | bifenthrin |
| M.44 | I-2672 | bifenthrin |

TABLE M-I-continued

| No. | Comp. I | Comp. B |
|---|---|---|
| M.45 | I-1 | cyfluthrin |
| M.46 | I-2 | cyfluthrin |
| M.47 | I-13 | cyfluthrin |
| M.48 | I-14 | cyfluthrin |
| M.49 | I-673 | cyfluthrin |
| M.50 | I-674 | cyfluthrin |
| M.51 | I-679 | cyfluthrin |
| M.52 | I-680 | cyfluthrin |
| M.53 | I-697 | cyfluthrin |
| M.54 | I-698 | cyfluthrin |
| M.55 | I-775 | cyfluthrin |
| M.56 | I-776 | cyfluthrin |
| M.57 | I-793 | cyfluthrin |
| M.58 | I-794 | cyfluthrin |
| M.59 | I-871 | cyfluthrin |
| M.60 | I-872 | cyfluthrin |
| M.61 | I-877 | cyfluthrin |
| M.62 | I-878 | cyfluthrin |
| M.63 | I-2563 | cyfluthrin |
| M.64 | I-2564 | cyfluthrin |
| M.65 | I-2671 | cyfluthrin |
| M.66 | I-2672 | cyfluthrin |
| M.67 | I-1 | lambda-cyhalothrin |
| M.68 | I-2 | lambda-cyhalothrin |
| M.69 | I-13 | lambda-cyhalothrin |
| M.70 | I-14 | lambda-cyhalothrin |
| M.71 | I-673 | lambda-cyhalothrin |
| M.72 | I-674 | lambda-cyhalothrin |
| M.73 | I-679 | lambda-cyhalothrin |
| M.74 | I-680 | lambda-cyhalothrin |
| M.75 | I-697 | lambda-cyhalothrin |
| M.76 | I-698 | lambda-cyhalothrin |
| M.77 | I-775 | lambda-cyhalothrin |
| M.78 | I-776 | lambda-cyhalothrin |
| M.79 | I-793 | lambda-cyhalothrin |
| M.80 | I-794 | lambda-cyhalothrin |
| M.81 | I-871 | lambda-cyhalothrin |
| M.82 | I-872 | lambda-cyhalothrin |
| M.83 | I-877 | lambda-cyhalothrin |
| M.84 | I-878 | lambda-cyhalothrin |
| M.85 | I-2563 | lambda-cyhalothrin |
| M.86 | I-2564 | lambda-cyhalothrin |
| M.87 | I-2671 | lambda-cyhalothrin |
| M.88 | I-2672 | lambda-cyhalothrin |
| M.89 | I-1 | cypermethrin |
| M.90 | I-2 | cypermethrin |
| M.91 | I-13 | cypermethrin |
| M.92 | I-14 | cypermethrin |
| M.93 | I-673 | cypermethrin |
| M.94 | I-674 | cypermethrin |
| M.95 | I-679 | cypermethrin |
| M.96 | I-680 | cypermethrin |
| M.97 | I-697 | cypermethrin |
| M.98 | I-698 | cypermethrin |
| M.99 | I-775 | cypermethrin |
| M.100 | I-776 | cypermethrin |
| M.101 | I-793 | cypermethrin |
| M.102 | I-794 | cypermethrin |
| M.103 | I-871 | cypermethrin |
| M.104 | I-872 | cypermethrin |
| M.105 | I-877 | cypermethrin |
| M.106 | I-878 | cypermethrin |
| M.107 | I-2563 | cypermethrin |
| M.108 | I-2564 | cypermethrin |
| M.109 | I-2671 | cypermethrin |
| M.110 | I-2672 | cypermethrin |
| M.111 | I-1 | alpha-cypermethrin |
| M.112 | I-2 | alpha-cypermethrin |
| M.113 | I-13 | alpha-cypermethrin |
| M.114 | I-14 | alpha-cypermethrin |
| M.115 | I-673 | alpha-cypermethrin |
| M.116 | I-674 | alpha-cypermethrin |
| M.117 | I-679 | alpha-cypermethrin |
| M.118 | I-680 | alpha-cypermethrin |
| M.119 | I-697 | alpha-cypermethrin |
| M.120 | I-698 | alpha-cypermethrin |
| M.121 | I-775 | alpha-cypermethrin |
| M.122 | I-776 | alpha-cypermethrin |

TABLE M-I-continued

| No. | Comp. I | Comp. B |
|---|---|---|
| M.123 | I-793 | alpha-cypermethrin |
| M.124 | I-794 | alpha-cypermethrin |
| M.125 | I-871 | alpha-cypermethrin |
| M.126 | I-872 | alpha-cypermethrin |
| M.127 | I-877 | alpha-cypermethrin |
| M.128 | I-878 | alpha-cypermethrin |
| M.129 | I-2563 | alpha-cypermethrin |
| M.130 | I-2564 | alpha-cypermethrin |
| M.131 | I-2671 | alpha-cypermethrin |
| M.132 | I-2672 | alpha-cypermethrin |
| M.133 | I-1 | beta-cypermethrin |
| M.134 | I-2 | beta-cypermethrin |
| M.135 | I-13 | beta-cypermethrin |
| M.136 | I-14 | beta-cypermethrin |
| M.137 | I-673 | beta-cypermethrin |
| M.138 | I-674 | beta-cypermethrin |
| M.139 | I-679 | beta-cypermethrin |
| M.140 | I-680 | beta-cypermethrin |
| M.141 | I-697 | beta-cypermethrin |
| M.142 | I-698 | beta-cypermethrin |
| M.143 | I-775 | beta-cypermethrin |
| M.144 | I-776 | beta-cypermethrin |
| M.145 | I-793 | beta-cypermethrin |
| M.146 | I-794 | beta-cypermethrin |
| M.147 | I-871 | beta-cypermethrin |
| M.148 | I-872 | beta-cypermethrin |
| M.149 | I-877 | beta-cypermethrin |
| M.150 | I-878 | beta-cypermethrin |
| M.151 | I-2563 | beta-cypermethrin |
| M.152 | I-2564 | beta-cypermethrin |
| M.153 | I-2671 | beta-cypermethrin |
| M.154 | I-2672 | beta-cypermethrin |
| M.155 | I-1 | zeta-cypermethrin |
| M.156 | I-2 | zeta-cypermethrin |
| M.157 | I-13 | zeta-cypermethrin |
| M.158 | I-14 | zeta-cypermethrin |
| M.159 | I-673 | zeta-cypermethrin |
| M.160 | I-674 | zeta-cypermethrin |
| M.161 | I-679 | zeta-cypermethrin |
| M.162 | I-680 | zeta-cypermethrin |
| M.163 | I-697 | zeta-cypermethrin |
| M.164 | I-698 | zeta-cypermethrin |
| M.165 | I-775 | zeta-cypermethrin |
| M.166 | I-776 | zeta-cypermethrin |
| M.167 | I-793 | zeta-cypermethrin |
| M.168 | I-794 | zeta-cypermethrin |
| M.169 | I-871 | zeta-cypermethrin |
| M.170 | I-872 | zeta-cypermethrin |
| M.171 | I-877 | zeta-cypermethrin |
| M.172 | I-878 | zeta-cypermethrin |
| M.173 | I-2563 | zeta-cypermethrin |
| M.174 | I-2564 | zeta-cypermethrin |
| M.175 | I-2671 | zeta-cypermethrin |
| M.176 | I-2672 | zeta-cypermethrin |
| M.177 | I-1 | deltamethrin |
| M.178 | I-2 | deltamethrin |
| M.179 | I-13 | deltamethrin |
| M.180 | I-14 | deltamethrin |
| M.181 | I-673 | deltamethrin |
| M.182 | I-674 | deltamethrin |
| M.183 | I-679 | deltamethrin |
| M.184 | I-680 | deltamethrin |
| M.185 | I-697 | deltamethrin |
| M.186 | I-698 | deltamethrin |
| M.187 | I-775 | deltamethrin |
| M.188 | I-776 | deltamethrin |
| M.189 | I-793 | deltamethrin |
| M.190 | I-794 | deltamethrin |
| M.191 | I-871 | deltamethrin |
| M.192 | I-872 | deltamethrin |
| M.193 | I-877 | deltamethrin |
| M.194 | I-878 | deltamethrin |
| M.195 | I-2563 | deltamethrin |
| M.196 | I-2564 | deltamethrin |
| M.197 | I-2671 | deltamethrin |
| M.198 | I-2672 | deltamethrin |
| M.199 | I-1 | esfenvalerate |
| M.200 | I-2 | esfenvalerate |
| M.201 | I-13 | esfenvalerate |
| M.202 | I-14 | esfenvalerate |
| M.203 | I-673 | esfenvalerate |
| M.204 | I-674 | esfenvalerate |
| M.205 | I-679 | esfenvalerate |
| M.206 | I-680 | esfenvalerate |
| M.207 | I-697 | esfenvalerate |
| M.208 | I-698 | esfenvalerate |
| M.209 | I-775 | esfenvalerate |
| M.210 | I-776 | esfenvalerate |
| M.211 | I-793 | esfenvalerate |
| M.212 | I-794 | esfenvalerate |
| M.213 | I-871 | esfenvalerate |
| M.214 | I-872 | esfenvalerate |
| M.215 | I-877 | esfenvalerate |
| M.216 | I-878 | esfenvalerate |
| M.217 | I-2563 | esfenvalerate |
| M.218 | I-2564 | esfenvalerate |
| M.219 | I-2671 | esfenvalerate |
| M.220 | I-2672 | esfenvalerate |
| M.221 | I-1 | etofenprox |
| M.222 | I-2 | etofenprox |
| M.223 | I-13 | etofenprox |
| M.224 | I-14 | etofenprox |
| M.225 | I-673 | etofenprox |
| M.226 | I-674 | etofenprox |
| M.227 | I-679 | etofenprox |
| M.228 | I-680 | etofenprox |
| M.229 | I-697 | etofenprox |
| M.230 | I-698 | etofenprox |
| M.231 | I-775 | etofenprox |
| M.232 | I-776 | etofenprox |
| M.233 | I-793 | etofenprox |
| M.234 | I-794 | etofenprox |
| M.235 | I-871 | etofenprox |
| M.236 | I-872 | etofenprox |
| M.237 | I-877 | etofenprox |
| M.238 | I-878 | etofenprox |
| M.239 | I-2563 | etofenprox |
| M.240 | I-2564 | etofenprox |
| M.241 | I-2671 | etofenprox |
| M.242 | I-2672 | etofenprox |
| M.243 | I-1 | fenpropathrin |
| M.244 | I-2 | fenpropathrin |
| M.245 | I-13 | fenpropathrin |
| M.246 | I-14 | fenpropathrin |
| M.247 | I-673 | fenpropathrin |
| M.248 | I-674 | fenpropathrin |
| M.249 | I-679 | fenpropathrin |
| M.250 | I-680 | fenpropathrin |
| M.251 | I-697 | fenpropathrin |
| M.252 | I-698 | fenpropathrin |
| M.253 | I-775 | fenpropathrin |
| M.254 | I-776 | fenpropathrin |
| M.255 | I-793 | fenpropathrin |
| M.256 | I-794 | fenpropathrin |
| M.257 | I-871 | fenpropathrin |
| M.258 | I-872 | fenpropathrin |
| M.259 | I-877 | fenpropathrin |
| M.260 | I-878 | fenpropathrin |
| M.261 | I-2563 | fenpropathrin |
| M.262 | I-2564 | fenpropathrin |
| M.263 | I-2671 | fenpropathrin |
| M.264 | I-2672 | fenpropathrin |
| M.265 | I-1 | flucythrinate |
| M.266 | I-2 | flucythrinate |
| M.267 | I-13 | flucythrinate |
| M.268 | I-14 | flucythrinate |
| M.269 | I-673 | flucythrinate |
| M.270 | I-674 | flucythrinate |
| M.271 | I-679 | flucythrinate |
| M.272 | I-680 | flucythrinate |
| M.273 | I-697 | flucythrinate |
| M.274 | I-698 | flucythrinate |
| M.275 | I-775 | flucythrinate |
| M.276 | I-776 | flucythrinate |
| M.277 | I-793 | flucythrinate |
| M.278 | I-794 | flucythrinate |

TABLE M-I-continued

| No. | Comp. I | Comp. B |
|---|---|---|
| M.279 | I-871 | flucythrinate |
| M.280 | I-872 | flucythrinate |
| M.281 | I-877 | flucythrinate |
| M.282 | I-878 | flucythrinate |
| M.283 | I-2563 | flucythrinate |
| M.284 | I-2564 | flucythrinate |
| M.285 | I-2671 | flucythrinate |
| M.286 | I-2672 | flucythrinate |
| M.287 | I-1 | tau-fluvalinate |
| M.288 | I-2 | tau-fluvalinate |
| M.289 | I-13 | tau-fluvalinate |
| M.290 | I-14 | tau-fluvalinate |
| M.291 | I-673 | tau-fluvalinate |
| M.292 | I-674 | tau-fluvalinate |
| M.293 | I-679 | tau-fluvalinate |
| M.294 | I-680 | tau-fluvalinate |
| M.295 | I-697 | tau-fluvalinate |
| M.296 | I-698 | tau-fluvalinate |
| M.297 | I-775 | tau-fluvalinate |
| M.298 | I-776 | tau-fluvalinate |
| M.299 | I-793 | tau-fluvalinate |
| M.300 | I-794 | tau-fluvalinate |
| M.301 | I-871 | tau-fluvalinate |
| M.302 | I-872 | tau-fluvalinate |
| M.303 | I-877 | tau-fluvalinate |
| M.304 | I-878 | tau-fluvalinate |
| M.305 | I-2563 | tau-fluvalinate |
| M.306 | I-2564 | tau-fluvalinate |
| M.307 | I-2671 | tau-fluvalinate |
| M.308 | I-2672 | tau-fluvalinate |
| M.309 | I-1 | silafluofen |
| M.310 | I-2 | silafluofen |
| M.311 | I-13 | silafluofen |
| M.312 | I-14 | silafluofen |
| M.313 | I-673 | silafluofen |
| M.314 | I-674 | silafluofen |
| M.315 | I-679 | silafluofen |
| M.316 | I-680 | silafluofen |
| M.317 | I-697 | silafluofen |
| M.318 | I-698 | silafluofen |
| M.319 | I-775 | silafluofen |
| M.320 | I-776 | silafluofen |
| M.321 | I-793 | silafluofen |
| M.322 | I-794 | silafluofen |
| M.323 | I-871 | silafluofen |
| M.324 | I-872 | silafluofen |
| M.325 | I-877 | silafluofen |
| M.326 | I-878 | silafluofen |
| M.327 | I-2563 | silafluofen |
| M.328 | I-2564 | silafluofen |
| M.329 | I-2671 | silafluofen |
| M.330 | I-2672 | silafluofen |
| M.331 | I-1 | tralomethrin |
| M.332 | I-2 | tralomethrin |
| M.333 | I-13 | tralomethrin |
| M.334 | I-14 | tralomethrin |
| M.335 | I-673 | tralomethrin |
| M.336 | I-674 | tralomethrin |
| M.337 | I-679 | tralomethrin |
| M.338 | I-680 | tralomethrin |
| M.339 | I-697 | tralomethrin |
| M.340 | I-698 | tralomethrin |
| M.341 | I-775 | tralomethrin |
| M.342 | I-776 | tralomethrin |
| M.343 | I-793 | tralomethrin |
| M.344 | I-794 | tralomethrin |
| M.345 | I-871 | tralomethrin |
| M.346 | I-872 | tralomethrin |
| M.347 | I-877 | tralomethrin |
| M.348 | I-878 | tralomethrin |
| M.349 | I-2563 | tralomethrin |
| M.350 | I-2564 | tralomethrin |
| M.351 | I-2671 | tralomethrin |
| M.352 | I-2672 | tralomethrin |
| M.353 | I-1 | acetamiprid |
| M.354 | I-2 | acetamiprid |
| M.355 | I-13 | acetamiprid |
| M.356 | I-14 | acetamiprid |
| M.357 | I-673 | acetamiprid |
| M.358 | I-674 | acetamiprid |
| M.359 | I-679 | acetamiprid |
| M.360 | I-680 | acetamiprid |
| M.361 | I-697 | acetamiprid |
| M.362 | I-698 | acetamiprid |
| M.363 | I-775 | acetamiprid |
| M.364 | I-776 | acetamiprid |
| M.365 | I-793 | acetamiprid |
| M.366 | I-794 | acetamiprid |
| M.367 | I-871 | acetamiprid |
| M.368 | I-872 | acetamiprid |
| M.369 | I-877 | acetamiprid |
| M.370 | I-878 | acetamiprid |
| M.371 | I-2563 | acetamiprid |
| M.372 | I-2564 | acetamiprid |
| M.373 | I-2671 | acetamiprid |
| M.374 | I-2672 | acetamiprid |
| M.375 | I-1 | clothianidin |
| M.376 | I-2 | clothianidin |
| M.377 | I-13 | clothianidin |
| M.378 | I-14 | clothianidin |
| M.379 | I-673 | clothianidin |
| M.380 | I-674 | clothianidin |
| M.381 | I-679 | clothianidin |
| M.382 | I-680 | clothianidin |
| M.383 | I-697 | clothianidin |
| M.384 | I-698 | clothianidin |
| M.385 | I-775 | clothianidin |
| M.386 | I-776 | clothianidin |
| M.387 | I-793 | clothianidin |
| M.388 | I-794 | clothianidin |
| M.389 | I-871 | clothianidin |
| M.390 | I-872 | clothianidin |
| M.391 | I-877 | clothianidin |
| M.392 | I-878 | clothianidin |
| M.393 | I-2563 | clothianidin |
| M.394 | I-2564 | clothianidin |
| M.395 | I-2671 | clothianidin |
| M.396 | I-2672 | clothianidin |
| M.397 | I-1 | dinotefuran |
| M.398 | I-2 | dinotefuran |
| M.399 | I-13 | dinotefuran |
| M.400 | I-14 | dinotefuran |
| M.401 | I-673 | dinotefuran |
| M.402 | I-674 | dinotefuran |
| M.403 | I-679 | dinotefuran |
| M.404 | I-680 | dinotefuran |
| M.405 | I-697 | dinotefuran |
| M.406 | I-698 | dinotefuran |
| M.407 | I-775 | dinotefuran |
| M.408 | I-776 | dinotefuran |
| M.409 | I-793 | dinotefuran |
| M.410 | I-794 | dinotefuran |
| M.411 | I-871 | dinotefuran |
| M.412 | I-872 | dinotefuran |
| M.413 | I-877 | dinotefuran |
| M.414 | I-878 | dinotefuran |
| M.415 | I-2563 | dinotefuran |
| M.416 | I-2564 | dinotefuran |
| M.417 | I-2671 | dinotefuran |
| M.418 | I-2672 | dinotefuran |
| M.419 | I-1 | imidacloprid |
| M.420 | I-2 | imidacloprid |
| M.421 | I-13 | imidacloprid |
| M.422 | I-14 | imidacloprid |
| M.423 | I-673 | imidacloprid |
| M.424 | I-674 | imidacloprid |
| M.425 | I-679 | imidacloprid |
| M.426 | I-680 | imidacloprid |
| M.427 | I-697 | imidacloprid |
| M.428 | I-698 | imidacloprid |
| M.429 | I-775 | imidacloprid |
| M.430 | I-776 | imidacloprid |
| M.431 | I-793 | imidacloprid |
| M.432 | I-794 | imidacloprid |
| M.433 | I-871 | imidacloprid |
| M.434 | I-872 | imidacloprid |

TABLE M-I-continued

| No. | Comp. I | Comp. B |
|---|---|---|
| M.435 | I-877 | imidacloprid |
| M.436 | I-878 | imidacloprid |
| M.437 | I-2563 | imidacloprid |
| M.438 | I-2564 | imidacloprid |
| M.439 | I-2671 | imidacloprid |
| M.440 | I-2672 | imidacloprid |
| M.441 | I-1 | thiamethoxam |
| M.442 | I-2 | thiamethoxam |
| M.443 | I-13 | thiamethoxam |
| M.444 | I-14 | thiamethoxam |
| M.445 | I-673 | thiamethoxam |
| M.446 | I-674 | thiamethoxam |
| M.447 | I-679 | thiamethoxam |
| M.448 | I-680 | thiamethoxam |
| M.449 | I-697 | thiamethoxam |
| M.450 | I-698 | thiamethoxam |
| M.451 | I-775 | thiamethoxam |
| M.452 | I-776 | thiamethoxam |
| M.453 | I-793 | thiamethoxam |
| M.454 | I-794 | thiamethoxam |
| M.455 | I-871 | thiamethoxam |
| M.456 | I-872 | thiamethoxam |
| M.457 | I-877 | thiamethoxam |
| M.458 | I-878 | thiamethoxam |
| M.459 | I-2563 | thiamethoxam |
| M.460 | I-2564 | thiamethoxam |
| M.461 | I-2671 | thiamethoxam |
| M.462 | I-2672 | thiamethoxam |
| M.463 | I-1 | nitenpyram |
| M.464 | I-2 | nitenpyram |
| M.465 | I-13 | nitenpyram |
| M.466 | I-14 | nitenpyram |
| M.467 | I-673 | nitenpyram |
| M.468 | I-674 | nitenpyram |
| M.469 | I-679 | nitenpyram |
| M.470 | I-680 | nitenpyram |
| M.471 | I-697 | nitenpyram |
| M.472 | I-698 | nitenpyram |
| M.473 | I-775 | nitenpyram |
| M.474 | I-776 | nitenpyram |
| M.475 | I-793 | nitenpyram |
| M.476 | I-794 | nitenpyram |
| M.477 | I-871 | nitenpyram |
| M.478 | I-872 | nitenpyram |
| M.479 | I-877 | nitenpyram |
| M.480 | I-878 | nitenpyram |
| M.481 | I-2563 | nitenpyram |
| M.482 | I-2564 | nitenpyram |
| M.483 | I-2671 | nitenpyram |
| M.484 | I-2672 | nitenpyram |
| M.485 | I-1 | thiacloprid |
| M.486 | I-2 | thiacloprid |
| M.487 | I-13 | thiacloprid |
| M.488 | I-14 | thiacloprid |
| M.489 | I-673 | thiacloprid |
| M.490 | I-674 | thiacloprid |
| M.491 | I-679 | thiacloprid |
| M.492 | I-680 | thiacloprid |
| M.493 | I-697 | thiacloprid |
| M.494 | I-698 | thiacloprid |
| M.495 | I-775 | thiacloprid |
| M.496 | I-776 | thiacloprid |
| M.497 | I-793 | thiacloprid |
| M.498 | I-794 | thiacloprid |
| M.499 | I-871 | thiacloprid |
| M.500 | I-872 | thiacloprid |
| M.501 | I-877 | thiacloprid |
| M.502 | I-878 | thiacloprid |
| M.503 | I-2563 | thiacloprid |
| M.504 | I-2564 | thiacloprid |
| M.505 | I-2671 | thiacloprid |
| M.506 | I-2672 | thiacloprid |
| M.507 | I-1 | ethiprole |
| M.508 | I-2 | ethiprole |
| M.509 | I-13 | ethiprole |
| M.510 | I-14 | ethiprole |
| M.511 | I-673 | ethiprole |
| M.512 | I-674 | ethiprole |
| M.513 | I-679 | ethiprole |
| M.514 | I-680 | ethiprole |
| M.515 | I-697 | ethiprole |
| M.516 | I-698 | ethiprole |
| M.517 | I-775 | ethiprole |
| M.518 | I-776 | ethiprole |
| M.519 | I-793 | ethiprole |
| M.520 | I-794 | ethiprole |
| M.521 | I-871 | ethiprole |
| M.522 | I-872 | ethiprole |
| M.523 | I-877 | ethiprole |
| M.524 | I-878 | ethiprole |
| M.525 | I-2563 | ethiprole |
| M.526 | I-2564 | ethiprole |
| M.527 | I-2671 | ethiprole |
| M.528 | I-2672 | ethiprole |
| M.529 | I-1 | fipronil |
| M.530 | I-2 | fipronil |
| M.531 | I-13 | fipronil |
| M.532 | I-14 | fipronil |
| M.533 | I-673 | fipronil |
| M.534 | I-674 | fipronil |
| M.535 | I-679 | fipronil |
| M.536 | I-680 | fipronil |
| M.537 | I-697 | fipronil |
| M.538 | I-698 | fipronil |
| M.539 | I-775 | fipronil |
| M.540 | I-776 | fipronil |
| M.541 | I-793 | fipronil |
| M.542 | I-794 | fipronil |
| M.543 | I-871 | fipronil |
| M.544 | I-872 | fipronil |
| M.545 | I-877 | fipronil |
| M.546 | I-878 | fipronil |
| M.547 | I-2563 | fipronil |
| M.548 | I-2564 | fipronil |
| M.549 | I-2671 | fipronil |
| M.550 | I-2672 | fipronil |
| M.551 | I-1 | abamectin |
| M.552 | I-2 | abamectin |
| M.553 | I-13 | abamectin |
| M.554 | I-14 | abamectin |
| M.555 | I-673 | abamectin |
| M.556 | I-674 | abamectin |
| M.557 | I-679 | abamectin |
| M.558 | I-680 | abamectin |
| M.559 | I-697 | abamectin |
| M.560 | I-698 | abamectin |
| M.561 | I-775 | abamectin |
| M.562 | I-776 | abamectin |
| M.563 | I-793 | abamectin |
| M.564 | I-794 | abamectin |
| M.565 | I-871 | abamectin |
| M.566 | I-872 | abamectin |
| M.567 | I-877 | abamectin |
| M.568 | I-878 | abamectin |
| M.569 | I-2563 | abamectin |
| M.570 | I-2564 | abamectin |
| M.571 | I-2671 | abamectin |
| M.572 | I-2672 | abamectin |
| M.573 | I-1 | emamectin benzoate |
| M.574 | I-2 | emamectin benzoate |
| M.575 | I-13 | emamectin benzoate |
| M.576 | I-14 | emamectin benzoate |
| M.577 | I-673 | emamectin benzoate |
| M.578 | I-674 | emamectin benzoate |
| M.579 | I-679 | emamectin benzoate |
| M.580 | I-680 | emamectin benzoate |
| M.581 | I-697 | emamectin benzoate |
| M.582 | I-698 | emamectin benzoate |
| M.583 | I-775 | emamectin benzoate |
| M.584 | I-776 | emamectin benzoate |
| M.585 | I-793 | emamectin benzoate |
| M.586 | I-794 | emamectin benzoate |
| M.587 | I-871 | emamectin benzoate |
| M.588 | I-872 | emamectin benzoate |
| M.589 | I-877 | emamectin benzoate |
| M.590 | I-878 | emamectin benzoate |

TABLE M-I-continued

| No. | Comp. I | Comp. B |
|---|---|---|
| M.591 | I-2563 | emamectin benzoate |
| M.592 | I-2564 | emamectin benzoate |
| M.593 | I-2671 | emamectin benzoate |
| M.594 | I-2672 | emamectin benzoate |
| M.595 | I-1 | lepimectin |
| M.596 | I-2 | lepimectin |
| M.597 | I-13 | lepimectin |
| M.598 | I-14 | lepimectin |
| M.599 | I-673 | lepimectin |
| M.600 | I-674 | lepimectin |
| M.601 | I-679 | lepimectin |
| M.602 | I-680 | lepimectin |
| M.603 | I-697 | lepimectin |
| M.604 | I-698 | lepimectin |
| M.605 | I-775 | lepimectin |
| M.606 | I-776 | lepimectin |
| M.607 | I-793 | lepimectin |
| M.608 | I-794 | lepimectin |
| M.609 | I-871 | lepimectin |
| M.610 | I-872 | lepimectin |
| M.611 | I-877 | lepimectin |
| M.612 | I-878 | lepimectin |
| M.613 | I-2563 | lepimectin |
| M.614 | I-2564 | lepimectin |
| M.615 | I-2671 | lepimectin |
| M.616 | I-2672 | lepimectin |
| M.617 | I-1 | chlorfenapyr |
| M.618 | I-2 | chlorfenapyr |
| M.619 | I-13 | chlorfenapyr |
| M.620 | I-14 | chlorfenapyr |
| M.621 | I-673 | chlorfenapyr |
| M.622 | I-674 | chlorfenapyr |
| M.623 | I-679 | chlorfenapyr |
| M.624 | I-680 | chlorfenapyr |
| M.625 | I-697 | chlorfenapyr |
| M.626 | I-698 | chlorfenapyr |
| M.627 | I-775 | chlorfenapyr |
| M.628 | I-776 | chlorfenapyr |
| M.629 | I-793 | chlorfenapyr |
| M.630 | I-794 | chlorfenapyr |
| M.631 | I-871 | chlorfenapyr |
| M.632 | I-872 | chlorfenapyr |
| M.633 | I-877 | chlorfenapyr |
| M.634 | I-878 | chlorfenapyr |
| M.635 | I-2563 | chlorfenapyr |
| M.636 | I-2564 | chlorfenapyr |
| M.637 | I-2671 | chlorfenapyr |
| M.638 | I-2672 | chlorfenapyr |
| M.639 | I-1 | flonicamid |
| M.640 | I-2 | flonicamid |
| M.641 | I-13 | flonicamid |
| M.642 | I-14 | flonicamid |
| M.643 | I-673 | flonicamid |
| M.644 | I-674 | flonicamid |
| M.645 | I-679 | flonicamid |
| M.646 | I-680 | flonicamid |
| M.647 | I-697 | flonicamid |
| M.648 | I-698 | flonicamid |
| M.649 | I-775 | flonicamid |
| M.650 | I-776 | flonicamid |
| M.651 | I-793 | flonicamid |
| M.652 | I-794 | flonicamid |
| M.653 | I-871 | flonicamid |
| M.654 | I-872 | flonicamid |
| M.655 | I-877 | flonicamid |
| M.656 | I-878 | flonicamid |
| M.657 | I-2563 | flonicamid |
| M.658 | I-2564 | flonicamid |
| M.659 | I-2671 | flonicamid |
| M.660 | I-2672 | flonicamid |
| M.661 | I-1 | pymetrozine |
| M.662 | I-2 | pymetrozine |
| M.663 | I-13 | pymetrozine |
| M.664 | I-14 | pymetrozine |
| M.665 | I-673 | pymetrozine |
| M.666 | I-674 | pymetrozine |
| M.667 | I-679 | pymetrozine |
| M.668 | I-680 | pymetrozine |
| M.669 | I-697 | pymetrozine |
| M.670 | I-698 | pymetrozine |
| M.671 | I-775 | pymetrozine |
| M.672 | I-776 | pymetrozine |
| M.673 | I-793 | pymetrozine |
| M.674 | I-794 | pymetrozine |
| M.675 | I-871 | pymetrozine |
| M.676 | I-872 | pymetrozine |
| M.677 | I-877 | pymetrozine |
| M.678 | I-878 | pymetrozine |
| M.679 | I-2563 | pymetrozine |
| M.680 | I-2564 | pymetrozine |
| M.681 | I-2671 | pymetrozine |
| M.682 | I-2672 | pymetrozine |
| M.683 | I-1 | spiromesifen |
| M.684 | I-2 | spiromesifen |
| M.685 | I-13 | spiromesifen |
| M.686 | I-14 | spiromesifen |
| M.687 | I-673 | spiromesifen |
| M.688 | I-674 | spiromesifen |
| M.689 | I-679 | spiromesifen |
| M.690 | I-680 | spiromesifen |
| M.691 | I-697 | spiromesifen |
| M.692 | I-698 | spiromesifen |
| M.693 | I-775 | spiromesifen |
| M.694 | I-776 | spiromesifen |
| M.695 | I-793 | spiromesifen |
| M.696 | I-794 | spiromesifen |
| M.697 | I-871 | spiromesifen |
| M.698 | I-872 | spiromesifen |
| M.699 | I-877 | spiromesifen |
| M.700 | I-878 | spiromesifen |
| M.701 | I-2563 | spiromesifen |
| M.702 | I-2564 | spiromesifen |
| M.703 | I-2671 | spiromesifen |
| M.704 | I-2672 | spiromesifen |
| M.705 | I-1 | spirotetramat |
| M.706 | I-2 | spirotetramat |
| M.707 | I-13 | spirotetramat |
| M.708 | I-14 | spirotetramat |
| M.709 | I-673 | spirotetramat |
| M.710 | I-674 | spirotetramat |
| M.711 | I-679 | spirotetramat |
| M.712 | I-680 | spirotetramat |
| M.713 | I-697 | spirotetramat |
| M.714 | I-698 | spirotetramat |
| M.715 | I-775 | spirotetramat |
| M.716 | I-776 | spirotetramat |
| M.717 | I-793 | spirotetramat |
| M.718 | I-794 | spirotetramat |
| M.719 | I-871 | spirotetramat |
| M.720 | I-872 | spirotetramat |
| M.721 | I-877 | spirotetramat |
| M.722 | I-878 | spirotetramat |
| M.723 | I-2563 | spirotetramat |
| M.724 | I-2564 | spirotetramat |
| M.725 | I-2671 | spirotetramat |
| M.726 | I-2672 | spirotetramat |
| M.727 | I-1 | flubendiamide |
| M.728 | I-2 | flubendiamide |
| M.729 | I-13 | flubendiamide |
| M.730 | I-14 | flubendiamide |
| M.731 | I-673 | flubendiamide |
| M.732 | I-674 | flubendiamide |
| M.733 | I-679 | flubendiamide |
| M.734 | I-680 | flubendiamide |
| M.735 | I-697 | flubendiamide |
| M.736 | I-698 | flubendiamide |
| M.737 | I-775 | flubendiamide |
| M.738 | I-776 | flubendiamide |
| M.739 | I-793 | flubendiamide |
| M.740 | I-794 | flubendiamide |
| M.741 | I-871 | flubendiamide |
| M.742 | I-872 | flubendiamide |
| M.743 | I-877 | flubendiamide |
| M.744 | I-878 | flubendiamide |
| M.745 | I-2563 | flubendiamide |
| M.746 | I-2564 | flubendiamide |

TABLE M-I-continued

| No. | Comp. I | Comp. B |
|---|---|---|
| M.747 | I-2671 | flubendiamide |
| M.748 | I-2672 | flubendiamide |
| M.749 | I-1 | chloranthraniliprole |
| M.750 | I-2 | chloranthraniliprole |
| M.751 | I-13 | chloranthraniliprole |
| M.752 | I-14 | chloranthraniliprole |
| M.753 | I-673 | chloranthraniliprole |
| M.754 | I-674 | chloranthraniliprole |
| M.755 | I-679 | chloranthraniliprole |
| M.756 | I-680 | chloranthraniliprole |
| M.757 | I-697 | chloranthraniliprole |
| M.758 | I-698 | chloranthraniliprole |
| M.759 | I-775 | chloranthraniliprole |
| M.760 | I-776 | chloranthraniliprole |
| M.761 | I-793 | chloranthraniliprole |
| M.762 | I-794 | chloranthraniliprole |
| M.763 | I-871 | chloranthraniliprole |
| M.764 | I-872 | chloranthraniliprole |
| M.765 | I-877 | chloranthraniliprole |
| M.766 | I-878 | chloranthraniliprole |
| M.767 | I-2563 | chloranthraniliprole |
| M.768 | I-2564 | chloranthraniliprole |
| M.769 | I-2671 | chloranthraniliprole |
| M.770 | I-2672 | chloranthraniliprole |
| M.771 | I-1 | cyantraniliprole |
| M.772 | I-2 | cyantraniliprole |
| M.773 | I-13 | cyantraniliprole |
| M.774 | I-14 | cyantraniliprole |
| M.775 | I-673 | cyantraniliprole |
| M.776 | I-674 | cyantraniliprole |
| M.777 | I-679 | cyantraniliprole |
| M.778 | I-680 | cyantraniliprole |
| M.779 | I-697 | cyantraniliprole |
| M.780 | I-698 | cyantraniliprole |
| M.781 | I-775 | cyantraniliprole |
| M.782 | I-776 | cyantraniliprole |
| M.783 | I-793 | cyantraniliprole |
| M.784 | I-794 | cyantraniliprole |
| M.785 | I-871 | cyantraniliprole |
| M.786 | I-872 | cyantraniliprole |
| M.787 | I-877 | cyantraniliprole |
| M.788 | I-878 | cyantraniliprole |
| M.789 | I-2563 | cyantraniliprole |
| M.790 | I-2564 | cyantraniliprole |
| M.791 | I-2671 | cyantraniliprole |
| M.792 | I-2672 | cyantraniliprole |
| M.793 | I-1 | A16.3 |
| M.794 | I-2 | A16.3 |
| M.795 | I-13 | A16.3 |
| M.796 | I-14 | A16.3 |
| M.797 | I-673 | A16.3 |
| M.798 | I-674 | A16.3 |
| M.799 | I-679 | A16.3 |
| M.800 | I-680 | A16.3 |
| M.801 | I-697 | A16.3 |
| M.802 | I-698 | A16.3 |
| M.803 | I-775 | A16.3 |
| M.804 | I-776 | A16.3 |
| M.805 | I-793 | A16.3 |
| M.806 | I-794 | A16.3 |
| M.807 | I-871 | A16.3 |
| M.808 | I-872 | A16.3 |
| M.809 | I-877 | A16.3 |
| M.810 | I-878 | A16.3 |
| M.811 | I-2563 | A16.3 |
| M.812 | I-2564 | A16.3 |
| M.813 | I-2671 | A16.3 |
| M.814 | I-2672 | A16.3 |
| M.815 | I-1 | pyrifluquinazon |
| M.816 | I-2 | pyrifluquinazon |
| M.817 | I-13 | pyrifluquinazon |
| M.818 | I-14 | pyrifluquinazon |
| M.819 | I-673 | pyrifluquinazon |
| M.820 | I-674 | pyrifluquinazon |
| M.821 | I-679 | pyrifluquinazon |
| M.822 | I-680 | pyrifluquinazon |
| M.823 | I-697 | pyrifluquinazon |
| M.824 | I-698 | pyrifluquinazon |
| M.825 | I-775 | pyrifluquinazon |
| M.826 | I-776 | pyrifluquinazon |
| M.827 | I-793 | pyrifluquinazon |
| M.828 | I-794 | pyrifluquinazon |
| M.829 | I-871 | pyrifluquinazon |
| M.830 | I-872 | pyrifluquinazon |
| M.831 | I-877 | pyrifluquinazon |
| M.832 | I-878 | pyrifluquinazon |
| M.833 | I-2563 | pyrifluquinazon |
| M.834 | I-2564 | pyrifluquinazon |
| M.835 | I-2671 | pyrifluquinazon |
| M.836 | I-2672 | pyrifluquinazon |
| M.837 | I-1 | sulfoxaflor |
| M.838 | I-2 | sulfoxaflor |
| M.839 | I-13 | sulfoxaflor |
| M.840 | I-14 | sulfoxaflor |
| M.841 | I-673 | sulfoxaflor |
| M.842 | I-674 | sulfoxaflor |
| M.843 | I-679 | sulfoxaflor |
| M.844 | I-680 | sulfoxaflor |
| M.845 | I-697 | sulfoxaflor |
| M.846 | I-698 | sulfoxaflor |
| M.847 | I-775 | sulfoxaflor |
| M.848 | I-776 | sulfoxaflor |
| M.849 | I-793 | sulfoxaflor |
| M.850 | I-794 | sulfoxaflor |
| M.851 | I-871 | sulfoxaflor |
| M.852 | I-872 | sulfoxaflor |
| M.853 | I-877 | sulfoxaflor |
| M.854 | I-878 | sulfoxaflor |
| M.855 | I-2563 | sulfoxaflor |
| M.856 | I-2564 | sulfoxaflor |
| M.857 | I-2671 | sulfoxaflor |
| M.858 | I-2672 | sulfoxaflor |
| M.859 | I-1 | afidopyropen |
| M.860 | I-2 | afidopyropen |
| M.861 | I-13 | afidopyropen |
| M.862 | I-14 | afidopyropen |
| M.863 | I-673 | afidopyropen |
| M.864 | I-674 | afidopyropen |
| M.865 | I-679 | afidopyropen |
| M.866 | I-680 | afidopyropen |
| M.867 | I-697 | afidopyropen |
| M.868 | I-698 | afidopyropen |
| M.869 | I-775 | afidopyropen |
| M.870 | I-776 | afidopyropen |
| M.871 | I-793 | afidopyropen |
| M.872 | I-794 | afidopyropen |
| M.873 | I-871 | afidopyropen |
| M.874 | I-872 | afidopyropen |
| M.875 | I-877 | afidopyropen |
| M.876 | I-878 | afidopyropen |
| M.877 | I-2563 | afidopyropen |
| M.878 | I-2564 | afidopyropen |
| M.879 | I-2671 | afidopyropen |
| M.880 | I-2672 | afidopyropen |

A further embodiment of the invention relates to mixtures of at least a compound of formula I with at least one compound B from the groups F.1 to F.11.

A preferred embodiment of the invention relates to mixtures of a compound of formula I with one compound B from the groups F.1 to F.11.

Binary mixtures of a compound of formula I and a compound B from the groups F.1 to F.11 are one preferred embodiment of the invention.

Ternary mixtures of a compound of formula I and two compounds B from the groups F.1 to F.11 are another preferred embodiment of the invention.

Ternary mixtures of a compound of formula I and a compound B from each of the groups A.1 to A.17 and F.1 to F.11 are another preferred embodiment of the invention.

A further embodiment of relates to mixtures of a compound of the formula I with at least one active compound B selected from the group F.1a), preferably from azoxystrobin, pyraclostrobin, fluoxastrobin, picoxystrobin and trifloxystrobin.

A further embodiment relates to mixtures of a compound of the formula I with at least one active compound B selected from the group of the F.1b), preferably cyazofamid.

A further embodiment relates to mixtures of a compound of the formula I with at least one active compound B selected from the group F.1c), preferably from boscalid, fluopyram, fluxapyroxad, penthiopyrad, and sedaxane.

A further embodiment relates to mixtures of a compound of the formula I with at least one active compound B selected from the group F.1d), preferably selected from silthiofam and ametoctradin.

A further embodiment relates to mixtures of a compound of the formula I with at least one active compound B selected from the group F.2a), preferably from difenoconazole, epoxiconazole, fluquinconazole, ipconazole, prothioconazole, tebuconazole, triticonazole, and prochloraz.

A further embodiment relates to mixtures of a compound of the formula I with at least one active compound B selected from the group F.2b).

A further embodiment relates to mixtures of a compound of the formula I with at least one active compound B selected from the group F.2c), preferably fenhexamid.

A further embodiment relates to mixtures of a compound of the formula I with at least one active compound B selected from the group F.3a), preferably from metalaxyl, and metalaxyl-M.

A further embodiment relates to mixtures of a compound of the formula I with at least one active compound B selected from the group F.3b).

A further embodiment relates to mixtures of a compound of the formula I with at least one active compound B selected from the group F.4a), preferably from carbendazim, and thiophanate-methyl.

A further embodiment relates to mixtures of a compound of the formula I with at least one active compound B selected from the group F.4b).

A further embodiment relates to mixtures of a compound of the formula I with at least one active compound B selected from the group F.5a), preferably selected from cyprodinil and pyrimethanil.

A further embodiment relates to mixtures of a compound of the formula I with at least one active compound B selected from the group F.5b).

A further embodiment relates to mixtures of a compound of the formula I with at least one active compound B selected from the group F.6a), preferably iprodione.

A further embodiment relates to mixtures of a compound of the formula I with at least one active compound B selected from the group F.6b).

A further embodiment relates to mixtures of a compound of the formula I with at least one active compound B selected from the group F.7a).

A further embodiment relates to mixtures of a compound of the formula I with at least one active compound B selected from the group F.7b).

A further embodiment relates to mixtures of a compound of the formula I with at least one active compound B selected from the group F.7c), preferably selected from benthiavalicarb and iprovalicarb.

A further embodiment relates to mixtures of a compound of the formula I with at least one active compound B selected from the group F.7d).

A further embodiment relates to mixtures of a compound of the formula I with at least one active compound B selected from the group F.8a).

A further embodiment relates to mixtures of a compound of the formula I with at least one active compound B selected from the group F.8b), preferably selected from thiram and mancozeb.

A further embodiment relates to mixtures of a compound of the formula I with at least one active compound B selected from the group F.8c), preferably chlorothalonil.

A further embodiment relates to mixtures of a compound of the formula I with at least one active compound B selected from the group F.8d).

A further embodiment relates to mixtures of a compound of the formula I with at least one active compound B selected from the group F.9.

A further embodiment relates to mixtures of a compound of the formula I with at least one active compound B selected from the group F.10.

A further embodiment relates to mixtures of a compound of the formula I with at least one active compound B selected from the group F.11 of fungicides of unknown mode of action.

A particular group of embodiments of relates to mixtures of a compound of the formula I with at least one active compound B selected from the group consisting of azoxystrobin, fluoxastrobin, picoxystrobin, pyraciostrobin, trifloxystrobin, fluxapyroxad, benthiavalicarb, iprovalicarb, fenhexamid, boscalid, mancozeb, ametoctradin, metalalxyl-m, pyrimethanil, cyprodinil, carbendazim, iprodion, cyazofamid, prochloraz, chlorothalonil, penthiopyrad, difenoconazole, epoxiconazole, ipconazole, prothioconazole and tebuconazole.

Especially preferred are inventive mixtures wherein the compound B is azoxystrobin and the compound I of formula I is a compound of Table I, Table II, Table III, or Table IV.

Especially preferred are inventive mixtures wherein the compound B is fluoxastrobin and the compound I of formula I is a compound of Table I, Table II, Table III, or Table IV.

Especially preferred are inventive mixtures wherein the compound B is picoxystrobin and the compound I of formula I is a compound of Table I, Table II, Table III, or Table IV.

Especially preferred are inventive mixtures wherein the compound B is pyraclostrobin and the compound I of formula I is a compound of Table I, Table II, Table III, or Table IV.

Especially preferred are inventive mixtures wherein the compound B is trifloxystrobin and the compound I of formula I is a compound of Table I, Table II, Table III, or Table IV.

Especially preferred are inventive mixtures wherein the compound B is fluoxapyroxad and the compound I of formula I is a compound of Table I, Table II, Table III, or Table IV.

Especially preferred are inventive mixtures wherein the compound B is benthiavalicarb and the compound I of formula I is a compound of Table I, Table II, Table III, or Table IV.

Especially preferred are inventive mixtures wherein the compound B is iprovalicarb and the compound I of formula I is a compound of Table I, Table II, Table III, or Table IV.

Especially preferred are inventive mixtures wherein the compound B is fenhexamid and the compound I of formula I is a compound of Table I, Table II, Table III, or Table IV.

Especially preferred are inventive mixtures wherein the compound B is boscalid and the compound I of formula I is a compound of Table I, Table II, Table III, or Table IV.

Especially preferred are inventive mixtures wherein the compound B is mancozeb and the compound I of formula I is a compound of Table I, Table II, Table III, or Table IV.

Especially preferred are inventive mixtures wherein the compound B is ametoctradin and the compound I of formula I is a compound of Table I, Table II, Table III, or Table IV.

Especially preferred are inventive mixtures wherein the compound B is metalaxyl-m and the compound I of formula I is a compound of Table I, Table II, Table III, or Table IV.

Especially preferred are inventive mixtures wherein the compound B is pyrimethanil and the compound I of formula I is a compound of Table I, Table II, Table III, or Table IV.

Especially preferred are inventive mixtures wherein the compound B is cyprodinil and the compound I of formula I is a compound of Table I, Table II, Table III, or Table IV.

Especially preferred are inventive mixtures wherein the compound B is carbendazim and the compound I of formula I is a compound of Table I, Table II, Table III, or Table IV.

Especially preferred are inventive mixtures wherein the compound B is iprodion and the compound I of formula I is a compound of Table I, Table II, Table III, or Table IV.

Especially preferred are inventive mixtures wherein the compound B is cyazofamid and the compound I of formula I is a compound of Table I, Table II, Table III, or Table IV.

Especially preferred are inventive mixtures wherein the compound B is prochloraz and the compound I of formula I is a compound of Table I, Table II, Table III, or Table IV.

Especially preferred are inventive mixtures wherein the compound B is chlorothalonil and the compound I of formula I is a compound of Table I, Table II, Table III, or Table IV.

Especially preferred are inventive mixtures wherein the compound B is penthiopyrad and the compound I of formula I is a compound of Table I, Table II, Table III, or Table IV.

Especially preferred are inventive mixtures wherein the compound B is difenoconazole and the compound I of formula I is a compound of Table I, Table II, Table III, or Table IV.

Especially preferred are inventive mixtures wherein the compound B is epoxiconazole and the compound I of formula I is a compound of Table I, Table II, Table III, or Table IV.

Especially preferred are inventive mixtures wherein the compound B is ipconazole and the compound I of formula I is a compound of Table I, Table II, Table III, or Table IV.

Especially preferred are inventive mixtures wherein the compound B is prothioconazole and the compound I of formula I is a compound of Table I, Table II, Table III, or Table IV.

Especially preferred are inventive mixtures wherein the compound B is tebuconazole and the compound I of formula I is a compound of Table I, Table II, Table III, or Table IV.

The following table M-F represents preferred combinations of the active compounds I of formula I as defined in table I and the active compounds B of groups F.1 to F.11 in mixtures according to the invention:

TABLE M-F

| No. | Comp. I | Comp. B |
|---|---|---|
| M.881 | I-1 | pyraclostrobin |
| M.882 | I-2 | pyraclostrobin |
| M.883 | I-13 | pyraclostrobin |
| M.884 | I-14 | pyraclostrobin |
| M.885 | I-673 | pyraclostrobin |
| M.886 | I-674 | pyraclostrobin |
| M.887 | I-679 | pyraclostrobin |
| M.888 | I-680 | pyraclostrobin |
| M.889 | I-697 | pyraclostrobin |
| M.890 | I-698 | pyraclostrobin |
| M.891 | I-775 | pyraclostrobin |
| M.892 | I-776 | pyraclostrobin |
| M.893 | I-793 | pyraclostrobin |
| M.894 | I-794 | pyraclostrobin |
| M.895 | I-871 | pyraclostrobin |
| M.896 | I-872 | pyraclostrobin |
| M.897 | I-877 | pyraclostrobin |
| M.898 | I-878 | pyraclostrobin |
| M.899 | I-2563 | pyraclostrobin |
| M.900 | I-2564 | pyraclostrobin |
| M.901 | I-2671 | pyraclostrobin |
| M.902 | I-2672 | pyraclostrobin |
| M.903 | I-1 | trifloxystrobin |
| M.904 | I-2 | trifloxystrobin |
| M.905 | I-13 | trifloxystrobin |
| M.906 | I-14 | trifloxystrobin |
| M.907 | I-673 | trifloxystrobin |
| M.908 | I-674 | trifloxystrobin |
| M.909 | I-679 | trifloxystrobin |
| M.910 | I-680 | trifloxystrobin |
| M.911 | I-697 | trifloxystrobin |
| M.912 | I-698 | trifloxystrobin |
| M.913 | I-775 | trifloxystrobin |
| M.914 | I-776 | trifloxystrobin |
| M.915 | I-793 | trifloxystrobin |
| M.916 | I-794 | trifloxystrobin |
| M.917 | I-871 | trifloxystrobin |
| M.918 | I-872 | trifloxystrobin |
| M.919 | I-877 | trifloxystrobin |
| M.920 | I-878 | trifloxystrobin |
| M.921 | I-2563 | trifloxystrobin |
| M.922 | I-2564 | trifloxystrobin |
| M.923 | I-2671 | trifloxystrobin |
| M.924 | I-2672 | trifloxystrobin |
| M.925 | I-1 | fluoxastrobin |
| M.926 | I-2 | fluoxastrobin |
| M.927 | I-13 | fluoxastrobin |
| M.928 | I-14 | fluoxastrobin |
| M.929 | I-673 | fluoxastrobin |
| M.930 | I-674 | fluoxastrobin |
| M.931 | I-679 | fluoxastrobin |
| M.932 | I-680 | fluoxastrobin |
| M.933 | I-697 | fluoxastrobin |
| M.934 | I-698 | fluoxastrobin |
| M.935 | I-775 | fluoxastrobin |
| M.936 | I-776 | fluoxastrobin |
| M.937 | I-793 | fluoxastrobin |
| M.938 | I-794 | fluoxastrobin |
| M.939 | I-871 | fluoxastrobin |
| M.940 | I-872 | fluoxastrobin |
| M.941 | I-877 | fluoxastrobin |
| M.942 | I-878 | fluoxastrobin |
| M.943 | I-2563 | fluoxastrobin |
| M.944 | I-2564 | fluoxastrobin |
| M.945 | I-2671 | fluoxastrobin |
| M.946 | I-2672 | fluoxastrobin |
| M.947 | I-1 | picoxystrobin |
| M.948 | I-2 | picoxystrobin |
| M.949 | I-13 | picoxystrobin |
| M.950 | I-14 | picoxystrobin |
| M.951 | I-673 | picoxystrobin |
| M.952 | I-674 | picoxystrobin |
| M.953 | I-679 | picoxystrobin |
| M.954 | I-680 | picoxystrobin |
| M.955 | I-697 | picoxystrobin |
| M.956 | I-698 | picoxystrobin |
| M.957 | I-775 | picoxystrobin |
| M.958 | I-776 | picoxystrobin |
| M.959 | I-793 | picoxystrobin |
| M.960 | I-794 | picoxystrobin |
| M.961 | I-871 | picoxystrobin |

TABLE M-F-continued

| No. | Comp. I | Comp. B |
|---|---|---|
| M.962 | I-872 | picoxystrobin |
| M.963 | I-877 | picoxystrobin |
| M.964 | I-878 | picoxystrobin |
| M.965 | I-2563 | picoxystrobin |
| M.966 | I-2564 | picoxystrobin |
| M.967 | I-2671 | picoxystrobin |
| M.968 | I-2672 | picoxystrobin |
| M.969 | I-1 | azoxystrobin |
| M.970 | I-2 | azoxystrobin |
| M.971 | I-13 | azoxystrobin |
| M.972 | I-14 | azoxystrobin |
| M.973 | I-673 | azoxystrobin |
| M.974 | I-674 | azoxystrobin |
| M.975 | I-679 | azoxystrobin |
| M.976 | I-680 | azoxystrobin |
| M.977 | I-697 | azoxystrobin |
| M.978 | I-698 | azoxystrobin |
| M.979 | I-775 | azoxystrobin |
| M.980 | I-776 | azoxystrobin |
| M.981 | I-793 | azoxystrobin |
| M.982 | I-794 | azoxystrobin |
| M.983 | I-871 | azoxystrobin |
| M.984 | I-872 | azoxystrobin |
| M.985 | I-877 | azoxystrobin |
| M.986 | I-878 | azoxystrobin |
| M.987 | I-2563 | azoxystrobin |
| M.988 | I-2564 | azoxystrobin |
| M.989 | I-2671 | azoxystrobin |
| M.990 | I-2672 | azoxystrobin |
| M.991 | I-1 | cyazofamid |
| M.992 | I-2 | cyazofamid |
| M.993 | I-13 | cyazofamid |
| M.994 | I-14 | cyazofamid |
| M.995 | I-673 | cyazofamid |
| M.996 | I-674 | cyazofamid |
| M.997 | I-679 | cyazofamid |
| M.998 | I-680 | cyazofamid |
| M.999 | I-697 | cyazofamid |
| M.1000 | I-698 | cyazofamid |
| M.1001 | I-775 | cyazofamid |
| M.1002 | I-776 | cyazofamid |
| M.1003 | I-793 | cyazofamid |
| M.1004 | I-794 | cyazofamid |
| M.1005 | I-871 | cyazofamid |
| M.1006 | I-872 | cyazofamid |
| M.1007 | I-877 | cyazofamid |
| M.1008 | I-878 | cyazofamid |
| M.1009 | I-2563 | cyazofamid |
| M.1010 | I-2564 | cyazofamid |
| M.1011 | I-2671 | cyazofamid |
| M.1012 | I-2672 | cyazofamid |
| M.1013 | I-1 | boscalid |
| M.1014 | I-2 | boscalid |
| M.1015 | I-13 | boscalid |
| M.1016 | I-14 | boscalid |
| M.1017 | I-673 | boscalid |
| M.1018 | I-674 | boscalid |
| M.1019 | I-679 | boscalid |
| M.1020 | I-680 | boscalid |
| M.1021 | I-697 | boscalid |
| M.1022 | I-698 | boscalid |
| M.1023 | I-775 | boscalid |
| M.1024 | I-776 | boscalid |
| M.1025 | I-793 | boscalid |
| M.1026 | I-794 | boscalid |
| M.1027 | I-871 | boscalid |
| M.1028 | I-872 | boscalid |
| M.1029 | I-877 | boscalid |
| M.1030 | I-878 | boscalid |
| M.1031 | I-2563 | boscalid |
| M.1032 | I-2564 | boscalid |
| M.1033 | I-2671 | boscalid |
| M.1034 | I-2672 | boscalid |
| M.1035 | I-1 | fluopyram |
| M.1036 | I-2 | fluopyram |
| M.1037 | I-13 | fluopyram |
| M.1038 | I-14 | fluopyram |
| M.1039 | I-673 | fluopyram |
| M.1040 | I-674 | fluopyram |
| M.1041 | I-679 | fluopyram |
| M.1042 | I-680 | fluopyram |
| M.1043 | I-697 | fluopyram |
| M.1044 | I-698 | fluopyram |
| M.1045 | I-775 | fluopyram |
| M.1046 | I-776 | fluopyram |
| M.1047 | I-793 | fluopyram |
| M.1048 | I-794 | fluopyram |
| M.1049 | I-871 | fluopyram |
| M.1050 | I-872 | fluopyram |
| M.1051 | I-877 | fluopyram |
| M.1052 | I-878 | fluopyram |
| M.1053 | I-2563 | fluopyram |
| M.1054 | I-2564 | fluopyram |
| M.1055 | I-2671 | fluopyram |
| M.1056 | I-2672 | fluopyram |
| M.1057 | I-1 | fluxapyroxad |
| M.1058 | I-2 | fluxapyroxad |
| M.1059 | I-13 | fluxapyroxad |
| M.1060 | I-14 | fluxapyroxad |
| M.1061 | I-673 | fluxapyroxad |
| M.1062 | I-674 | fluxapyroxad |
| M.1063 | I-679 | fluxapyroxad |
| M.1064 | I-680 | fluxapyroxad |
| M.1065 | I-697 | fluxapyroxad |
| M.1066 | I-698 | fluxapyroxad |
| M.1067 | I-775 | fluxapyroxad |
| M.1068 | I-776 | fluxapyroxad |
| M.1069 | I-793 | fluxapyroxad |
| M.1070 | I-794 | fluxapyroxad |
| M.1071 | I-871 | fluxapyroxad |
| M.1072 | I-872 | fluxapyroxad |
| M.1073 | I-877 | fluxapyroxad |
| M.1074 | I-878 | fluxapyroxad |
| M.1075 | I-2563 | fluxapyroxad |
| M.1076 | I-2564 | fluxapyroxad |
| M.1077 | I-2671 | fluxapyroxad |
| M.1078 | I-2672 | fluxapyroxad |
| M.1079 | I-1 | penthiopyrad |
| M.1080 | I-2 | penthiopyrad |
| M.1081 | I-13 | penthiopyrad |
| M.1082 | I-14 | penthiopyrad |
| M.1083 | I-673 | penthiopyrad |
| M.1084 | I-674 | penthiopyrad |
| M.1085 | I-679 | penthiopyrad |
| M.1086 | I-680 | penthiopyrad |
| M.1087 | I-697 | penthiopyrad |
| M.1088 | I-698 | penthiopyrad |
| M.1089 | I-775 | penthiopyrad |
| M.1090 | I-776 | penthiopyrad |
| M.1091 | I-793 | penthiopyrad |
| M.1092 | I-794 | penthiopyrad |
| M.1093 | I-871 | penthiopyrad |
| M.1094 | I-872 | penthiopyrad |
| M.1095 | I-877 | penthiopyrad |
| M.1096 | I-878 | penthiopyrad |
| M.1097 | I-2563 | penthiopyrad |
| M.1098 | I-2564 | penthiopyrad |
| M.1099 | I-2671 | penthiopyrad |
| M.1100 | I-2672 | penthiopyrad |
| M.1101 | I-1 | sedaxane |
| M.1102 | I-2 | sedaxane |
| M.1103 | I-13 | sedaxane |
| M.1104 | I-14 | sedaxane |
| M.1105 | I-673 | sedaxane |
| M.1106 | I-674 | sedaxane |
| M.1107 | I-679 | sedaxane |
| M.1108 | I-680 | sedaxane |
| M.1109 | I-697 | sedaxane |
| M.1110 | I-698 | sedaxane |
| M.1111 | I-775 | sedaxane |
| M.1112 | I-776 | sedaxane |
| M.1113 | I-793 | sedaxane |
| M.1114 | I-794 | sedaxane |
| M.1115 | I-871 | sedaxane |
| M.1116 | I-872 | sedaxane |
| M.1117 | I-877 | sedaxane |

TABLE M-F-continued

| No. | Comp. I | Comp. B |
|---|---|---|
| M.1118 | I-878 | sedaxane |
| M.1119 | I-2563 | sedaxane |
| M.1120 | I-2564 | sedaxane |
| M.1121 | I-2671 | sedaxane |
| M.1122 | I-2672 | sedaxane |
| M.1123 | I-1 | silthiofam |
| M.1124 | I-2 | silthiofam |
| M.1125 | I-13 | silthiofam |
| M.1126 | I-14 | silthiofam |
| M.1127 | I-673 | silthiofam |
| M.1128 | I-674 | silthiofam |
| M.1129 | I-679 | silthiofam |
| M.1130 | I-680 | silthiofam |
| M.1131 | I-697 | silthiofam |
| M.1132 | I-698 | silthiofam |
| M.1133 | I-775 | silthiofam |
| M.1134 | I-776 | silthiofam |
| M.1135 | I-793 | silthiofam |
| M.1136 | I-794 | silthiofam |
| M.1137 | I-871 | silthiofam |
| M.1138 | I-872 | silthiofam |
| M.1139 | I-877 | silthiofam |
| M.1140 | I-878 | silthiofam |
| M.1141 | I-2563 | silthiofam |
| M.1142 | I-2564 | silthiofam |
| M.1143 | I-2671 | silthiofam |
| M.1144 | I-2672 | silthiofam |
| M.1145 | I-1 | ametoctradin |
| M.1146 | I-2 | ametoctradin |
| M.1147 | I-13 | ametoctradin |
| M.1148 | I-14 | ametoctradin |
| M.1149 | I-673 | ametoctradin |
| M.1150 | I-674 | ametoctradin |
| M.1151 | I-679 | ametoctradin |
| M.1152 | I-680 | ametoctradin |
| M.1153 | I-697 | ametoctradin |
| M.1154 | I-698 | ametoctradin |
| M.1155 | I-775 | ametoctradin |
| M.1156 | I-776 | ametoctradin |
| M.1157 | I-793 | ametoctradin |
| M.1158 | I-794 | ametoctradin |
| M.1159 | I-871 | ametoctradin |
| M.1160 | I-872 | ametoctradin |
| M.1161 | I-877 | ametoctradin |
| M.1162 | I-878 | ametoctradin |
| M.1163 | I-2563 | ametoctradin |
| M.1164 | I-2564 | ametoctradin |
| M.1165 | I-2671 | ametoctradin |
| M.1166 | I-2672 | ametoctradin |
| M.1167 | I-1 | epoxiconazol |
| M.1168 | I-2 | epoxiconazol |
| M.1169 | I-13 | epoxiconazol |
| M.1170 | I-14 | epoxiconazol |
| M.1171 | I-673 | epoxiconazol |
| M.1172 | I-674 | epoxiconazol |
| M.1173 | I-679 | epoxiconazol |
| M.1174 | I-680 | epoxiconazol |
| M.1175 | I-697 | epoxiconazol |
| M.1176 | I-698 | epoxiconazol |
| M.1177 | I-775 | epoxiconazol |
| M.1178 | I-776 | epoxiconazol |
| M.1179 | I-793 | epoxiconazol |
| M.1180 | I-794 | epoxiconazol |
| M.1181 | I-871 | epoxiconazol |
| M.1182 | I-872 | epoxiconazol |
| M.1183 | I-877 | epoxiconazol |
| M.1184 | I-878 | epoxiconazol |
| M.1185 | I-2563 | epoxiconazol |
| M.1186 | I-2564 | epoxiconazol |
| M.1187 | I-2671 | epoxiconazol |
| M.1188 | I-2672 | epoxiconazol |
| M.1189 | I-1 | difenoconazol |
| M.1190 | I-2 | difenoconazol |
| M.1191 | I-13 | difenoconazol |
| M.1192 | I-14 | difenoconazol |
| M.1193 | I-673 | difenoconazol |
| M.1194 | I-674 | difenoconazol |
| M.1195 | I-679 | difenoconazol |
| M.1196 | I-680 | difenoconazol |
| M.1197 | I-697 | difenoconazol |
| M.1198 | I-698 | difenoconazol |
| M.1199 | I-775 | difenoconazol |
| M.1200 | I-776 | difenoconazol |
| M.1201 | I-793 | difenoconazol |
| M.1202 | I-794 | difenoconazol |
| M.1203 | I-871 | difenoconazol |
| M.1204 | I-872 | difenoconazol |
| M.1205 | I-877 | difenoconazol |
| M.1206 | I-878 | difenoconazol |
| M.1207 | I-2563 | difenoconazol |
| M.1208 | I-2564 | difenoconazol |
| M.1209 | I-2671 | difenoconazol |
| M.1210 | I-2672 | difenoconazol |
| M.1211 | I-1 | ipconazole |
| M.1212 | I-2 | ipconazole |
| M.1213 | I-13 | ipconazole |
| M.1214 | I-14 | ipconazole |
| M.1215 | I-673 | ipconazole |
| M.1216 | I-674 | ipconazole |
| M.1217 | I-679 | ipconazole |
| M.1218 | I-680 | ipconazole |
| M.1219 | I-697 | ipconazole |
| M.1220 | I-698 | ipconazole |
| M.1221 | I-775 | ipconazole |
| M.1222 | I-776 | ipconazole |
| M.1223 | I-793 | ipconazole |
| M.1224 | I-794 | ipconazole |
| M.1225 | I-871 | ipconazole |
| M.1226 | I-872 | ipconazole |
| M.1227 | I-877 | ipconazole |
| M.1228 | I-878 | ipconazole |
| M.1229 | I-2563 | ipconazole |
| M.1230 | I-2564 | ipconazole |
| M.1231 | I-2671 | ipconazole |
| M.1232 | I-2672 | ipconazole |
| M.1233 | I-1 | prothioconazole |
| M.1234 | I-2 | prothioconazole |
| M.1235 | I-13 | prothioconazole |
| M.1236 | I-14 | prothioconazole |
| M.1237 | I-673 | prothioconazole |
| M.1238 | I-674 | prothioconazole |
| M.1239 | I-679 | prothioconazole |
| M.1240 | I-680 | prothioconazole |
| M.1241 | I-697 | prothioconazole |
| M.1242 | I-698 | prothioconazole |
| M.1243 | I-775 | prothioconazole |
| M.1244 | I-776 | prothioconazole |
| M.1245 | I-793 | prothioconazole |
| M.1246 | I-794 | prothioconazole |
| M.1247 | I-871 | prothioconazole |
| M.1248 | I-872 | prothioconazole |
| M.1249 | I-877 | prothioconazole |
| M.1250 | I-878 | prothioconazole |
| M.1251 | I-2563 | prothioconazole |
| M.1252 | I-2564 | prothioconazole |
| M.1253 | I-2671 | prothioconazole |
| M.1254 | I-2672 | prothioconazole |
| M.1255 | I-1 | tebuconazole |
| M.1256 | I-2 | tebuconazole |
| M.1257 | I-13 | tebuconazole |
| M.1258 | I-14 | tebuconazole |
| M.1259 | I-673 | tebuconazole |
| M.1260 | I-674 | tebuconazole |
| M.1261 | I-679 | tebuconazole |
| M.1262 | I-680 | tebuconazole |
| M.1263 | I-697 | tebuconazole |
| M.1264 | I-698 | tebuconazole |
| M.1265 | I-775 | tebuconazole |
| M.1266 | I-776 | tebuconazole |
| M.1267 | I-793 | tebuconazole |
| M.1268 | I-794 | tebuconazole |
| M.1269 | I-871 | tebuconazole |
| M.1270 | I-872 | tebuconazole |
| M.1271 | I-877 | tebuconazole |
| M.1272 | I-878 | tebuconazole |
| M.1273 | I-2563 | tebuconazole |

TABLE M-F-continued

| No. | Comp. I | Comp. B |
|---|---|---|
| M.1274 | I-2564 | tebuconazole |
| M.1275 | I-2671 | tebuconazole |
| M.1276 | I-2672 | tebuconazole |
| M.1277 | I-1 | fluquinconazole |
| M.1278 | I-2 | fluquinconazole |
| M.1279 | I-13 | fluquinconazole |
| M.1280 | I-14 | fluquinconazole |
| M.1281 | I-673 | fluquinconazole |
| M.1282 | I-674 | fluquinconazole |
| M.1283 | I-679 | fluquinconazole |
| M.1284 | I-680 | fluquinconazole |
| M.1285 | I-697 | fluquinconazole |
| M.1286 | I-698 | fluquinconazole |
| M.1287 | I-775 | fluquinconazole |
| M.1288 | I-776 | fluquinconazole |
| M.1289 | I-793 | fluquinconazole |
| M.1290 | I-794 | fluquinconazole |
| M.1291 | I-871 | fluquinconazole |
| M.1292 | I-872 | fluquinconazole |
| M.1293 | I-877 | fluquinconazole |
| M.1294 | I-878 | fluquinconazole |
| M.1295 | I-2563 | fluquinconazole |
| M.1296 | I-2564 | fluquinconazole |
| M.1297 | I-2671 | fluquinconazole |
| M.1298 | I-2672 | fluquinconazole |
| M.1299 | I-1 | triticonazole |
| M.1300 | I-2 | triticonazole |
| M.1301 | I-13 | triticonazole |
| M.1302 | I-14 | triticonazole |
| M.1303 | I-673 | triticonazole |
| M.1304 | I-674 | triticonazole |
| M.1305 | I-679 | triticonazole |
| M.1306 | I-680 | triticonazole |
| M.1307 | I-697 | triticonazole |
| M.1308 | I-698 | triticonazole |
| M.1309 | I-775 | triticonazole |
| M.1310 | I-776 | triticonazole |
| M.1311 | I-793 | triticonazole |
| M.1312 | I-794 | triticonazole |
| M.1313 | I-871 | triticonazole |
| M.1314 | I-872 | triticonazole |
| M.1315 | I-877 | triticonazole |
| M.1316 | I-878 | triticonazole |
| M.1317 | I-2563 | triticonazole |
| M.1318 | I-2564 | triticonazole |
| M.1319 | I-2671 | triticonazole |
| M.1320 | I-2672 | triticonazole |
| M.1321 | I-1 | prochloraz |
| M.1322 | I-2 | prochloraz |
| M.1323 | I-13 | prochloraz |
| M.1324 | I-14 | prochloraz |
| M.1325 | I-673 | prochloraz |
| M.1326 | I-674 | prochloraz |
| M.1327 | I-679 | prochloraz |
| M.1328 | I-680 | prochloraz |
| M.1329 | I-697 | prochloraz |
| M.1330 | I-698 | prochloraz |
| M.1331 | I-775 | prochloraz |
| M.1332 | I-776 | prochloraz |
| M.1333 | I-793 | prochloraz |
| M.1334 | I-794 | prochloraz |
| M.1335 | I-871 | prochloraz |
| M.1336 | I-872 | prochloraz |
| M.1337 | I-877 | prochloraz |
| M.1338 | I-878 | prochloraz |
| M.1339 | I-2563 | prochloraz |
| M.1340 | I-2564 | prochloraz |
| M.1341 | I-2671 | prochloraz |
| M.1342 | I-2672 | prochloraz |
| M.1343 | I-1 | fenhexamid |
| M.1344 | I-2 | fenhexamid |
| M.1345 | I-13 | fenhexamid |
| M.1346 | I-14 | fenhexamid |
| M.1347 | I-673 | fenhexamid |
| M.1348 | I-674 | fenhexamid |
| M.1349 | I-679 | fenhexamid |
| M.1350 | I-680 | fenhexamid |
| M.1351 | I-697 | fenhexamid |
| M.1352 | I-698 | fenhexamid |
| M.1353 | I-775 | fenhexamid |
| M.1354 | I-776 | fenhexamid |
| M.1355 | I-793 | fenhexamid |
| M.1356 | I-794 | fenhexamid |
| M.1357 | I-871 | fenhexamid |
| M.1358 | I-872 | fenhexamid |
| M.1359 | I-877 | fenhexamid |
| M.1360 | I-878 | fenhexamid |
| M.1361 | I-2563 | fenhexamid |
| M.1362 | I-2564 | fenhexamid |
| M.1363 | I-2671 | fenhexamid |
| M.1364 | I-2672 | fenhexamid |
| M.1365 | I-1 | metalaxyl |
| M.1366 | I-2 | metalaxyl |
| M.1367 | I-13 | metalaxyl |
| M.1368 | I-14 | metalaxyl |
| M.1369 | I-673 | metalaxyl |
| M.1370 | I-674 | metalaxyl |
| M.1371 | I-679 | metalaxyl |
| M.1372 | I-680 | metalaxyl |
| M.1373 | I-697 | metalaxyl |
| M.1374 | I-698 | metalaxyl |
| M.1375 | I-775 | metalaxyl |
| M.1376 | I-776 | metalaxyl |
| M.1377 | I-793 | metalaxyl |
| M.1378 | I-794 | metalaxyl |
| M.1379 | I-871 | metalaxyl |
| M.1380 | I-872 | metalaxyl |
| M.1381 | I-877 | metalaxyl |
| M.1382 | I-878 | metalaxyl |
| M.1383 | I-2563 | metalaxyl |
| M.1384 | I-2564 | metalaxyl |
| M.1385 | I-2671 | metalaxyl |
| M.1386 | I-2672 | metalaxyl |
| M.1387 | I-1 | metalaxyl-M |
| M.1388 | I-2 | metalaxyl-M |
| M.1389 | I-13 | metalaxyl-M |
| M.1390 | I-14 | metalaxyl-M |
| M.1391 | I-673 | metalaxyl-M |
| M.1392 | I-674 | metalaxyl-M |
| M.1393 | I-679 | metalaxyl-M |
| M.1394 | I-680 | metalaxyl-M |
| M.1395 | I-697 | metalaxyl-M |
| M.1396 | I-698 | metalaxyl-M |
| M.1397 | I-775 | metalaxyl-M |
| M.1398 | I-776 | metalaxyl-M |
| M.1399 | I-793 | metalaxyl-M |
| M.1400 | I-794 | metalaxyl-M |
| M.1401 | I-871 | metalaxyl-M |
| M.1402 | I-872 | metalaxyl-M |
| M.1403 | I-877 | metalaxyl-M |
| M.1404 | I-878 | metalaxyl-M |
| M.1405 | I-2563 | metalaxyl-M |
| M.1406 | I-2564 | metalaxyl-M |
| M.1407 | I-2671 | metalaxyl-M |
| M.1408 | I-2672 | metalaxyl-M |
| M.1409 | I-1 | carbendazim |
| M.1410 | I-2 | carbendazim |
| M.1411 | I-13 | carbendazim |
| M.1412 | I-14 | carbendazim |
| M.1413 | I-673 | carbendazim |
| M.1414 | I-674 | carbendazim |
| M.1415 | I-679 | carbendazim |
| M.1416 | I-680 | carbendazim |
| M.1417 | I-697 | carbendazim |
| M.1418 | I-698 | carbendazim |
| M.1419 | I-775 | carbendazim |
| M.1420 | I-776 | carbendazim |
| M.1421 | I-793 | carbendazim |
| M.1422 | I-794 | carbendazim |
| M.1423 | I-871 | carbendazim |
| M.1424 | I-872 | carbendazim |
| M.1425 | I-877 | carbendazim |
| M.1426 | I-878 | carbendazim |
| M.1427 | I-2563 | carbendazim |
| M.1428 | I-2564 | carbendazim |
| M.1429 | I-2671 | carbendazim |

TABLE M-F-continued

| No. | Comp. I | Comp. B |
|---|---|---|
| M.1430 | I-2672 | carbendazim |
| M.1431 | I-1 | thiophanate-methyl |
| M.1432 | I-2 | thiophanate-methyl |
| M.1433 | I-13 | thiophanate-methyl |
| M.1434 | I-14 | thiophanate-methyl |
| M.1435 | I-673 | thiophanate-methyl |
| M.1436 | I-674 | thiophanate-methyl |
| M.1437 | I-679 | thiophanate-methyl |
| M.1438 | I-680 | thiophanate-methyl |
| M.1439 | I-697 | thiophanate-methyl |
| M.1440 | I-698 | thiophanate-methyl |
| M.1441 | I-775 | thiophanate-methyl |
| M.1442 | I-776 | thiophanate-methyl |
| M.1443 | I-793 | thiophanate-methyl |
| M.1444 | I-794 | thiophanate-methyl |
| M.1445 | I-871 | thiophanate-methyl |
| M.1446 | I-872 | thiophanate-methyl |
| M.1447 | I-877 | thiophanate-methyl |
| M.1448 | I-878 | thiophanate-methyl |
| M.1449 | I-2563 | thiophanate-methyl |
| M.1450 | I-2564 | thiophanate-methyl |
| M.1451 | I-2671 | thiophanate-methyl |
| M.1452 | I-2672 | thiophanate-methyl |
| M.1453 | I-1 | cyprodinil |
| M.1454 | I-2 | cyprodinil |
| M.1455 | I-13 | cyprodinil |
| M.1456 | I-14 | cyprodinil |
| M.1457 | I-673 | cyprodinil |
| M.1458 | I-674 | cyprodinil |
| M.1459 | I-679 | cyprodinil |
| M.1460 | I-680 | cyprodinil |
| M.1461 | I-697 | cyprodinil |
| M.1462 | I-698 | cyprodinil |
| M.1463 | I-775 | cyprodinil |
| M.1464 | I-776 | cyprodinil |
| M.1465 | I-793 | cyprodinil |
| M.1466 | I-794 | cyprodinil |
| M.1467 | I-871 | cyprodinil |
| M.1468 | I-872 | cyprodinil |
| M.1469 | I-877 | cyprodinil |
| M.1470 | I-878 | cyprodinil |
| M.1471 | I-2563 | cyprodinil |
| M.1472 | I-2564 | cyprodinil |
| M.1473 | I-2671 | cyprodinil |
| M.1474 | I-2672 | cyprodinil |
| M.1475 | I-1 | pyrimethanil |
| M.1476 | I-2 | pyrimethanil |
| M.1477 | I-13 | pyrimethanil |
| M.1478 | I-14 | pyrimethanil |
| M.1479 | I-673 | pyrimethanil |
| M.1480 | I-674 | pyrimethanil |
| M.1481 | I-679 | pyrimethanil |
| M.1482 | I-680 | pyrimethanil |
| M.1483 | I-697 | pyrimethanil |
| M.1484 | I-698 | pyrimethanil |
| M.1485 | I-775 | pyrimethanil |
| M.1486 | I-776 | pyrimethanil |
| M.1487 | I-793 | pyrimethanil |
| M.1488 | I-794 | pyrimethanil |
| M.1489 | I-871 | pyrimethanil |
| M.1490 | I-872 | pyrimethanil |
| M.1491 | I-877 | pyrimethanil |
| M.1492 | I-878 | pyrimethanil |
| M.1493 | I-2563 | pyrimethanil |
| M.1494 | I-2564 | pyrimethanil |
| M.1495 | I-2671 | pyrimethanil |
| M.1496 | I-2672 | pyrimethanil |
| M.1497 | I-1 | iprodione |
| M.1498 | I-2 | iprodione |
| M.1499 | I-13 | iprodione |
| M.1500 | I-14 | iprodione |
| M.1501 | I-673 | iprodione |
| M.1502 | I-674 | iprodione |
| M.1503 | I-679 | iprodione |
| M.1504 | I-680 | iprodione |
| M.1505 | I-697 | iprodione |
| M.1506 | I-698 | iprodione |
| M.1507 | I-775 | iprodione |
| M.1508 | I-776 | iprodione |
| M.1509 | I-793 | iprodione |
| M.1510 | I-794 | iprodione |
| M.1511 | I-871 | iprodione |
| M.1512 | I-872 | iprodione |
| M.1513 | I-877 | iprodione |
| M.1514 | I-878 | iprodione |
| M.1515 | I-2563 | iprodione |
| M.1516 | I-2564 | iprodione |
| M.1517 | I-2671 | iprodione |
| M.1518 | I-2672 | iprodione |
| M.1519 | I-1 | benthiavalicarb |
| M.1520 | I-2 | benthiavalicarb |
| M.1521 | I-13 | benthiavalicarb |
| M.1522 | I-14 | benthiavalicarb |
| M.1523 | I-673 | benthiavalicarb |
| M.1524 | I-674 | benthiavalicarb |
| M.1525 | I-679 | benthiavalicarb |
| M.1526 | I-680 | benthiavalicarb |
| M.1527 | I-697 | benthiavalicarb |
| M.1528 | I-698 | benthiavalicarb |
| M.1529 | I-775 | benthiavalicarb |
| M.1530 | I-776 | benthiavalicarb |
| M.1531 | I-793 | benthiavalicarb |
| M.1532 | I-794 | benthiavalicarb |
| M.1533 | I-871 | benthiavalicarb |
| M.1534 | I-872 | benthiavalicarb |
| M.1535 | I-877 | benthiavalicarb |
| M.1536 | I-878 | benthiavalicarb |
| M.1537 | I-2563 | benthiavalicarb |
| M.1538 | I-2564 | benthiavalicarb |
| M.1539 | I-2671 | benthiavalicarb |
| M.1540 | I-2672 | benthiavalicarb |
| M.1541 | I-1 | iprovalicarb |
| M.1542 | I-2 | iprovalicarb |
| M.1543 | I-13 | iprovalicarb |
| M.1544 | I-14 | iprovalicarb |
| M.1545 | I-673 | iprovalicarb |
| M.1546 | I-674 | iprovalicarb |
| M.1547 | I-679 | iprovalicarb |
| M.1548 | I-680 | iprovalicarb |
| M.1549 | I-697 | iprovalicarb |
| M.1550 | I-698 | iprovalicarb |
| M.1551 | I-775 | iprovalicarb |
| M.1552 | I-776 | iprovalicarb |
| M.1553 | I-793 | iprovalicarb |
| M.1554 | I-794 | iprovalicarb |
| M.1555 | I-871 | iprovalicarb |
| M.1556 | I-872 | iprovalicarb |
| M.1557 | I-877 | iprovalicarb |
| M.1558 | I-878 | iprovalicarb |
| M.1559 | I-2563 | iprovalicarb |
| M.1560 | I-2564 | iprovalicarb |
| M.1561 | I-2671 | iprovalicarb |
| M.1562 | I-2672 | iprovalicarb |
| M.1563 | I-1 | thiram |
| M.1564 | I-2 | thiram |
| M.1565 | I-13 | thiram |
| M.1566 | I-14 | thiram |
| M.1567 | I-673 | thiram |
| M.1568 | I-674 | thiram |
| M.1569 | I-679 | thiram |
| M.1570 | I-680 | thiram |
| M.1571 | I-697 | thiram |
| M.1572 | I-698 | thiram |
| M.1573 | I-775 | thiram |
| M.1574 | I-776 | thiram |
| M.1575 | I-793 | thiram |
| M.1576 | I-794 | thiram |
| M.1577 | I-871 | thiram |
| M.1578 | I-872 | thiram |
| M.1579 | I-877 | thiram |
| M.1580 | I-878 | thiram |
| M.1581 | I-2563 | thiram |
| M.1582 | I-2564 | thiram |
| M.1583 | I-2671 | thiram |
| M.1584 | I-2672 | thiram |
| M.1585 | I-1 | mancozeb |

TABLE M-F-continued

| No. | Comp. I | Comp. B |
|---|---|---|
| M.1586 | I-2 | mancozeb |
| M.1587 | I-13 | mancozeb |
| M.1588 | I-14 | mancozeb |
| M.1589 | I-673 | mancozeb |
| M.1590 | I-674 | mancozeb |
| M.1591 | I-679 | mancozeb |
| M.1592 | I-680 | mancozeb |
| M.1593 | I-697 | mancozeb |
| M.1594 | I-698 | mancozeb |
| M.1595 | I-775 | mancozeb |
| M.1596 | I-776 | mancozeb |
| M.1597 | I-793 | mancozeb |
| M.1598 | I-794 | mancozeb |
| M.1599 | I-871 | mancozeb |
| M.1600 | I-872 | mancozeb |
| M.1601 | I-877 | mancozeb |
| M.1602 | I-878 | mancozeb |
| M.1603 | I-2563 | mancozeb |
| M.1604 | I-2564 | mancozeb |
| M.1605 | I-2671 | mancozeb |
| M.1606 | I-2672 | mancozeb |
| M.1607 | I-1 | chlorothalonil |
| M.1608 | I-2 | chlorothalonil |
| M.1609 | I-13 | chlorothalonil |
| M.1610 | I-14 | chlorothalonil |
| M.1611 | I-673 | chlorothalonil |
| M.1612 | I-674 | chlorothalonil |
| M.1613 | I-679 | chlorothalonil |
| M.1614 | I-680 | chlorothalonil |
| M.1615 | I-697 | chlorothalonil |
| M.1616 | I-698 | chlorothalonil |
| M.1617 | I-775 | chlorothalonil |
| M.1618 | I-776 | chlorothalonil |
| M.1619 | I-793 | chlorothalonil |
| M.1620 | I-794 | chlorothalonil |
| M.1621 | I-871 | chlorothalonil |
| M.1622 | I-872 | chlorothalonil |
| M.1623 | I-877 | chlorothalonil |
| M.1624 | I-878 | chlorothalonil |
| M.1625 | I-2563 | chlorothalonil |
| M.1626 | I-2564 | chlorothalonil |
| M.1627 | I-2671 | chlorothalonil |
| M.1628 | I-2672 | chlorothalonil |

The mixtures of the present invention have excellent activity against a broad spectrum of phytopathogenic fungi and animal pests.

The inventive compounds and the mixtures of the present invention have excellent activity against a broad spectrum of animal pests.

They are in particular suitable for efficiently controlling invertebrate pests. Particularier, they are suitable for efficiently controlling arthropodal pests such as arachnids, myriapedes and insects as well as nematodes.

In particular, they are suitable for controlling insect pests, such as insects from the order of lepidopterans (Lepidoptera), for example *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibemia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicomis, Diabrotica semipunctata, Diabrotica* 12-punctata *Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius califomicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti Aedes albopictus Aedes vexans, Anastrepha ludens, Anopheles maculipennis, Anopheles crudcans, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nignpalpus, Culex quinquefasciatus, Culex tarsalis, Culiseta inomata, Culiseta melanura, Dacus cucurbitae, Dacus oleae, Dasineura brasscae, Delia antique, Delia coarcata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Linomyza sativae, Linomyza trifolii, Lucilia caprina, Lucilia cuprina, Luclia sericata, Lycoria pectoralis, Mansonia titilanus Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhodalis, Sarcophaga* spp., *Simulium vittatum, Stonoxys calcitrans, Tabanus bovinus, Tabanus atratus, Tabanus lineola*, and *Tabanus similis, Tipula oleracea*, and *Tipua paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (*Blattaria—Blattodea*), e.g. *Blattela germanica, Blattella asahinae, Penpianeta americana, Penrplaneta japonica, Penpianeta brunnea, Periplaneta fuligginosa, Periplaneta australasiae,* and *Blatta orientalis;* bugs, aphids, leafhoppers, whiteflies, scale insects, cicadas (*Hemiptera*), e.g. *Acrastemum hilare, Blissus leucopterus, Cyrtopelits notatus, Dysdercus cingulatus, Dysdercus internedius, Eurygaster integriceps, Euschistus impictdiventris, Leptoglossus phyllopus, Lygus lineolaris, Lygus pratensis, Nezara vindula, Piesma quadrata, Sotubea insularis, Thyanta perditor, Acyrthosiphon onobrychis, Adelges laricis, Aphidula nastuii, Aphis fabae, Aphis forbesi, Aphis pomi, Aphis gossyphi, Aphis grossulanae, Aphis schneiden; Aphis spiraecola, Aphis sambucd Acyrthosiphon pisum, Aulaoothum solani, Bemisia argentifoli, Brachycaudus cardui, Brachycaudus helichrysi, Brachycaudus persicae, Brachycaudus prunicola, Brevioryne brassicae, Capitophorus horni, Cerosipha gossypi, Chaetosiphon fragaefolii, Cryptomyzus ribis, Dreyfusia nordmannianae, Dreyfusia piceae, Dysaphis radiola, Dysaulacorthum pseudosoani, Dysaphis plantaginea, Dysaphis pyri; Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nign; Nilaparvata lugens, Pemphigus bursanus, Perkinsiella saccharicida, Phorodon humuli, Psylla mali, Psylla piri, Rhopalomyzus ascalonicus, Rhopalosiphum maidis, Rhopalosiphum padi Rhopalosiphum insertum, Sappaphis mala, Sappaphis mali; Schizaphis graminum, Schizoneura lanuginosa, Sitobion avenae, Trialeurodes vaporariorum, Toxoptera aurantiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri Solenopsis xyloni Pogonomyrmex barbatus, Pogonomyrmex califomicus, Pheidole megacephala, Dasymutilla occidentalis, Bombus* spp., *Vespula squamosa, Paravespula vulgans, Paravespula pennsylvanica, Paravespula germanica, Dolichovespula macuata, Vespa crabro, Polistes rubiginosa, Camponotus floridanus,* and *Linepithema humile;* crickets, grasshoppers, locusts (*Orthoptera*), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (*Acanna*), e.g. of the families Argasidae, Ixodidae and Sarcoptidae, such as *Amblyomma americanum, Amblyonma vaniegatum, Ambryomma macuatum, Argas persicus, Boophilus annulatus, Boophilus decoloratus, Boophilus microplus, Dermacentor silvarum, Dermacentor andersoni, Dermacentor variabils, Hyalomma truncatum, Ixodes ricinus, Ixodes rubicundus, Ixodes scapuars, Ixodes holocydus, Ixodes pacicus, Ornithodorus moubata, Omithodorus hermsi Ormithodorus turicata, Ornithonyssus bacoti, Otobius megnini Dermanyssus gallinae, Psoroptes ovis, Rhipicephalus sanguineus, Rhipicephalus appendiculatus, Rhipicephalus evertsi, Sarcoptes scabie,* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis, Tetranychidae* spp. such as *Tetranychus cinnabarinus, Tetranychus kanzawai, Tetranychus pacicus, Tetranychus telanus* and *Tetranychus urticae, Panonychus ulmi, Panonychus citri,* and *Oligonychus pratensis* Araneida, e.g. *Latrodedus mactans,* and *Loxosceles reclusa,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (*Thysanura*), e.g. *Lepisma saccharina* and *Thermobia domestica,* centipedes (*Chilopoda*), e.g. *Scutigera coleoptrata,* millipedes (*Diplopoda*), e.g. *Narceus* spp., earwigs (*Dermaptera*), e.g. *forficula auricularia,* lice (*Phthiraptera*), e.g. *Pediculus humanus capitis, Pediculus humanus corporis, Pthirus pubis, Haematopinus eurystemus, Haematopinus suis, Linognathus vituli, Bovicola bovis, Menopon gallinae, Menacanthus stramineus* and *Solenopotes capillatus.*

Collembola (*springtails*), e.g. *Onychiurus* ssp.

They are also suitable for controlling nematodes: plant parasitic nematodes such as root knot nematodes, *Meloidogyne hapa, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachki, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multianctus* and other *Helicotylenchus* species; Sheath and sheathoid nematodes, *Hemicydiophora* species and *Hemicriconemoides* species; *Hirshmanniella* species; Lance nematodes, *Hoploaimus* species; false rootknot nematodes, *Nacobbus* species; Needle nematodes, *Longidonis elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

They are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri*, and *oligonychus pratensis*.

The mixtures of the present invention have excellent activity against a broad spectrum of phytopathogenic fungi Ascomycetes, Basidiomycetes, Deuteromycetes and Peronosporomycetes (syn. Oomycetes). Some of them are systemically effective and can be employed in crop protection as foliar fungicides, as fungicides for seed dressing and as soil fungicides. They can also be used for treating seed. They are particularly important in the control of a multitude of fungi on various cultivated plants, such as wheat, rye, barley, oats, rice, corn, lawns, bananas, cotton, soybean, coffee, sugar cane, grapevines, fruits and ornamental plants, and vegetables such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, for example, *A. solani* or *A. alternata* on potatoes and tomatoes;
*Aphanomyces* species on sugar beet and vegetables;
*Ascochyta* species on cereals and vegetables;
*Bipolaris* and *Drechslera* species on corn, cereals, rice and lawns, for example, *D. maydis* on corn;
*Blumeria graminis* (powdery mildew) on cereals;
*Botrytis cinerea* (gray mold) on strawberries, vegetables, flowers and grapevines;
*Bremia lactucae* on lettuce;
*Ceroospora* species on corn, soybeans, rice and sugar beet;
*Cochliobolus* species on corn, cereals, rice, for example *Cochliobolus sativus* on cereals, *Cochliobolus miyabeanus* on rice;
*Colletotricum* species on soybeans and cotton;
*Drechslera* species, *Pyrenophora* species on corn, cereals, rice and lawns, for example, *D. teres* on barley or *D. tritici-repentis* on wheat;
*Esca* on grapevines, caused by *Phaeoacremonium chlamydosporium, Ph. Aleophilum* and *Formitipora punctata* (syn. *Phellinus punctatus*)
*Exserohilum* species on corn;
*Erysiphe cichoraceanrm* and *Sphaerotheca fuliginea* on cucumbers;
*Fusarium* and *Verticillium* species on various plants, for example, *F. graminearum* or *F. culmorum* on cereals or *F. oxysporum* on a multitude of plants, such as, for example, tomatoes;
*Gaeumanomyces graminis* on cereals;
*Gibberella* species on cereals and rice (for example *Gibberella fujikuroi* on rice)
*Grainstaining complex* on rice;
*Helminthosporium* species on corn and rice;
*Michrodochium nivale* on cereals;
*Mycosphaerella* species on cereals, bananas and peanuts, for example, *M. graminicola* on wheat or *M. fijiensis* on bananas;
*Peronospora* species on cabbage and bulbous plants, for example, *P. brassicae* on cabbage or *P. destructor* on onions;
*Phakopsara pachyrhizi* and *Phakopsara meibomiae* on soybeans;
*Phomopsis* species on soybeans and sunflowers;
*Phytophthora infestans* on potatoes and tomatoes;
*Phytophthora* species on various plants, for example, *P. capsici* on bell pepper;
*Plasmopara viticola* on grapevines;
*Podosphaera leucoticha* on apples;
*Pseudocercosporella herpotrichoides* on cereals;
*Pseudoperonospora* on various plants, for example, *P. cubensis* on cucumber or *P. humili* on hops;
*Puccinia* species on various plants, for example, *P. triticina, P. striformins, P. hordei* or *P. graminis* on cereals or *P. asparagi* on asparagus;
*Pyricularia oryzae, Corticium sasakii, Sarocladium oryzae, S. attenuatum, Entyloma oryzae* on rice;
*Pyricularia grisea* on lawns and cereals;
*Pythium* spp. on lawns, rice, corn, cotton, oilseed rape, sunflowers, sugar beet, vegetables and other plants, for example, *P. ultiumum* on various plants, *P. aphanidermatum* on lawns;
*Rhizoctonia* species on cotton, rice, potatoes, lawns, corn, oilseed rape, sugar beet, vegetables and on various plants, for example, R. so/anion beet and various plants;
*Rhynchosporium secalis* on barley, rye and triticale;
*Sclerotinia* species on oilseed rape and sunflowers;
*Septoria tritici* and *Stagonospora nodorum* on wheat;
*Erysiphe* (syn. *Uncinula*) *necator* on grapevines;
*Setospaeria* species on corn and lawns;
*Sphacelotheca reilinia* on corn;
*Thievaliopsis* species on soybeans and cotton;
*Tilletia* species on cereals;
*Ustilago* species on cereals, corn and sugar cane, for example, *U. maydis* on corn;
*Venturia* species (scab) on apples and pears, for example, *V. inaequalis* on apples.

The mixtures according to the invention are also suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces carevisae*.

Moreover, the inventive mixtures are especially useful for the control of Lepidoptera, Coleoptera, Diptera, Thysanoptera and Hemiptera.

In particular the inventive mixtures are useful for the control of Thysanoptera and Hemiptera, especially Hemiptera.

The mixtures according to the present invention can be converted into the customary formulations, for example solutions, emulsions, suspensions, dusts, powders, pastes and granules. The use form depends on the particular intended purpose; in each case, it should ensure a fine and even distribution of the compounds according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation tech-nology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active com-pound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP (N-methyl-pyrrolidone), NOP (N-octyl-pyrrolidone), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropyl-ene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bacte-ricides such as can be added to the formulation.

Suitable antifoaming agents are for example antifoaming agents based on silicon or magnesium stearate.

A suitable preservative is e.g. dichlorophen.

An example of a gelling agent is carrageen (Satiagel®)

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, cal-cium sulfate, magnesium sulfate, magnesium oxide, ground synthetic materials, fertiliz-ers, such as, for example, ammonium sulfate, ammonium phosphate, ammonium ni-trate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. In this case, the active compounds are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compounds by weight, preferably 0.1 to 40% by weight.

The term "seed treatment" comprises all suitable seed treatment techniques known in the art, such as seed dressing, seed coating, seed dusting, seed soaking and seed pelleting.

The mixtures of the present invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active com-pound, or even to apply the active compound without additives.

The following are examples of formulations:

1. Products for dilution with water for foliar applications. For seed treatment purposes, such products may be applied to the seed diluted or undiluted.

A) Water-soluble concentrates (SL, LS)

10 parts by weight of the active compound(s) are dissolved in 90 parts by weight of water or a water-soluble solvent. As an alternative, wetters or other auxiliaries are added. The active com-pound(s) dissolve(s) upon dilution with water, whereby a formulation with 10% (w/w) of active compound (s) is obtained.

B) Dispersible concentrates (DC)

20 parts by weight of the active compound(s) are dissolved in 70 parts by weight of cyclohexanone with addition of 10 parts by weight of a dispersant, for example polyvi-nylpyr-rolidone. Dilution with water gives a dispersion, whereby a formulation with 20% (w/w) of active compound(s) is obtained.

C) Emulsifiable concentrates (EC)

15 parts by weight of the active compound(s) are dissolved in 7 parts by weight of xy-lene with addition of calcium dodecylbenzenesulfonate and castor oil ethoxylate (in each case 5 parts by weight). Dilution with water gives an emulsion, whereby a formu-lation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of wa-ter by means of an emulsifier machine (e.g. Ultraturrax) and made into a homogeneous emulsion. Dilution with water gives an emulsion, whereby a formula-tion with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active com-pound(s) suspension. Dilution with water gives a stable suspension of the active compound(s), whereby a formula-tion with 20% (w/w) of active com-pound(s) is obtained.

F) Water-dispersible granules and water-soluble granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluid-ized bed). Dilution with water gives a stable dispersion or solution of the active com-pound(s), whereby a formulation with 50% (w/w) of active compound(s) is obtained.

G) Water-dispersible powders and water-soluble powders (WP, SP, SS, WS)

75 parts by weight of the active compound(s) are ground in a rotor-stator mill with addi-tion of 25 parts by weight of dispersants, wetters and silica gel. Dilution with water gives a stable dispersion or solution of the active compound(s), whereby a formulation with 75% (w/w) of active com-pound(s) is obtained.

H) Gel-Formulation (GF)

In an agitated ball mill, 20 parts by weight of the active compound(s) are comminuted with addition of 10 parts by weight of dispersants, 1 part by weight of gelling agent wetters and 70 parts by weight of water or of an organic solvent to give a fine active compound(s) suspension. Dilu-tion with water gives a stable suspension of the active compound(s), whereby a formulation with 20% (w/w) of active compound(s) is obtained.

2. Products to be applied undiluted for foliar applications. For seed treatment pur-poses, such products may be applied to the seed diluted or undiluted.

I) Dustable powders (DP, DS)

5 parts by weight of the active compound(s) are ground finely and mixed intimately with 95 parts by weight of finely divided kaolin. This gives a dustable product having 5% (w/w) of active com-pound(s).

J) Granules (GR, FG, GG, MG)

0.5 part by weight of the active compound(s) is ground finely and associated with 95.5 parts by weight of carriers, whereby a formulation with 0.5% (w/w) of active com-pound(s) is obtained. Current methods are extrusion, spray-drying or the fluidized bed. This gives granules to be applied undiluted for foliar use.

K) ULV solutions (UL)

10 parts by weight of the active compound(s) are dissolved in 90 parts by weight of an organic solvent, for example xylene. This gives a product having 10% (w/w) of active compound(s), which is applied undiluted for foliar use.

Various types of oils, wetters, adjuvants, herbicides, fun-gicides, other pesticides, or bactericides may be added to the active ingredients, if appropriate just immediately prior to use (tank mix). These agents usually are admixed with the agents according to the invention in a weight ratio of 1:10 to 10:1.

The compounds I and the one or more compound(s) B can be applied simultaneously, that is jointly or separately, or in succession, the sequence, in the case of separate application, generally not having any effect on the result of the control measures.

The compounds of the present invention, the composi-tions comprising them or the mixtures of the present inven-tion are employed as such or in form of compositions by treating the insects, the fungi or the plants, plant propagation materials, such as seeds, soil, surfaces, materials or rooms to be protected from insecticidal attack with a pesticidally effective amount of the active compounds. The application can be carried out both before and after the infection of the plants, plant propagation materials, such as seeds, soil, surfaces, materials or rooms by the insects.

The present invention also includes a method of combat-ing animal pests and harmful fungi which comprises con-tacting the fungi and/or animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture according to the present invention or a compound of the invention. The compounds of the present invention, com-positions comprising them, the inventive mixtures or com-positions of these mixtures can also be employed for pro-tecting plants from attack or infestation by invertebrate pests such as insects, acarids or nematodes comprising contacting a plant, or soil or water in which the plant is growing.

The pyrazole compound A selected from compounds I and the one or more compound(s) B are usually applied in a weight ratio of from 500:1 to 1:100, preferably from 20:1 to 1:50, in particular from 5:1 to 1:20.

In ternary mixtures the pyrazole compound A selected from compounds I compounds I and B are usually present in ratio ranges of from 500:1:1, to 500:100:1 to 500:100:1 to 1:100:100 to 1:100:1 to 1:1:100.

Depending on the desired effect, the application rates of the mixtures according to the invention are from 5 g/ha to 2000 g/ha, preferably from 50 to 1500 g/ha, in particular from 50 to 750 g/ha.

The compounds according to the present invention and the mixtures according to the invention are effective through both contact and ingestion.

According to a preferred embodiment of the invention, the mixtures according to the present invention are employed via soil application. According to a further preferred embodiment of the invention, the compounds according to the present invention are employed via soil application. Soil application is especially favorable for use against ants, termites, crickets, or cockroaches.

According to another preferred embodiment of the invention, for use against non crop pests such as ants, termites, wasps, flies, mosquitoes, crickets, locusts, or cockroaches the mixtures according to the present invention or the compounds of the present invention are prepared into a bait preparation. The compounds according to the invention may also be applied against said non-crop pests.

The bait can be a liquid, a solid or a semisolid preparation (e.g. a gel).

Another aspect of the present invention is when preparing the mixtures, it is preferred to employ the pure active compounds I and B, to which further active compounds, e.g. against harmful fungi or having herbicidal activity, or growth-regulating agents or fertilizers can be added.

Compositions comprising an inventive compound of the formula I may further contain other active ingredients than those listed above. Compositions of this invention may further contain other active ingredients than those listed above. For example fungicides, herbicides, fertilizers such as ammonium nitrate, urea, potash, and superphosphate, phytotoxicants and plant growth regulators and safeners. These additional ingredients may be used sequentially or in combination with the above-described compositions, if appropriate also added only immediately prior to use (tank mix). For example, the plant(s) may be sprayed with a composition of this invention either before or after being treated with other active ingredients.

The mixtures according to the invention or compositions comprising the inventive compound I can be applied to any and all developmental stages, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, seed, soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures and/or compositions used in the invention. A pesticidally effective amount of the mixtures and/or compositions will also vary according to the prevailing conditions such as desired pesticidal effect and duration, weather, target species, locus, mode of application, and the like.

The inventive compounds I or the inventive mixtures or compositions of these mixtures can also be employed for protecting plants from attack or infestation by invertrebrate pests such as insects, acarids or nematodes comprising contacting a plant, or soil or water in which the plant is growing.

The inventive compounds or mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non crop pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive mixtures, optionally a repellent and at least one binder.

The compounds according to the invention, compositions comprising them, the inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient(s) ranges from 0.0001 to 500 g per 100 $m^2$, preferably from 0.001 to 20 g per 100 $m^2$.

Customary application rates in the protection of materials are, for example, from 0.01 g to 1000 g of active compound(s) per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient(s) is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weights %, preferably from 0.01 to 50 weight % and most preferably from 0.01 to 15 weight %.

For use in treating crop plants, the rate of application of the mixture of the active ingredients of this invention may be in the range of 0.1 g to 4000 g per hectare, desirably from 25 g to 600 g per hectare, more desirably from 50 g to 500 g per hectare.

In the context of the present invention, the term plant refers to an entire plant, a part of the plant or the plant propagation material.

The mixtures of the present invention and the compositions comprising them are particularly important in the control of a multitude of insects on various cultivated plants.

Plants which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be protected before transplantation by a total or partial treatment by immersion or pouring.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox.

Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of insects, especially to beetles (Coeloptera), two-winged insects (Diptera), and butterflies (Lepidoptera).

The term "cultivated plants" is to be understood also including plants that are by the use of recombinant DNA techniques capable to synthesize one or more proteins to in-crease the resistance or tolerance of those plants to bacterial, viral or fungal pathogens. Examples of such proteins are the so-called "pathogenesis-related proteins" (PR proteins, see, for example EP-A 392 225), plant disease resistance genes (for example potato cultivars, which express resistance genes acting against *Phytophthora infestans* derived from the mexican wild potato *Solanum bulbocastanum*) or T4-lyso-zym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e. g. Nexera rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

Some of the inventive mixtures have systemic action and can therefore be used for the protection of the plant shoot against foliar pests as well as for the treatment of the seed and roots against soil pests.

The mixtures according to the present invention are therefore suitable for the treatment of seeds in order to protect the seed from insect pest, in particular from soil-living insect pests and the resulting plant's roots and shoots against soil pests and foliar insects.

The protection of the resulting plant's roots and shoots is preferred.

More preferred is the protection of resulting plant's shoots from piercing and sucking insects.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with mixtures according to the present invention. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active com-pound(s). The term "coated with and/or containing" generally signifies that the active ingredient(s) are for the most part on the surface of the propagation product at the time of application, although a greater or lesser part of the ingredient may penetrate into the propagation product, depending on the method of application. When the said propagation products are (re)planted, it may absorb the active ingredient.

Suitable seeds are seeds of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the mixtures according to the invention may also be used for the treatment seeds from plants, which tolerate the action of herbicides or fungicides or insecticides owing to breeding, including genetic engineering methods. For example, the active mixtures can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259).

Furthermore, the compounds of the invention and the mixtures according to the present invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the mixtures is carried out by spraying or by dusting the seeds before sowing of the plants and before emergence of the plants.

In the treatment of seeds the corresponding formulations are applied by treating the seeds with an effective amount of the mixture according to the present invention. Herein, the application rates of the active compound(s) are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

Compositions, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient(s), 1-200 g/l Surfactant, 0 to 200 g/l antifreezing agent, 0 to 400 g/l of binder, 0 to 200 g/l of a pigment and up to 1 liter of a solvent, preferably water.

Preferred FS formulations of compounds of formula I for seed treatment usually comprise from 0.1 to 80% by weight (1 to 800 g/l) of the active ingredient(s), from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an antifoam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention also relates to seed comprising mixtures according to the present invention. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

The mixtures of the present invention or the inventive compounds are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of mixture of the present invention or a composition comprising it or the inventive compound.

The invention also provides a process for the preparation of a composition for treating, controlling, preventing or protecting animals against infestation or infection by parasites which comprises a parasiticidally effective amount of a mixture of the present invention or a composition comprising it or a compound according to the invention.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that mixtures of the present invention are suitable for combating endo- and ectoparasites in and on animals. Surprisingly it has now been found that the inventive compounds I are suitable for combating endo- and ectoparasites in and on animals.

Inventive compounds or mixtures of the present invention and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Inventive compounds I, mixtures of the present invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The inventive compounds, the mixtures of the present invention and compositions comprising them are suitable for systemic and/or non-systemic control of ecto- and/or endoparasites. They are active against all or some stages of development.

The mixtures of the present invention are especially useful for combating ectoparasites.

The mixture of the present invention is especially useful for combating parasites of the following orders and species, respectively:

fleas (*Siphonaptera*), e.g. *Ctenocephalides felis, Ctenocephalides canis, Xenopsylla cheopis, Pulex iritans, Tunga penetrans*, and *Nosopsyllus fasciatus*, cockroaches (*Blattaria—Blattodea*), e.g. *Blattella germanica, Blattella asahinae, Periplaneta americana, Periplaneta japonica, Peiplaneta brunnea, Peiplaneta fuligginosa, Peiplaneta australasiae*, and *Blatta orientalis*, flies, mosquitoes (Diptera), e.g. *Aedes aegypti; Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vidna, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inomata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Luclia caprina, Lucilia cuprina, Lucilia sericata,*

*Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (*Phthiraptera*), e.g. *Pediculus humanus capitis, Pediculus humanus corpos, Pthirus pubis, Haematopinus eurystemus, Haematopinus suis, Linognathus vitul, Bovicola bovis, Menopon gallinae, Menacanthus stramineus* and *Solenopotes capillatus.* ticks and parasitic mites (*Parasitiformes*): ticks (*Ixodida*), e.g. *Ixodes scapulais, Ixodes holocyclus, Ixodes pacicus, Rhiphicephalus sanguineus, Dermacentor andersoni, Dermacentor variabilis, Amblyomma americanum, Ambryomma maculatum, Omithodorus hermsi, Ornithodorus turicata* and parasitic mites (*Mesostigmata*), e.g. *Omithonyssus bacoti* and *Dermanyssus gallinae,*

Actinedida (*Prostigmata*) und Acaridida (*Astigmata*) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Calogphus* spp., *Hypodedes* spp., *Pterolichus* spp., *Psoroptes* spp., *Chonoptes* spp., *Otodectes* spp., *Sarcoptes* spp., *Notoedres* spp., *Knemidocoptes* spp., *Cytodites* spp., and *Laminosioptes* spp, Bugs (*Heteropterida*): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Amblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (*Trichosyringida*), e.g. Trichinellidae (*Trichinella* spp.), (Trichuridae) *Trichuris* spp., *Capillara* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Tichostrongylus* spp., *Haemonchus contortus., Osteitagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muelleus capillaris, Protostrongylus* spp., *Angiostrongylus* spp., *Parelaphostrongylus* spp. *Aleurostrongylus abstrusus*, and *Dioctophyma renae,*

Intestinal roundworms (*Ascaridida*), e.g. *Ascaris lumbrooides, Ascaris suum, Ascaridia galli, Parascans equonim, Enterobius vermiculans* (Threadworm), *Toxocara canis, Toxascaris leonine, Skrabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (*Acanthocephala*), e.g. *Acanthocephalus* spp., *Macracanthorhynchus hirudinaceus* and *Oncicola* spp, Planarians (*Plathelminthes*):

Flukes (*Trematoda*), e.g. *Faciola* spp., *Fasciolodes magna, Paragonimus* spp., *Dicrocooelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds according to the invention, the mixtures of the present invention and compositions containing them are particularly useful for the control of pests from the orders Diptera, Siphonaptera and Ixodida.

Moreover, the use of compounds according to the invention, mixtures of the present invention and compositions containing them for combating mosquitoes is especially preferred.

The use of compounds according to the invention, mixtures of the present invention and compositions containing them for combating flies is a further preferred embodiment of the present invention.

Furthermore, the use of the compounds according to the invention, mixtures of the present invention and compositions containing them for combating fleas is especially preferred.

The use of compounds according to the invention, the mixtures of the present invention and compositions containing them for combating ticks is a further preferred embodiment of the present invention.

The mixtures of the present invention also are especially useful for combating endoparasites (roundworms nematoda, thorny headed worms and planarians).

Administration can be carried out both prophylactically and therapeutically.

Administration of the active compound(s) is carried out directly or in the form of suitable preparations, orally, topically/dermally or parenterally.

For oral administration to warm-blooded animals, the compound according to the invention, mixtures of the present invention may be formulated as animal feeds, animal feed premixes, animal feed concentrates, pills, solutions, pastes, suspensions, drenches, gels, tablets, boluses and capsules. In addition, the mixtures of the present invention may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the compounds of the invention, mixtures of the present invention may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the mixtures of the present invention may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the active compounds.

The compounds according to the invention, mixtures of the present invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the active compounds. In addition, the active compound mixtures may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethytformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, N-alkylpyrrolidones such as methylpyrrolidone, N-butylpyrrolidone or N-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin;
anionic surfactants, such as sodium lauryl sulfate, fatty alcohol ether sulfates, mono/dialkyl polyglycol ether orthophosphoric acid ester monoethanolamine salt;
cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound(s) is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvi-nylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95 wt % of the active compounds of the mixtures of the present invention.

Generally it is favorable to apply the active compounds of the mixtures of the present invention in total amounts of 0.5 mg/kg to 100 mg/kg per day, preferably 1 mg/kg to 50 mg/kg per day.

Ready-to-use preparations contain the active compounds of the mixtures of the present invention acting against parasites, preferably ectoparasites, in concentrations of 10 ppm to 80 per cent by weight, preferably from 0.1 to 65 per cent by weight, more preferably from 1 to 50 per cent by weight, most preferably from 5 to 40 per cent by weight.

Preparations which are diluted before use contain the active compounds of the mixtures of the present invention acting against ectoparasites in concentrations of 0.5 to 90 per cent by weight, preferably of 1 to 50 per cent by weight.

Furthermore, the preparations comprise the active compounds of the mixtures of the present invention against endoparasites in concentrations of 10 ppm to 2 per cent by weight, preferably of 0.05 to 0.9 per cent by weight, very particularly preferably of 0.005 to 0.25 per cent by weight.

In a preferred embodiment of the present invention, the compositions comprising the mixtures of the present invention are applied dermally/topically.

In a further preferred embodiment, the topical application is conducted in the form of com-pound-containing shaped articles such as collars, medallions, ear tags, bands for fixing at body parts, and adhesive strips and foils.

Generally it is favorable to apply solid formulations which release the active compounds of the mixtures of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

EXAMPLES

The present invention is now illustrated in further details by the following examples, without imposing any limitation thereto.

Example 1

Preparation of N,5-dimethyl-N-pyridazin-4-yl-1-(1-spiro[2.2]pentan-5-ylethyl)pyrazole-4-carboxamide
[I-22]

A solution of 594 mg 5-methyl-1-(1-spiro[2.2]pentan-5-ylethyl)pyrazole-4-carbonyl chloride in 5 mL THF was added dropwise to a solution of 271 mg N-methylpyridazin-4-amine and 315 mg triethylamine in 30 mL THF at 0° C. The mixture was stirred at 20-25° C. for about 20 h, the solvent was evaporated and the residue was diluted with 70 mL dichloromethane, washed with 2×10 mL water, dried over MgSO₄ and evaporated. Purification by flash chromatography (CH₂Cl₂/MeOH) gave 522 mg of the title compound. HPLC-MS: RT 0.842 min, m/z [MH]+ 312.2

Compounds can in general be characterized e.g. by coupled High Performance Liquid Chromatography/mass spectrometry (HPLC/MS), by ¹H-NMR and/or by their melting points.

Analytical HPLC column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

MS-method: ESI positive.

RT=HPLC retention time; m/z of the [M+H]+, [M+Na]+ or [M+K]+ peaks.

Further compounds examples of the present invention were prepared by analogy to the above described synthetic methods and the hereunder table illustrates, without imposing any limitation thereto, compounds examples of formula (I) including their corresponding characterization data:

SP1 and SP2 have the following meaning in the hereunder Table:

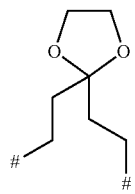
SP1

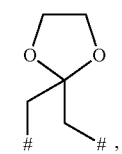
SP2 wherein
# denotes the bond to the skeleton of formula (I)

TABLE I

Compounds of formula (I) numbered C-1 to C-32 and wherein R² is CH₃ and R⁵ is H:

| No | R¹ | R³ | R⁴ | RT [min] | m/z [MH]+ |
|---|---|---|---|---|---|
| C-1 | CH₂CH₃ | 1-OCH₃—cC₃H₄ | CH₃ | 0.766 | 330.0 |
| C-2 | CH₃ | 1-OCH₃—cC₃H₄ | CH₃ | 0.703 | 313.3 |
| C-3 | H | 1-OCH₃—cC₃H₄ | CH₃ | 0.727 | 302.0 |
| C-4 | CH₃ | CF₂CH₃ | CH₃ | 0.760 | 310.2 |
| C-5 | CH₂CH₃ | CF₂CH₃ | CH₃ | 0.813 | 324.3 |
| C-6 | H | CF₂CH₃ | CH₃ | 0.762 | 296.2 |
| C-7 | H | SP1 | | 0.738 | 344.2 |
| C-8 | CH₃ | SP1 | | 0.728 | 358.3 |
| C-9 | CH₂CH₃ | SP1 | | 0.798 | 372.2 |
| C-10 | CH₃ | —CH₂OCH₂OCH₂— | | 0.830 | 336.2 |
| C-11 | CH₃ | SP2 | | 0.715 | 330.2 |
| C-12 | H | CF(CH₃)₂ | CH₃ | 0.755 | 292.1 |
| C-13 | CH₃ | CF(CH₃)₂ | CH₃ | 0.750 | 306.2 |
| C-14 | CH₂CH₃ | CF(CH₃)₂ | CH₃ | 0.811 | 320.2 |
| C-15 | CH₂CH₃ | SP2 | | 0.747 | 344.2 |
| C-16 | H | SP2 | | 0.705 | 316.1 |
| C-17 | CH₂CH₃ | —CH₂OCH₂OCH₂— | | 0.662 | 318.2 |
| C-18 | H | —CH₂OCH₂OCH₂— | | 0.629 | 290.1 |
| C-19 | CH₂OCH₃ | CHFCH₃ | CH₃ | 0.766 | 322.2 |
| C-20 | CH₂OCH₂CH₃ | CHFCH₃ | CH₃ | 0.797 | 336.3 |
| C-21 | H | spiro[2.2]pentan-5-yl | CH₃ | 0.839 | 298.2 |
| C-22 | CH₃ | spiro[2.2]pentan-5-yl | CH₃ | 0.842 | 312.2 |
| C-23 | CH₃ | 5-cyanospiro[2.2]pentan-5-yl | CH₃ | 0.727 | 337.2 |
| C-24 | H | 5-cyanospiro[2.2]pentan-5-yl | CH₃ | 0.726 | 323.2 |
| C-25 | CH₂CH₃ | 5-cyanospiro[2.2]pentan-5-yl | CH₃ | 0.781 | 351.2 |
| C-26 | CH₂CH₃ | spiro[2.2]pentan-5-yl | CH₃ | 0.924 | 326.2 |
| C-27 | H | C(CH₃)₂OCH₃ | CH₃ | 0.773 | 304.1 |
| C-28 | CH₃ | C(CH₃)₂OCH₃ | CH₃ | 0.771 | 318.2 |
| C-29 | CH₂CH₃ | C(CH₃)₂OCH₃ | CH₃ | 0.781 | 351.2 |
| C-30 | H | 2-(methoxymethyl)spiro[2.2]pentan-5-yl | CH₃ | 0.809 | 342.4 |
| C-31 | CH₃ | 2-(methoxymethyl)spiro[2.2]pentan-5-yl | CH₃ | 0.819 | 356.2 |
| C-32 | CH₂CH₃ | 2-(methoxymethyl)spiro[2.2]pentan-5-yl | CH₃ | 0.861 | 370.2 |

Synergism can be described as an interaction where the combined effect of two or more compounds is greater than the sum of the individual effects of each of the compounds. The presence of a synergistic effect in terms of percent control or efficacy, between two mixing partners (X and Y) can be calculated using the Colby equation (Colby, S. R., 1967, Calculating Synergistic and Antagonistic Responses in Herbicide Combinations, Weeds, 15, 20-22):

$$E = X + Y - \frac{XY}{100}$$

When the observed combined control effect is greater than the expected combined control effect (E), then the combined effect is synergistic.

The following tests can demonstrate the control efficacy of compounds, mixtures or compositions of this invention on specific pests and fungi. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests and/or harmful fungi.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

B.1 Cowpea Aphid (*Aphis craccivora*)

The active compounds were formulated in 50:50 (vol:vol) acetone:water. The test solution was prepared at the day of use. Potted cowpea plants colonized with 100-150 aphids of various stages were sprayed after the pest population had been recorded. Population reduction was assessed after 24, 72, and 120 hours.

In this test, the compounds C-1, C-2, C-3, C-4, C-5, C-6, C-7, C-8, C-9, C-10, C-11, C-12, C-13, C-14, C-15, C-16, C-17, C-18, C-19, C-21, C-22, C-23, C-24, C-25, C-26, C-27, C-28, and C-29 respectively at 500 ppm showed at least 75% mortality in comparison with untreated controls.

B.2 Cotton Aphid (*Aphis gossypii*, Mixed Life Stages)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone: 50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds C-2, C-3, C-4, C-5, C-6, C-7, C-8, C-9, and C-10 respectively at 10 ppm showed at least 75% mortality in comparison with untreated controls.

B.3 Silverleaf Whitefly (*Bemisia argentifolii*, Adult)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone: 50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the C-1, C-2, C-3, C-4, C-5, C-6, C-7, C-8, and C-9 respectively at 10 ppm showed at least 75% mortality in comparison with untreated controls.

B.4 Vetch Aphid (*Megoura viciae*)

The active compounds were formulated in 1:3 (vol:vol) DMSO:water with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiter plates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds C-1, C-2, C-3, C-4, C-5, C-6, C-7, C-8, C-9, C-10, C-11, C-12, C-13, C-14, C-15, C-16, C-17, C-18, C-19, C-21, C-22, C-23, C-24, C-25, C-26, C-27, C-28, C-29, C-30, C-31, and C-32 respectively at 2500 ppm showed at least 75% mortality in comparison with untreated controls.

B.5 Green Peach Aphid (*Myzus persicae*)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone: 50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24 hour photoperiod at 25° C. and 20-40% relative humidity. Aphid mortality on the treated plants, relative to mortality on untreated control plants, was determined after 5 days.

In this test, compounds C-1, C-2, C-3, C-4, C-5, C-6, C-7, C-8, C-9, and C-10 respectively at 10 ppm showed at least 75% mortality in comparison with untreated controls.

B.7 Rice Plant Hopper (*Nilaparvata lugens*)

Rice seedlings were cleaned and washed 24 hours before spraying. The active compounds were formulated in 50:50 acetone: water and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, C-10, and C-15 respectively at 500 ppm showed 75% mortality in comparison with untreated controls.

B.8 Orchid Thrips (*Dichromothrips corbetti*)

The active compounds were formulated as a 50:50 (vol: vol) acetone:water solution. Surfactant (Alkamuls EL 620) was added at the rate of 0.1% (vol/vol). Vanda orchids petals were cleaned, washed and air dried prior to spraying. Petals were dipped into the test solution for 3 seconds, air dried, placed inside a resealable plastic and inoculated with 20 adults. The treated petals were kept inside the holding room at 28-29° C. and relative humidity of 50-60%. Percent mortality was recorded after 72 hours.

In this test, compounds C-4, C-5, and C-9 at 500 ppm showed at least 75% mortality in comparison with untreated controls.

B.9 Rice Green Leafhopper (*Nephotettix virescens*)

Rice seedlings were cleaned and washed 24 hours before spraying. The active compounds were formulated in 50:50 acetone: water, and 0.1% vol/vol surfactant (EL 620) was added. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compound C-26 at 500 ppm showed at least 75% mortality in comparison with untreated controls.

Test 1—Control of Vetch Aphid

For evaluating control of vetch aphid (*Megoura viciae*) through contact or systemic means the test unit consisted of 24-well-microtiter plates containing broad bean leaf disks.

The compounds or mixtures were formulated using a solution containing 75% water and 25% Dimethylsulfoxide (DMSO). Different concentrations of formulated compounds or mixtures were sprayed onto the leaf disks at 2.5 μl, using a custom built micro atomizer, at two replications.

For experimental mixtures in these tests identical volumes of both mixing partners at the desired concentrations respectively, were mixed together.

After application, the leaf disks were air-dried and 5-8 adult aphids placed on the leaf disks inside the microtiter plate wells. The aphids were then allowed to suck on the treated leaf disks and incubated at 23+1° C., 50+5% relative humidity (RH) for 5 days. Aphid mortality and fecundity was then visually assessed.

Test 2—Control of Green Peach Aphid

For evaluating control of green peach aphid (*Myzus persicae*) through systemic means the test unit consisted of 96-well-microtiter plates containing liquid artificial diet under an artificial membrane.

The compounds or mixtures were formulated using a solution containing 75% water and 25% DMSO. Different concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23+1° C., 50+5% RH for 3 days. Aphid mortality and fecundity was then visually assessed.

Test 3—Control of Boll Weevil

For evaluating control of boll weevil (*Anthonomus grandis*) the test unit consisted of 24-well-microtiter plates containing an insect diet and 20-30 *A. grandis* eggs.

The compounds or mixtures were formulated using a solution containing 75% water and 25% DMSO. Different concentrations of formulated compounds or mixtures were sprayed onto the insect diet at 20 μl, using a custom built micro atomizer, at two replications.

For experimental mixtures in these tests identical volumes of both mixing partners at the desired concentrations respectively, were mixed together.

After application, microtiter plates were incubated at 23+1° C., 50+5% RH for 5 days. Egg and larval mortality was then visually assessed.

In this test, compounds C-4, C-5, C-6, C-22, C-25, and C-26 respectively at 2500 ppm showed at least 75% mortality in comparison with untreated controls.

Test 4—Control of Mediterranean Fruitfly

For evaluating control of Mediterranean fruitfly (*Ceratitis capitata*) the test unit consisted of 96-well-microtiter plates containing an insect diet and 50-80 *C. capitata* eggs.

The compounds or mixtures were formulated using a solution containing 75% water and 25% DMSO. Different concentrations of formulated compounds or mixtures were sprayed onto the insect diet at 5 μl, using a custom built micro atomizer, at two replications.

For experimental mixtures in these tests identical volumes of both mixing partners at the desired concentrations respectively, were mixed together.

After application, microtiter plates were incubated at 28+1° C., 80+5% RH for 5 days. Egg and larval mortality was then visually assessed.

Test 5—Control of Tobacco Budworm

For evaluating control of tobacco budworm (*Heliothis virescens*) the test unit consisted of 96-well-microtiter plates containing an insect diet and 15-25 *H. virescens* eggs.

The compounds or mixtures were formulated using a solution containing 75% water and 25% DMSO. Different concentrations of formulated compounds or mixtures were sprayed onto the insect diet at 10 μl, using a custom built micro atomizer, at two replications.

For experimental mixtures in these tests identical volumes of both mixing partners at the desired concentrations respectively, were mixed together.

After application, microtiter plates were incubated at 28+1° C., 80+5% RH for 5 days. Egg and larval mortality was then visually assessed.

Tests 6 to 9: Microtests

The active compounds were formulated separately as a stock solution having a concentration of 10000 ppm in dimethyl sulfoxide.

The measured parameters were compared to the growth of the active compound-free control variant (100%) and the fungus-free and active compound-free blank value to determine the relative growth in % of the pathogens in the respective active compounds. These percentages were converted into efficacies.

Test 6—Activity Against the Grey Mold *Botrytis cinerea* in the Microtiterplate Test The stock solutions were mixed according to the ratio, pipetted onto a micro titer plate (MTP) and diluted with water to the stated concentrations. A spore suspension of *Botrci cinerea* in an aqueous biomalt solution was then added. The plates were placed in a water vapor-saturated chamber at a temperature of 18° C. Using an absorption photometer, the MTPs were measured at 405 nm 7 days after the inoculation.

Test 7—Activity Against Rice Blast Pyricularia *Oryzae* in the Microtiterplate Test The stock solutions were mixed according to the ratio, pipetted onto a micro titer plate (MTP) and diluted with water to the stated concentrations. A spore suspension of Pyricularia *oryzae* in an aqueous biomalt solution was then added. The plates were placed in a water vapor-saturated chamber at a temperature of 18° C. Using an absorption photometer, the MTPs were measured at 405 nm 7 days after the inoculation Test 8+Activity Against Early Blight on Tomatoes Caused by *Altemaria solani*

Microtest: the active compounds were formulated separately as a stock solution having a concentration of 10000 ppm in dimethyl sulfoxide.

The stock solutions were mixed according to the ratio, pipetted onto a micro titer plate (MTP) and diluted with water to the stated concentrations. A spore suspension of *Altemaria solani* in an aqueous biomalt solution was then added. The plates were placed in a water vapor-saturated chamber at a temperature of 18° C. Using an absorption photometer, the MTPs were measured at 405 nm 7 days after the inoculation. The evaluation as described in Test 8 was made to give the following results:

| Active compound/ active mixture | Concentration (ppm) | Mixture | Observed efficacy | Calculated efficacy according to Colby (%) |
|---|---|---|---|---|
| I-674 | 63 | — | 1 | |
| I-698 | 63 | — | 3 | |
| | 1 | — | 7 | |
| I-680 | 63 | — | 3 | |
| Pyraclostrobin | 0.016 | — | 16 | |
| Triticonazol | 0.063 | — | 27 | |
| Fludioxonil | 0.063 | — | 26 | |
| I-674 + Pyraclostrobin | 63 0.016 | 4000:1 | 62 | 17 |
| I-698 + Triticonazol | 1 0.063 | 16:1 | 56 | 32 |
| I-698 + Fludioxonil | 63 0.063 | 1000:1 | 54 | 28 |
| I-680 + Fludioxonil | 63 0.063 | 1000:1 | 52 | 28 |

Test 9—Activity Against Leaf Blotch on Wheat Caused by *Septoria tritici*

The stock solutions were mixed according to the ratio, pipetted onto a micro titer plate (MTP) and diluted with water to the stated concentrations. A spore suspension of *Septoria tritici* in an aqueous biomalt solution was then added. The plates were placed in a water vapor-saturated chamber at a temperature of 18° C. Using an absorption photometer, the MTPs were measured at 405 nm 7 days after the inoculation.

Test 10—Control of *Rhizoctonia solani*

The compounds were dissolved in Acetone. Seeds of com were treated in a treater as standard equipment. The products and concentrations are listed below. After the treatment the seeds were sown in pots, and rye seeds (infected with *Rhizoctonia* solani) were placed next to the seeds (1 seed per corn seed).

After cultivation in the greenhouse for 14 days at 20° C. and a relative humidity of 70% the plant height of the plants were measured.

The evaluation as described in Test 8 was made to give the following results:

| Active compound/ active mixture | Concentration (g a.i./100 kg seeds) | Mixture | Observed efficacy (%) | Calculated efficacy according to Colby (%) |
|---|---|---|---|---|
| I-674 | 63 | — | 5 | |
| I-698 | 250 | — | 3 | |
| I-680 | 63 | — | 0 | |
| Pyraclostrobin | 63 | — | 49 | |
| Triticonazol | 16 | — | 20 | |
| Fluxapyroxad | 4 | — | 74 | |
| Mefenoxam | 63 | — | 0 | |
| I-674 + Pyraclostrobin | 63 63 | 1:1 | 74 | 51 |
| I-698 + Triticonazol | 250 16 | 16:1 | 38 | 23 |
| I-698 + Fluxapyroxad | 250 4 | 63:1 | 93 | 75 |
| I-680 + Mefenoxam | 63 63 | 1:1 | 18 | 0 |

Test 11—Control of Brown Rust on Wheat Caused by *Puadnia recondita*

Seeds of wheat were treated in a treater as standard equipment. The products and concentrations are listed below. At the same day the plants were seeded in pots. 14 days later at 19° C. and 70% humidity the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area.

| Active compound/ active mixture | Concentration (g a.i./100 kg seeds) | Mixture | Observed efficacy (%) | Calculated efficacy according to Colby (%) |
|---|---|---|---|---|
| Untreated | 90% Disease | | | |
| I-674 | 250 | — | 0 | |
| I-698 | 63 | — | 4 | |
| I-680 | 250 | — | 0 | |
| Triticonazol | 16 | — | 49 | |
| Fluxapyroxad | 1 | — | 16 | |
| I-674 + Triticonazol | 250 16 | 16:1 | 92 | 49 |
| I-698 + Fluxapyroxad | 63 1 | 63:1 | 44 | 20 |
| I-680 + Triticonazole | 250 16 | 16:1 | 69 | 49 |

Test 12—Control of Powdery Mildew on Wheat Caused by *Blumeria graminis* f. sp. *tritici*

Seeds of wheat were treated in a treater as standard equipment. The products and concentrations are listed below. At the same day the plants were seeded in pots. 14 days later at 19° C. and 70% humidity the plants were inoculated with spores of *Blumeria graminis* f. sp. *tritici* (=syn. *Erysiphe garminis* f. sp. *tritici*) by shaking heavily infestated stock plants over the treated pots. After cultivation in the greenhouse for 7 days at 22-26° C. and a relative humidity between 60 to 90% the extent of fungal attack on the leaves was visually assessed as % diseased leaf area.

The evaluation as described in Test 8 was made to give the following results:

| Active compound/ active mixture | Concentration (g a.i./100 kg seeds) | Mixture | Observed efficacy (%) | Calculated efficacy according to Colby (%) |
|---|---|---|---|---|
| Untreated | 82% Disease | | | |
| I-674 | 250 | — | 21 | |
| | 4 | — | 9 | |
| I-698 | 250 | — | 15 | |
| I-680 | 250 | — | 15 | |
| Thiabendazol | 250 | — | 2 | |
| Mefenoxam | 4 | — | 0 | |
| Triticonazol | 16 | — | 60 | |
| I-674 + Thiabendazol | 250 250 | 1:1 | 51 | 23 |
| I-674 + Mefenoxam | 4 4 | 1:1 | 33 | 9 |
| I-698 + Thiabendazol | 250 250 | 1:1 | 51 | 17 |
| I-698 + Triticonazol | 250 16 | 63:1 | 94 | 66 |
| I-680 + Triticonazol | 250 16 | 63:1 | 92 | 66 |

Test 13—Activity Against Greenbug Aphid, *Schizaphis graminum*: Wheat seed treatment Technical material was dissolved in acetone at sub-lethal doses. 50 µL of solution was added to a 20-ml scintillation vial, 15 wheat seeds were added, and the seeds were coated by vortexing the vial for 1 minute. The seeds were allowed to dry and planted later the same day. Seeds were planted individually in a moistened, fertilized soil mixture of 1:1 North Carolina loamy sand (Sandhill soil):play sand in 40.32 cm² pots. Pots were arranged in a randomized complete block design in the greenhouse and top-watered daily. Plant emergence and shoot phytotoxicity were evaluated 4, 7, and 14 days after treatment (DAT). At 14 DAT (true leaf stage), each plant was infested with 10 greenbug aphids (*Schizaphis graminum*) of mixed stages. Plants were maintained on light carts in a randomized complete block design and bottom-watered as needed. Twelve replicates (pots) were prepared for plant emergence and five replicates were prepared for infestation. Live aphids were counted 4 DAI and the mean percent population reduction relative to the solvent blank control was calculated.

The evaluation as described in Test 8 was made to give the following results:

Activity with insecticides of the group A.1 to A.17:

| Active compound/active mixture | Concentraton (g a.i./ 100 kg seeds) | Mixture | Observed efficacy (%) | Calculated efficacy according to Colby (%) |
|---|---|---|---|---|
| I-674 | 33.7 | — | 28 | |
| I-698 | 150 | — | 74 | |
| I-680 | 2.9 | — | 23 | |
| Clothianidin | 3.7 | — | 38 | |
| Cyantraniliprole | 75 | — | 36 | |
| Fipronil | 75 | — | 24 | |
| Imidacloprid | 1.2 | — | 32 | |
| Thiamethoxam | 4.4 | — | 16 | |
| chloran-thraniliprole | 75 | — | 30 | |
| I-680 + Clothianidin | 2.9 3.7 | 1:2.3 | 64 | 52 |
| I-674 + Cyantraniliprole | 33.7:75 | 1:2.2 | 66 | 54 |
| I-680 + Fipronil | 2.9 75 | 1:25.9 | 45 | 41 |
| I-698 + Imidacloprid | 150 1.2 | 125:1 | 87 | 82 |
| I-680 + Imidacloprid | 2.9 1.2 | 2.4:1 | 50 | 47 |
| I-698 + Thiamethoxam | 150 4.4 | 34:1 | 82 | 78 |
| I-680 + chloranthraniliprole | 2.9 75 | 1:25.9 | 59 | 46 |

Activity with fungicides of the groups F.1 to F.11:

| Active compound / active mixture | Concentration (g a.i./ 100 kg seeds) | Mixture | Observed efficacy (%) | Calculated efficacy according to Colby (%) |
|---|---|---|---|---|
| I-674 | 33.7 | — | 21 | |
| I-698 | 150 | — | 51 | |
| I-680 | 2.9 | — | 7 | |
| Fludioxonil | 5 | — | 3 | |
| Fluxapyroxad | 20 | — | 0 | |
| Mefenoxam | 15 | — | 6 | |
| Pyraclostrobin | 20 | — | 0 | |
| Thiabendazole | 20 | — | 13 | |
| Triticonazole | 5 | — | 7 | |
| I-680 + Fludioxonil | 2.9:5 | 1:1.7 | 12 | 10 |
| I-698 + Fluxapyroxad | 150 75 | 2:1 | 62 | 50 |
| I-680 + Mefenoxam | 2.9 15 | 1:5.2 | 30 | 12 |
| I-698 + Pyraclostrobin | 150 20 | 7.5:1 | 65 | 44 |
| I-674 + Thiabendazole | 33.7 20 | 1.7:1 | 46 | 32 |
| I-680 + Triticonazole | 2.9 5 | 1:1.9 | 21 | 14 |

The invention claimed is:

1. A compound of formula I,

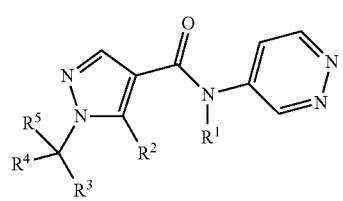

(I)

wherein
$R^1$ is H, $C_1$-$C_2$-alkyl, or $C_1$-$C_2$-alkoxymethyl;
$R^2$ is $CH_3$, $CH_2F$, $CHF_2$, or $CF_3$;

$R^3$ is a monospiro or dispiro 5- to 10-membered carbo- or heterocycle, which may contain 1 or 2 heteroatom moieties selected from N—$R^c$, O, and $S(O)_k$, with k being 0, 1, or 2, which carbo- or heterocycle is unsubstituted or may be substituted by 1, 2, 3 or 4 radicals $R^{a3}$; or $R^3$ and $R^4$ together with the carbon atom, to which they are attached, form a monospiro or dispiro 5- to 10-membered carbo- or heterocycle, which may contain 1 or 2 heteroatom moieties selected from N—$R^c$, O, and $S(O)_k$, with k being 0, 1, or 2, which carbo- or heterocycle is unsubstituted or may be substituted by 1, 2, 3 or 4 radicals $R^{a3}$;

$R^{a1}$ is CN, $NO_2$, $C(O)NH_2$, $C(S)NH_2$, $C_1$-$C_2$-alkylcarbonyloxy, $C_1$-$C_4$-alkoxy, $C_1$-$C_2$-haloalkoxy, $C_1$-$C_2$-alkyloxycarbonyl, or $S(O)_n R^b$;

$R^{a3}$ is halogen, $C_1$-$C_2$-alkyl, $C_1$-$C_2$-haloalkyl, $C_1$-$C_2$-alkoxy-$C_1$-$C_2$-alkyl, $C_1$-$C_2$-alkyliden, =O, =S, =$NR^b$, =$NOR^b$, =$NSR^b$, or a group mentioned for $R^{a1}$;

n is 0, 1, or 2;

$R^b$ is H, $C_1$-$C_2$-alkyl, $C_1$-$C_2$-haloalkyl, $C_3$-$C_6$-cycloalkyl, or $C_1$-$C_4$-alkoxy, $R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;

$R^4$ is $C_1$-$C_4$-alkyl or $C_1$-$C_4$-haloalkyl;

$R^5$ is H, $CH_3$, CN, F, $OCH_3$, $SCH_3$, $CF_3$, $OCF_3$, or $SCF_3$;

or a stereoisomer, a salt, a tautomer or an N-oxide thereof.

2. The compound of claim 1, wherein $R^3$ is spiro[2.2]pentyl, which is unsubstituted or carries one or two radicals $R^{a3}$, or 7-dispiro[2.0.2.1]-heptyl which is unsubstituted or carries a radical $R^{a3}$.

3. The compound of claim 1, where $R^4$ is $CH_3$, $C_2H_5$, $CHF_2$ or $CF_3$.

4. A compound of formula I as defined in claim 1 wherein
$R^1$ is H, $C_1$-$C_2$-alkyl, or $C_1$-$C_2$-alkoxymethyl;
$R^2$ is $CH_3$, $CH_2F$, $CHF_2$, or $CF_3$;
$R^3$ and $R^4$ together with the carbon atom, to which they are attached, form a monospiro or dispiro 5- to 10-membered carbo- or heterocycle, which may contain 1 or 2 heteroatom moieties selected from N—$R^c$, O, and $S(O)_k$, with k being 0, 1, or 2, which carbo- or heterocycle is unsubstituted or may be substituted by 1, 2, 3 or 4 radicals $R^{a3}$;
$R^{a3}$ is CN, $C_1$-$C_2$-alkyl, $C_1$-$C_2$-haloalkyl, $C_1$-$C_2$-alkoxy-$C_1$-$C_2$-alkyl, or $C_1$-$C_2$-alkyliden;
$R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;
$R^5$ is H, $CH_3$, CN, F, $OCH_3$, $SCH_3$, $CF_3$, $OCF_3$, or $SCF_3$;
the stereoisomers, salts, tautomers and N-oxides thereof.

5. The compound of claim 4, where $R^3$ and $R^4$ together with the carbon atom, to which they are attached, form a monospiro or dispiro 5- to 10-membered carbocycle which is unsubstituted or substituted by 1 or 2 radicals $R^{a3}$.

6. The compound of claim 4, where $R^3$ and $R^4$ together with the carbon atom, to which they are attached, form spiro[2.2]pentyl, which is unsubstituted or carries a radical $R^{a3}$ or 7-dispiro[2.0.2.1]-heptyl which is unsubstituted or carries one or two radicals $R^{a3}$, wherein the spiro[2.2]pentyl is selected from the group consisting of 2-methylene-spiro [2.2]pentyl, 4-methyl-spiro[2.2]pentyl, 4,4-dimethyl-spiro [2.2]pentyl, 4-(methoxymethy)-spiro [2.2]pentyl, and 4-(trifluoromethyl)-spiro[2.2]pentyl.

7. The compound of claim 1, where $R^1$ is $CH_3$, or $C_2H_5$.

8. The compound of claim 1, where $R^2$ is $CH_3$, $CHF_2$, or $CF_3$.

9. A composition comprising a compound according to claim 1 and at least one inert liquid and/or solid carrier.

10. A method for combating or controlling invertebrate pests, which method comprises contacting said pest or its food supply, habitat or breeding grounds with a pesticidally effective amount of a compound according to claim 1.

11. A method for protecting growing plants or plant propagation materials from attack or infestation by invertebrate pests, which method comprises contacting a plant, a plant propagation material or soil or water in which the plant is growing, with a pesticidally effective amount of a compound according to claim 1.

12. A method for protection of plant propagation material comprising contacting the plant propagation material with a compound according to claim 1 in an amount of from 0.1 g to 10 kg per 100 kg of plant propagation material.

13. The method of claim 10, wherein, in the compound of formula (I), $R^3$ is spiro[2.2]pentyl, which is unsubstituted or carries one or two radicals $R^{a3}$, or 7-dispiro[2.0.2.1]-heptyl which is unsubstituted or carries a radical $R^{a3}$.

14. The method of claim 10, wherein, in the compound of formula (I), $R^4$ is $CH_3$, $C_2H_5$, $CHF_2$ or $CF_3$.

15. The method of claim 10, wherein, in the compound of formula (I),
$R^1$ is H, $C_1$-$C_2$-alkyl, or $C_1$-$C_2$-alkoxymethyl;
$R^2$ is $CH_3$, $CH_2F$, $CHF_2$, or $CF_3$;
$R^3$ and $R^4$ together with the carbon atom, to which they are attached, form a monospiro or dispiro 5- to 10-membered carbo- or heterocycle, which may contain 1 or 2 heteroatom moieties selected from N—$R^c$, O, and $S(O)_k$, with k being 0, 1, or 2, which carbo- or heterocycle is unsubstituted or may be substituted by 1, 2, 3 or 4 radicals $R^{a3}$;
$R^{a3}$ is CN, $C_1$-$C_2$-alkyl, $C_1$-$C_2$-haloalkyl, $C_1$-$C_2$-alkoxy-$C_1$-$C_2$-alkyl, or $C_1$-$C_2$-alkyliden;
$R^c$ is H, $C_1$-$C_2$-alkyl, $C_1$-$C_2$-haloalkyl, $C_1$-$C_2$-alkylcarbonyl, or $C_1$-$C_2$-alkoxycarbonyl;
$R^5$ is H, $CH_3$, CN, F, $OCH_3$, $SCH_3$, $CF_3$, $OCF_3$, or $SCF_3$;
the stereoisomers, salts, tautomers and N-oxides thereof.

16. The method of claim 15, wherein, in the compound of formula (I), $R^3$ and $R^4$ together with the carbon atom, to which they are attached, form a monospiro or dispiro 5-to 10-membered carbocycle which is unsubstituted or substituted by 1 or 2 radicals $R^{a3}$.

17. The method of claim 15, wherein, in the compound of formula (I), $R^3$ and $R^4$ together with the carbon atom, to which they are attached, form a spiro[2.2]pentyl, which is unsubstituted or carries a radical $R^{a3}$ or 7-dispiro[2.0.2.1]-heptyl which is unsubstituted or carries one or two radicals $R^{a3}$,
wherein the spiro[2.2]pentyl is selected from the group consisting of 2-methylene-spiro [2.2]pentyl, 4-methyl-spiro[2.2]pentyl, 4,4-dimethyl-spiro[2.2]pentyl, 4-(methoxymethyl)-spiro [2.2]pentyl, and 4-(trifluoromethy)-spiro[2.2]pentyl.

18. The method of claim 10, wherein, in the compound of formula (I), $R^1$ is $CH_3$, or $C_2H_5$.

19. The method of claim 10, wherein, in the compound of formula (I), $R^2$ is $CH_3$, $CHF_2$, or $CF_3$.

20. The compound of claim 2, wherein $R^3$ is a radical selected from the group consisting of spiro[2.2]pentyl, 2-methylene-spiro[2.2]pentyl, 1-cyano-spiro[2.2]pentyl, 1-(trifluoromethy)-spiro[2.2]pentyl, 4-methyl-spiro[2.2] pentyl, 4,4-dimethyl-spiro[2.2]pentyl, 4-(methoxymethy)-spiro[2.2]pentyl, 4-(trifluoromethy)-spiro[2.2]pentyl, and 7-dispiro[2.0.2.1]-heptyl.

21. The method of claim 13, wherein, in the compound of formula (I), $R^3$ is a radical selected from the group consisting of spiro[2.2]pentyl, 2-methylene-spiro[2.2]pentyl, 1-cyano-spiro[2.2]pentyl, 1-(trifluoromethy)-spiro[2.2]pentyl, 4-methyl-spiro[2.2]pentyl, 4,4-dimethyl-spiro[2.2]pentyl, 4-(methoxymethy)-spiro[2.2]pentyl, 4-(trifluoromethy)-spiro[2.2]pentyl, and 7-dispiro[2.0.2.1]-heptyl.

\* \* \* \* \*